(12) United States Patent
Dobelmann-Mara et al.

(10) Patent No.: US 11,014,900 B2
(45) Date of Patent: *May 25, 2021

(54) HYDROPHILIC COMPOUNDS FOR OPTICALLY ACTIVE DEVICES

(71) Applicant: MERCK PATENT GMBH, Darmstadt (DE)

(72) Inventors: Lars Dobelmann-Mara, Darmstadt (DE); Stefan Riedmueller, Frankfurt am Main (DE); Martin Schraub, Alsbach-Haehnlein (DE)

(73) Assignee: MERCK PATENT GMBH, Darmstadt (DE)

( * ) Notice: Subject to any disclaimer, the term of this patent is extended or adjusted under 35 U.S.C. 154(b) by 10 days.

This patent is subject to a terminal disclaimer.

(21) Appl. No.: 16/486,340

(22) PCT Filed: Feb. 14, 2018

(86) PCT No.: PCT/EP2018/053627
§ 371 (c)(1),
(2) Date: Aug. 15, 2019

(87) PCT Pub. No.: WO2018/149853
PCT Pub. Date: Aug. 23, 2018

(65) Prior Publication Data
US 2020/0231559 A1 Jul. 23, 2020

(30) Foreign Application Priority Data

Feb. 15, 2017 (EP) .................................... 17156324

(51) Int. Cl.
| | | |
|---|---|---|
| *C07D 307/79* | (2006.01) | |
| *A61L 27/16* | (2006.01) | |
| *C07D 209/08* | (2006.01) | |
| *C07D 209/12* | (2006.01) | |
| *C07D 333/54* | (2006.01) | |
| *C07D 407/12* | (2006.01) | |
| *C07D 409/04* | (2006.01) | |
| *C07D 409/06* | (2006.01) | |
| *C07D 409/14* | (2006.01) | |
| *C07F 7/18* | (2006.01) | |
| *C08F 120/36* | (2006.01) | |
| *C08F 124/00* | (2006.01) | |
| *C08F 126/06* | (2006.01) | |
| *C08F 128/06* | (2006.01) | |

(52) U.S. Cl.
CPC ............ *C07D 307/79* (2013.01); *A61L 27/16* (2013.01); *C07D 209/08* (2013.01); *C07D 209/12* (2013.01); *C07D 333/54* (2013.01); *C07D 407/12* (2013.01); *C07D 409/04* (2013.01); *C07D 409/06* (2013.01); *C07D 409/14* (2013.01); *C07F 7/1804* (2013.01); *C08F 120/36* (2013.01); *C08F 124/00* (2013.01); *C08F 126/06* (2013.01); *C08F 128/06* (2013.01)

(58) Field of Classification Search
CPC .................................................... C07D 307/79
USPC ........................................................ 526/256
See application file for complete search history.

(56) References Cited

U.S. PATENT DOCUMENTS

| | | |
|---|---|---|
| 5,290,892 A | 3/1994 | Namdaran et al. |
| 5,331,073 A | 7/1994 | Weinschenk et al. |
| 5,693,095 A | 12/1997 | Freeman et al. |
| 8,109,999 B2 | 2/2012 | Hampp |
| 10,457,658 B2 * | 10/2019 | Dobelmann-Mara ........ C08F 20/40 |
| 10,829,451 B2 * | 11/2020 | Dobelmann-Mara ........ C07D 215/227 |
| 2010/0324165 A1 | 12/2010 | Ritter et al. |
| 2011/0092612 A1 | 4/2011 | Miki |

FOREIGN PATENT DOCUMENTS

| | | |
|---|---|---|
| CN | 105753837 A | 7/2016 |
| WO | 07033831 A1 | 3/2007 |
| WO | 09074520 A2 | 6/2009 |
| WO | 16200401 A1 | 12/2016 |

OTHER PUBLICATIONS

M. Schraub et al., European Polymer Journal, vol. 51, 2014, pp. 21-27.
C.H. Krauch et al., Chemische Berichte Jahrg, vol. 99, 1966, pp. 1723.
A. Bouquet et al., Tetrahedron, vol. 37, 1981, pp. 75-81.
David L. Oldroyd et al., Tetrahedron Letters, vol. 34, No. 7, 1993, pp. 1087-1090.
Lee et al., Journal of Applied Polymer Science, 2012, vol. 124, 4339-4345.
International search report PCT/EP2018/053627 dated Apr. 5, 2018 (pp. 1-3).

* cited by examiner

*Primary Examiner* — Nizal S Chandrakumar
(74) *Attorney, Agent, or Firm* — Millen White Zelano & Branigan, PC; Brion P. Heaney

(57) ABSTRACT

The present invention relates to novel compounds, particularly to compounds comprising a photoactive unit, said novel compounds being particularly suitable for compositions and ophthalmic devices as well as to compositions and ophthalmic devices comprising such compounds.

38 Claims, No Drawings

HYDROPHILIC COMPOUNDS FOR OPTICALLY ACTIVE DEVICES

FIELD OF THE INVENTION

The present invention relates to novel compounds, particularly to compounds comprising a photoactive unit, said novel compounds being particularly suitable for compositions and ophthalmic devices as well as to compositions and ophthalmic devices comprising such compounds.

BACKGROUND OF THE INVENTION

Cataract is a general term for an affection of the eye that leads to a loss of vision and in the extreme to blindness by clouding of the normally clear lens of the eye. It is the major cause of blindness in the world, affecting more than 100 million people. Due to the fact that its major cause is age and the population's average age is increasing, it is expected that the number of cataracts will continue to increase substantially in the future.

Effective treatment of cataract is only possible by surgical intervention, whereby the natural lens of the eye is removed through an incision in the cornea and replaced with an artificial lens, often also referred to as "intraocular lens". In preparation of surgery current state-of-the-art surgical methods employ eye mapping so as to approximate the refractive power best suited to the respective patient.

Even though cataract surgery is one of the most widely used and safest surgical procedures it is not without specific post-surgery problems. It frequently happens that the refractive power of the implanted intraocular lens (IOL) is insufficient for restoring good vision. Such problems may, for example, be caused by changes in eye geometry as consequence of the surgery as well as irregular wound healing and positioning errors that result in the artificial lens not having the optimal optical properties. As a result the patient will still require corrective vision aids, e.g. glasses, to be able to see correctly. In some cases the resulting refractive power of the implanted artificial lens is so far removed from the required refractive power that further surgery will be required. Particularly for aged persons this is not desirable because the body's capability for healing is reduced with increasing age. Furthermore, there is the risk of attracting endophthalmitis, an inflammation of the eye, which can even lead to a complete loss of vision or worse, loss of the eye.

There is therefore a need in the health sector for optically active devices, and particularly for artificial intraocular lenses, that would allow for non-invasive adjustment of refractive power after implantation of the lens, thereby preferably further reducing the need for post-surgery vision aids.

Some developments in this sense have already been made, as for example evidenced by WO 2007/033831 A1, WO 2009/074520 A2 or US 2010/0324165 A1.

US 2011/0092612 A describes 3- or 4-(2-benzothiophenyl)-1-phenyl acrylates and methacrylates as photoreactive compounds.

CN 105753837 A describes liquid crystal compositions comprising benzothiophene dimethacrylates.

WO 2016/200401 A1 describes liquid crystal materials having photoalignment properties such as 6-(4-(benzofuran-2-yl)phenoxy)hexyl methacrylate.

M. Schraub et al, European Polymer Journal 51 (2014) 21-27 describes the photochemistry of 3-phenyl-coumarin containing polymethacrylates.

C. H. Krauch et al, Chemische Berichte Jahrg. 99, 1966, 1723 describe photochemical reactions on coumaron.

A. Bouquet et al, Tetrahedron, 1981, vol. 37, 75 to 81 describe the photochemical behavior of several benzo[b]thiophenes in neutral solutions or in the presence of primary and tertiary amines.

David L. Oldroyd et al, Tetrahedron Letters, 1993, vol. 34, no. 7, 1087-1090 describe photochemical dimerization reactions of N-Acylindoles.

Mi Sun Lee and Jin-Chul Kim, Journal of Applied Polymer Science, 2012, vol. 124, 4339 to 4345 describe poly (vinyl alcohol) (PVA) having coumarin pendants by reacting the polymer with epoxypropoxy coumarin (EPC) in a strong alkali condition with EPC/PVA molar ratio of 200/1 and an aqueous solution of PVA-EPC (5%, w/v) which became a semi-solid hydrogel by the irradiation of a light for 1 hour. Such chemically crosslinked PVA hydrogels are deemed to become relevant as a vehicle which releases a drug in response to a UV light irradiation. It may be used in the photo anticancer therapy.

However, the compounds disclosed so far suffer from being too stiff and too brittle so that they can't be rolled or folded and are thus not fit to be implanted by state of the art cataract surgical methods, particularly by state of the art micro-incision cataract surgical methods.

Consequently, it is an objective of the present application to provide for novel compounds suitable for ophthalmic devices.

It is also an objective of the present application to provide for compounds, the optical properties of which may be changed, preferably by non-invasive techniques.

It is a further objective of the present application to provide for novel compounds having advantages over currently known compounds, preferably in combination with being suitable for ophthalmic devices.

Advantages such as better flexibility and objectives of the compounds of the present application will be evident to the skilled person from the following detailed description as well as from the examples.

SUMMARY OF THE INVENTION

The present inventors have now found that the above objects may be attained either individually or in any combination by the compounds and ophthalmic devices of the present application.

The invention relates to compounds of formula (I)

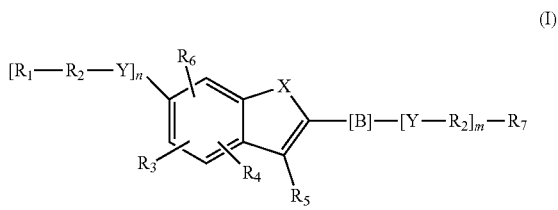

wherein
X is O, S or $NR_0$,
Y is independently of each other O, S or a bond,
n is 0 or 1,
m is 0 or 1,
n+m is 1 or 2,
—[B]— is selected from the group consisting of formula (1) to formula (4),

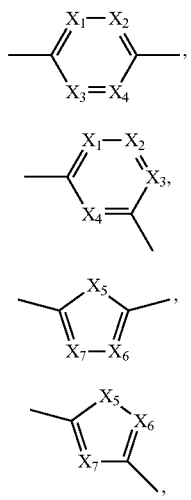

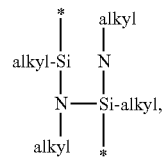

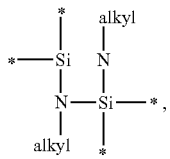

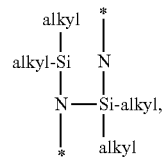

$X_1$, $X_2$, $X_3$, $X_4$ are each independently of each other $CR'$ or N,
$X_5$ is each independently O, S, C=O or $NR_0$,
$X_6$, $X_7$ are each independently $CR'$ or N,
R is at each occurrence independently selected from the group consisting of H, OH or a linear or branched hydroxyalkyl group having 1 to 4 C atoms,
$R'$ is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms,
$R_0$ is at each occurrence independently selected from the group consisting of a linear or branched alkyl group having 1 to 10 C atoms or a cycloalkyl group having 3 to 6 C atoms,
$R_1$ is a polymerizable group selected from the group consisting of
an alkenyl group of formula (5),

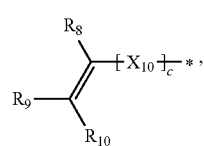

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1;
trialkoxysilyl groups or dialkoxyalkylsilyl groups where the alkyl and/or alkoxy groups are each independently linear or branched having 1 to 6 C atoms; and silyl groups of formula (6), (7) or (8), where alkyl means at each occurrence independently of each other a linear or branched alkyl group having 1 to 6 C atoms and the asterisk "*" denotes at each occurrence independently of each other a linkage to the linker $[-R_2-Y]_n$ and/or $[Y-R_2-]_m$,
$-R_2-$ is $-(C(R)_2)_o-$ or $-(C(R)_2)_p-X_8-(C(R)_2)_q-(X_9)_s-(C(R)_2)_r-$, wherein at least one R is OH or a linear or branched hydroxyalkyl group having 1 to 4 C atoms,
o is selected from the group consisting of 1 to 20,
$X_8$, $X_9$ are at each occurrence independently O, S or $NR_0$,
s is 0 or 1,
p, q are at each occurrence independently selected from the group consisting of 1 to 10,
r is at each occurrence independently selected from the group consisting of 0 to 10, wherein the overall number of atoms for $-(C(R)_2)_p-X_8-(C(R)_2)_q-(X_9)_s-(C(R)_2)_r-$ is up to 20 atoms,
$R_3$, $R_4$, $R_5$, $R_6$ are at each occurrence independently $R'$,
$R_7$ is $R'$ in case m is 0 and
$R_7$ is $R_1$ in case m is 1.

The invention relates further to compositions comprising at least one of said compounds of formula (I) and/or their polymerized forms as well as to articles comprising at least one polymerized compound of formula (I).

In addition, the invention relates to a process for forming such article, said process comprising the steps of
providing a composition comprising at least one compound of formula (I) and/or an oligomer or polymer as described before;
subsequently forming the article of said composition.

Furthermore, the invention relates to a process for changing the optical properties of an article according to the invention, said process comprising the steps of
providing an article comprising at least one polymerized compound of formula (I), and
subsequently exposing said article to irradiation having a wavelength of at least 200 nm and at most 1500 nm.

DETAILED DESCRIPTION OF THE INVENTION

The compounds of formula (I) and all preferred embodiments of compounds of formula (I) according to the present invention include all stereoisomers or racemic mixtures.

The compounds of formula (I) provide several advantages over prior art materials
- by adding a linker —[B]— to the benzo[b]furan, benzo[b]thiophene or benzo[b]pyrrol ring system their melting point or glass transition temperature will decrease and π stacking will be disturbed, thus being better foldable or bendable,
- by incorporating OH or hydroxyalkyl groups they can be made hydrophilic allowing an uptake of water decreasing the glistening of the material.

In comparison to known coumarin-type photoactive chromophores, compounds according to the invention are more stable toward UV-irradiation due to lower absorption range. Furthermore the chemical and hydrolytical stability is higher and given due to their intrinsic chemical nature e.g. due to lack of positions prone to nucleophilic attacks, like $sp^2$ centers and the absence of cyclic lactone structure motifs, compared to coumarin-type photoactive chromophores.

Polymers that are foldable at room temperature generally exhibit glass transition temperatures ($T_g$) lower than room temperature (ca. 21° C.). They are easily deformable at this temperature without causing physical damage to the polymer, for example by inducing creep, stress or fissures. For polymers in intraocular lenses, $T_g$s of less than or equal to 15° C. are preferred.

Polymers used in intraocular lens manufacturing have preferably relative high refractive indices, which enable the fabrication of thinner intraocular lenses. Preferably, the polymer used in an intraocular lens will have a refractive index greater than about 1.5 and presently most preferably greater than about 1.55.

In case an asterisk ("*") is used within the description of the present invention, it denotes a linkage to an adjacent unit or group or, in case of a polymer, to an adjacent repeating unit or any other group.

A linear or branched alkyl group having 1 to 10 C atoms denotes an alkyl group having 1, 2, 3, 4, 5, 6, 7, 8, 9 or 10 C atoms, for example methyl, ethyl, iso-propyl, n-propyl, iso-butyl, n-butyl, tert-butyl, n-pentyl, 1-, 2- or 3-methylbutyl, 1,1-, 1,2- or 2,2-dimethylpropyl, 1-ethylpropyl, n-hexyl, n-heptyl, n-octyl, ethylhexyl, n-nonyl or n-decyl. A linear or branched alkyl group having 1 to 20 C atoms include all examples for a linear or branched alkyl group having 1 to 10 C atoms including any alkyl group having 11, 12, 13, 14, 15, 16, 17, 18, 19 and 20 C atoms such as n-undecyl, n-dodecyl, n-tridecyl, n-tetradecyl, n-pentadecyl, n-hexadecyl, n-heptadecyl, n-octadecyl, n-nonadecyl and n-eicosyl.

The term partially halogenated alkyl group denotes that at least one H atom of the alkyl group is replaced by F, Cl, Br or I. Preferably, the alkyl group is partially fluorinated meaning that at least one H atom of the alkyl group is replaced by F.

The term completely halogenated alkyl group denotes that all H atoms of the alkyl group are replaced by F, Cl, Br and/or I. Preferably, the alkyl group is completely fluorinated meaning that all H atoms of the alkyl group are replaced by F. A preferred completely fluorinated alkyl group is trifluoromethyl.

The term halogenated or preferably fluorinated corresponds additionally to other groups such as a halogenated cycloalkyl group, a halogenated alkoxy group or a halogenated thioalkyl group.

A linear or branched hydroxyalkyl group having 1 to 20 C atoms denotes an alkyl group having 1, 2, 3, 4, 5, 6, 7, 8, 9, 10, 11, 12, 13, 14, 15, 16, 17, 18, 19 or 20 C atoms wherein at least one H atom is replaced by a hydroxyl group (—OH). The hydroxyl group is preferably replaced on the last C atom of the alkyl group, for example hydroxymethyl, 2-hydroxyethyl, 3-hydroxy-propyl, 4-hydroxy-butyl, 5-hydroxy-pentyl, 4-hydroxy-1-, -2- or -3-methylbutyl, 3-hydroxy-1,1-, -1,2- or -2,2-dimethylpropyl, 3-hydroxy-1-ethylpropyl, 6-hydroxy-hexyl, 7-hydroxy-heptyl, 8-hydroxy-octyl, 6-hydroxy-1-ethylhexyl, 9-hydroxy-nonyl, 10-hydroxy-decyl, 11-hydroxy-undecyl, 12-hydroxy-dodecyl, 13-hydroxy-tridecyl, 14-hydroxy-tetradecyl, 15-hydroxy-pentadecyl, 16-hydroxy-hexadecyl, 17-hydroxy-heptadecyl, 18-hydroxy-octadecyl, 19-hydroxy-nonadecyl and 20-hydroxy-eicosyl. Preferred hydroxyalkyl groups are hydroxymethyl and 3-hydroxy-propyl.

A cycloalkyl group having 3 to 6 C atoms includes cyclopropyl, cyclobutyl, cyclopentyl and cyclohexyl which may be partially or completely halogenated or fluorinated as explained before.

A linear or branched alkoxy group having 1 to 20 C atoms denotes an O-alkyl group having 1, 2, 3, 4, 5, 6, 7, 8, 9, 10, 11, 12, 13, 14, 15, 16, 17, 18, 19 or 20 C atoms, for example methoxy, ethoxy, iso-propoxy, n-propoxy, iso-butoxy, n-butoxy, tert-butoxy, n-pentyloxy, 1-, 2- or 3-methylbutyloxy, 1,1-, 1,2- or 2,2-dimethylpropoxy, 1-ethylpropoxy, n-hexyloxy, n-heptyloxy, n-octyloxy, ethylhexyloxy, n-nonyloxy, n-decyloxy, n-undecyloxy, n-dodecyloxy, n-tridecyloxy, n-tetradecyloxy, n-pentadecyloxy, n-hexadecyloxy, n-heptadecyloxy, n-octadecyloxy, n-nonadecyloxy and n-eicosyloxy which may be partially or completely halogenated or preferably may be partially or completely fluorinated. A preferred completely fluorinated alkoxy group is trifluoromethoxy.

A linear or branched thioalkyl group having 1 to 20 C atoms denotes a S-alkyl group having 1, 2, 3, 4, 5, 6, 7, 8, 9, 10, 11, 12, 13, 14, 15, 16, 17, 18, 19 or 20 C atoms, for example thiomethyl, 1-thioethyl, 1-thio-iso-propyl, 1-thio-n-propoyl, 1-thio-iso-butyl, 1-thio-n-butyl, 1-thio-tert-butyl, 1-thio-n-pentyl, 1-thio-1-, -2- or -3-methylbutyl, 1-thio-1,1-, -1,2- or -2,2-dimethylpropyl, 1-thio-1-ethylpropyl, 1-thio-n-hexyl, 1-thio-n-heptyl, 1-thio-n-octyl, 1-thio-ethylhexyl, 1-thio-n-nonyl, 1-thio-n-decyl, 1-thio-n-undecyl, 1-thio-n-dodecyl, 1-thio-n-tridecyl, 1-thio-n-tetradecyl, 1-thio-n-pentadecyl, 1-thio-n-hexadecyl, 1-thio-n-heptadecyl, 1-thio-n-octadecyl, 1-thio-n-nonadecyl and 1-thio-n-eicosyl which may be partially or completely halogenated or preferably may be partially or completely fluorinated. A preferred completely fluorinated thioether group is trifluoromethyl thioether.

Preferred alkyl and alkoxy radicals have 1, 2, 3, 4, 5, 6, 7, 8, 9 or 10 C atoms.

A polymerizable group is a group which can be subject to or can undergo polymerization thus forming an oligomer or a polymer.

Polymerization is the process of taking individual monomers and chaining them together to make longer units. These longer units are called polymers. The compounds of formula (I) as described before and preferably described below are suitable monomers.

Within the gist of the invention, the polymerizable group $R_1$ once oligomerized or polymerized thus forms or is part of the backbone of the oligomer or polymer comprising polymerized compounds of formula (I).

Suitable polymerizable groups contain at least one double bond or at least one triple bond thus forming polymers where the linking is formed via carbon-carbon bonds. Alternatively, a suitable polymerizable group may contain silicon thus forming polysiloxanes or polysilazanes.

The suitable polymerizable groups are selected from the group consisting of
an alkenyl group of formula (5),

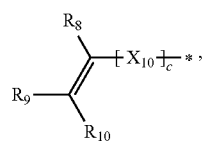

(5)

wherein
$X_{10}$ is selected from the group consisting of O, S, C(=O), C(=O)O,
$R_8$, $R_9$, $R_{10}$ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1;
trialkoxysilyl groups or dialkoxyalkylsilyl groups where the alkyl and/or alkoxy groups are each independently linear or branched having 1 to 6 C atoms; and
silyl groups of formula (6), (7) or (8),

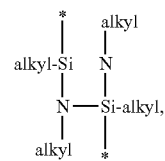

(6)

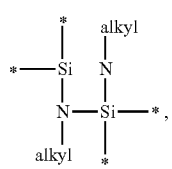

(7)

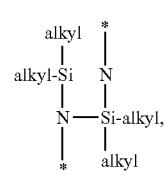

(8)

where alkyl means at each occurrence independently of each other a linear or branched alkyl group having 1 to 6 C atoms and the asterisk "*" denotes at each occurrence independently of each other a linkage to the linker [—$R_2$—Y]$_n$ and/or [Y—$R_2$-]$_m$ as described before or preferably described before.

A preferred polymerizable group is selected from the group consisting of trimethoxysilyl, triethoxysilyl, diethoxymethylsilyl and the alkenyl group of formula (5) as described before and preferably described below.

Aryl with 6 to 14 C atoms is an aryl group preferably selected from the group consisting of phenyl, naphthyl or anthryl, particularly preferably phenyl.

The linker —[B]— is selected from the group of formulae (1) to (4), wherein $X_1$, $X_2$, $X_3$, $X_4$ are each independently of each other CR' or N, $X_5$ is each independently O, S, C=O or $NR_0$ and $X_6$ and $X_7$ are each independently CR' or N, wherein R' and $R_0$ have a meaning as described before or preferably described below.

Preferred examples for the linker —[B]— are therefore selected from the group of formulae (B-1) to (B-34),

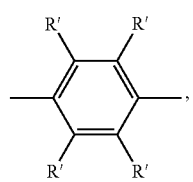

(B-1)

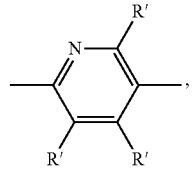

(B-2)

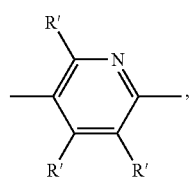

(B-3)

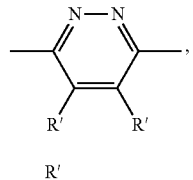

(B-4)

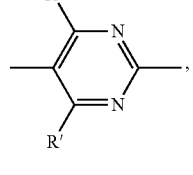

(B-5)

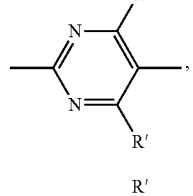

(B-6)

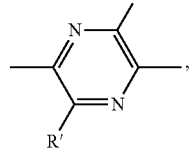

(B-7)

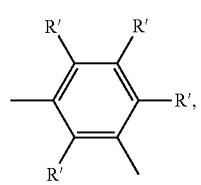
(B-8)
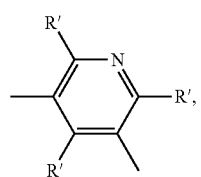
(B-9)
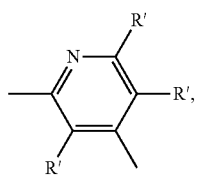
(B-10)
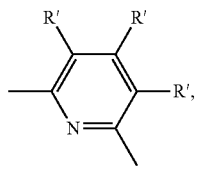
(B-11)
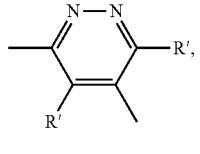
(B-12)
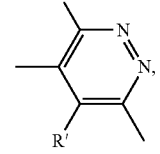
(B-13)
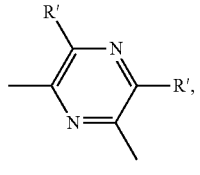
(B-14)
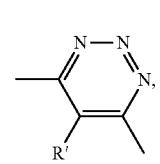
(B-15)
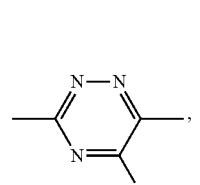
(B-16)
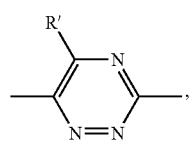
(B-17)
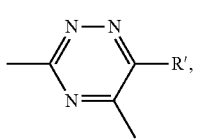
(B-18)
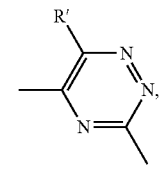
(B-19)
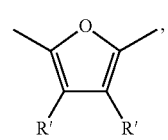
(B-20)
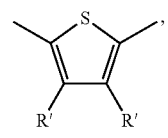
(B-21)
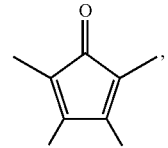
(B-22)
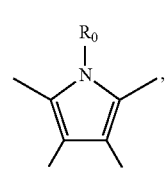
(B-23)
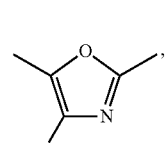
(B-24)
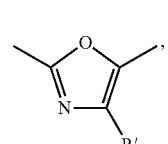
(B-25)
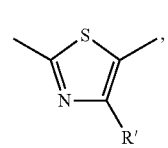
(B-26)

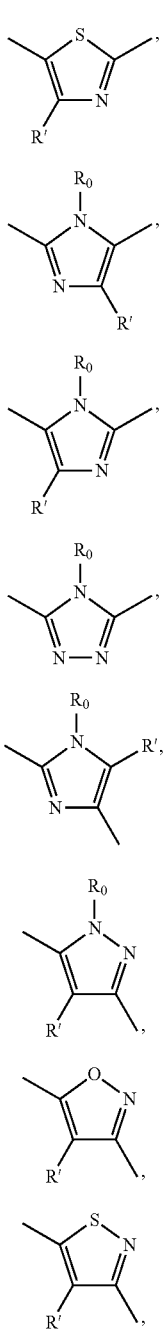

(B-27), (B-28), (B-29), (B-30), (B-31), (B-32), (B-33), (B-34)

wherein R' and R₀ have a meaning as described before or preferably described below.

Compounds of formula (I) as described before are preferred where the linker —[B]— corresponds to formula (1) or (2) and $X_1$, $X_2$, $X_3$ and $X_4$ have a meaning as described before. Therefore, compounds of formula (I) are preferred where the linker —[B]— corresponds to formulae (B-1) to (B-19).

The invention therefore relates additionally to compounds of formula (I) as described before wherein —[B]— corresponds to formula (1) and (2) and $X_1$, $X_2$, $X_3$ and $X_4$ have a meaning as described before.

Compounds of formula (I) as described before are particularly preferred where the linker —[B]— corresponds to formula (1) or (2) and $X_1$, $X_3$ and $X_4$ are CR' and R' has at each occurrence independently a meaning as described before or preferably described below. Therefore, compounds of formula (I) are particularly preferred where the linker —[B]— corresponds to formulae (B-1), (B-3), (B-8) or (B-9).

The invention therefore relates additionally to compounds of formula (I) as described before wherein —[B]— corresponds to formula (1) and (2) and $X_1$, $X_3$ and $X_4$ are CR' and R' has at each occurrence independently a meaning as described before or preferably described below.

Compounds of formula (I) as described or preferably described before are especially preferred where the linker —[B]— corresponds to formula (1) or (2) and $X_2$ is CR' and R' has at each occurrence independently a meaning as described before or preferably described below. Therefore, compounds of formula (I) are especially preferred where the linker —[B]— corresponds to formulae (B-1), (B-2), (B-6), (B-7), (B-8), (B-10) or (B-11). Additionally, compounds of formula (I) having a linker —[B]— which corresponds to formula (B-1) or (B-8) are very particularly preferred and R' has at each occurrence independently a meaning as described before or preferably described below. Within this very particular preferred compounds of formula (I), it is preferred to select the linker of formula (B-1) and R' has at each occurrence independently a meaning as described before or preferably described below.

The invention therefore relates additionally to compounds of formula (I) as described or preferably described before wherein —[B]— corresponds to formula (1) and (2) and $X_2$ is CR' and R' has at each occurrence independently a meaning as described before or preferably described below.

R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms.

It is preferred that at least one R' in —[B]— as described before or preferably described before is different from H and is selected from the group consisting of F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms. It is particularly preferred that at least two substituents R' are different from H and are independently selected from the group consisting of F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, a linear or branched, non-halogenated, partially or completely halogenated thioalkyl group having 1 to 20 C atoms. With regard to said substituent R', R' is at each occurrence independently preferably selected from the group consisting of H, F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

It is preferred that at least one R' in —[B] as described before or preferably described before is different from H and is selected from the group consisting of F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

It is particularly preferred that at least two substituents R' are different from H and are independently selected from the group consisting of F, a linear or branched, non-halogenated, partially or completely halogenated alkyl group having 1 to 10 C atoms, a linear or branched hydroxyalkyl group having 1 to 10 C atoms, a linear or branched, non-halogenated and a partially or completely halogenated alkoxy group having 1 to 10 C atoms.

R' is at each occurrence independently particularly preferably selected from the group consisting of H, F, methyl, ethyl, n-propyl, n-butyl, n-pentyl, n-hexyl, n-heptyl, n-octyl, trifluormethyl, pentafluorethyl, heptafluorpropyl, methoxy, ethoxy, propoxy, trifluormethoxy, pentafluorethoxy, 2-hydroxy-ethyl, 3-hydroxy-propyl, 4-hydroxy-butyl and 5-hydroxy-pentyl.

R' is at each occurrence independently very particularly preferably selected from the group consisting of H, F, ethyl, n-pentyl, trifluoromethyl, methoxy, trifluoromethoxy and 3-hydroxy-propyl.

Compounds of formula (I) with linkers —[B]— as defined before or preferably defined before are further preferred through their substitution pattern on the linker —[B]— preferably through the substituent R' which is independent at each occurrence.

Therefore, the invention is further directed to compounds of formula (I) as described before where —[B]— corresponds to formulae (1) to (4) and wherein at least one R' within $X_1$, $X_2$, $X_3$. $X_4$, $X_6$ or $X_7$ is not H.

Therefore, the invention is further directed to compounds of formula (I) as described before where —[B]— corresponds to formulae (B-1) to (B-29) or (B-31) to (B-34) or to preferred linkers as described before, wherein at least one R' is not H, all other R' and $R_0$ have a meaning as described before or preferably described before or below.

The substituent R' within $X_1$ or $X_3$ in formula (1) is particularly preferred not H and has a meaning as described before.

The substituent R' within $X_7$ in formula (3) is particularly preferred not H and has a meaning as described before.

As described before, the substituents $R_3$, $R_4$, $R_5$ and $R_6$ are at each occurrence independently R' where R' has a meaning or a preferred or particularly preferred meaning as described before.

$R_5$ is preferably H or F. $R_5$ is particularly preferably H.

As described before, the substituent $R_7$ corresponds to R' in case m is 0 wherein R' has a meaning or a preferred or particularly preferred meaning as described before. Preferably in case m is 0, $R_7$ corresponds to R' which is not H and has a meaning as described before or preferably described before or below.

In all cases when R' is preferably not H, it is selected from the preferred group consisting of F, methyl, ethyl, n-propyl, n-butyl, n-pentyl, n-hexyl, n-heptyl, n-octyl, trifluormethyl, pentafluorethyl, heptafluorpropyl, methoxy, ethoxy, propoxy, trifluormethoxy, pentafluorethoxy, 2-hydroxy-ethyl, 3-hydroxy-propyl, 4-hydroxy-butyl and 5-hydroxy-pentyl or from the particular preferred group consisting of F, ethyl, n-pentyl, trifluoromethyl, methoxy, trifluoromethoxy and 3-hydroxy-propyl.

Therefore, the invention is further directed to compounds of formula (I) as described before where —[B]— corresponds to formulae (1) to (4) and wherein at least one R' within $X_1$, $X_2$, $X_3$. $X_4$, $X_6$ or $X_7$ is not H and $R_7$ is not H in case m is 0.

Therefore, the invention is further directed to compounds of formula (I) as described before where —[B]— corresponds to formulae (B-1) to (B-29) or (B-31) to (B-34) or to preferred linkers as described before, wherein at least one R' is not H and $R_7$ is not H in case m is 0 and $R_0$ has a meaning as described before or as preferably described below.

As described before, the substituent $R_7$ corresponds to $R_1$ in case m is 1 wherein $R_1$ has a meaning or a preferred meaning as described before or further below. Compounds of formula (I) in which m is 1 are preferred having a linker —[B]— selected from the group consisting of formula (1) to (4) wherein at least one substituent R' within $X_1$, $X_2$, $X_3$, $X_4$, $X_6$ or $X_7$ is not H and in which at least one substituent $R_3$, $R_4$ or $R_6$ is not H.

Therefore, the invention is further directed to compounds of formula (I) as described before where —[B]— corresponds to formulae (1) to (4) and wherein at least one R' within $X_1$, $X_2$, $X_3$. $X_4$, $X_6$ or $X_7$ is not H, in which at least one substituent $R_3$, $R_4$ or $R_6$ is not H and $R_7$ corresponds to $R_1$ in case m is 1.

Therefore, the invention is further directed to compounds of formula (I) as described before where —[B]— corresponds to formulae (B-1) to (B-29) or (B-31) to (B-34) or to preferred linkers as described before, wherein at least one R' is not H, in which at least one substituent $R_3$, $R_4$ or $R_6$ is not H and $R_7$ corresponds to $R_1$ in case m is 1 wherein $R_0$ and $R_1$ has a meaning as described before or further below.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]furan ring system in case X is O.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]thiophene ring system in case X is S.

Compounds of formula (I) with linkers —[B]— as defined before or preferably defined before with the described or preferred substitution pattern on the linker —[B]— and its substituents $R_3$, $R_4$, $R_5$ and $R_6$ as described before or preferably described before are based on a benzo[b]pyrrol ring system in case X is $NR_0$ and $R_0$ is independently selected from the group consisting of a linear or branched alkyl group having 1 to 10 C atoms or a cycloalkyl group having 3 to 6 C atoms.

$R_0$ is at each occurrence independently preferably methyl, ethyl, iso-propyl, 2-methyl-propyl, n-butyl, n-pentyl, 4-methyl-pentyl or cyclopropyl.

In case X is $NR_0$, $R_0$ is particularly preferably ethyl, iso-propyl, 2-methyl-propyl, n-pentyl or 4-methyl-pentyl.

In case $X_5$ is $NR_0$, $R_0$ is particularly preferably methyl or n-butyl.

In case $X_8$ or $X_9$ is $NR_0$, $R_0$ is particularly preferably methyl.

Compounds of formula (I) with linkers and substituents as described before or preferably described before or below are preferred when X is O or S.

Compounds of formula (I) with linkers and substituents as described before or preferably described before or below are particularly preferred when X is O.

In one preferred embodiment of the invention, the compounds of formula (I) as described before or preferably described before contain one polymerizable group $R_1$. This is the case for compounds of formula (I) in which n is 1 or m is 1 and the sum of n and m is 1. Such compounds can be preferably used as monomers for the preparation of a blank which may be transformed to an ophthalmic device such as an eye-implant or specifically an intraocular lens or to the ophthalmic device as such as described before.

The invention is therefore additionally directed to compounds of formula (I) wherein n is 1 and m is 0 which can preferably be described according to formula (I'), (I')

wherein $R_1$, —$R_2$—, Y, $R_3$, $R_4$, $R_5$, $R_6$, X, —[B]— and $R_7$ have a meaning as described before or preferably described before or below.

The invention is therefore additionally directed to compounds of formula (I) wherein n is 0 and m is 1 which can preferably be described according to formula (I''), (I'')

wherein $R_1$, —$R_2$—, Y, $R_3$, $R_4$, $R_5$, $R_6$, X, —[B]— and $R_7$ have a meaning as described before or preferably described before or below.

In another preferred embodiment of the invention, the compounds of formula (I) as described before or preferably described before contain two polymerizable groups $R_1$. This is the case for compounds of formula (I) in which n is 1 and m is 1 and the sum of n and m is 2. Such compounds can be preferably used as cross-linking agent for the preparation of a blank which may be transformed to an ophthalmic device such as an eye-implant or specifically an intraocular lens or to the ophthalmic device as such as described before.

The invention is therefore additionally directed to compounds of formula (I) wherein n is 1 and m is 1 which can preferably be described according to formula (I'''), (I''')

wherein $R_1$, —$R_2$—, Y, $R_3$, $R_4$, $R_5$, $R_6$, X, —[B]— and $R_7$ have a meaning as described before or preferably described before or below.

Compounds of formula (I), (I'), (I'') and (I''') with linkers —[B]— and substituents as described before or preferably described before have a polymerizable group as described before or preferably described before or below and have at least one linking element Y—$R_2$—.

Y is at each occurrence independently O, S or a bond.

The linking element —$R_2$— is selected from the group consisting of —$(C(R)_2)_o$— and —$(C(R)_2)_p$—$X_8$—$(C(R)_2)_q$—$(X_9)_s$—$(C(R)_2)_r$—, wherein at least one R is OH or a linear or branched hydroxyalkyl group having 1 to 4 C atoms and o is selected from the group consisting of 1 to 20, $X_8$ and $X_9$ are at each occurrence O, S or $NR_0$, s is 0 or 1, p and q are at each occurrence independently selected from the group consisting of 1 to 10 and r is at each occurrence independently selected from the group consisting of 0 to 10, wherein the overall number of atoms for —$(C(R)_2)_p$—$X_8$—$(C(R)_2)_q$—$(X_9)_s$—$(C(R)_2)_r$— is up to 20 C atoms.

R is at each occurrence independently selected from the group consisting of H, OH or a linear or branched hydroxyalkyl group having 1 to 4 C atoms.

R is preferably at each occurrence independently selected from the group consisting of H, OH, hydroxymethyl, 2-hydroxy-ethyl, 3-hydroxypropyl and 4-hydroxybutyl. R is particularly preferably at each occurrence independently H, OH or hydroxymethyl.

Preferably, o is selected from the group consisting of 3, 4, 5, 6, 7, 8, 9 and 10. Particularly preferably, o is selected from the group consisting of 6 to 10.

Preferably, s is 1.

Preferably, $X_8$ and $X_9$ are O.

Preferably, p and r are 3, 4, 5 or 6, particularly preferably 3.

Preferably, q is 2, 3, 4, 5 or 6.

Suitable examples for —$R_2$— are —(CHOH)—(CH$_2$)—, —(CH$_2$)—(CHOH)—, —(CH$_2$)—(CHOH)—(CH$_2$)—, —(CH$_2$)—(CHOH)—(CH$_2$)$_2$—, —(CH$_2$)—(CHOH)—(CH$_2$)$_3$—, —(CH$_2$)—(CHOH)—(CH$_2$)$_4$—, —(CH$_2$)—(CHOH)—(CH$_2$)$_5$—, —(CH$_2$)—(CHOH)—(CH$_2$)$_6$—, —(CH$_2$)—(CHOH)—(CH$_2$)$_7$—, —(CH$_2$)—(CHOH)—(CH$_2$)$_8$—, —(CH$_2$)$_2$—(CHOH)—(CH$_2$)—, —(CH$_2$)$_3$—(CHOH)—(CH$_2$)—, —(CH$_2$)$_4$—(CHOH)—(CH$_2$)—, —(CH$_2$)$_5$—(CHOH)—(CH$_2$)—, —(CH$_2$)$_6$—(CHOH)—(CH$_2$)—, —(CH$_2$)$_7$—(CHOH)—(CH$_2$)—, —(CH$_2$)$_8$—(CHOH)—(CH$_2$)—, —(CH$_2$)$_2$—(CHOH)—(CH$_2$)$_2$—, —(CH$_2$)$_3$—(CHOH)—(CH$_2$)$_3$—, —(CH$_2$)$_4$—(CHOH)—(CH$_2$)$_4$—, —(CH$_2$)$_5$—(CHOH)—(CH$_2$)$_5$—, —[CH(CH$_2$OH)]—(CH$_2$)—, —(CH$_2$)—, —[CH(CH$_2$OH)]—, —(CH$_2$)—[CH(CH$_2$OH)]—(CH$_2$)—, —(CH$_2$)—[CH(CH$_2$OH)]—(CH$_2$)$_2$—, —(CH$_2$)—[CH(CH$_2$OH)]—(CH$_2$)$_3$—, —(CH$_2$)—[CH(CH$_2$OH)]—(CH$_2$)$_4$—, —(CH$_2$)—[CH(CH$_2$OH)]—(CH$_2$)$_5$—, —(CH$_2$)—[CH(CH$_2$OH)]—(CH$_2$)$_6$—, —(CH$_2$)—[CH(CH$_2$OH)]

—(CH$_2$)$_7$—, —(CH$_2$)—[CH(CH$_2$OH)]—(CH$_2$)$_8$—, —(CH$_2$)$_2$—[CH(CH$_2$OH)]—(CH$_2$)—, —(CH$_2$)$_3$—[CH(CH$_2$OH)]—(CH$_2$)—, —(CH$_2$)$_4$—[CH(CH$_2$OH)]—(CH$_2$)—, —(CH$_2$)$_5$—[CH(CH$_2$OH)]—(CH$_2$)—, —(CH$_2$)$_6$—[CH(CH$_2$OH)]—(CH$_2$)—, —(CH$_2$)$_7$—[CH(CH$_2$OH)]—(CH$_2$)—, —(CH$_2$)$_8$—[CH(CH$_2$OH)]—(CH$_2$)—, —(CH$_2$)$_2$—[CH(CH$_2$OH)]—(CH$_2$)$_2$—, —(CH$_2$)$_3$—[CH(CH$_2$OH)]—(CH$_2$)$_3$—, —(CH$_2$)$_4$—[CH(CH$_2$OH)]—(CH$_2$)$_4$—, —(CH$_2$)$_5$—[CH(CH$_2$OH)]—(CH$_2$)$_5$—, —(CH$_2$)—(CHOH)—(CHOH)—(CH$_2$)—, —(CH$_2$)$_2$—(CHOH)—(CHOH)—(CH$_2$)$_2$—, —(CH$_2$)$_3$—(CHOH)—(CHOH)—(CH$_2$)$_3$—, —(CH$_2$)$_4$—(CHOH)—(CHOH)—(CH$_2$)$_4$—, —(CH$_2$)—(CHOH)—(CHOH)—(CH$_2$)$_3$—, —(CH$_2$)—(CHOH)—(CHOH)—(CH$_2$)$_4$—, —(CH$_2$)—(CHOH)—(CHOH)—(CH$_2$)$_5$—, —(CH$_2$)—(CHOH)—(CHOH)—(CH$_2$)$_6$—, —(CH$_2$)—(CHOH)—(CHOH)—(CH$_2$)$_7$—, —(CH$_2$)$_3$—(CHOH)—(CHOH)—(CH$_2$)—, —(CH$_2$)$_4$—(CHOH)—(CHOH)—(CH$_2$)—, —(CH$_2$)$_5$—(CHOH)—(CHOH)—(CH$_2$)—, —(CH$_2$)$_6$—(CHOH)—(CHOH)—(CH$_2$)—, —(CH$_2$)$_7$—(CHOH)—(CHOH)—(CH$_2$)—, —(CH$_2$)$_2$—(CHOH)—(CHOH)—(CH$_2$)$_3$—, —(CH$_2$)$_2$—(CHOH)—(CHOH)—(CH$_2$)$_4$—, —(CH$_2$)$_2$—(CHOH)—(CHOH)—(CH$_2$)$_5$—, —(CH$_2$)$_2$—(CHOH)—(CHOH)—(CH$_2$)$_6$—, —(CH$_2$)$_3$—(CHOH)—(CHOH)—(CH$_2$)$_2$—, —(CH$_2$)$_4$—(CHOH)—(CHOH)—(CH$_2$)$_2$—, —(CH$_2$)$_5$—(CHOH)—(CHOH)—(CH$_2$)$_2$—, —(CH$_2$)$_6$—(CHOH)—(CHOH)—(CH$_2$)$_2$—, —(CH$_2$)$_3$—(CHOH)—(CHOH)—(CH$_2$)$_4$—, —(CH$_2$)$_4$—(CHOH)—(CHOH)—(CH$_2$)$_3$—, —(CH$_2$)$_3$—(CHOH)—(CHOH)—(CH$_2$)$_5$—, —(CH$_2$)$_5$—(CHOH)—(CHOH)—(CH$_2$)$_3$—, —(CH$_2$)—(CHOH)—(CH$_2$)—(CHOH)—(CH$_2$)—, —(CH$_2$)$_2$—(CHOH)—(CH$_2$)—(CHOH)—(CH$_2$)$_2$—, —(CH$_2$)$_3$—(CHOH)—(CH$_2$)—(CHOH)—(CH$_2$)$_3$—, —(CH$_2$)$_4$—(CHOH)—(CH$_2$)—(CHOH)—(CH$_2$)$_4$—, —(CH$_2$)—(CHOH)—(CH$_2$)—(CHOH)—(CH$_2$)$_3$—, —(CH$_2$)—(CHOH)—(CH$_2$)—(CHOH)—(CH$_2$)$_4$—, —(CH$_2$)—(CHOH)—(CH$_2$)—(CHOH)—(CH$_2$)$_5$—, —(CH$_2$)—(CHOH)—(CH$_2$)—(CHOH)—(CH$_2$)$_6$—, —(CH$_2$)—(CHOH)—(CH$_2$)—(CHOH)—(CH$_2$)$_7$—, —(CH$_2$)$_3$—(CHOH)—(CH$_2$)—(CHOH)—(CH$_2$)—, —(CH$_2$)$_4$—(CHOH)—(CH$_2$)—(CHOH)—(CH$_2$)—, —(CH$_2$)$_5$—(CHOH)—(CH$_2$)—(CHOH)—(CH$_2$)—, —(CH$_2$)$_6$—(CHOH)—(CH$_2$)—(CHOH)—(CH$_2$)—, —(CH$_2$)$_7$—(CHOH)—(CH$_2$)—(CHOH)—(CH$_2$)—, —(CH$_2$)$_2$—(CHOH)—(CH$_2$)—(CHOH)—(CH$_2$)$_3$—, —(CH$_2$)$_2$—(CHOH)—(CH$_2$)—(CHOH)—(CH$_2$)$_4$—, —(CH$_2$)$_2$—(CHOH)—(CH$_2$)—(CHOH)—(CH$_2$)$_5$—, —(CH$_2$)$_2$—(CHOH)—(CH$_2$)—(CHOH)—(CH$_2$)$_6$—, —(CH$_2$)$_3$—(CHOH)—(CH$_2$)—(CHOH)—(CH$_2$)$_2$—, —(CH$_2$)$_4$—(CHOH)—(CH$_2$)—(CHOH)—(CH$_2$)$_2$—, —(CH$_2$)$_5$—(CHOH)—(CH$_2$)—(CHOH)—(CH$_2$)$_2$—, —(CH$_2$)$_6$—(CHOH)—(CH$_2$)—(CHOH)—(CH$_2$)$_2$—, —(CH$_2$)$_3$—(CHOH)—(CH$_2$)—(CHOH)—(CH$_2$)$_4$—, —(CH$_2$)$_4$—(CHOH)—(CH$_2$)—(CHOH)—(CH$_2$)$_3$—, —(CH$_2$)—(CHOH)—(CH$_2$)$_2$—(CHOH)—(CH$_2$)—, —(CH$_2$)$_2$—(CHOH)—(CH$_2$)$_2$—(CHOH)—(CH$_2$)$_2$—, —(CH$_2$)$_3$—(CHOH)—(CH$_2$)$_2$—(CHOH)—(CH$_2$)$_3$—, —(CH$_2$)$_4$—(CHOH)—(CH$_2$)$_2$—(CHOH)—(CH$_2$)$_4$—, —(CH$_2$)—(CHOH)—(CH$_2$)$_2$—(CHOH)—(CH$_2$)$_3$—, —(CH$_2$)—(CHOH)—(CH$_2$)$_2$—(CHOH)—(CH$_2$)$_4$—, —(CH$_2$)—(CHOH)—(CH$_2$)$_2$—(CHOH)—(CH$_2$)$_5$—, —(CH$_2$)—(CHOH)—(CH$_2$)$_2$—(CHOH)—(CH$_2$)$_6$—, —(CH$_2$)—(CHOH)—(CH$_2$)$_2$—(CHOH)—(CH$_2$)$_7$—, —(CH$_2$)$_3$—(CHOH)—(CH$_2$)$_2$—(CHOH)—(CH$_2$)—, —(CH$_2$)$_4$—(CHOH)—(CH$_2$)$_2$—(CHOH)—(CH$_2$)—, —(CH$_2$)$_5$—(CHOH)—(CH$_2$)$_2$—(CHOH)—(CH$_2$)—, —(CH$_2$)$_6$—(CHOH)—(CH$_2$)$_2$—(CHOH)—(CH$_2$)—, —(CH$_2$)$_7$—(CHOH)—(CH$_2$)$_2$—(CHOH)—(CH$_2$)—, —(CH$_2$)$_2$—(CHOH)—(CH$_2$)$_2$—(CHOH)—(CH$_2$)$_3$—, —(CH$_2$)$_2$—(CHOH)—(CH$_2$)$_2$—(CHOH)—(CH$_2$)$_4$—, —(CH$_2$)$_2$—(CHOH)—(CH$_2$)$_2$—(CHOH)—(CH$_2$)$_5$—, —(CH$_2$)$_2$—(CHOH)—(CH$_2$)$_2$—(CHOH)—(CH$_2$)$_6$—, —(CH$_2$)$_3$—(CHOH)—(CH$_2$)$_2$—(CHOH)—(CH$_2$)$_2$—, —(CH$_2$)$_4$—(CHOH)—(CH$_2$)$_2$—(CHOH)—(CH$_2$)$_2$—, —(CH$_2$)$_5$—(CHOH)—(CH$_2$)$_2$—(CHOH)—(CH$_2$)$_2$—, —(CH$_2$)$_6$—(CHOH)—(CH$_2$)$_2$—(CHOH)—(CH$_2$)$_2$—, —(CH$_2$)$_3$—(CHOH)—(CH$_2$)$_2$—(CHOH)—(CH$_2$)$_4$—, —(CH$_2$)$_4$—(CHOH)—(CH$_2$)$_2$—(CHOH)—(CH$_2$)$_3$—, —(CH$_2$)—(CHOH)—(CH$_2$)—[CH(CH$_2$OH)]—(CH$_2$)—, —(CH$_2$)$_2$—(CHOH)—(CH$_2$)—[CH(CH$_2$OH)]—(CH$_2$)$_2$—, —(CH$_2$)$_3$—(CHOH)—(CH$_2$)—[CH(CH$_2$OH)]—(CH$_2$)$_3$—, —(CH$_2$)$_4$—(CHOH)—(CH$_2$)—[CH(CH$_2$OH)]—(CH$_2$)$_4$—, —(CH$_2$)—(CHOH)—(CH$_2$)—[CH(CH$_2$OH)]—(CH$_2$)$_3$—, —(CH$_2$)—(CHOH)—(CH$_2$)—[CH(CH$_2$OH)]—(CH$_2$)$_4$—, —(CH$_2$)—(CHOH)—(CH$_2$)—[CH(CH$_2$OH)]—(CH$_2$)$_5$—, —(CH$_2$)—(CHOH)—(CH$_2$)—[CH(CH$_2$OH)]—(CH$_2$)$_6$—, —(CH$_2$)—(CHOH)—(CH$_2$)—[CH(CH$_2$OH)]—(CH$_2$)$_7$—, —(CH$_2$)$_3$—(CHOH)—(CH$_2$)—[CH(CH$_2$OH)]—(CH$_2$)—, —(CH$_2$)$_4$—(CHOH)—(CH$_2$)—[CH(CH$_2$OH)]—(CH$_2$)—, —(CH$_2$)$_5$—(CHOH)—(CH$_2$)—[CH(CH$_2$OH)]—(CH$_2$)—, —(CH$_2$)$_6$—(CHOH)—(CH$_2$)—[CH(CH$_2$OH)]—(CH$_2$)—, —(CH$_2$)$_7$—(CHOH)—(CH$_2$)—[CH(CH$_2$OH)]—(CH$_2$)—, —(CH$_2$)$_2$—(CHOH)—(CH$_2$)—[CH(CH$_2$OH)]—(CH$_2$)$_3$—, —(CH$_2$)$_2$—(CHOH)—(CH$_2$)—[CH(CH$_2$OH)]—(CH$_2$)$_4$—, —(CH$_2$)$_2$—(CHOH)—(CH$_2$)—[CH(CH$_2$OH)]—(CH$_2$)$_5$—, —(CH$_2$)$_2$—(CHOH)—(CH$_2$)—[CH(CH$_2$OH)]—(CH$_2$)$_6$—, —(CH$_2$)$_3$—(CHOH)—(CH$_2$)—[CH(CH$_2$OH)]—(CH$_2$)$_2$—, —(CH$_2$)$_4$—(CHOH)—(CH$_2$)—[CH(CH$_2$OH)]—(CH$_2$)$_2$—, —(CH$_2$)$_5$—(CHOH)—(CH$_2$)—[CH(CH$_2$OH)]—(CH$_2$)$_2$—, —(CH$_2$)$_6$—(CHOH)—(CH$_2$)—[CH(CH$_2$OH)]—(CH$_2$)$_2$—, —(CH$_2$)$_3$—(CHOH)—(CH$_2$)—[CH(CH$_2$OH)]—(CH$_2$)$_4$—, —(CH$_2$)$_4$—(CHOH)—(CH$_2$)—[CH(CH$_2$OH)]—(CH$_2$)$_3$—, —(CH$_2$)—(CHOH)—(CH$_2$)$_2$—[CH(CH$_2$OH)]—(CH$_2$)—, —(CH$_2$)$_2$—(CHOH)—(CH$_2$)$_2$—[CH(CH$_2$OH)]—(CH$_2$)$_2$—, —(CH$_2$)$_3$—(CHOH)—(CH$_2$)$_2$—[CH(CH$_2$OH)]—(CH$_2$)$_3$—, —(CH$_2$)$_4$—(CHOH)—(CH$_2$)$_2$—[CH(CH$_2$OH)]—(CH$_2$)$_4$—, —(CH$_2$)—(CHOH)—(CH$_2$)$_2$—[CH(CH$_2$OH)]—(CH$_2$)$_3$—, —(CH$_2$)—(CHOH)—(CH$_2$)$_2$—[CH(CH$_2$OH)]—(CH$_2$)$_4$—, —(CH$_2$)—(CHOH)—(CH$_2$)$_2$—[CH(CH$_2$OH)]—(CH$_2$)$_5$—, —(CH$_2$)—(CHOH)—(CH$_2$)$_2$—[CH(CH$_2$OH)]—(CH$_2$)$_6$—, —(CH$_2$)—(CHOH)—(CH$_2$)$_2$—[CH(CH$_2$OH)]—(CH$_2$)$_7$—, —(CH$_2$)$_3$—(CHOH)—(CH$_2$)$_2$—[CH(CH$_2$OH)]—(CH$_2$)—, —(CH$_2$)$_4$—(CHOH)—(CH$_2$)$_2$—[CH(CH$_2$OH)]—(CH$_2$)—, —(CH$_2$)$_5$—(CHOH)—(CH$_2$)$_2$—[CH(CH$_2$OH)]—(CH$_2$)—, —(CH$_2$)$_6$—(CHOH)—(CH$_2$)$_2$—[CH(CH$_2$OH)]—(CH$_2$)—, —(CH$_2$)$_7$—(CHOH)—(CH$_2$)$_2$—[CH(CH$_2$OH)]—(CH$_2$)—, —(CH$_2$)$_2$—(CHOH)—(CH$_2$)$_2$—[CH(CH$_2$OH)]—(CH$_2$)$_3$—, —(CH$_2$)$_2$—(CHOH)—(CH$_2$)$_2$—[CH(CH$_2$OH)]—(CH$_2$)$_4$—, —(CH$_2$)$_2$—(CHOH)—(CH$_2$)$_2$—[CH(CH$_2$OH)]—(CH$_2$)$_5$—, —(CH$_2$)$_2$—(CHOH)—(CH$_2$)$_2$—[CH(CH$_2$OH)]—(CH$_2$)$_6$—, —(CH$_2$)$_3$—(CHOH)—(CH$_2$)$_2$—[CH(CH$_2$OH)]—(CH$_2$)$_2$—, —(CH$_2$)$_4$—(CHOH)—(CH$_2$)$_2$—[CH(CH$_2$OH)]—(CH$_2$)$_2$—, —(CH$_2$)$_5$—(CHOH)—(CH$_2$)$_2$—[CH(CH$_2$OH)]—(CH$_2$)$_2$—, —(CH$_2$)$_6$—(CHOH)—(CH$_2$)$_2$—[CH(CH$_2$OH)]—(CH$_2$)$_2$—, —(CH$_2$)$_3$—(CHOH)—(CH$_2$)$_2$—[CH(CH$_2$OH)]—(CH$_2$)$_4$—, —(CH$_2$)$_4$—(CHOH)—(CH$_2$)$_2$—[CH(CH$_2$OH)]—(CH$_2$)$_3$—, —(CH$_2$)—[CH(CH$_2$OH)]—(CH$_2$)$_2$—(CHOH)—(CH$_2$)—, —(CH$_2$)$_2$—[CH(CH$_2$OH)]—(CH$_2$)$_2$—(CHOH)—(CH$_2$)$_2$—, —(CH$_2$)$_3$—[CH(CH$_2$OH)]—(CH$_2$)$_2$—(CHOH)—(CH$_2$)$_3$—, —(CH$_2$)$_4$—[CH(CH$_2$OH)]—(CH$_2$)$_2$—(CHOH)—(CH$_2$)$_4$—, —(CH$_2$)—[CH(CH$_2$OH)]—(CH$_2$)$_2$—

(CHOH)—(CH₂)₃—, —(CH₂)—[CH(CH₂OH)]—(CH₂)₂—(CHOH)—(CH₂)₄—, —(CH₂)—[CH(CH₂OH)]—(CH₂)₂—(CHOH)—(CH₂)₅—, —(CH₂)—[CH(CH₂OH)]—(CH₂)₂—(CHOH)—(CH₂)₆—, —(CH₂)—[CH(CH₂OH)]—(CH₂)₂—(CHOH)—(CH₂)₇—, —(CH₂)₃—[CH(CH₂OH)]—(CH₂)₂—(CHOH)—(CH₂)₂—, —(CH₂)₄—[CH(CH₂OH)]—(CH₂)₂—(CHOH)—(CH₂)₂—, —(CH₂)₅—[CH(CH₂OH)]—(CH₂)₂—(CHOH)—(CH₂)₂—, —(CH₂)₆—[CH(CH₂OH)]—(CH₂)₂—(CHOH)—(CH₂)₂—, —(CH₂)₇—[CH(CH₂OH)]—(CH₂)₂—(CHOH)—(CH₂)₂—, —(CH₂)₂—[CH(CH₂OH)]—(CH₂)₂—(CHOH)—(CH₂)₃—, —(CH₂)₂—[CH(CH₂OH)]—(CH₂)₂—(CHOH)—(CH₂)₄—, —(CH₂)₂—[CH(CH₂OH)]—(CH₂)₂—(CHOH)—(CH₂)₅—, —(CH₂)₂—[CH(CH₂OH)]—(CH₂)₂—(CHOH)—(CH₂)₆—, —(CH₂)₃—[CH(CH₂OH)](CH₂)₂—(CHOH)—(CH₂)₂—, —(CH₂)₄—[CH(CH₂OH)]—(CH₂)₂—(CHOH)—(CH₂)₂—, —(CH₂)₅—[CH(CH₂OH)]—(CH₂)₂—(CHOH)—(CH₂)₂—, —(CH₂)₆—[CH(CH₂OH)](CH₂)₂—(CHOH)—(CH₂)₂—, —(CH₂)₃—[CH(CH₂OH)]—(CH₂)₂—(CHOH)—(CH₂)₄—, —(CH₂)₄—[CH(CH₂OH)]—(CH₂)₂—(CHOH)—(CH₂)₃—, —(CH₂)—[CH(CH₂OH)]—(CH₂)—(CHOH)—(CH₂)—, —(CH₂)₂—[CH(CH₂OH)]—(CH₂)—(CHOH)—(CH₂)₂—, —(CH₂)₃—[CH(CH₂OH)]—(CH₂)—(CHOH)—(CH₂)₃—, —(CH₂)₄—[CH(CH₂OH)]—(CH₂)—(CHOH)—(CH₂)₄—, —(CH₂)—[CH(CH₂OH)]—(CH₂)—(CHOH)—(CH₂)₃—, —(CH₂)—[CH(CH₂OH)]—(CH₂)—(CHOH)—(CH₂)₄—, —(CH₂)—[CH(CH₂OH)]—(CH₂)—(CHOH)—(CH₂)₅—, —(CH₂)—[CH(CH₂OH)]—(CH₂)—(CHOH)—(CH₂)₆—, —(CH₂)—[CH(CH₂OH)]—(CH₂)—(CHOH)—(CH₂)₇—, —(CH₂)₃—[CH(CH₂OH)]—(CH₂)—(CHOH)—(CH₂)—, —(CH₂)₄—[CH(CH₂OH)]—(CH₂)—(CHOH)—(CH₂)—, —(CH₂)₅—[CH(CH₂OH)]—(CH₂)—(CHOH)—(CH₂)—, —(CH₂)₆—[CH(CH₂OH)]—(CH₂)—(CHOH)—(CH₂)—, —(CH₂)₇—[CH(CH₂OH)]—(CH₂)—(CHOH)—(CH₂)—, —(CH₂)₂—[CH(CH₂OH)]—(CH₂)—(CHOH)—(CH₂)₃—, —(CH₂)₂—[CH(CH₂OH)]—(CH₂)—(CHOH)—(CH₂)₄—, —(CH₂)₂—[CH(CH₂OH)]—(CH₂)—(CHOH)—(CH₂)₅—, —(CH₂)₃—[CH(CH₂OH)]—(CH₂)—(CHOH)—(CH₂)₆—, —(CH₂)₄—[CH(CH₂OH)]—(CH₂)—(CHOH)—(CH₂)₂—, —(CH₂)₅—[CH(CH₂OH)]—(CH₂)—(CHOH)—(CH₂)₂—, —(CH₂)₆—[CH(CH₂OH)]—(CH₂)—(CHOH)—(CH₂)₂—, —(CH₂)₃—[CH(CH₂OH)]—(CH₂)—(CHOH)—(CH₂)₂—, —(CH₂)₄—[CH(CH₂OH)]—(CH₂)—(CHOH)—(CH₂)₂—, —(CH₂)—(CHOH)—(CHOH)—(CH₂)—(CHOH)—(CHOH)—(CH₂)—, —(CH₂)₂—(CHOH)—(CHOH)—(CH₂)—(CHOH)—(CHOH)—(CH₂)₂—, —(CH₂)₃—(CHOH)—(CHOH)—(CH₂)—(CHOH)—(CHOH)—(CH₂)₃—, —(CH₂)₄—(CHOH)—(CHOH)—(CH₂)—(CHOH)—(CHOH)—(CH₂)₄—, —(CH₂)—(CHOH)—(CHOH)—(CH₂)—(CHOH)—(CHOH)—(CH₂)₃—, —(CH₂)—(CHOH)—(CHOH)—(CH₂)—(CHOH)—(CHOH)—(CH₂)₄—, —(CH₂)—(CHOH)—(CHOH)—(CH₂)—(CHOH)—(CHOH)—(CH₂)₅—, —(CH₂)—(CHOH)—(CHOH)—(CH₂)—(CHOH)—(CHOH)—(CH₂)₆—, —(CH₂)—(CHOH)—(CHOH)—(CH₂)—(CHOH)—(CHOH)—(CH₂)₇—, —(CH₂)₃—(CHOH)—(CHOH)—(CH₂)—(CHOH)—(CHOH)—(CH₂)—, —(CH₂)₄—(CHOH)—(CHOH)—(CH₂)—(CHOH)—(CHOH)—(CH₂)—, —(CH₂)₅—(CHOH)—(CHOH)—(CH₂)—(CHOH)—(CHOH)—(CH₂)—, —(CH₂)₆—(CHOH)—(CHOH)—(CH₂)—(CHOH)—(CHOH)—(CH₂)—, —(CH₂)₇—(CHOH)—(CHOH)—(CH₂)—(CHOH)—(CHOH)—(CH₂)—, —(CH₂)₂—(CHOH)—(CHOH)—(CH₂)—(CHOH)—(CHOH)—(CH₂)₃—, —(CH₂)₂—(CHOH)—(CHOH)—(CH₂)—(CHOH)—(CHOH)—(CH₂)₄—, —(CH₂)₂—(CHOH)—(CHOH)—(CH₂)—(CHOH)—(CHOH)—(CH₂)₅—, —(CH₂)₂—(CHOH)—(CHOH)—(CH₂)—(CHOH)—(CHOH)—(CH₂)₆—, —(CH₂)₃—(CHOH)—(CHOH)—(CH₂)—(CHOH)—(CHOH)—(CH₂)₂—, —(CH₂)₄—(CHOH)—(CHOH)—(CH₂)—(CHOH)—(CHOH)—(CH₂)₂—, —(CH₂)₅—(CHOH)—(CHOH)—(CH₂)—(CHOH)—(CHOH)—(CH₂)₂—, —(CH₂)₆—(CHOH)—(CHOH)—(CH₂)—(CHOH)—(CHOH)—(CH₂)₂—, —(CH₂)₃—(CHOH)—(CHOH)—(CH₂)—(CHOH)—(CHOH)—(CH₂)₄—, —(CH₂)₄—(CHOH)—(CHOH)—(CH₂)—(CHOH)—(CHOH)—(CH₂)₃—, —(CH₂)₃—(CHOH)—(CHOH)—(CH₂)—(CHOH)—(CHOH)—(CH₂)₅—, —(CH₂)₅—(CHOH)—(CHOH)—(CH₂)—(CHOH)—(CHOH)—(CH₂)₃—, —(CH₂)—(CHOH)—(CH₂)—O—(CH₂)₂—O—(CH₂)—(CHOH)—(CH₂)—, —(CH₂)₂—(CHOH)—(CH₂)—O—(CH₂)₂—O—(CH₂)—(CHOH)—(CH₂)₂—, —(CH₂)₃—(CHOH)—(CH₂)—O—(CH₂)₂—O—(CH₂)—(CHOH)—(CH₂)₃—, —(CH₂)₄—(CHOH)—(CH₂)—O—(CH₂)₂—O—(CH₂)—(CHOH)—(CH₂)₄—, —(CH₂)—(CHOH)—(CH₂)—O—(CH₂)₂—O—(CH₂)—(CHOH)—(CH₂)₃—, —(CH₂)—(CHOH)—(CH₂)—O—(CH₂)₂—O—(CH₂)—(CHOH)—(CH₂)₄—, —(CH₂)—(CHOH)—(CH₂)—O—(CH₂)₂—O—(CH₂)—(CHOH)—(CH₂)₅—, —(CH₂)—(CHOH)—(CH₂)—O—(CH₂)₂—O—(CH₂)—(CHOH)—(CH₂)₆—, —(CH₂)—(CHOH)—(CH₂)—O—(CH₂)₂—O—(CH₂)—(CHOH)—(CH₂)₇—, —(CH₂)₃—(CHOH)—(CH₂)—O—(CH₂)₂—O—(CH₂)—(CHOH)—(CH₂)—, —(CH₂)₄—(CHOH)—(CH₂)—O—(CH₂)₂—O—(CH₂)—(CHOH)—(CH₂)—, —(CH₂)₅—(CHOH)—(CH₂)—O—(CH₂)₂—O—(CH₂)—(CHOH)—(CH₂)—, —(CH₂)₆—(CHOH)—(CH₂)—O—(CH₂)₂—O—(CH₂)—(CHOH)—(CH₂)—, —(CH₂)₇—(CHOH)—(CH₂)—O—(CH₂)₂—O—(CH₂)—(CHOH)—(CH₂)—, —(CH₂)₂—(CHOH)—(CH₂)—O—(CH₂)₂—O—(CH₂)—(CHOH)—(CH₂)₃—, —(CH₂)₂—(CHOH)—(CH₂)—O—(CH₂)₂—O—(CH₂)—(CHOH)—(CH₂)₄—, —(CH₂)₂—(CHOH)—(CH₂)—O—(CH₂)₂—O—(CH₂)—(CHOH)—(CH₂)₅—, —(CH₂)₂—(CHOH)—(CH₂)—O—(CH₂)₂—O—(CH₂)—(CHOH)—(CH₂)₆—, —(CH₂)₃—(CHOH)—(CH₂)—O—(CH₂)₂—O—(CH₂)—(CHOH)—(CH₂)₂—, —(CH₂)₄—(CHOH)—(CH₂)—O—(CH₂)₂—O—(CH₂)—(CHOH)—(CH₂)₂—, —(CH₂)₅—(CHOH)—(CH₂)—O—(CH₂)₂—O—(CH₂)—(CHOH)—(CH₂)₂—, —(CH₂)₆—(CHOH)—(CH₂)—O—(CH₂)₂—O—(CH₂)—(CHOH)—(CH₂)₂—, —(CH₂)₃—(CHOH)—(CH₂)—O—(CH₂)₂—O—(CH₂)—(CHOH)—(CH₂)₄—, —(CH₂)₄—(CHOH)—(CH₂)—O—(CH₂)₂—O—(CH₂)—(CHOH)—(CH₂)₃—, —(CH₂)₃—(CHOH)—(CH₂)—O—(CH₂)₂—O—(CH₂)—(CHOH)—(CH₂)₅—, —(CH₂)₅—(CHOH)—(CH₂)—O—(CH₂)₂—O—(CH₂)—(CHOH)—(CH₂)₃—, —(CH₂)—(CHOH)—(CH₂)—O—(CH₂)₃—O—(CH₂)—(CHOH)—(CH₂)—, —(CH₂)₂—(CHOH)—(CH₂)—O—(CH₂)₃—O—(CH₂)—(CHOH)—(CH₂)₂—, —(CH₂)₃—(CHOH)—(CH₂)—O—(CH₂)₃—O—(CH₂)—(CHOH)—(CH₂)₃—, —(CH₂)₄—(CHOH)—(CH₂)—O—(CH₂)₃—O—(CH₂)—(CHOH)—(CH₂)₄—, —(CH₂)—(CHOH)—(CH₂)—O—(CH₂)₃—O—(CH₂)—(CHOH)—(CH₂)₃—, —(CH₂)—(CHOH)—(CH₂)—O—(CH₂)₃—O—(CH₂)—(CHOH)—(CH₂)₄—, —(CH₂)—(CHOH)—(CH₂)—O—(CH₂)₃—O—(CH₂)—(CHOH)—(CH₂)₅—, —(CH₂)—(CHOH)—(CH₂)—O—(CH₂)₃—O—(CH₂)—(CHOH)—(CH₂)₆—, —(CH₂)—(CHOH)—(CH₂)—O—(CH₂)₃—O—(CH₂)—(CHOH)—(CH₂)₇—, —(CH₂)₃—(CHOH)—(CH₂)—O—(CH₂)₃—O—(CH₂)—(CHOH)—(CH₂)—, —(CH₂)₄—(CHOH)—(CH₂)—O—(CH₂)₃—O—(CH₂)—(CHOH)—(CH₂)—, —(CH₂)₅—(CHOH)—

—(CH₂)—O—(CH₂)₃—O—(CH₂)—(CHOH)—(CH₂)—, —(CH₂)₆—(CHOH)—(CH₂)—O—(CH₂)₃—O—(CH₂)—(CHOH)—(CH₂)—, —(CH₂)₇—(CHOH)—(CH₂)—O—(CH₂)₃—O—(CH₂)—(CHOH)—(CH₂)—, —(CH₂)₂—(CHOH)—(CH₂)—O—(CH₂)₃—O—(CH₂)—(CHOH)—(CH₂)₃—, —(CH₂)₂—(CHOH)—(CH₂)—O—(CH₂)₃—O—(CH₂)—(CHOH)—(CH₂)₄—, —(CH₂)₂—(CHOH)—(CH₂)—O—(CH₂)₃—O—(CH₂)—(CHOH)—(CH₂)₅—, —(CH₂)₂—(CHOH)—(CH₂)—O—(CH₂)₃—O—(CH₂)—(CHOH)—(CH₂)₆—, —(CH₂)₃—(CHOH)—(CH₂)—O—(CH₂)₃—O—(CH₂)—(CHOH)—(CH₂)₂—, —(CH₂)₄—(CHOH)—(CH₂)—O—(CH₂)₃—O—(CH₂)—(CHOH)—(CH₂)₂—, —(CH₂)₅—(CHOH)—(CH₂)—O—(CH₂)₃—O—(CH₂)—(CHOH)—(CH₂)₂—, —(CH₂)₆—(CHOH)—(CH₂)—O—(CH₂)₃—O—(CH₂)—(CHOH)—(CH₂)₂—, —(CH₂)₃—(CHOH)—(CH₂)—O—(CH₂)₃—O—(CH₂)—(CHOH)—(CH₂)₄—, —(CH₂)₄—(CHOH)—(CH₂)—O—(CH₂)₃—O—(CH₂)—(CHOH)—(CH₂)₃—, —(CH₂)₃—(CHOH)—(CH₂)—O—(CH₂)₃—O—(CH₂)—(CHOH)—(CH₂)₅—, —(CH₂)₅—(CHOH)—(CH₂)—O—(CH₂)₃—O—(CH₂)—(CHOH)—(CH₂)₃—, —(CH₂)—(CHOH)—(CH₂)—O—(CH₂)₄—O—(CH₂)—(CHOH)—(CH₂)—, —(CH₂)₂—(CHOH)—(CH₂)—O—(CH₂)₄—O—(CH₂)—(CHOH)—(CH₂)₂—, —(CH₂)₃—(CHOH)—(CH₂)—O—(CH₂)₄—O—(CH₂)—(CHOH)—(CH₂)₃—, —(CH₂)₄—(CHOH)—(CH₂)—O—(CH₂)₄—O—(CH₂)—(CHOH)—(CH₂)₄—, —(CH₂)—(CHOH)—(CH₂)—O—(CH₂)₄—O—(CH₂)—(CHOH)—(CH₂)₃—, —(CH₂)—(CHOH)—(CH₂)—O—(CH₂)₄—O—(CH₂)—(CHOH)—(CH₂)₄—, —(CH₂)—(CHOH)—(CH₂)—O—(CH₂)₄—O—(CH₂)—(CHOH)—(CH₂)₅—, —(CH₂)—(CHOH)—(CH₂)—O—(CH₂)₄—O—(CH₂)—(CHOH)—(CH₂)₆—, —(CH₂)—(CHOH)—(CH₂)—O—(CH₂)₄—O—(CH₂)—(CHOH)—(CH₂)₇—, —(CH₂)₃—(CHOH)—(CH₂)—O—(CH₂)₄—O—(CH₂)—(CHOH)—(CH₂)—, —(CH₂)₄—(CHOH)—(CH₂)—O—(CH₂)₄—O—(CH₂)—(CHOH)—(CH₂)—, —(CH₂)₅—(CHOH)—(CH₂)—O—(CH₂)₄—O—(CH₂)—(CHOH)—(CH₂)—, —(CH₂)₆—(CHOH)—(CH₂)—O—(CH₂)₄—O—(CH₂)—(CHOH)—(CH₂)—, —(CH₂)₇—(CHOH)—(CH₂)—O—(CH₂)₄—O—(CH₂)—(CHOH)—(CH₂)—, —(CH₂)₂—(CHOH)—(CH₂)—O—(CH₂)₄—O—(CH₂)—(CHOH)—(CH₂)₃—, —(CH₂)₂—(CHOH)—(CH₂)—O—(CH₂)₄—O—(CH₂)—(CHOH)—(CH₂)₄—, —(CH₂)₂—(CHOH)—(CH₂)—O—(CH₂)₄—O—(CH₂)—(CHOH)—(CH₂)₅—, —(CH₂)₂—(CHOH)—(CH₂)—O—(CH₂)₄—O—(CH₂)—(CHOH)—(CH₂)₆—, —(CH₂)₃—(CHOH)—(CH₂)—O—(CH₂)₄—O—(CH₂)—(CHOH)—(CH₂)₄—, —(CH₂)₄—(CHOH)—(CH₂)—O—(CH₂)₄—O—(CH₂)—(CHOH)—(CH₂)₂—, —(CH₂)₅—(CHOH)—(CH₂)—O—(CH₂)₄—O—(CH₂)—(CHOH)—(CH₂)₂—, —(CH₂)₆—(CHOH)—(CH₂)—O—(CH₂)₄—O—(CH₂)—(CHOH)—(CH₂)₂—, —(CH₂)₃—(CHOH)—(CH₂)—O—(CH₂)₄—O—(CH₂)—(CHOH)—(CH₂)₄—, —(CH₂)₄—(CHOH)—(CH₂)—O—(CH₂)₄—O—(CH₂)—(CHOH)—(CH₂)₃—, —(CH₂)₃—(CHOH)—(CH₂)—O—(CH₂)₄—O—(CH₂)—(CHOH)—(CH₂)₅—, —(CH₂)₅—(CHOH)—(CH₂)—O—(CH₂)₄—O—(CH₂)—(CHOH)—(CH₂)₃—, —(CH₂)—(CHOH)—(CH₂)—O—(CH₂)₅—O—(CH₂)—(CHOH)—(CH₂)—, —(CH₂)₂—(CHOH)—(CH₂)—O—(CH₂)₅—O—(CH₂)—(CHOH)—(CH₂)₂—, —(CH₂)—(CHOH)—(CH₂)—O—(CH₂)₅—O—(CH₂)—(CHOH)—(CH₂)₅—, —(CH₂)—(CHOH)—(CH₂)—O—(CH₂)₅—O—(CH₂)—(CHOH)—(CH₂)₆—, —(CH₂)—(CHOH)—(CH₂)—O—(CH₂)₅—O—(CH₂)—(CHOH)—(CH₂)₇—, —(CH₂)₃—(CHOH)—(CH₂)—O—(CH₂)₅—O—(CH₂)—(CHOH)—(CH₂)—, —(CH₂)₄—(CHOH)—(CH₂)—O—(CH₂)₅—O—(CH₂)—(CHOH)—(CH₂)—, —(CH₂)₅—(CHOH)—(CH₂)—O—(CH₂)₅—O—(CH₂)—(CHOH)—(CH₂)—, —(CH₂)₆—(CHOH)—(CH₂)—O—(CH₂)₅—O—(CH₂)—(CHOH)—(CH₂)—, —(CH₂)₇—(CHOH)—(CH₂)—O—(CH₂)₅—O—(CH₂)—(CHOH)—(CH₂)—, —(CH₂)₂—(CHOH)—(CH₂)—O—(CH₂)₅—O—(CH₂)—(CHOH)—(CH₂)₃—, —(CH₂)₂—(CHOH)—(CH₂)—O—(CH₂)₅—O—(CH₂)—(CHOH)—(CH₂)₄—, —(CH₂)₂—(CHOH)—(CH₂)—O—(CH₂)₅—O—(CH₂)—(CHOH)—(CH₂)₅—, —(CH₂)₂—(CHOH)—(CH₂)—O—(CH₂)₅—O—(CH₂)—(CHOH)—(CH₂)₆—, —(CH₂)₃—(CHOH)—(CH₂)—O—(CH₂)₅—O—(CH₂)—(CHOH)—(CH₂)₂—, —(CH₂)₄—(CHOH)—(CH₂)—O—(CH₂)₅—O—(CH₂)—(CHOH)—(CH₂)₂—, —(CH₂)₅—(CHOH)—(CH₂)—O—(CH₂)₅—O—(CH₂)—(CHOH)—(CH₂)₂—, —(CH₂)₆—(CHOH)—(CH₂)—O—(CH₂)₅—O—(CH₂)—(CHOH)—(CH₂)₂—, —(CH₂)₃—(CHOH)—(CH₂)—O—(CH₂)₅—O—(CH₂)—(CHOH)—(CH₂)₄—, —(CH₂)₄—(CHOH)—(CH₂)—O—(CH₂)₅—O—(CH₂)—(CHOH)—(CH₂)₃—, —(CH₂)₃—(CHOH)—(CH₂)—O—(CH₂)₅—O—(CH₂)—(CHOH)—(CH₂)₅—, —(CH₂)₅—(CHOH)—(CH₂)—O—(CH₂)₅—O—(CH₂)—(CHOH)—(CH₂)₃—, —(CH₂)—(CHOH)—(CH₂)—O—(CH₂)₆—O—(CH₂)—(CHOH)—(CH₂)—, —(CH₂)₂—(CHOH)—(CH₂)—O—(CH₂)₆—O—(CH₂)—(CHOH)—(CH₂)₂—, —(CH₂)₃—(CHOH)—(CH₂)—O—(CH₂)₆—O—(CH₂)—(CHOH)—(CH₂)₃—, —(CH₂)₄—(CHOH)—(CH₂)—O—(CH₂)₆—O—(CH₂)—(CHOH)—(CH₂)₄—, —(CH₂)—(CHOH)—(CH₂)—O—(CH₂)₆—O—(CH₂)—(CHOH)—(CH₂)₃—, —(CH₂)—(CHOH)—(CH₂)—O—(CH₂)₆—O—(CH₂)—(CHOH)—(CH₂)₄—, —(CH₂)—(CHOH)—(CH₂)—O—(CH₂)₆—O—(CH₂)—(CHOH)—(CH₂)₅—, —(CH₂)—(CHOH)—(CH₂)—O—(CH₂)₆—O—(CH₂)—(CHOH)—(CH₂)₆—, —(CH₂)—(CHOH)—(CH₂)—O—(CH₂)₆—O—(CH₂)—(CHOH)—(CH₂)₇—, —(CH₂)₃—(CHOH)—(CH₂)—O—(CH₂)₆—O—(CH₂)—(CHOH)—(CH₂)—, —(CH₂)₄—(CHOH)—(CH₂)—O—(CH₂)₆—O—(CH₂)—(CHOH)—(CH₂)—, —(CH₂)₅—(CHOH)—(CH₂)—O—(CH₂)₆—O—(CH₂)—(CHOH)—(CH₂)—, —(CH₂)₆—(CHOH)—(CH₂)—O—(CH₂)₆—O—(CH₂)—(CHOH)—(CH₂)—, —(CH₂)₇—(CHOH)—(CH₂)—O—(CH₂)₆—O—(CH₂)—(CHOH)—(CH₂)—, —(CH₂)₂—(CHOH)—(CH₂)—O—(CH₂)₆—O—(CH₂)—(CHOH)—(CH₂)₃—, —(CH₂)₂—(CHOH)—(CH₂)—O—(CH₂)₆—O—(CH₂)—(CHOH)—(CH₂)₄—, —(CH₂)₂—(CHOH)—(CH₂)—O—(CH₂)₆—O—(CH₂)—(CHOH)—(CH₂)₅—, —(CH₂)₂—(CHOH)—(CH₂)—O—(CH₂)₆—O—(CH₂)—(CHOH)—(CH₂)₆—, —(CH₂)₅—(CHOH)—(CH₂)—O—(CH₂)₆—O—(CH₂)—(CHOH)—(CH₂)₂—, —(CH₂)₆—(CHOH)—(CH₂)—O—(CH₂)₆—O—(CH₂)—(CHOH)—(CH₂)₂—, —(CH₂)₃—(CHOH)—(CH₂)—O—(CH₂)₆—O—(CH₂)—(CHOH)—(CH₂)₄—, —(CH₂)₄—(CHOH)—(CH₂)—O—(CH₂)₆—O—(CH₂)—(CHOH)—(CH₂)₃—, —(CH₂)₃—(CHOH)—(CH₂)—O—(CH₂)₆—O—(CH₂)—(CHOH)—(CH₂)₅— and —(CH₂)₅—(CHOH)—(CH₂)—O—(CH₂)₆—O—(CH₂)—(CHOH)—(CH₂)₃—.

Preferred examples for —R₂— are —(CH₂)—(CHOH)—(CH₂)—, —(CH₂)—(CHOH)—(CH₂)₄—, —(CH₂)₄—(CHOH)—(CH₂)—, —(CH₂)—[CH(CH₂OH)]—(CH₂)—, —(CH₂)—[CH(CH₂OH)]—(CH₂)₄—, —(CH₂)₂—[CH (CH₂OH)]—(CH₂)—, —(CH₂)₃—(CHOH)—(CHOH)—(CH₂)₃—, —(CH₂)₃—(CHOH)—(CHOH)—(CH₂)₄—, —(CH₂)₃—(CHOH)—(CH₂)—(CHOH)—(CH₂)₃—, —(CH₂)—(CHOH)—(CH₂)₂—(CHOH)—(CH₂)—, —(CH₂)—(CHOH)—(CH₂)—[CH(CH₂OH)]—(CH₂)₃—, —(CH₂)—(CHOH)—(CH₂)₂—[CH(CH₂OH)]—(CH₂)—, —(CH₂)—(CHOH)—(CHOH)—(CH₂)—(CHOH)—(CHOH)—(CH₂)₃—, —(CH₂)₂—(CHOH)—(CHOH)—(CH₂)—(CHOH)—(CHOH)—(CH₂)₃—, —(CH₂)—(CHOH)—(CH₂)—O—(CH₂)₂—O—(CH₂)—(CHOH)—(CH₂)— and —(CH₂)—(CHOH)—(CH₂)—O—(CH₂)₆—O—(CH₂)—(CHOH)—(CH₂)—.

Compounds of formula (I), (I'), (I") and (I'") with linkers —[B]— and substituents as described before or preferably described before having a polymerizable group as described before or preferably described before or below are preferred in case the substituent —R₂— within the at least one linking element Y—R₂— corresponds to —(C(R)₂)ₒ—, wherein at least one R is OH or a linear or branched hydroxyalkyl group having 1 to 4 C atoms, and all other R and o have a meaning as described before.

The invention therefore relates to compounds of formula (I), (I'), (I") and (I'") as described before or preferably described before wherein —R₂— is at each occurrence independently —(C(R)₂)ₒ—, wherein at least one R is OH or a linear or branched hydroxyalkyl group having 1 to 4 C atoms and R and o have a meaning as described before.

The linking element —(C(R)₂)ₒ— as —R₂— is particularly preferably selected from the group consisting of —(CH₂)—(CHOH)—(CH₂)—, —(CH₂)—(CHOH)—(CH₂)₄—, —(CH₂)₄—(CHOH)—(CH₂)—, —(CH₂)—[CH(CH₂OH)]—(CH₂)—, —(CH₂)—[CH(CH₂OH)]—(CH₂)₄—, —(CH₂)₂—[CH(CH₂OH)]—(CH₂)—, —(CH₂)₃—(CHOH)—(CHOH)—(CH₂)₃—, —(CH₂)₃—(CHOH)—(CHOH)—(CH₂)₄—, —(CH₂)₃—(CHOH)—(CH₂)—(CHOH)—(CH₂)₃—, —(CH₂)—(CHOH)—(CH₂)—(CHOH)—(CH₂)—, —(CH₂)₂—(CHOH)—(CH₂)—(CHOH)—(CH₂)—[CH(CH₂OH)]—(CH₂)₃—, —(CH₂)—(CHOH)—(CH₂)₂—[CH(CH₂OH)]—(CH₂)—, —(CH₂)—(CHOH)—(CH₂)—(CHOH)—(CHOH)—(CH₂)—(CHOH)—(CHOH)—(CH₂)₃— and —(CH₂)₂—(CHOH)—(CHOH)—(CH₂)—(CHOH)—(CHOH)—(CH₂)₃.

The substituent Y—R₂—R₁ is particularly preferably selected from the group consisting of O—R₂—R₁, —R₂—R₁, and S—R₂—R₁, wherein —R₂— has a meaning as described before or preferably or particularly preferably described before and wherein R₁ is a polymerizable group selected from the group consisting of a trialkoxysilyl group, a dialkoxyalkylsilyl group, a silyl group of formula (6), (7) or (8) as described before where the alkyl and/or alkoxy groups are each independently linear or branched having 1 to 6 C atoms, or an alkenyl group of formula (5),

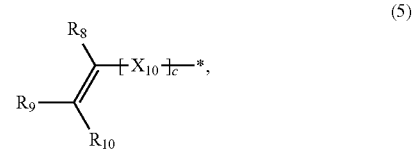

(5)

wherein
X₁₀ is selected from the group consisting of O, S, C(=O), C(=O)O,
R₈, R₉, R₁₀ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1.

The substituent Y—R₂—R₁ is preferably selected from the group consisting of O—R₂—R₁, and —R₂—R₁, wherein —R₂— is selected from the group consisting of —(CH₂)—(CHOH)—(CH₂)—, —(CH₂)—(CHOH)—(CH₂)₄—, —(CH₂)₄—(CHOH)—(CH₂)—, —(CH₂)—[CH(CH₂OH)]—(CH₂)—, —(CH₂)—[CH(CH₂OH)]—(CH₂)₄—, —(CH₂)₂—[CH(CH₂OH)]—(CH₂)—, —(CH₂)₃—(CHOH)—(CHOH)—(CH₂)₃—, —(CH₂)₃—(CHOH)—(CHOH)—(CH₂)₄—, —(CH₂)₃—(CHOH)—(CH₂)—(CHOH)—(CH₂)₃—, —(CH₂)—(CHOH)—(CH₂)—(CHOH)—(CH₂)—, —(CH₂)₂—(CHOH)—(CH₂)—, —(CH₂)—(CHOH)—(CH₂)—[CH(CH₂OH)]—(CH₂)₃—, —(CH₂)—(CHOH)—(CH₂)₂—[CH(CH₂OH)]—(CH₂)—, —(CH₂)—(CHOH)—(CHOH)—(CH₂)—(CHOH)—(CHOH)—(CH₂)₃—, —(CH₂)₂—(CHOH)—(CHOH)—(CH₂)—(CHOH)—(CHOH)—(CH₂)₃—, —(CH₂)—(CHOH)—(CH₂)—O—(CH₂)₂—O—(CH₂)—(CHOH)—(CH₂)— and —(CH₂)—(CHOH)—(CH₂)—O—(CH₂)₆—O—(CH₂)—(CHOH)—(CH₂)— and wherein R₁ is a polymerizable group selected from the group consisting of a trialkoxysilyl group, a dialkoxyalkylsilyl group, a silyl group of formula (6), (7) or (8) as described before where the alkyl and/or alkoxy groups are each independently linear or branched having 1 to 6 C atoms, or an alkenyl group of formula (5),

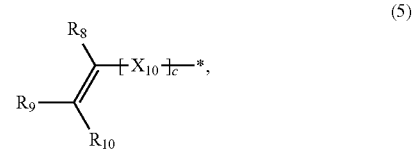

(5)

wherein
X₁₀ is selected from the group consisting of O, S, C(=O), C(=O)O,
R₈, R₉, R₁₀ are at each occurrence independently of each other selected from the group consisting of H, F, a linear or branched, non-fluorinated, partially or completely fluorinated alkyl having 1 to 20 C atoms or aryl with 6 to 14 C atoms,
c is 0 or 1.

Preferably, R₉ and R₁₀ are H.
Preferably, R₈ is H, methyl, ethyl or phenyl.
Preferably, X₁₀ is C(=O) or C(=O)O.

Preferred alkenyl groups of formula (5) are therefore represented by any one selected from the group consisting of formulae (5-1), (5-2), (5-3), (5-4), (5-5), (5-6), (5-7) (58), and (5-9):

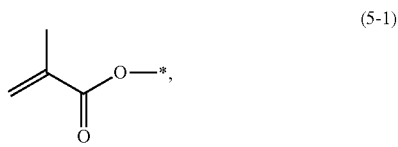

(5-1)

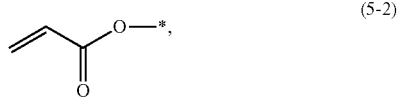

(5-2)

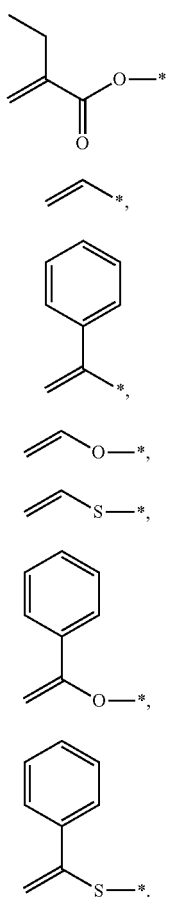

The alkenyl group represented by formula (5-1) is called methacrylate. The alkenyl group represented by formula (5-2) is called acrylate.

The preferred groups $R_1$ are preferably combined with preferred groups of the linking element —$R_2$— and/or the linking element Y—$R_2$—. Combinations are excluded where two O atoms or one O atom and one S atom are directly bonded to each other as known for a skilled artisan in the field of organic chemistry.

The substituent Y—$R_2$—$R_1$ is therefore particularly preferably selected from the group consisting of O—(CH$_2$)—(CHOH)—(CH$_2$)—R$_1$, O—(CH$_2$)—(CHOH)—(CH$_2$)$_4$—R$_1$, O—(CH$_2$)$_4$—(CHOH)—(CH$_2$)—R$_1$, O—(CH$_2$)—[CH(CH$_2$OH)]—(CH$_2$)—R$_1$, O—(CH$_2$)—[CH(CH$_2$OH)]—(CH$_2$)$_4$—R$_1$, O—(CH$_2$)$_2$—[CH(CH$_2$OH)]—(CH$_2$)—R$_1$, O—(CH$_2$)$_3$—(CHOH)—(CHOH)—(CH$_2$)$_3$—R$_1$, O—(CH$_2$)$_3$—(CHOH)—(CHOH)—(CH$_2$)$_4$—R$_1$, O—(CH$_2$)$_3$—(CHOH)—(CH$_2$)—(CHOH)—(CH$_2$)$_3$—R$_1$, O—(CH$_2$)—(CHOH)—(CH$_2$)$_2$—(CHOH)—(CH$_2$)—R$_1$, O—(CH$_2$)—(CHOH)—(CH$_2$)—[CH(CH$_2$OH)]—(CH$_2$)$_3$—R$_1$, O—(CH$_2$)—(CHOH)—(CH$_2$)$_2$—[CH(CH$_2$OH)]—(CH$_2$)—R$_1$, O—(CH$_2$)—(CHOH)—(CHOH)—(CH$_2$)—(CHOH)—(CHOH)—(CH$_2$)$_3$—R$_1$, O—(CH$_2$)$_2$—(CHOH)—(CHOH)—(CH$_2$)—(CHOH)—(CHOH)—(CH$_2$)$_3$—R$_1$, O—(CH$_2$)—(CHOH)—(CH$_2$)—O—(CH$_2$)$_2$—O—(CH$_2$)—(CHOH)—(CH$_2$)—R$_1$ and O—(CH$_2$)—(CHOH)—(CH$_2$)—O—(CH$_2$)$_6$—O—(CH$_2$)—(CHOH)—(CH$_2$)—R$_1$ wherein $R_1$ is selected from the group consisting of an alkenyl of formula (5-1), (5-2), (5-3), (5-4), (5-5), (5-6), (5-7), (5-8), or (5-9);

—(CH$_2$)—(CHOH)—(CH$_2$)—R$_1$, —(CH$_2$)—(CHOH)—(CH$_2$)$_4$—R$_1$, —(CH$_2$)$_4$—(CHOH)—(CH$_2$)—R$_1$, —(CH$_2$)—[CH(CH$_2$OH)]—(CH$_2$)—R$_1$, —(CH$_2$)—[CH(CH$_2$OH)]—(CH$_2$)$_4$—R$_1$, —(CH$_2$)$_2$—[CH(CH$_2$OH)]—(CH$_2$)—R$_1$, —(CH$_2$)$_3$—(CHOH)—(CHOH)—(CH$_2$)$_3$—R$_1$, —(CH$_2$)$_3$—(CHOH)—(CHOH)—(CH$_2$)$_4$—R$_1$, —(CH$_2$)$_3$—(CHOH)—(CH$_2$)—(CHOH)—(CH$_2$)$_3$—R$_1$, —(CH$_2$)—(CHOH)—(CH$_2$)$_2$—(CHOH)—(CH$_2$)—R$_1$, —(CH$_2$)—(CHOH)—(CH$_2$)—[CH(CH$_2$OH)]—(CH$_2$)$_3$—R$_1$, —(CH$_2$)—(CHOH)—(CH$_2$)$_2$—[CH(CH$_2$OH)]—(CH$_2$)—R$_1$, —(CH$_2$)—(CHOH)—(CHOH)—(CH$_2$)—(CHOH)—(CHOH)—(CH$_2$)$_3$—R$_1$, —(CH$_2$)$_2$—(CHOH)—(CHOH)—(CH$_2$)—(CHOH)—(CHOH)—(CH$_2$)$_3$—R$_1$, —(CH$_2$)—(CHOH)—(CH$_2$)—O—(CH$_2$)$_2$—O—(CH$_2$)—(CHOH)—(CH$_2$)—R$_1$ and —(CH$_2$)—(CHOH)—(CH$_2$)—O—(CH$_2$)$_6$—O—(CH$_2$)—(CHOH)—(CH$_2$)—R$_1$ wherein $R_1$ is selected from the group consisting of an alkenyl of formula (5-1), (5-2), (5-3), (5-4), (5-5), (5-6), (5-7), (5-8), or (5-9);

S—(CH$_2$)—(CHOH)—(CH$_2$)—R$_1$, S—(CH$_2$)—(CHOH)—(CH$_2$)$_4$—R$_1$, S—(CH$_2$)$_4$—(CHOH)—(CH$_2$)—R$_1$, S—(CH$_2$)—[CH(CH$_2$OH)]—(CH$_2$)—R$_1$, S—(CH$_2$)—[CH(CH$_2$OH)]—(CH$_2$)$_4$—R$_1$, S—(CH$_2$)$_2$—[CH(CH$_2$OH)]—(CH$_2$)—R$_1$, S—(CH$_2$)$_3$—(CHOH)—(CHOH)—(CH$_2$)$_3$—R$_1$, S—(CH$_2$)$_3$—(CHOH)—(CHOH)—(CH$_2$)$_4$—R$_1$, S—(CH$_2$)$_3$—(CHOH)—(CH$_2$)—(CHOH)—(CH$_2$)$_3$—R$_1$, S—(CH$_2$)—(CHOH)—(CH$_2$)$_2$—(CHOH)—(CH$_2$)—R$_1$, S—(CH$_2$)—(CHOH)—(CH$_2$)—[CH(CH$_2$OH)]—(CH$_2$)$_3$—R$_1$, S—(CH$_2$)—(CHOH)—(CH$_2$)$_2$—[CH(CH$_2$OH)]—(CH$_2$)—R$_1$, S—(CH$_2$)—(CHOH)—(CHOH)—(CH$_2$)—(CHOH)—(CHOH)—(CH$_2$)$_3$—R$_1$, S—(CH$_2$)$_2$—(CHOH)—(CHOH)—(CH$_2$)—(CHOH)—(CHOH)—(CH$_2$)$_3$—R$_1$, S—(CH$_2$)—(CHOH)—(CH$_2$)—O—(CH$_2$)$_2$—O—(CH$_2$)—(CHOH)—(CH$_2$)—R$_1$ and S—(CH$_2$)—(CHOH)—(CH$_2$)—O—(CH$_2$)$_6$—O—(CH$_2$)—(CHOH)—(CH$_2$)—R$_1$ wherein $R_1$ is selected from the group consisting of an alkenyl of formula (5-1), (5-2), (5-3), (5-4), (5-5), (5-6), (5-7), (5-8), or (5-9).

Very particularly preferably, the compounds of formula (I), (I'), (I'') and (I''') comprise a polymerizable group $R_1$ which is a methacryl or an acryl group represented by formula (5-1) and (5-2).

The invention therefore relates further to compounds of formula (I), (I'), (I'') and/or (I''') as described before or preferably described before wherein $R_1$ is at each occurrence independently an acryl or methacryl group.

Examples for compounds of formula (I), (I'), (I'') and/or (I''') are the following compounds 0-01 to 0-104 and N-01 to N-51:

O-01

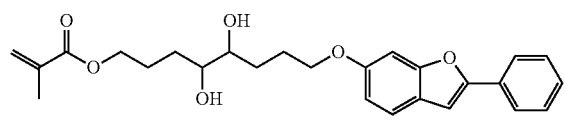

O-02

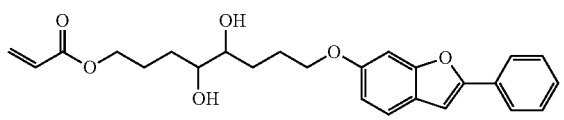

-continued
O-03
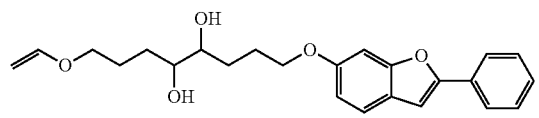
O-04
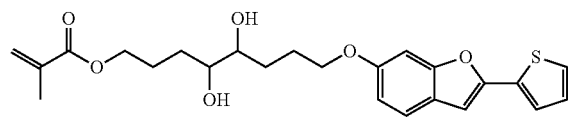
O-05
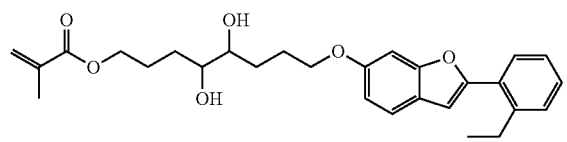
O-06
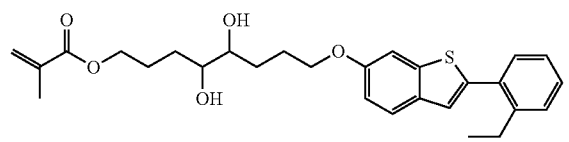
O-07
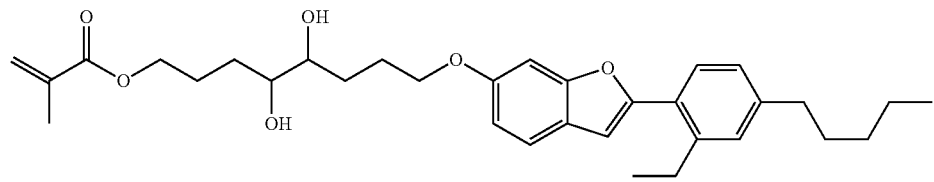
O-08
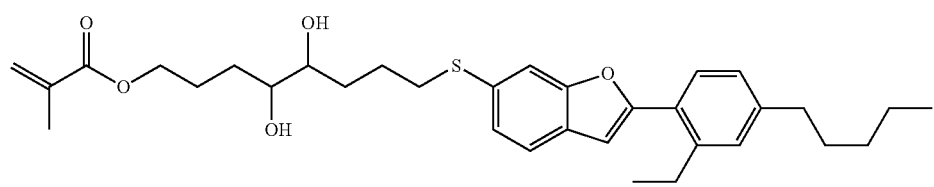
O-09
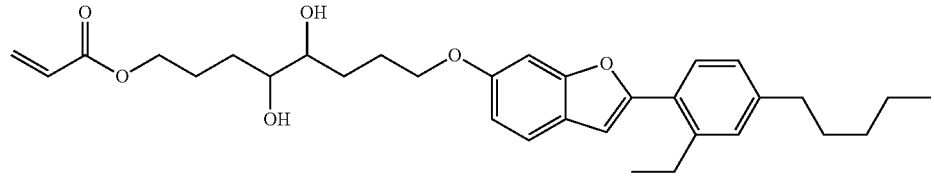
O-10
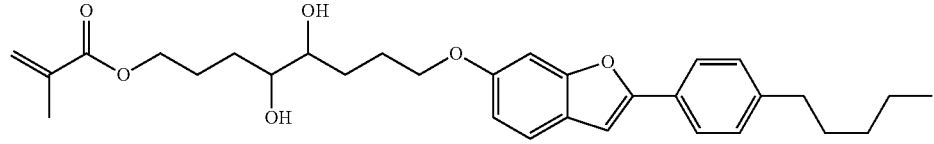
O-11
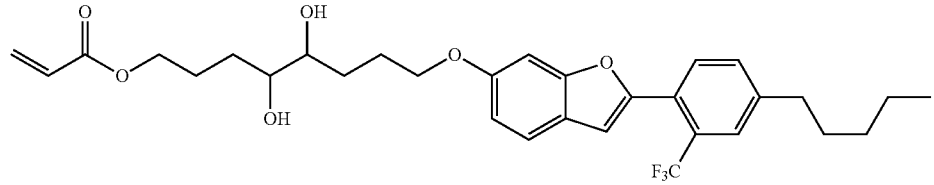
O-12
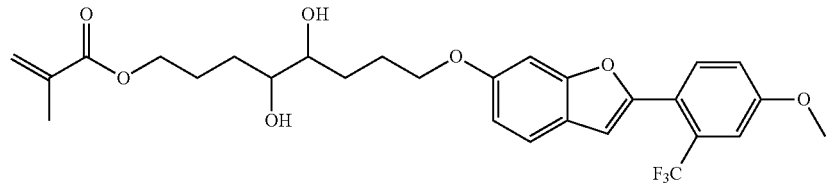
O-13
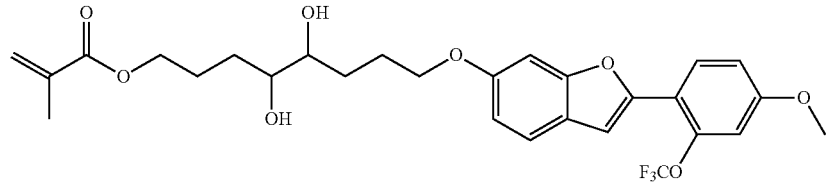

-continued
O-14
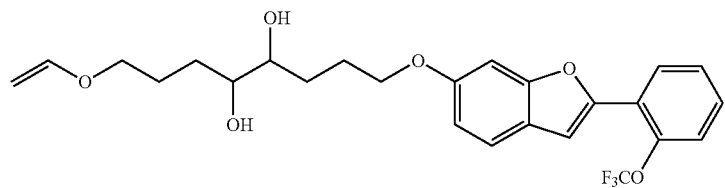
O-15
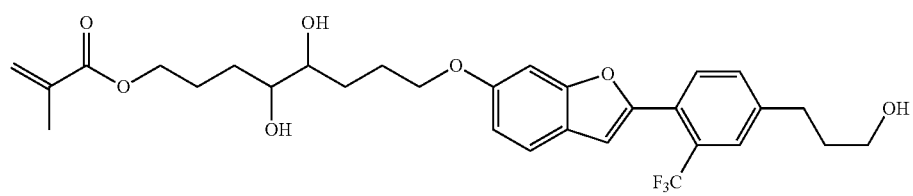
O-16
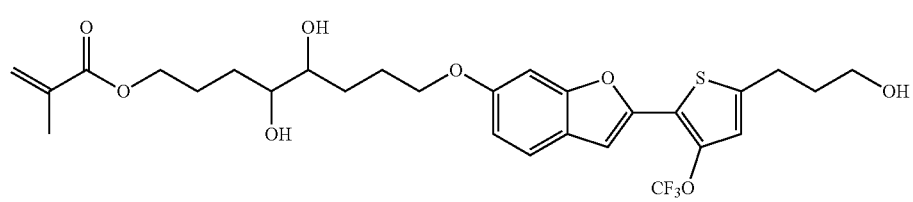
O-17
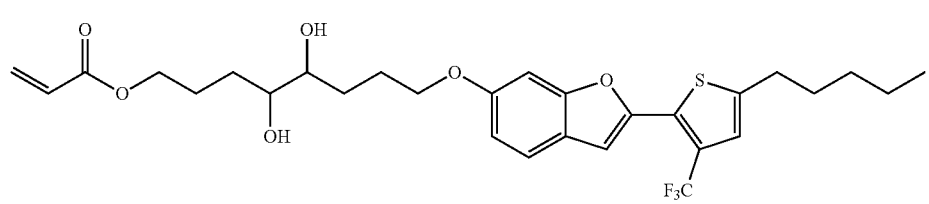
O-18
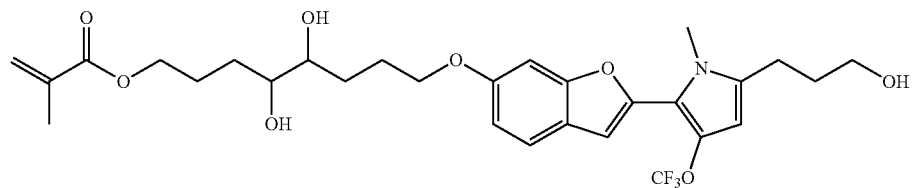
O-19
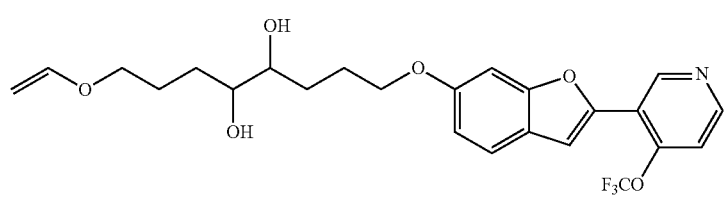
O-20
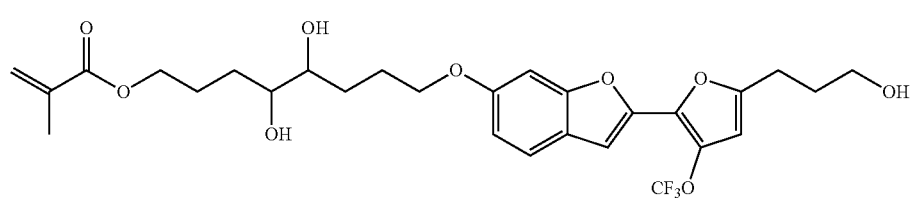
O-21
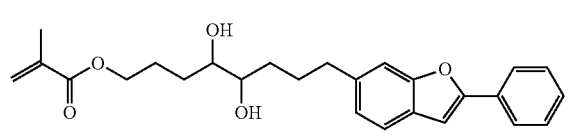
O-22
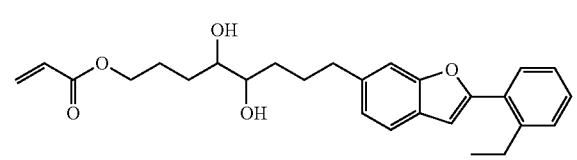

-continued
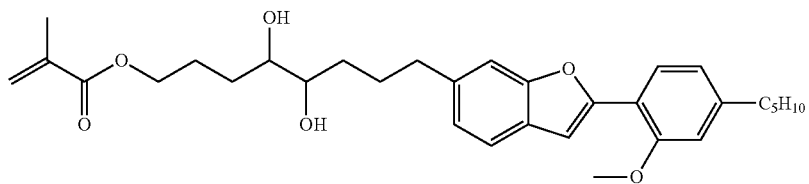 O-23
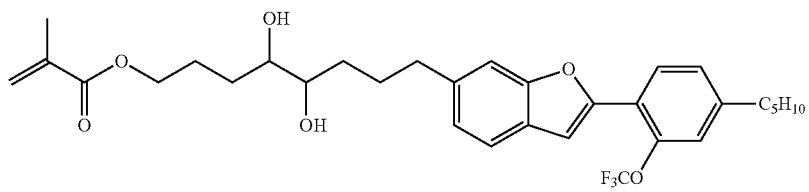 O-24
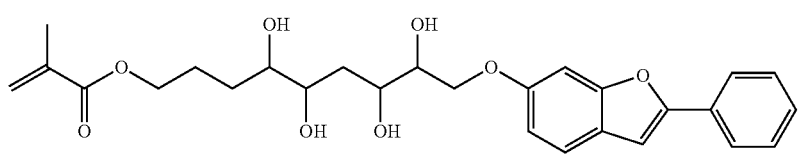 O-25
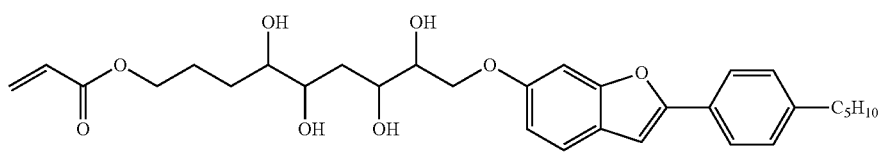 O-26
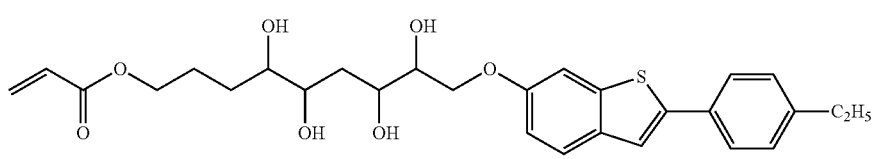 O-27
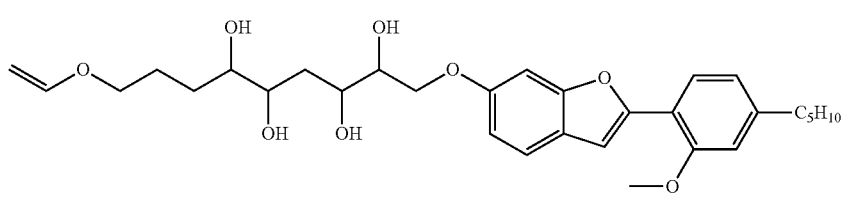 O-28
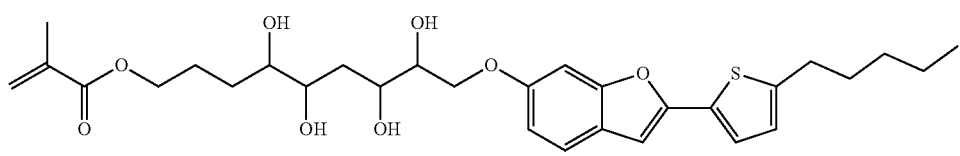 O-29
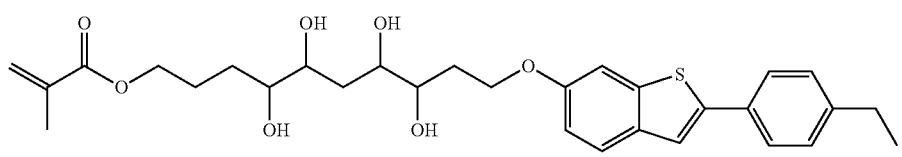 O-30
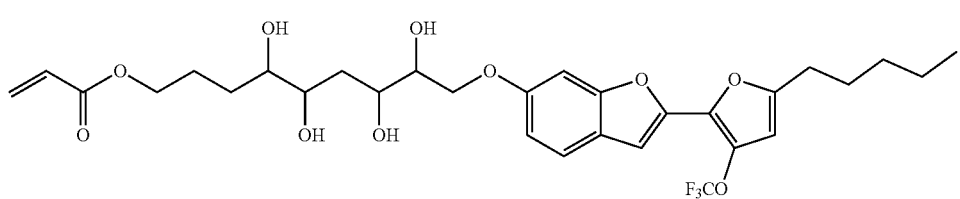 O-31

-continued
O-32
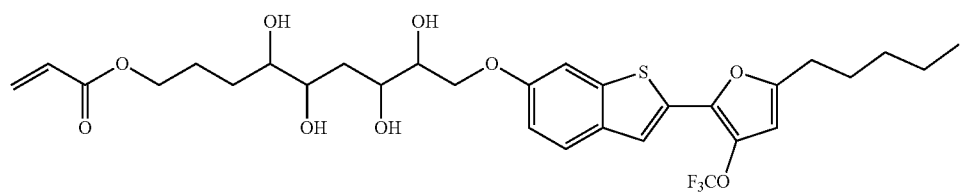
O-33
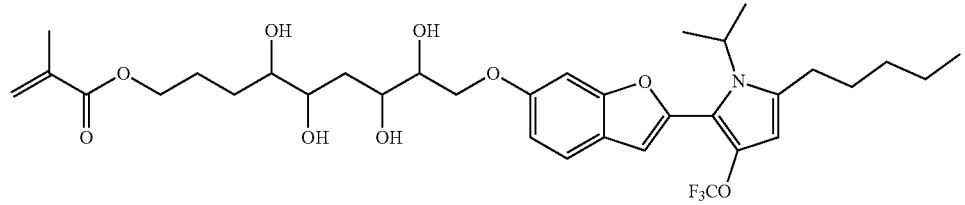
O-34
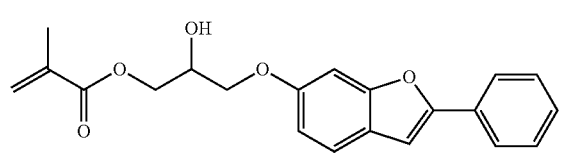
O-35
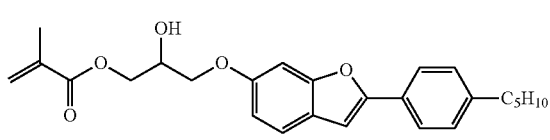
O-36
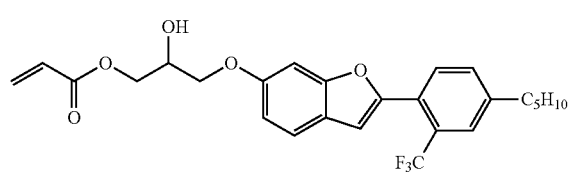
O-37
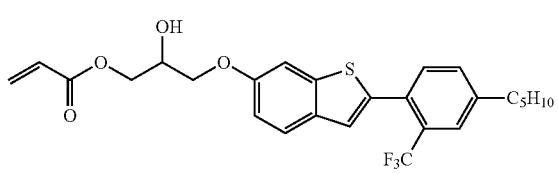
O-38
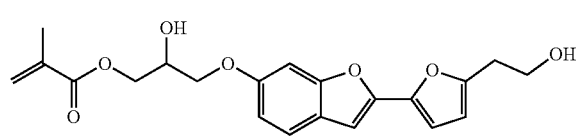
O-39
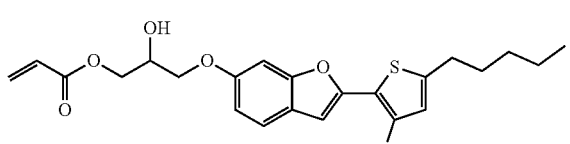
O-40
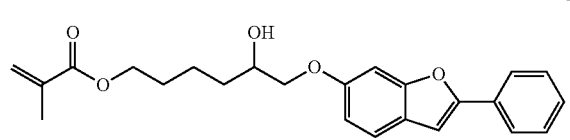
O-41
O-42
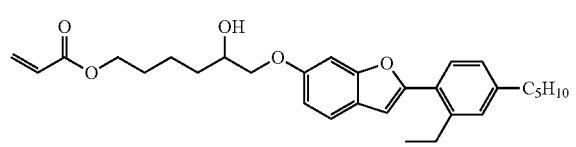
O-43
O-44
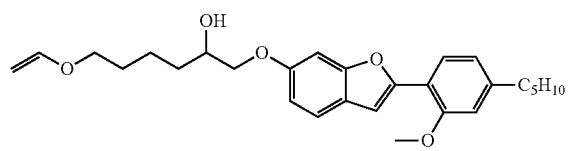
O-45
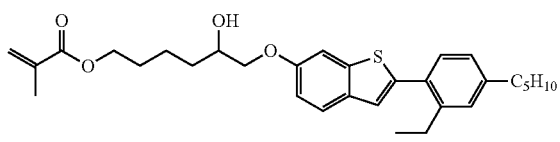

-continued
O-46
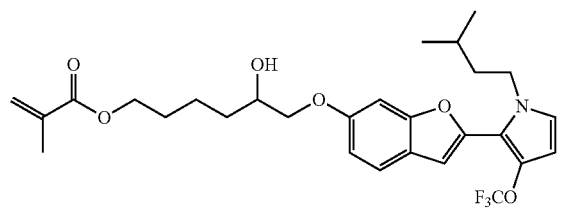
O-47
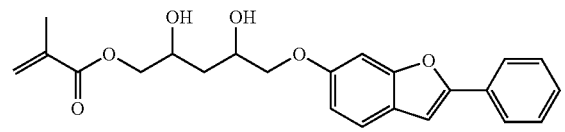
O-48
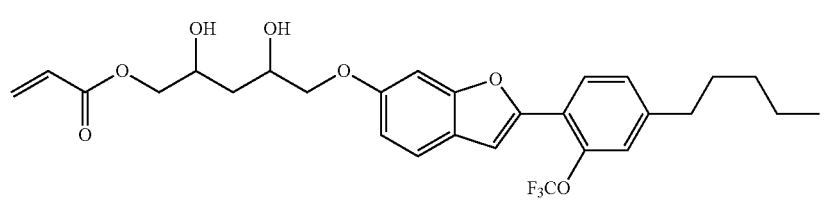
O-49
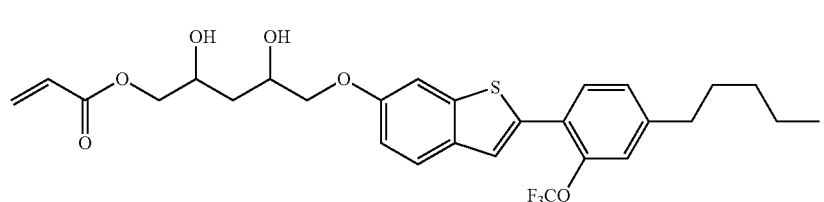
O-50
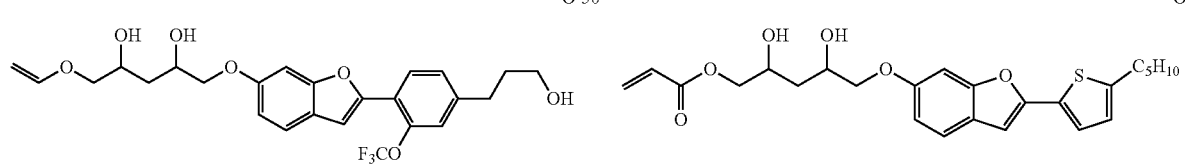
O-51
O-52
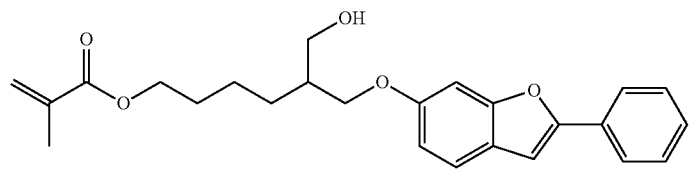
O-53
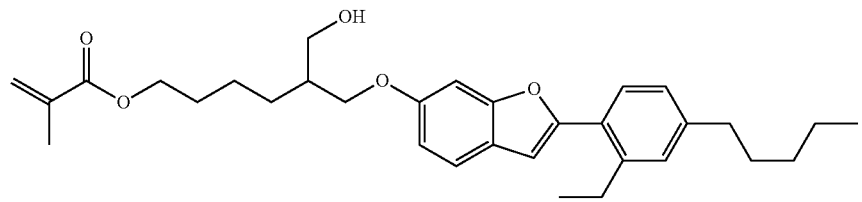
O-54
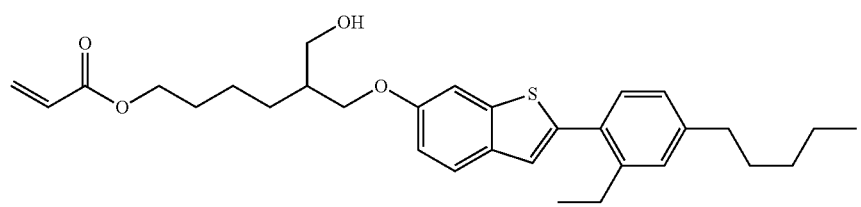
O-55
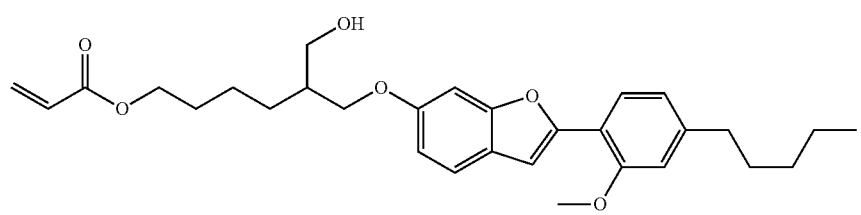

-continued
O-56
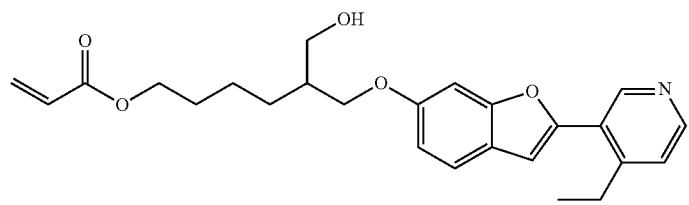
O-57
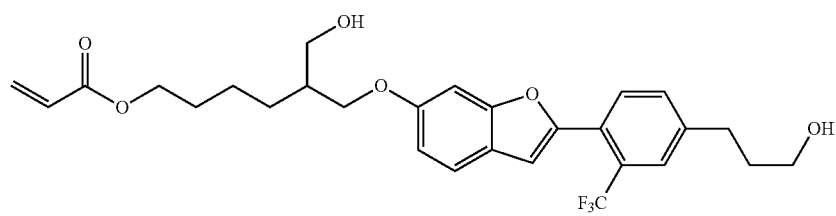
O-58
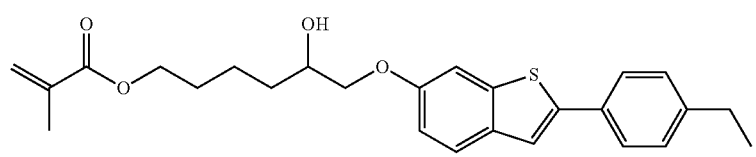
O-59
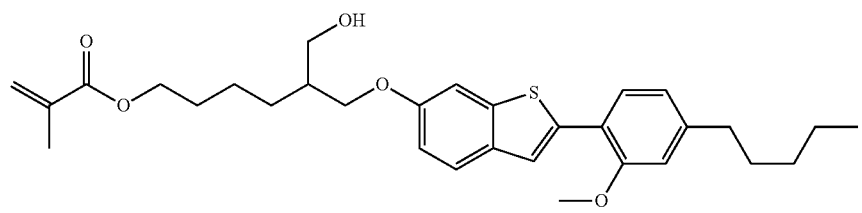
O-60
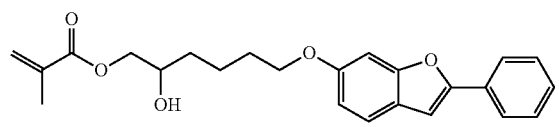
O-61
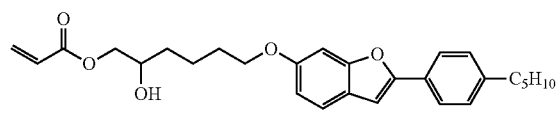
O-62
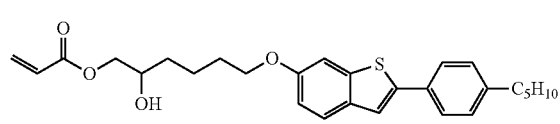
O-63
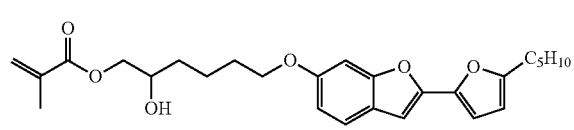
O-64
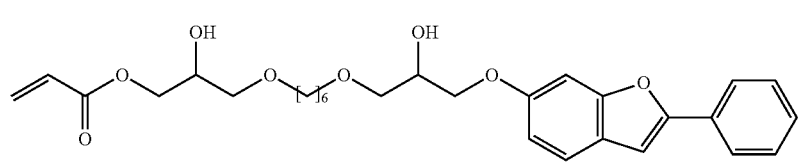
O-65
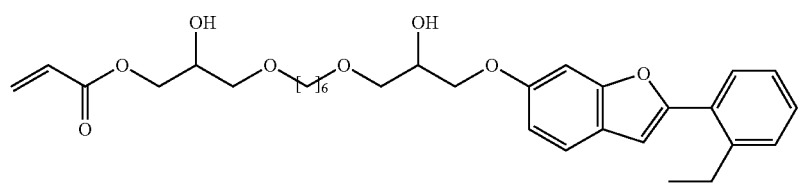
O-66
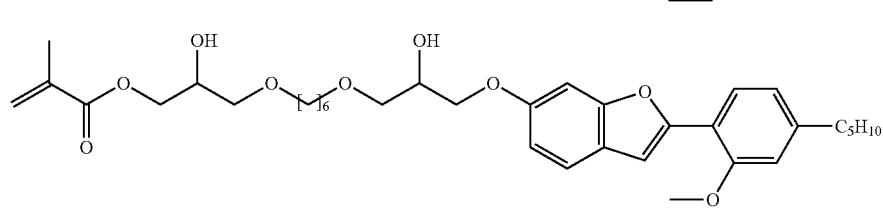

-continued
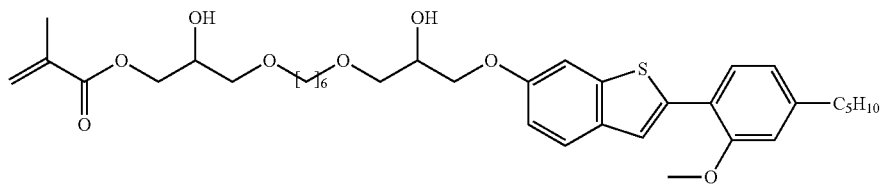
O-67
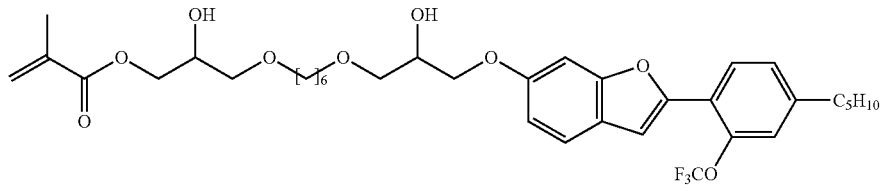
O-68
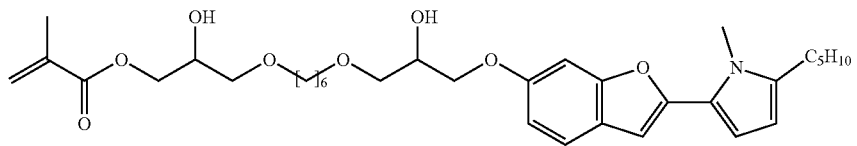
O-69
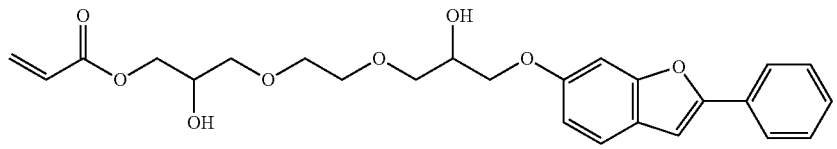
O-70
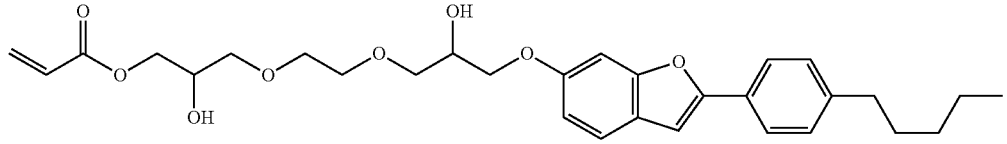
O-71
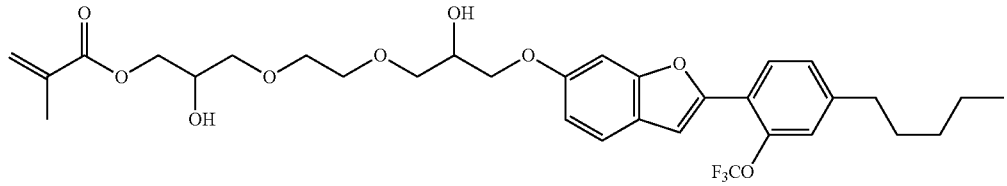
O-72
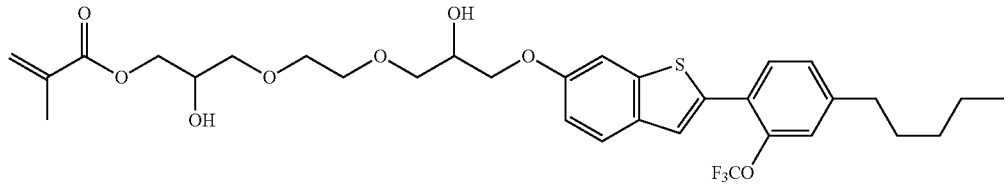
O-73
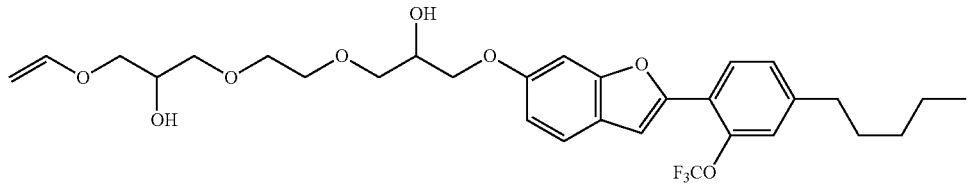
O-74
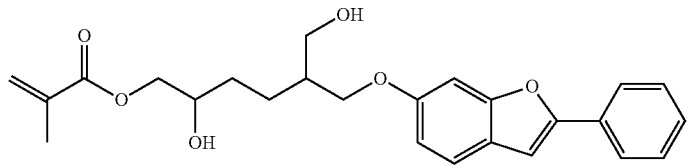
O-75

-continued
O-76
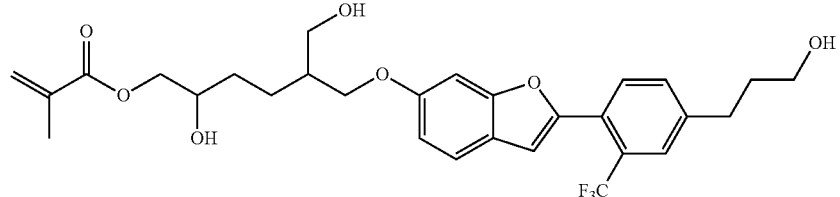
O-77
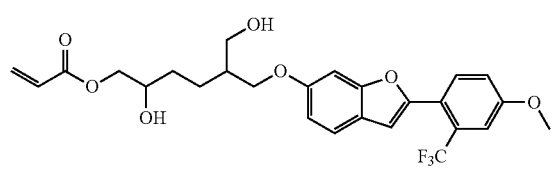
O-78
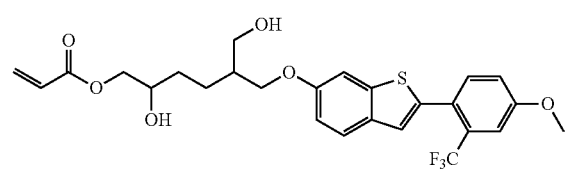
O-79
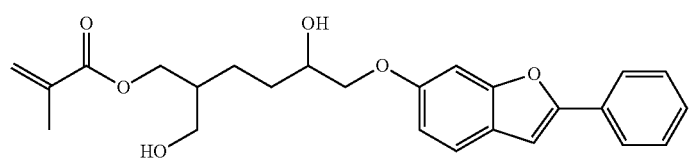
O-80
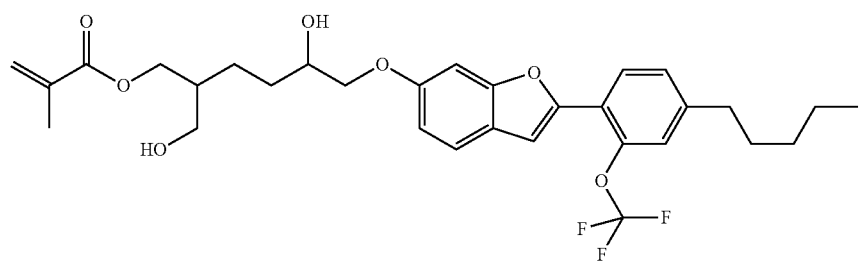
O-81
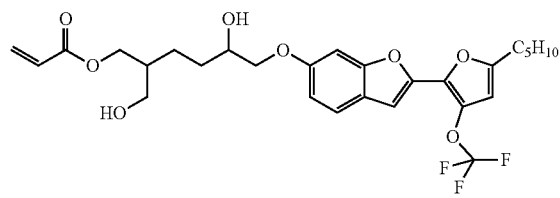
O-82
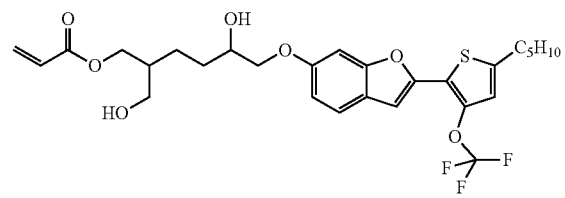
O-83
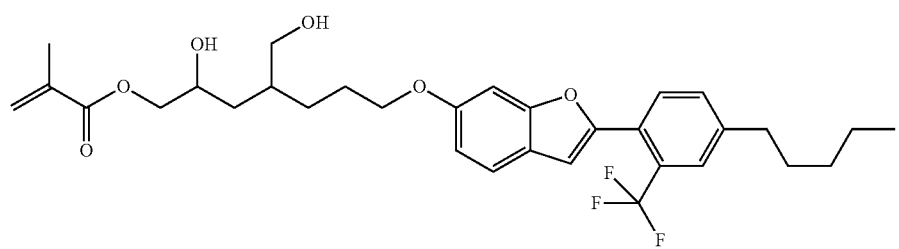
O-84
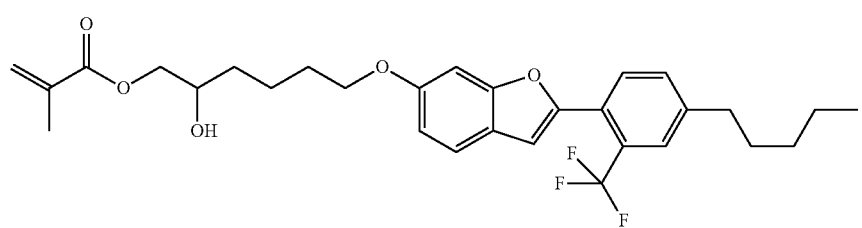

-continued
O-85
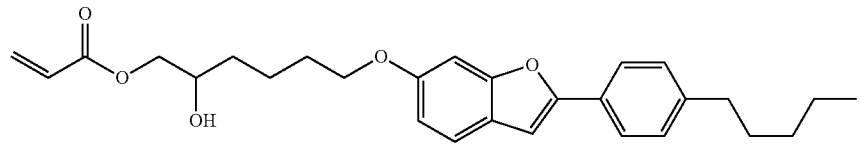
O-86
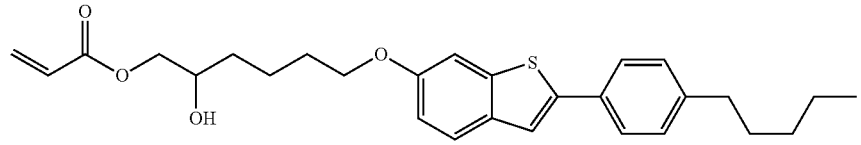
O-87
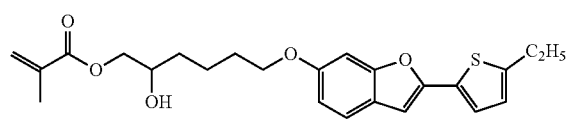
O-88
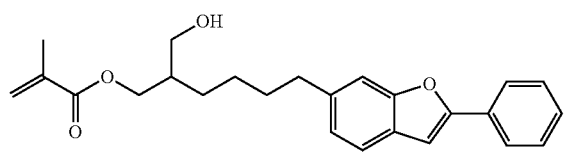
O-89
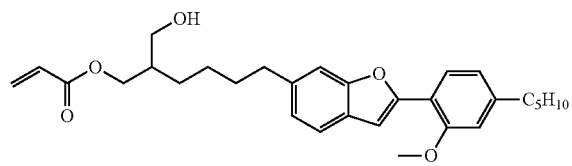
O-90
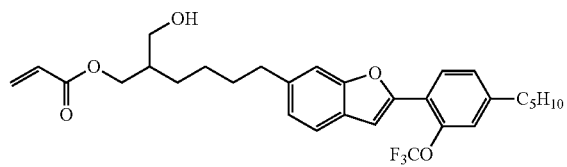
O-91
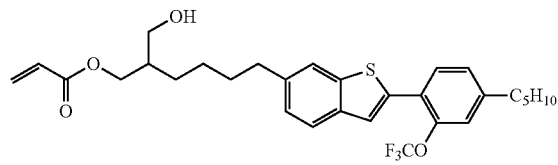
O-92
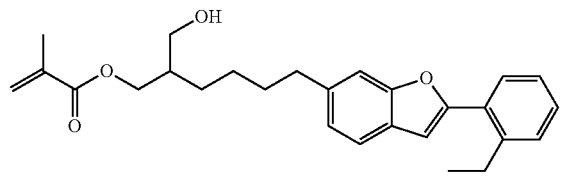
O-93
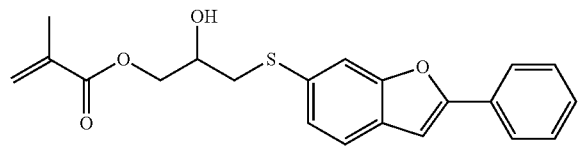
O-94
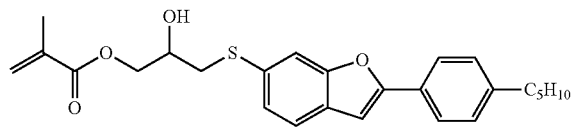
O-95
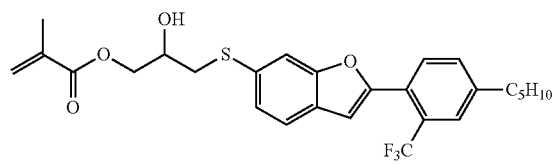
O-96
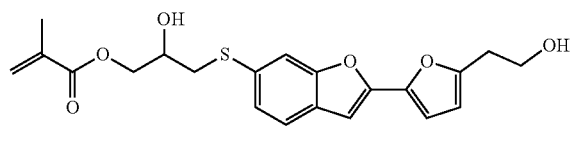
O-97
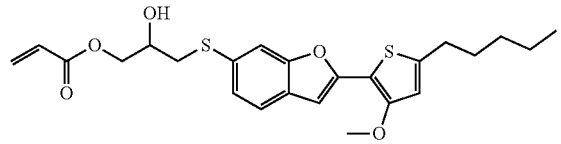
O-98
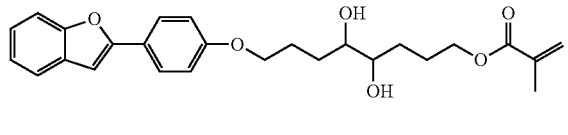
O-99
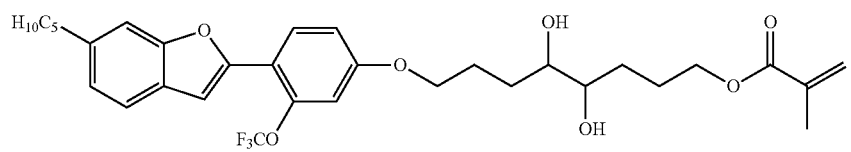

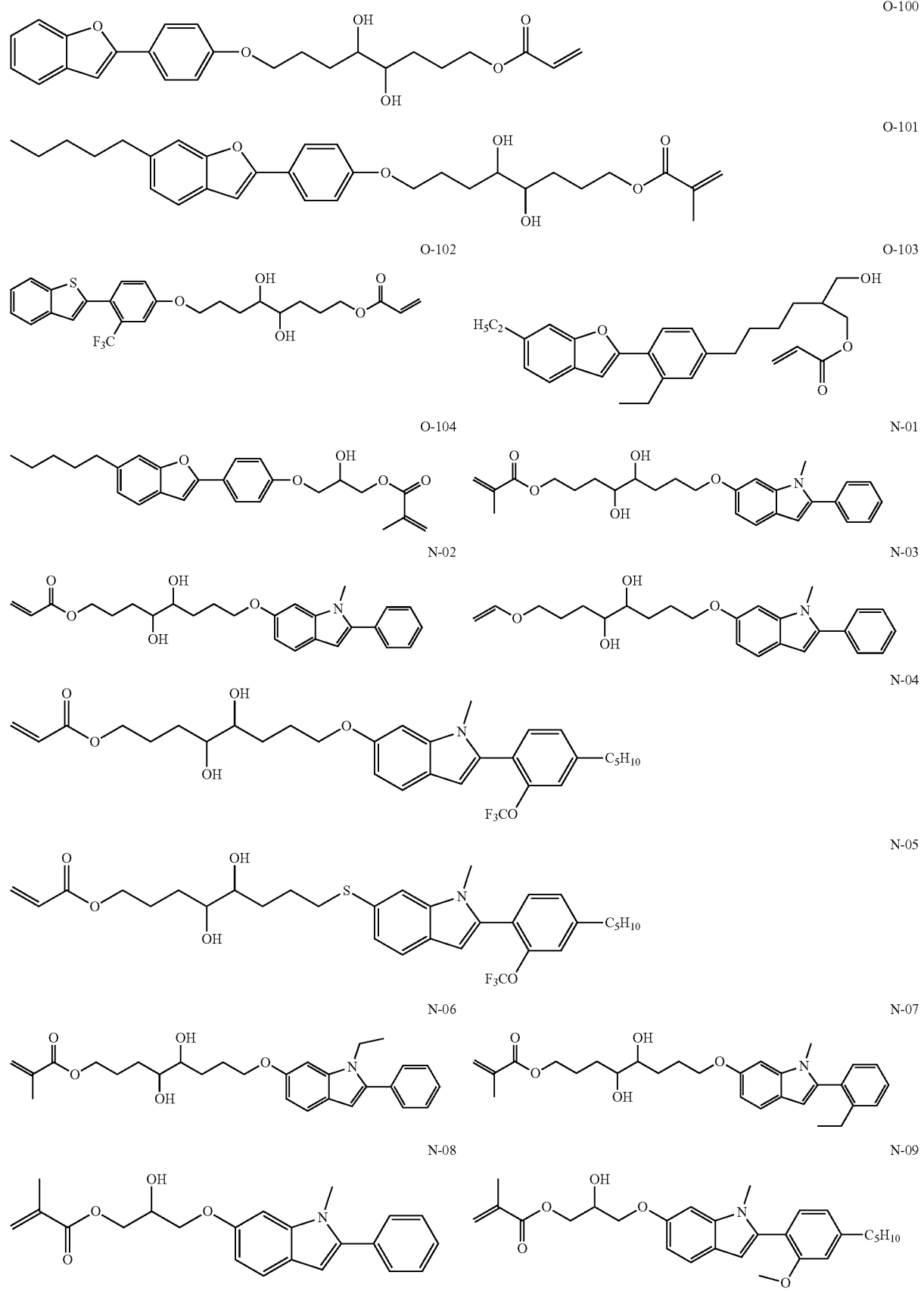

-continued
N-10
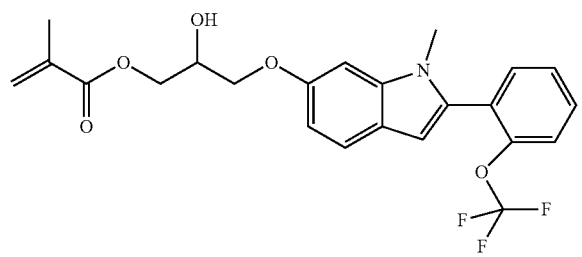
N-11
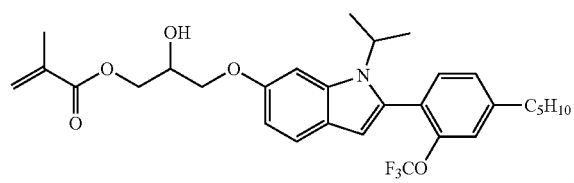
N-12
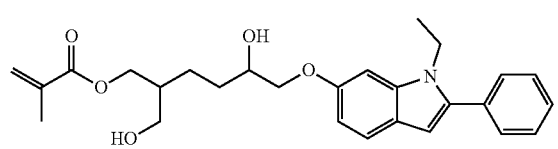
N-13
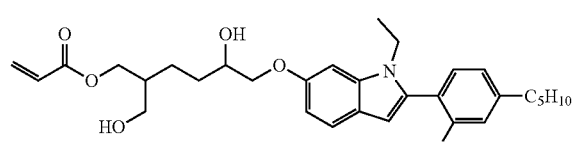
N-14
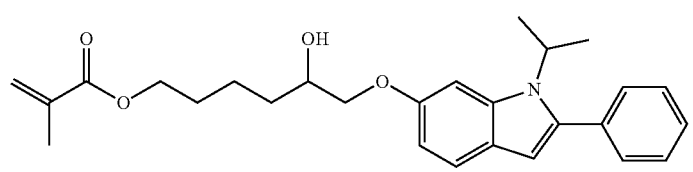
N-15
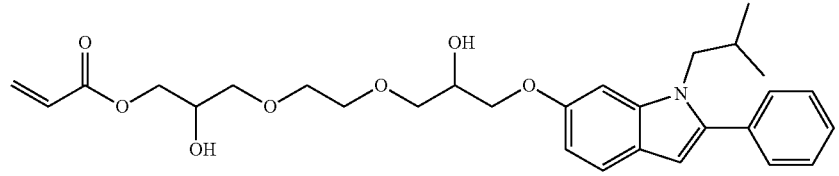
N-16
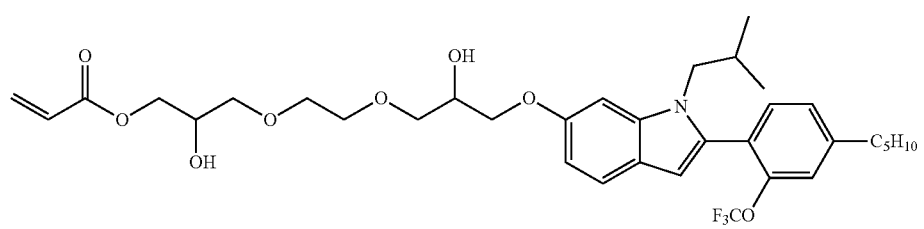
N-17
N-18
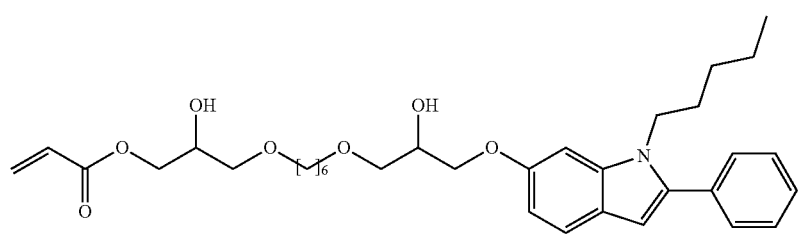

-continued
N-19
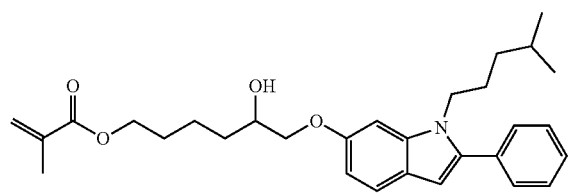
N-20
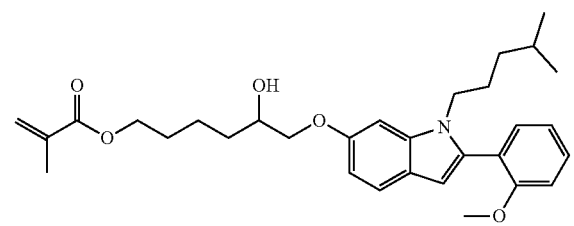
N-21
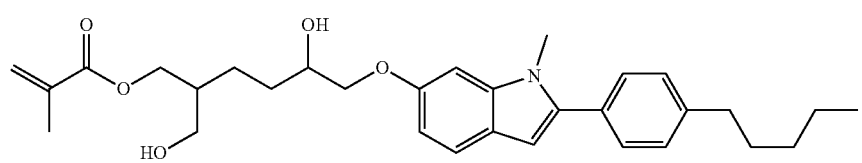
N-22
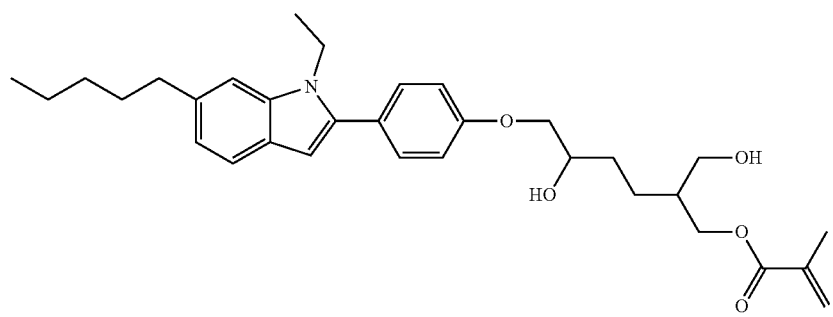
N-23
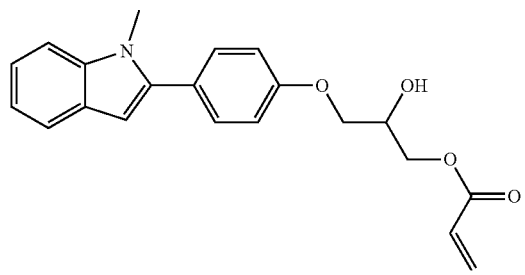
N-24
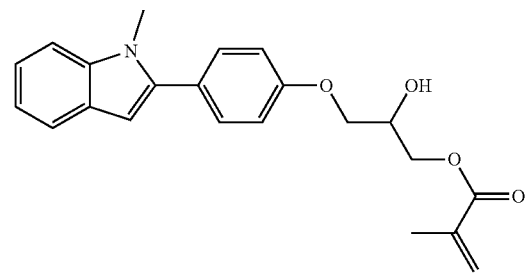
N-25
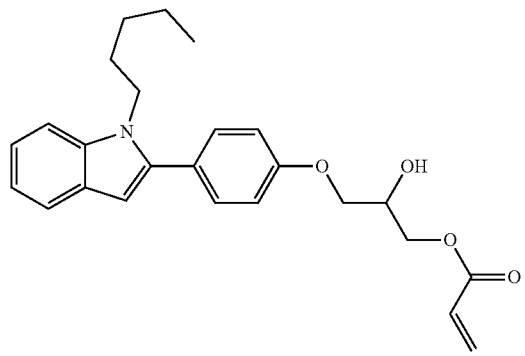
N-26
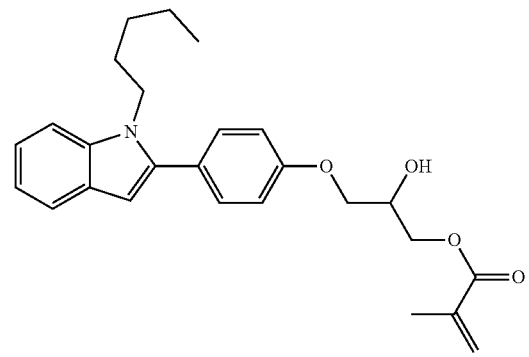
N-27
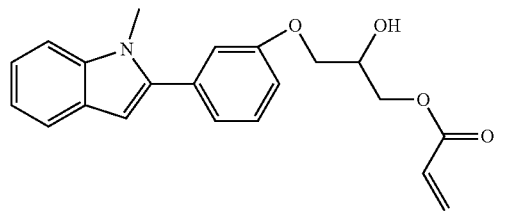
N-28
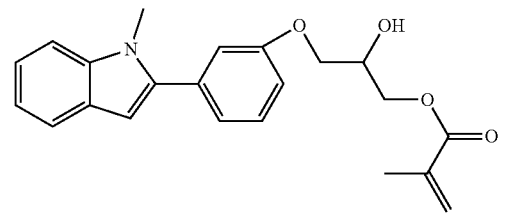

-continued
N-29
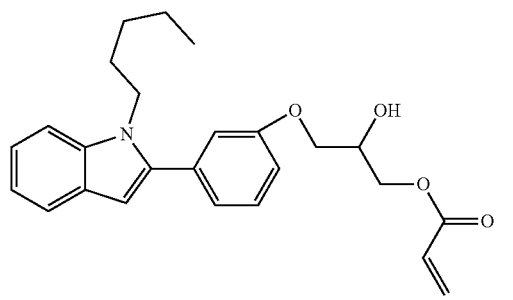
N-30
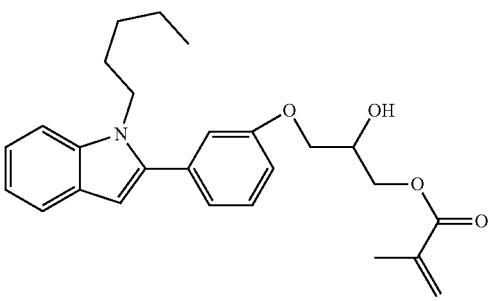
N-31
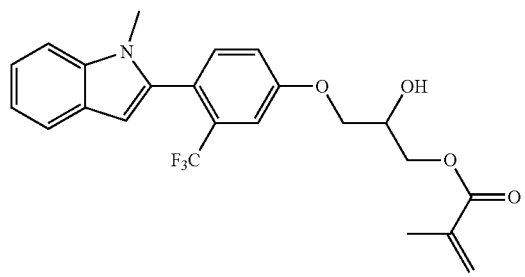
N-32
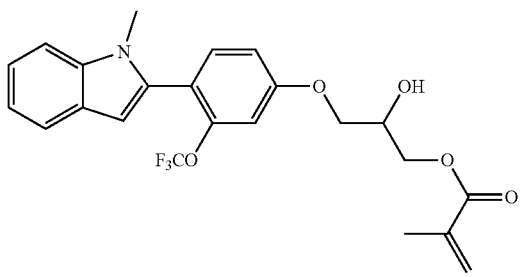
N-33
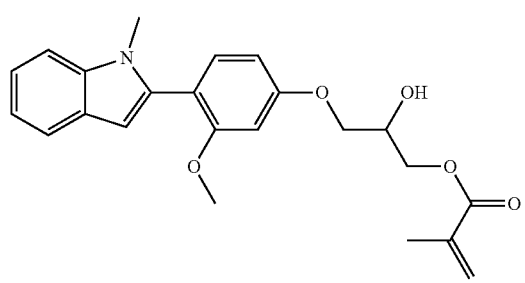
N-34
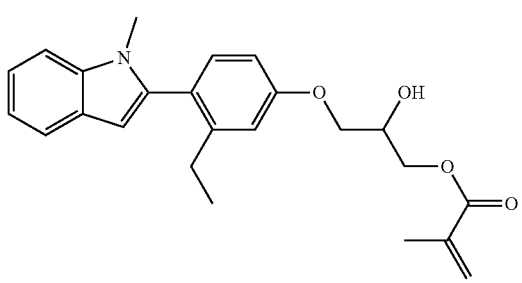
N-35
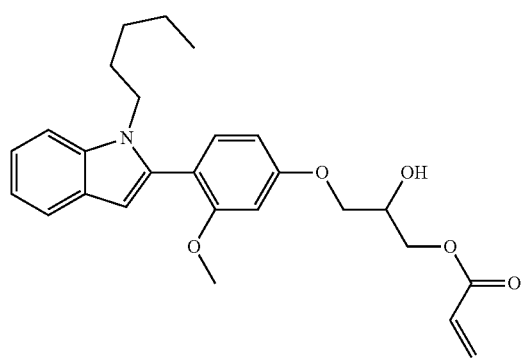
N-36
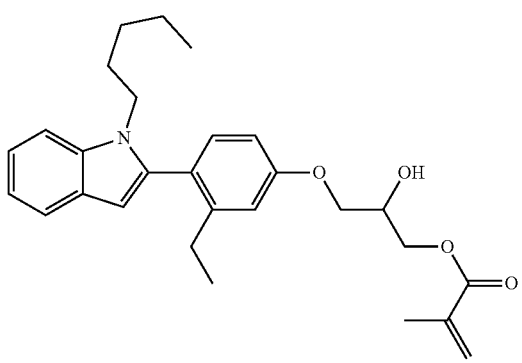
N-37
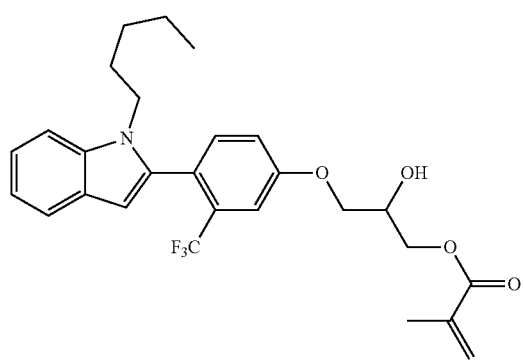
N-38
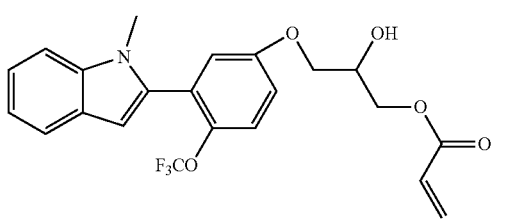

N-39
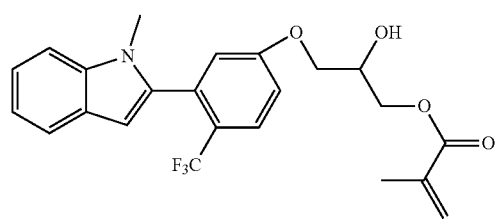
N-40
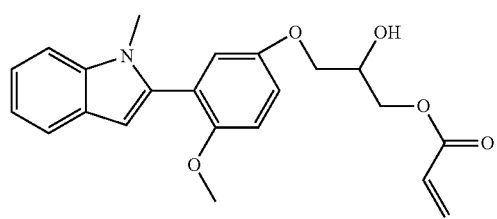
N-41
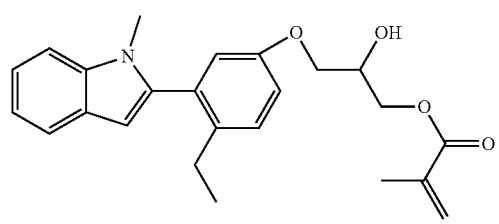
N-42
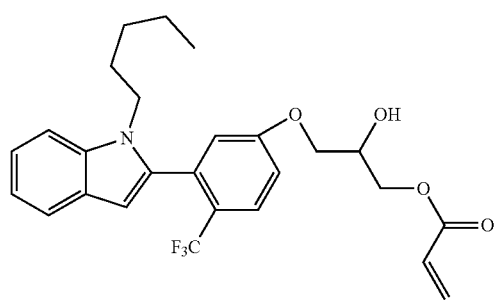
N-43
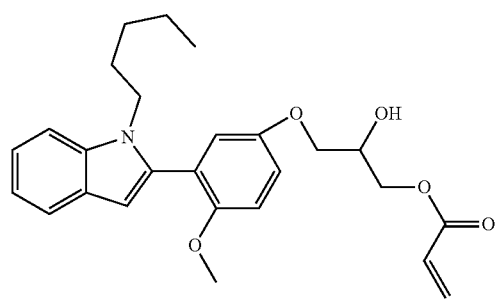
N-44
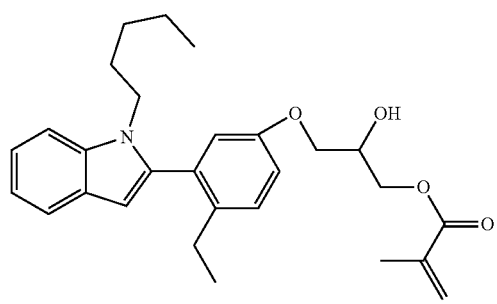
N-45
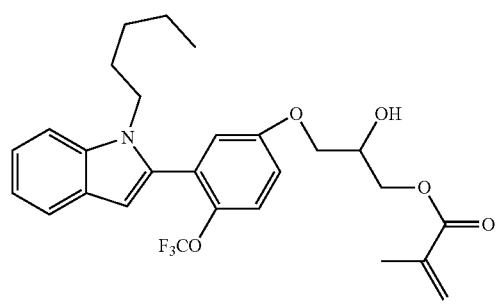
N-46
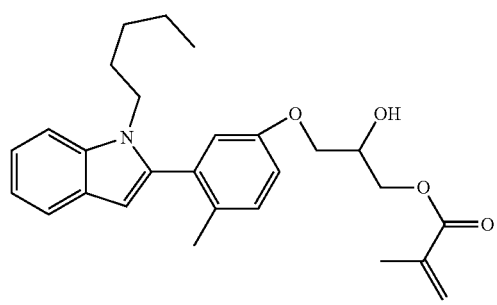
N-47
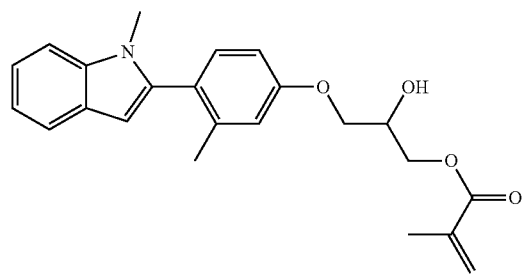
N-48
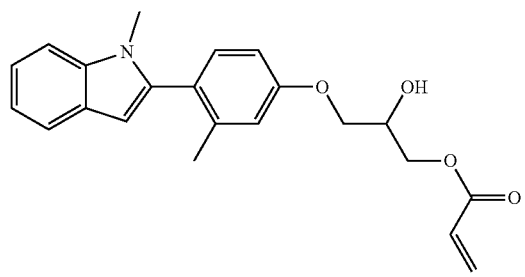

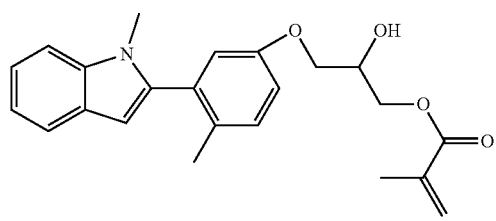
N-49
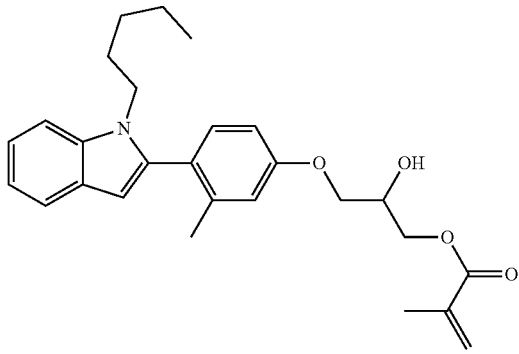
N-50
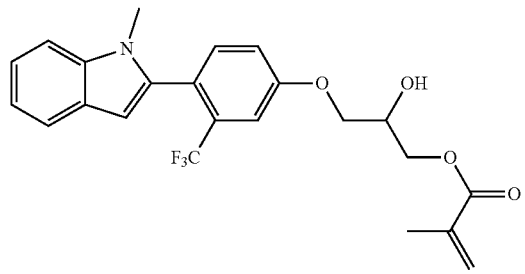
N-51
The compounds of the present application may be synthesized by methods well known to the skilled person. Preferably, all syntheses are carried out under an inert atmosphere using dried solvents.
An exemplary reaction sequence is shown in Scheme 1 for the compound O-10.
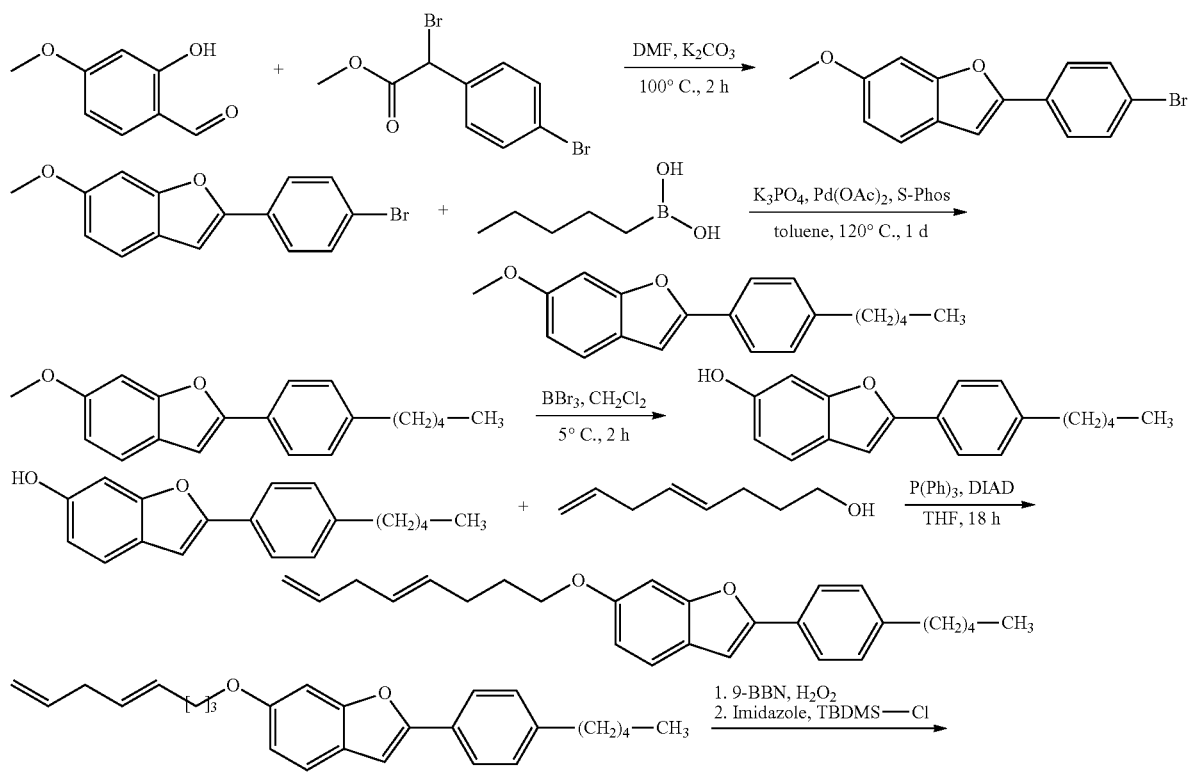

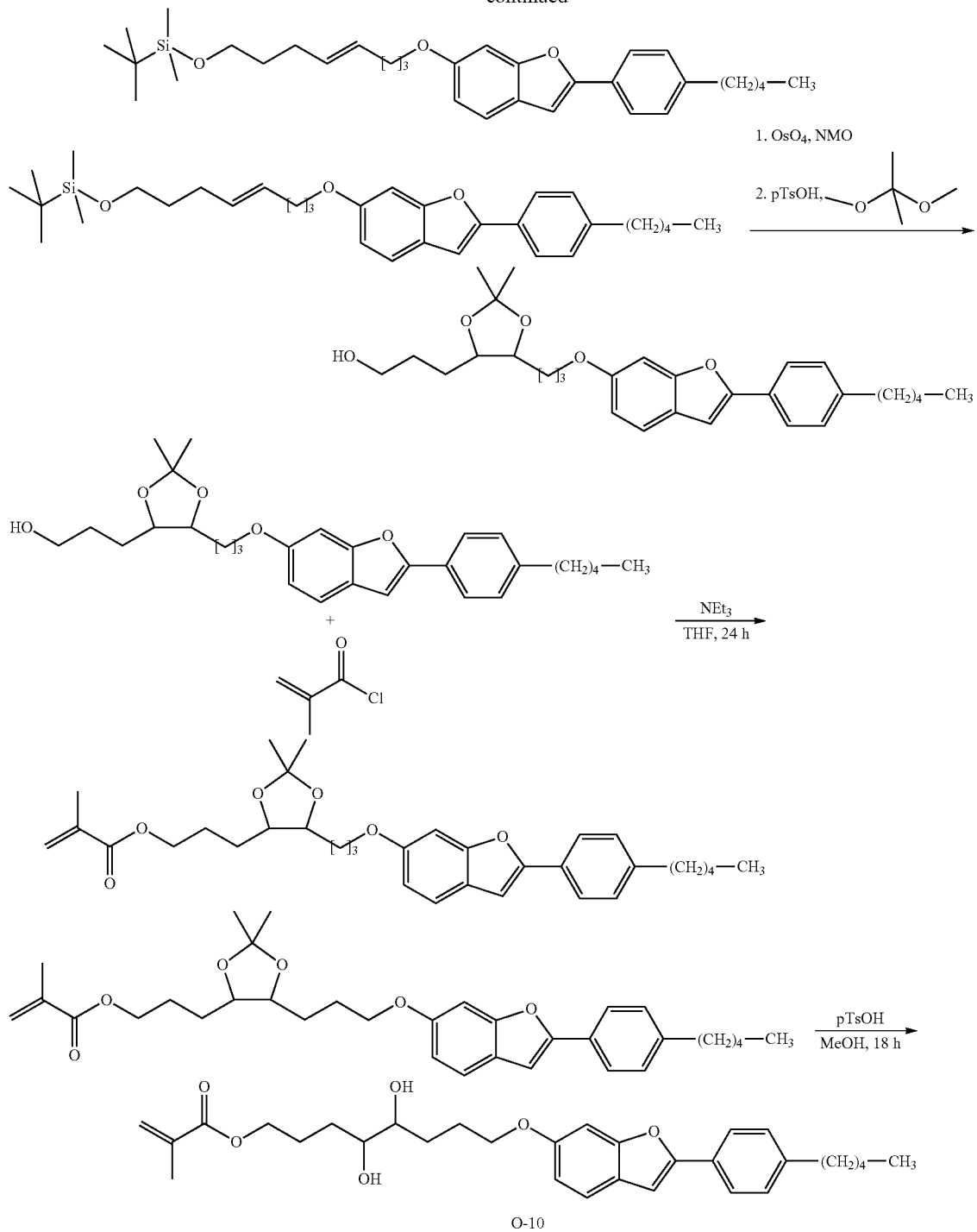

O-10

The first type of reaction is a classical ring closure via nucleophilic substitution, aldol-addition followed by decarboxylation. In the second step, a pentyl substituent is introduced via palladium-catalyzed Suzuki reaction. The third type of reaction is an ether cleavage in the presence of borontribromide. The fourth type of reaction is a Mitsunobu reaction, introducing an unsaturated alkyl linker. In the following step, Brown hydroboration yields the terminal hydroxyl group. A TMDMS-group is introduced as protective group. The remaining alkene is transformed to the corresponding 1,2-diol in an Upjohn dihydroxylation. Acetonide is introduced as protection group, and in the same step, TBDMS-group is removed. Hydroxyl-functional compound with acetonide protecting group is then reacted with methacryloyl chloride to produce an unsaturated methacrylate monomer. In the last step, the acetonide protecting group is removed by stirring in acidified methanol yielding a hydrophilic monomer.

All these types of reaction and their reaction conditions are well known to a skilled person and can be easily optimized for the specific starting materials forming the compounds of formula (I). More details can be found in the experimental section.

An exemplary reaction sequence is shown in Scheme 2 for the compound O-58.

Scheme 2

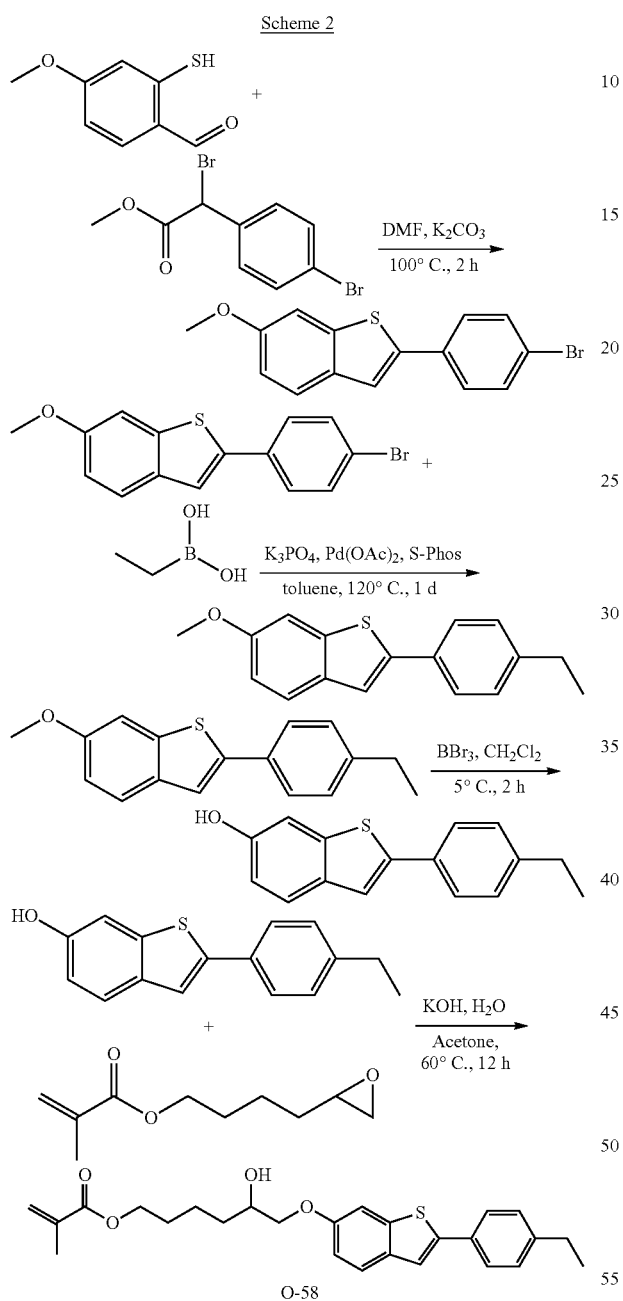

optimized for the specific starting materials forming the compounds of formula (I). More details can be found in the experimental section.

An exemplary reaction sequence is shown in Scheme 3 for the compound N-21.

Scheme 3

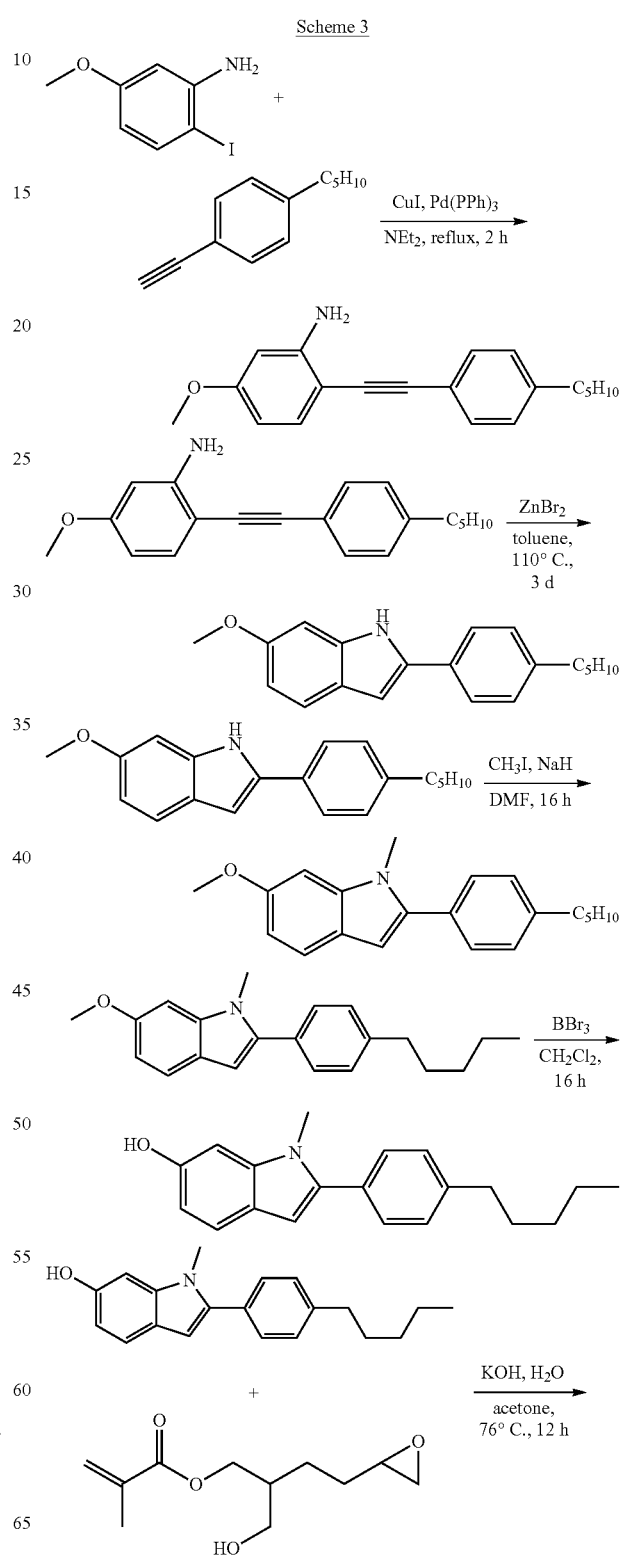

The first type of reaction is a classical ring closure via nucleophilic substitution, aldol-addition followed by decarboxylation. In the second step, an ethyl substituent is introduced via palladium-catalyzed Suzuki reaction. The third type of reaction is an ether cleavage in the presence of borontribromide. The fourth type of reaction is a basic epoxide opening yielding the free hydroxyl group in beta-position.

All these types of reaction and their reaction conditions are well known to a skilled person and can be easily

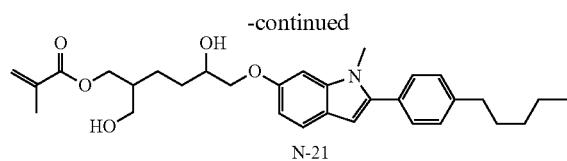

N-21

The first type of reaction is a Sonogashira. The second step is a zinc mediated ring closure reaction. The third type of reaction is a base mediated alkylation reaction. The fourth type of reaction is an ether cleavage in the presence of borontribromide. The fifth type of reaction is a basic epoxide opening yielding the free hydroxyl group in beta-position.

All these types of reaction and their reaction conditions are well known to a skilled person and can be easily optimized for the specific starting materials forming the compounds of formula (I). More details can be found in the experimental section.

An exemplary reaction sequence is shown in Scheme 4 for 2-hydroxy-3-(4-(1-alkyl-1H-indol-2-yl)phenoxy)propyl acrylate/methacrylate:

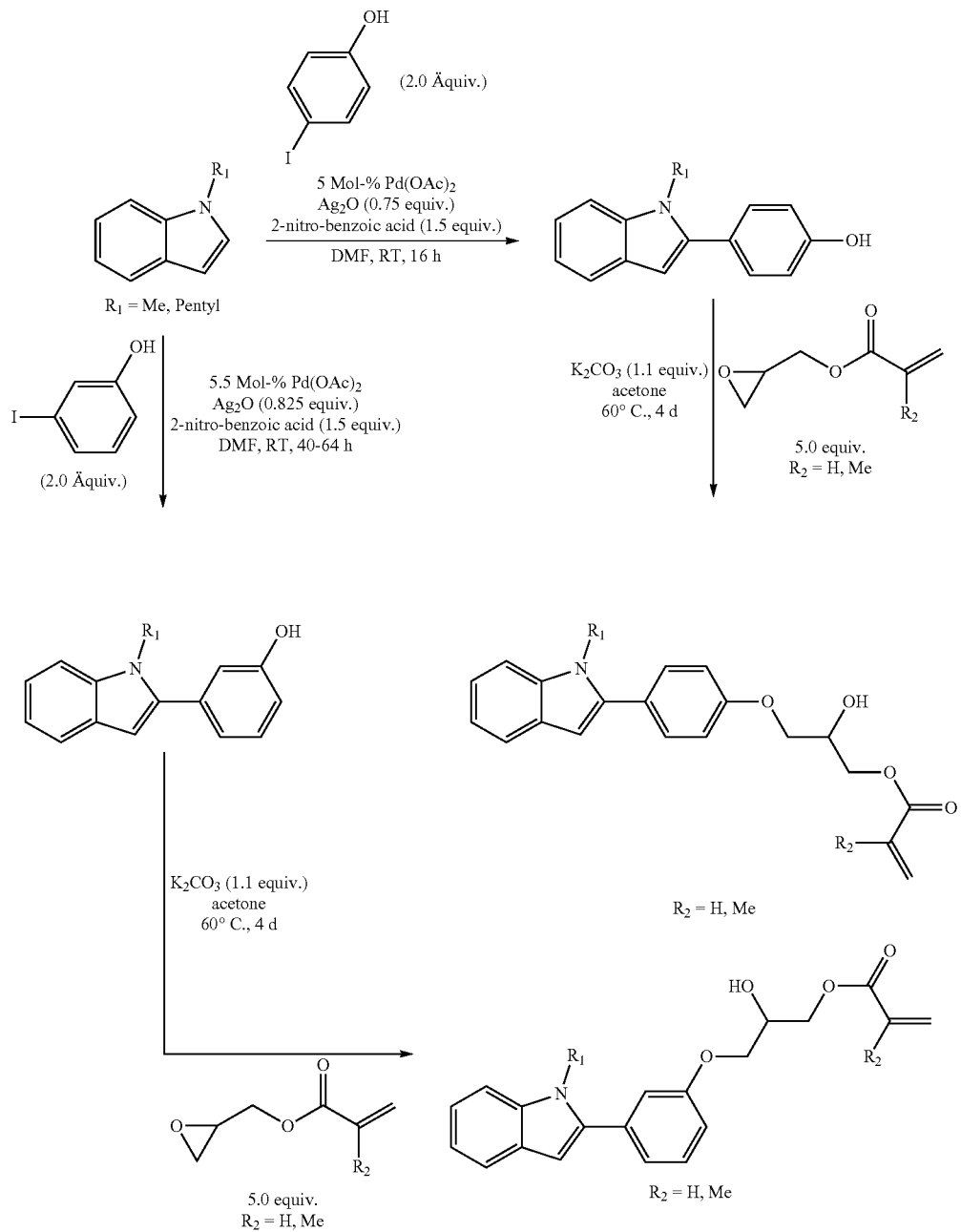

Me in Scheme 4 means methyl.

Me in scheme 4 means methyl.

As described before, the compounds of formula (I), (I'), (I") and/or (I''') as described before or preferably described before contain a polymerizable group and are predestinated as monomers for an oligomerization or a polymerization.

The invention is therefore further directed to an oligomer or polymer comprising polymerized compounds of formula (I), (I'), (I") and/or (I''') as described before or preferably described before.

The term "polymer" generally means a molecule of high relative molecular mass, the structure of which essentially comprises the multiple repetition of units derived, actually or conceptually, from molecules of low relative molecular mass (PAC, 1996, 68, 2291). The term "polymer" includes homopolymers and co-polymers. The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having ≥30 repeating units, and an oligomer means a compound with >1 and <30 repeating units.

Above and below, in formulae showing a polymer, an oligomer, a compound of formula (I) or a monomeric unit formed from a compound of formula (I), an asterisk ("*") denotes a linkage to the adjacent repeating unit in the polymer chain or oligomer chain or to a terminal end group.

Suitable terminal end groups are known to the skilled artisan and depend on the polymerization method used.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, tetrahydrofuran is used as solvent. The degree of polymerization (n) means the number average degree of polymerization given as $n=M_n/M_U$, wherein $M_U$ is the molecular weight of the single repeating unit as described in J. M. G. Cowie, *Polymers: Chemistry & Physics of Modern Materials*, Blackie, Glasgow, 1991. The polydispersity (PDI) means the ratio of weight average molecular weight $M_w$, divided by the number average molecular weight $M_n$ and is described with the letter D. The value of D is dimensionless and describes the broadness of the molecular weight distribution. The value of D can be calculated from the obtained values ($M_w$, $M_n$) from the GPC analysis.

In the polymers according to the the present invention, the total number of repeating units n is preferably ≥30, very preferably ≥100, most preferably ≥200, and preferably up to 5000, very preferably up to 3000, most preferably up to 2000, including any combination of the aforementioned lower and upper limits of n.

The polymers of the present invention include homopolymers, statistical co-polymers, random co-polymers, alternating co-polymers and block co-polymers, and combinations of the aforementioned.

Throughout the description and claims of this specification, the words "comprise" and "contain" and variations of the words, for example "comprising" and "comprises", mean "including but not limited to", and are not intended to (and do not) exclude other components Preferably the polymerizable group $R_1$ forms the regioregular, alternated, regiorandom, statistical, block or random homopolymer or co-polymer backbone or is part of the polymer backbone where $R_1$ has a meaning as described or preferably described before. Particularly preferably, such oligomer or polymer comprises a constitutional unit $M^0$ of formulae (5-p-1), (5-p-2), (5-p-3),

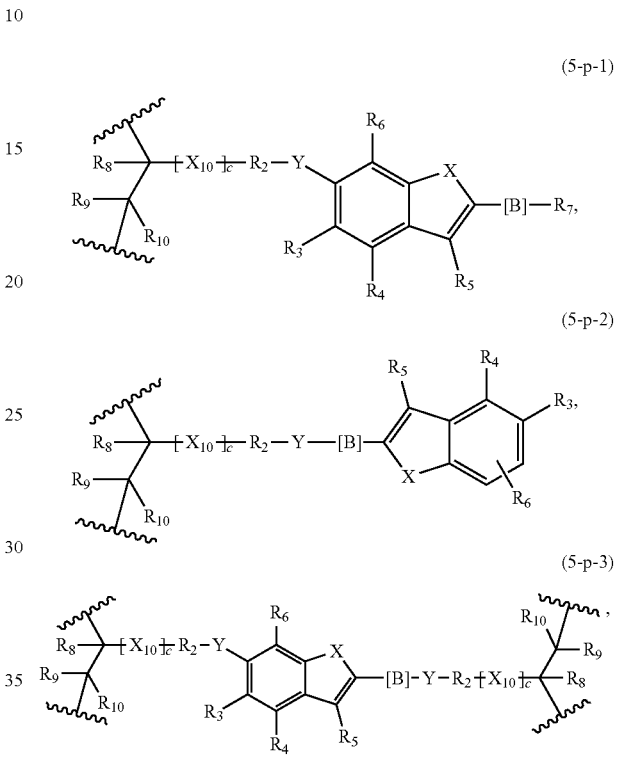

wherein
—$R_2$—, Y, $R_3$, $R_4$, $R_5$, $R_6$, X, —[B]—, $R_7$, $X_{10}$, $R_8$, $R_9$, $R_{10}$ and c have a meaning or a preferred meaning as described or preferably described before. Combinations are excluded where two O atoms or an O atom and a S atom are directly linked to each other as known for a skilled artisan in the field of organic chemistry.

The co-polymer may be an oligomer or polymer comprising one or more polymerized compounds of formula (I), (I'), (I") or (I''') or a constitutional unit $M^0$ of formulae (5-p-1), (5-p-2), (5-p-3), which may be the same or different from one another, and one or more constitutional units $M^2$, which may be the same or different from one another.

Said one or more constitutional units $M^2$ are chemically different from the units $M^0$. Preferably, said one or more constitutional units $M^2$ are derived by polymerization of one or more monomers selected from the group consisting of styrene, ethoxyethyl methacrylate (EOEMA), methyl methacrylate (MMA), n-alkyl acrylates (the n-alkyl group comprising 2-20 C-atoms), n-alkyl methacrylates (the n-alkyl group comprising 2-20 C-atoms), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EG-PEA), Bisphenol A diacrylate-1 EO/Phenol (BPADA), 2-[3'-2'H-benzotriazol-2'-yl)-4'-hydroxyphenyl]ethyl methacrylate (BTPEM), trialkoxyalkenylsilane, dialkoxyalkylalkenylsilane or a silane of formula (9) and (10),

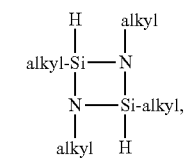
(9)

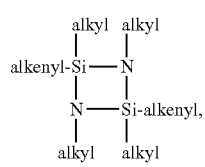
(10)

where the alkyl and/or alkoxy groups are at each occurrence independently of each other linear or branched having 1 to 6 C atoms and where the alkenyl group is at each occurrence independently linear having 2 to 4 C atoms.

Particularly preferably, said one or more constitutional units $M^2$ are derived by polymerization of one or more monomers selected from the group consisting of styrene, ethoxyethyl methacrylate (EOEMA), methyl methacrylate (MMA), n-alkyl acrylates (the n-alkyl group comprising 2-20 C-atoms), n-alkyl methacrylates (the n-alkyl group comprising 2-20 C-atoms), ethoxyethyl methacrylate (EOEMA), methyl methacrylate (MMA), ethoxyethoxy ethylacrylate (EEEA), 2-hydroxyethyl methacrylate (HEMA), tetrahydrofuryl methacrylate (THFMA), glycidylmethacrylate (GMA), 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate (EGPEA), Bisphenol A diacrylate-1 EO/Phenol (BPADA) and 2-[3'-2'H-benzotriazol-2'-yl]-4'-hydroxyphenyl]ethyl methacrylate (BTPEM) in combination with inventive monomers containing an alkenyl group of formula (5) as described or preferably described before.

Particularly preferably, said one or more constitutional units $M^2$ are derived by polymerization of one or more monomers selected from the group consisting of trialkoxyalkenylsilane, dialkoxyalkylalkenylsilane or a silane of formula (9) and (10),

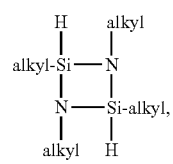
(9)

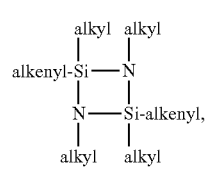
(10)

where the alkyl and/or alkoxy groups are at each occurrence independently of each other linear or branched having 1 to 6 C atoms and where the alkenyl group is at each occurrence independently linear having 2 to 4 C atoms in combination with inventive monomers containing a polymerizable group containing at least one Si atom.

Alternatively the oligomer or polymer according to the invention is a homopolymer, i.e. an oligomer or polymer comprising one or more constitutional unit $M^0$ of formula of formulae (5-p-1), (5-p-2), (5-p-3), wherein all constitutional units $M^0$ are the same.

Exemplary polymeric compounds may be selected from the following formulae (P-01) to (P-156):

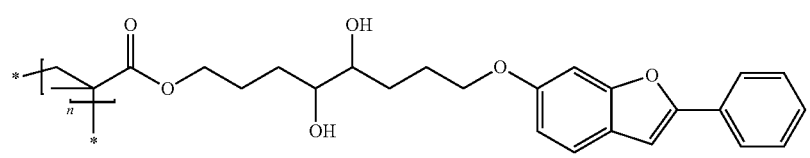
P-01

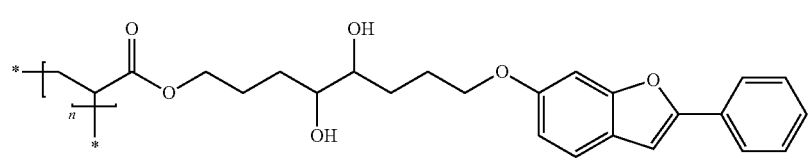
P-02

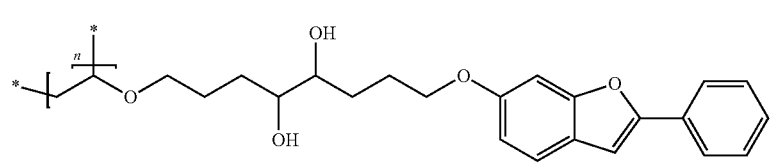
P-03

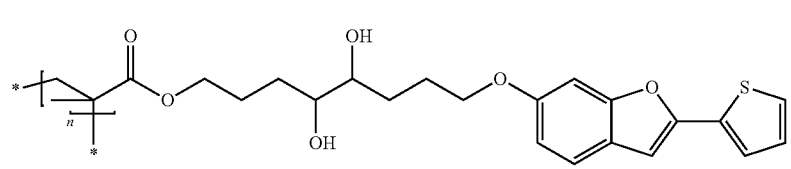
P-04

-continued
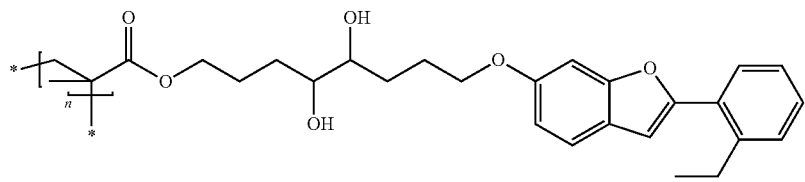
P-05
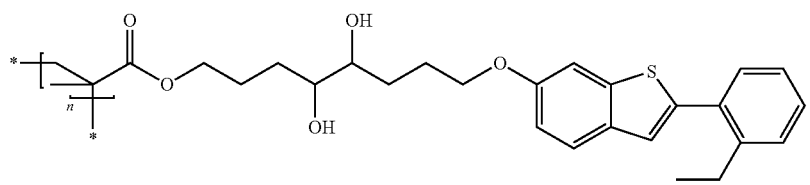
P-06
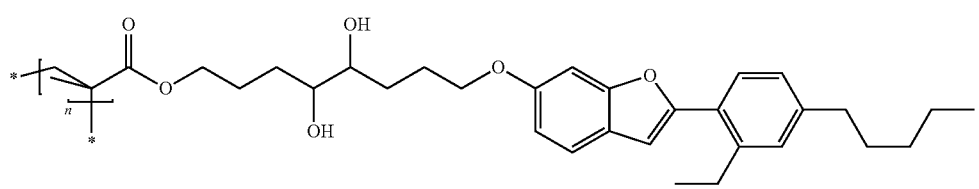
P-07
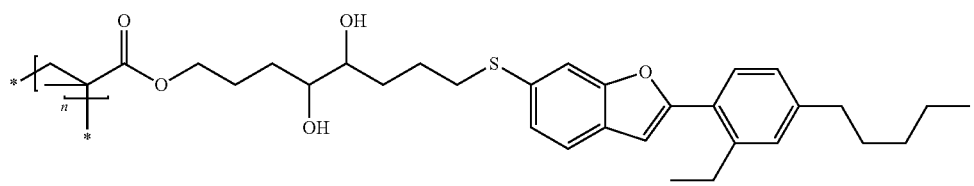
P-08
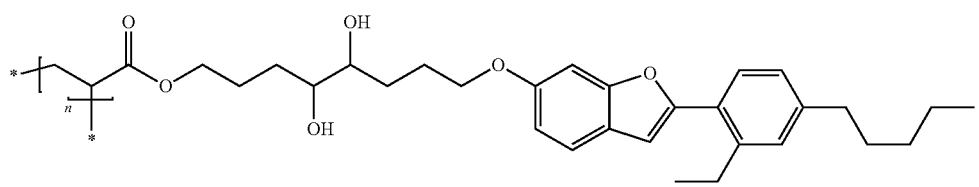
P-09
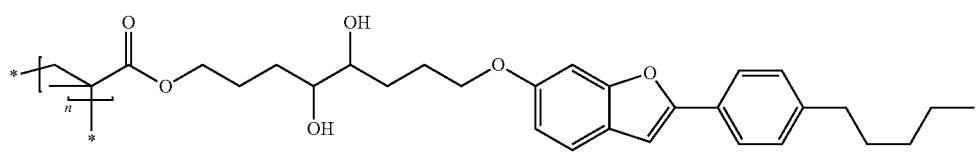
P-10
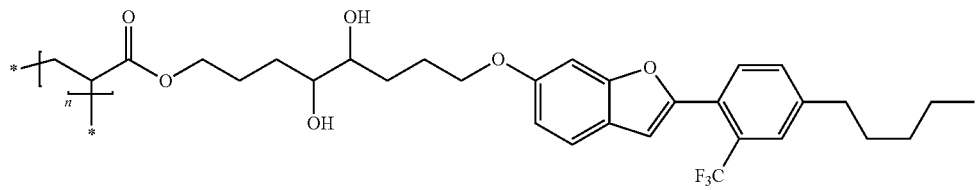
P-11
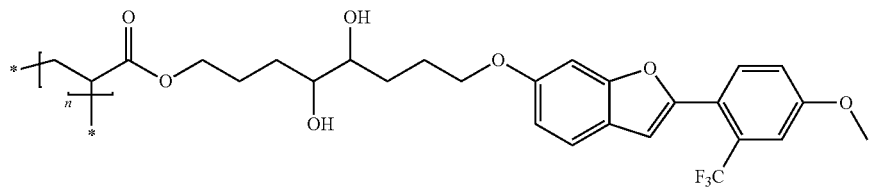
P-12

-continued
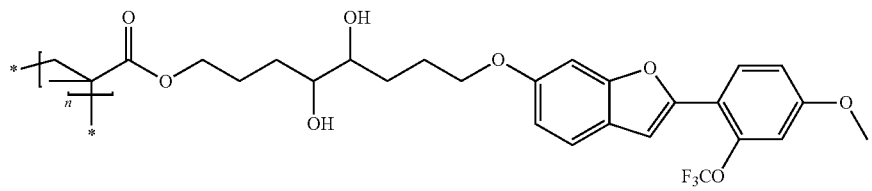 P-13
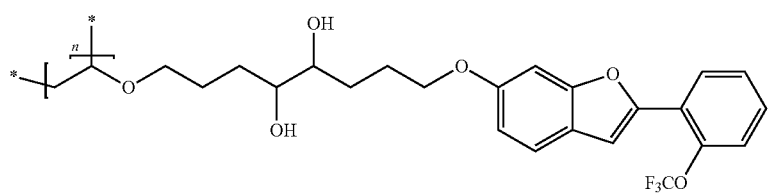 P-14
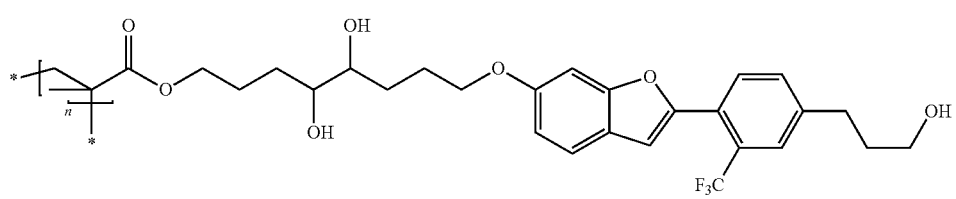 P-15
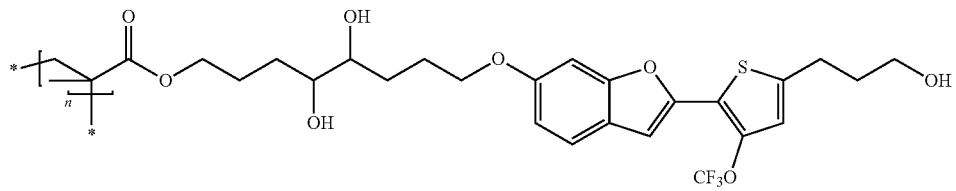 P-16
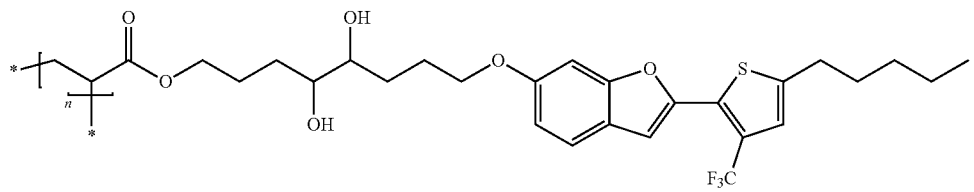 P-17
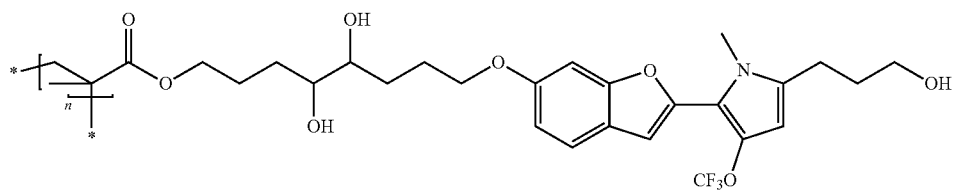 P-18
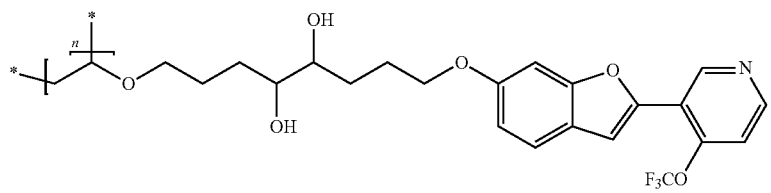 P-19
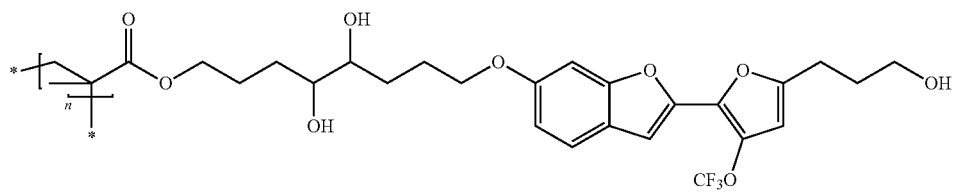 P-20

P-21
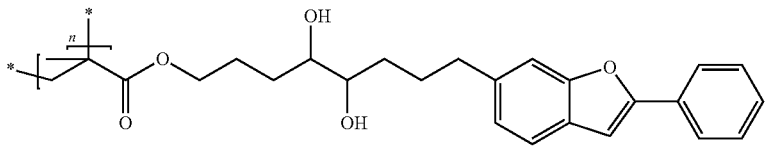
P-22
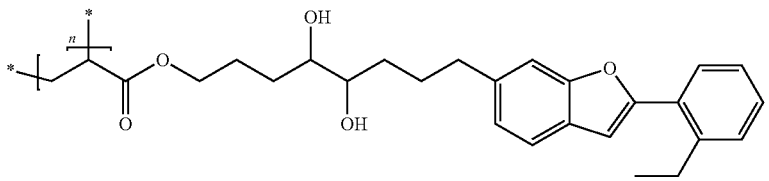
P-23
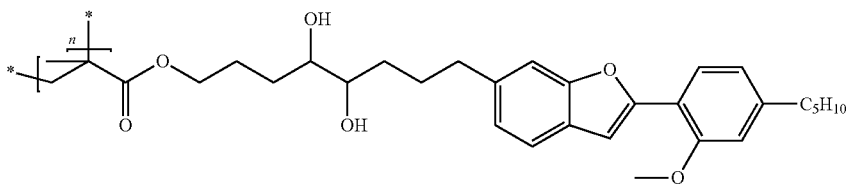
P-24
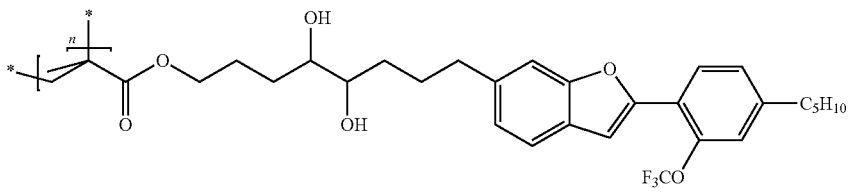
P-25
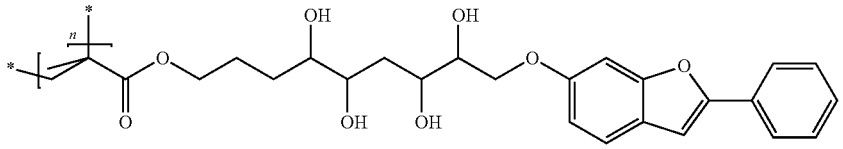
P-26
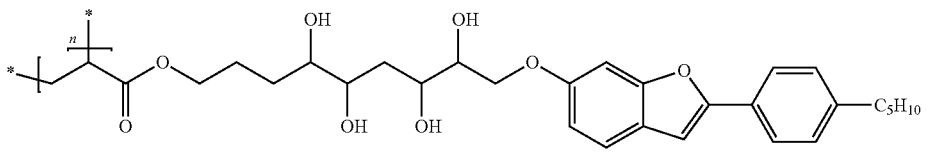
P-27
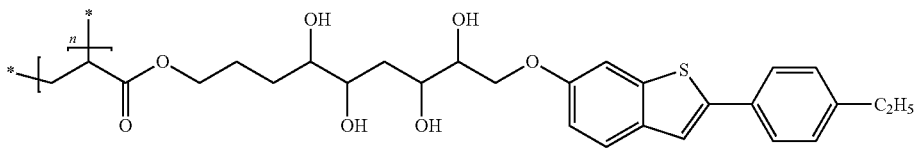
P-28
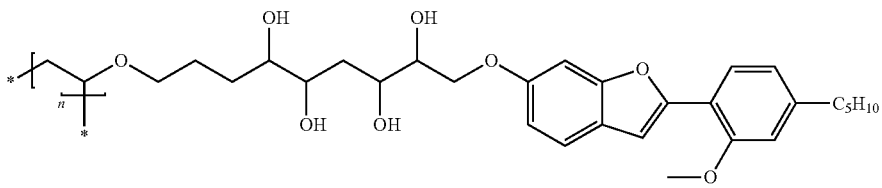
P-29
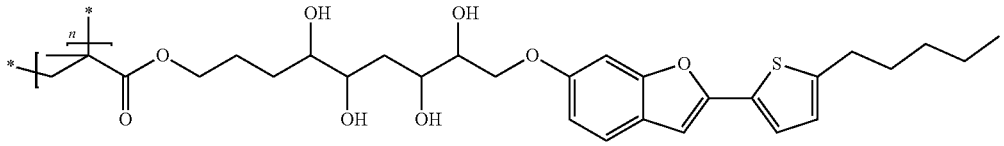

-continued
P-30
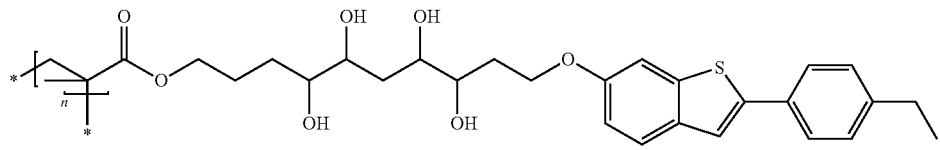
P-31
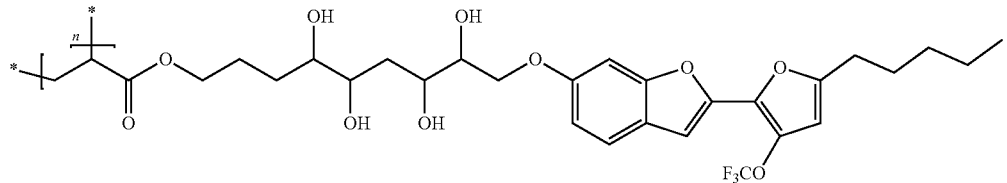
P-32
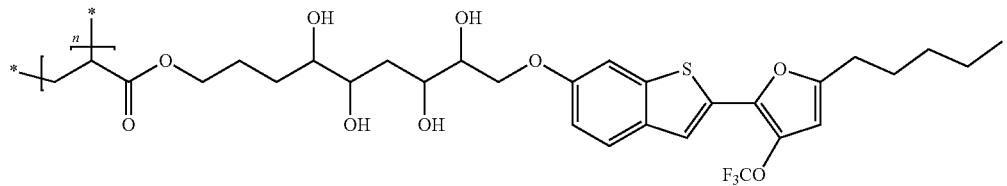
P-33
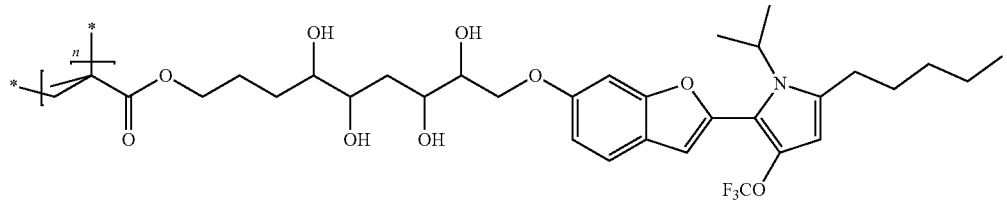
P-34
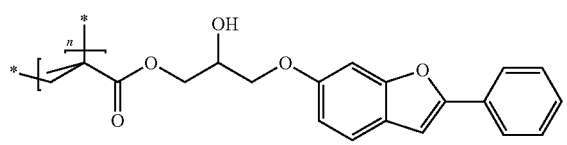
P-35
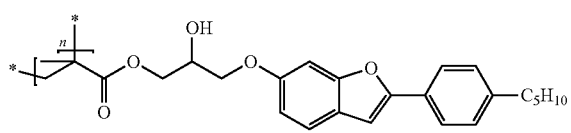
P-36
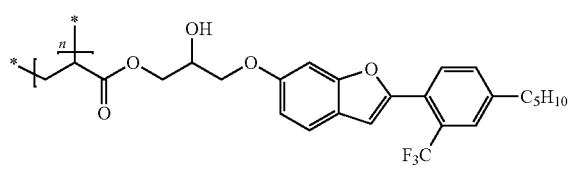
P-37
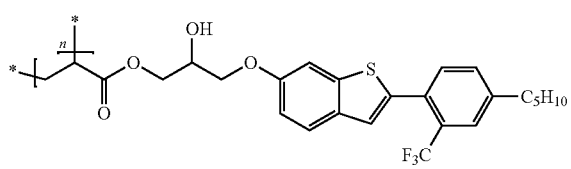
P-38
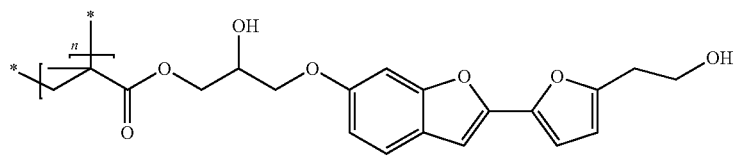
P-39
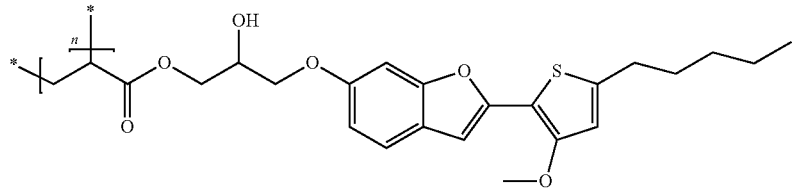

-continued
P-40
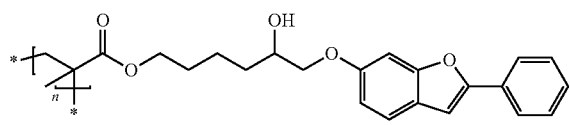
P-41
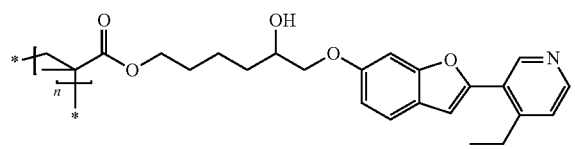
P-42
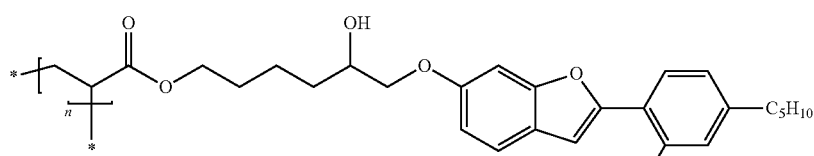
P-43
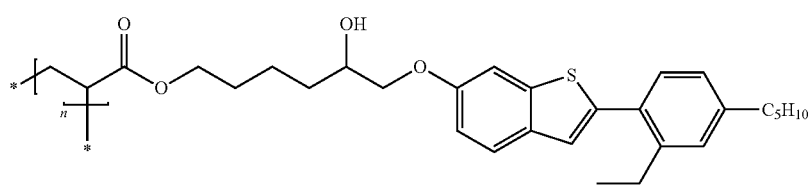
P-44
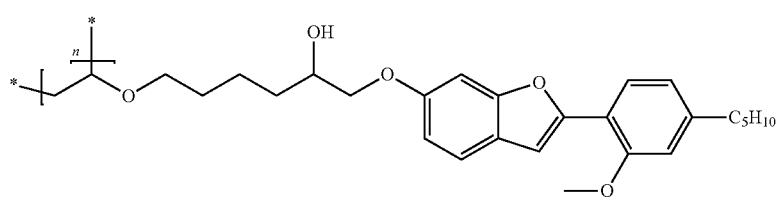
P-45
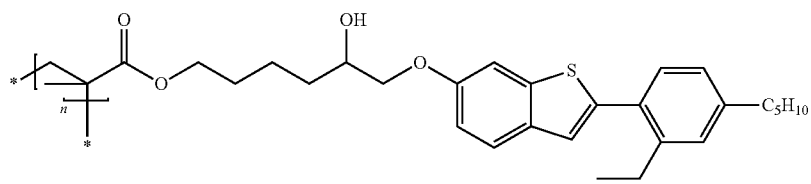
P-46
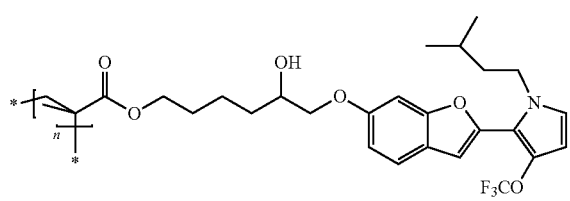
P-47
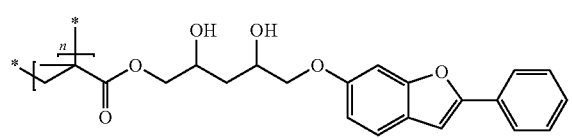
P-48
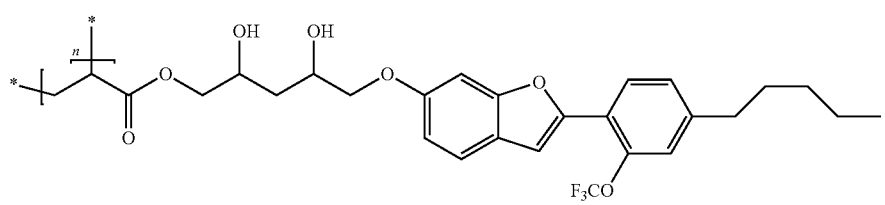
P-49
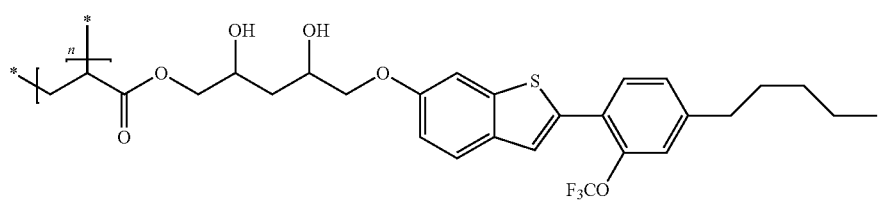

-continued
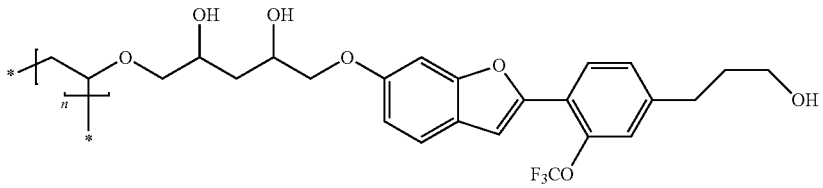
P-50
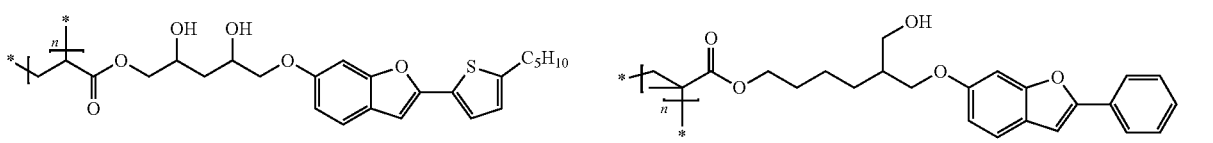
P-51      P-52
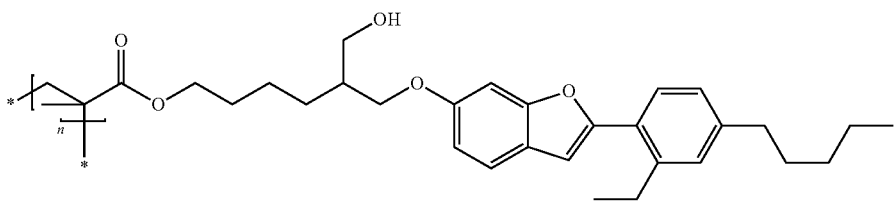
P-53
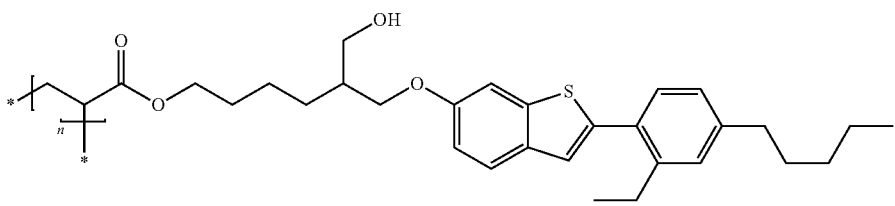
P-54
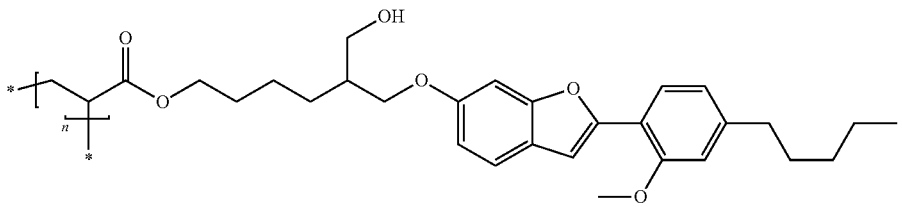
P-55
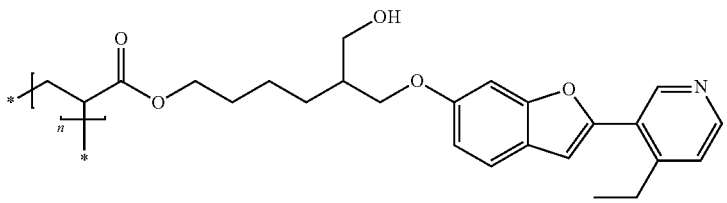
P-56
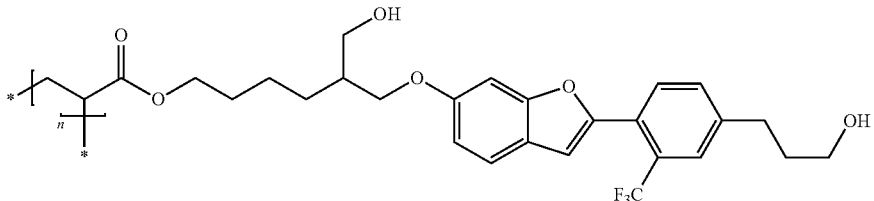
P-57
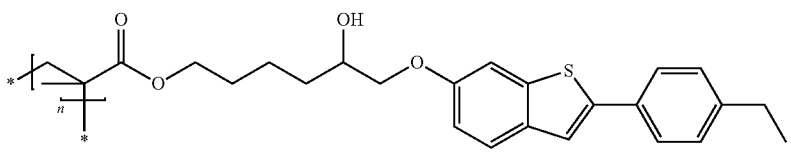
P-58

-continued
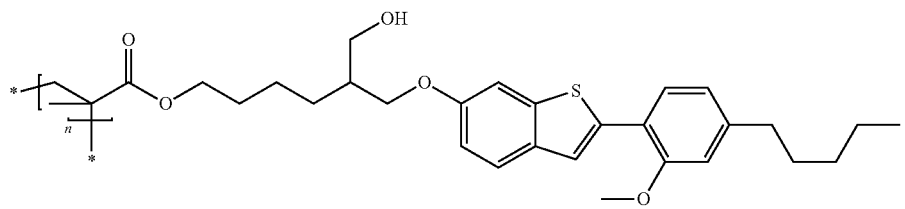
P-59
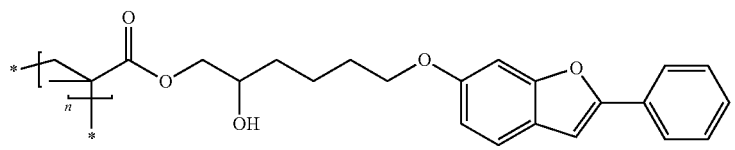
P-60
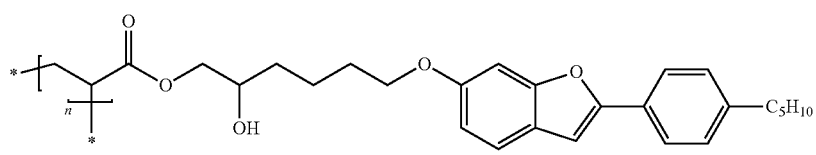
P-61
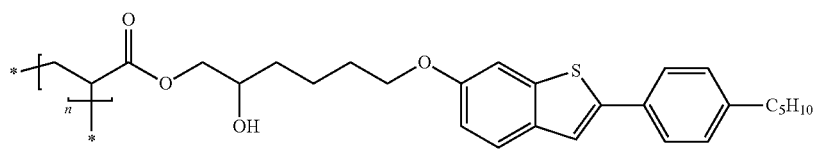
P-62
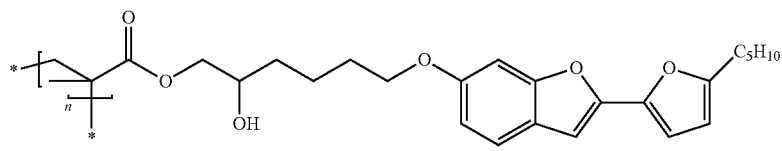
P-63
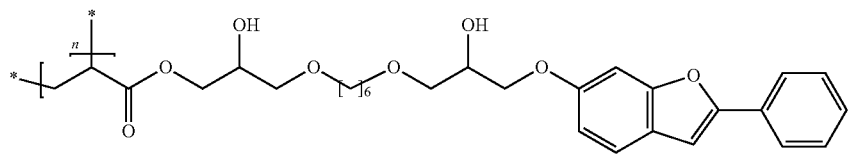
P-64
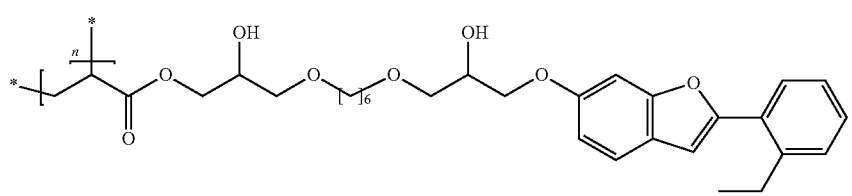
P-65
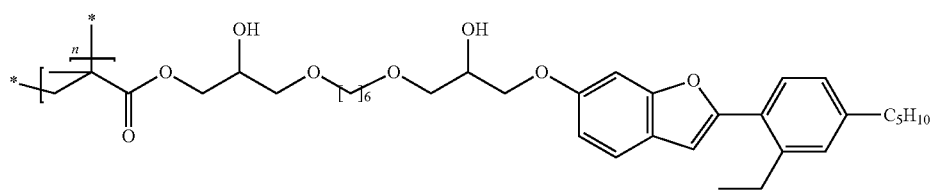
P-66
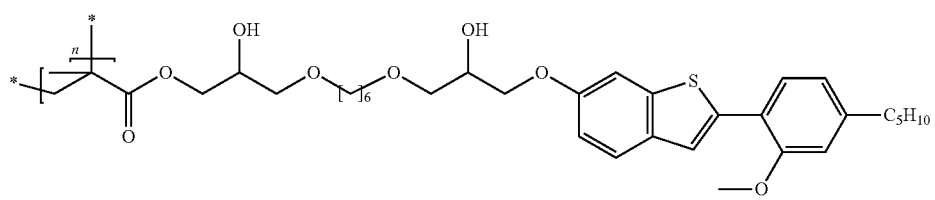
P-67

-continued
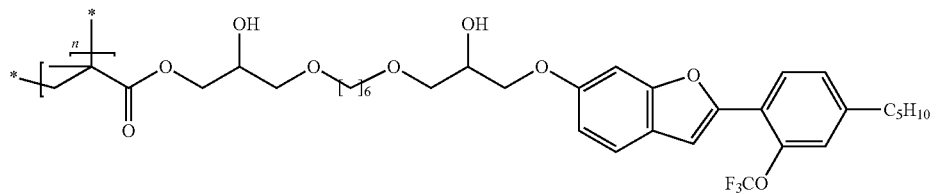
P-68
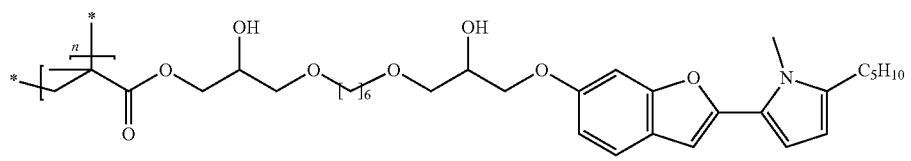
P-69
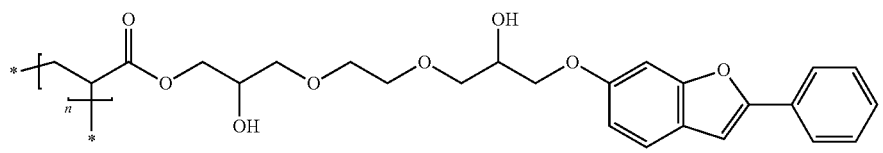
P-70
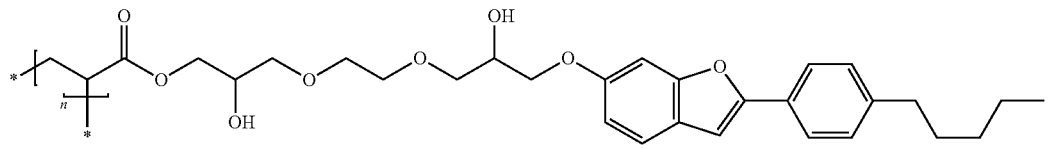
P-71
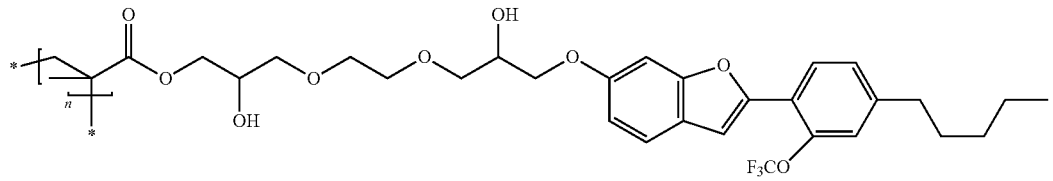
P-72
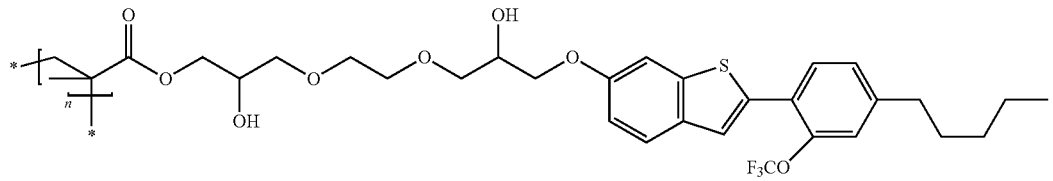
P-73
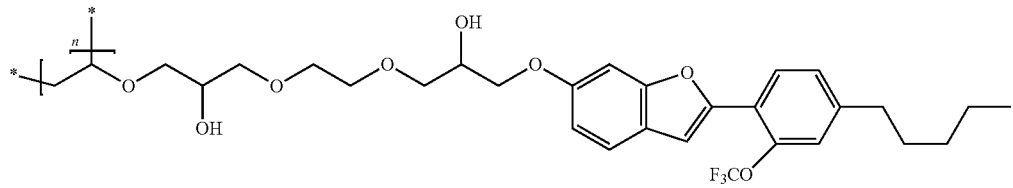
P-74
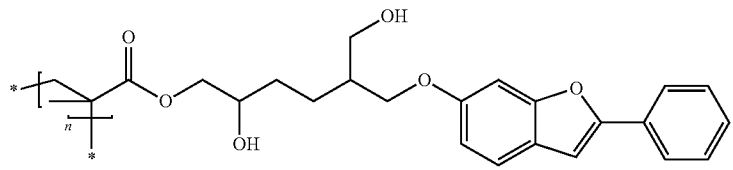
P-75

-continued
P-76
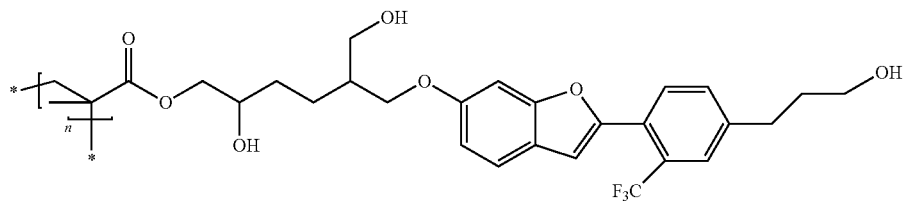
P-77
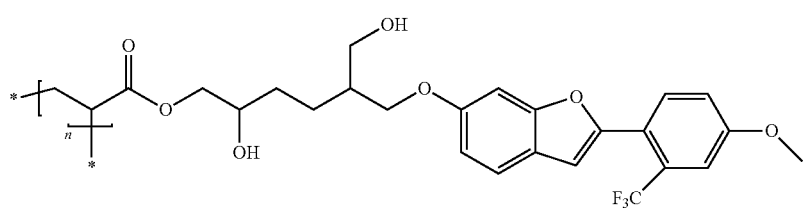
P-78
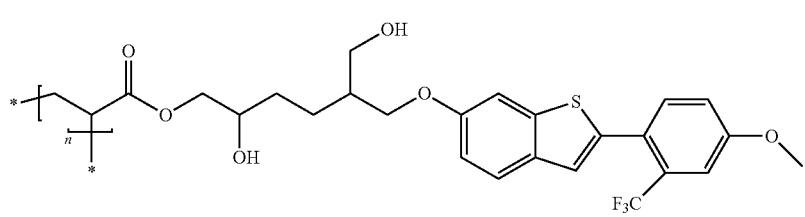
P-79
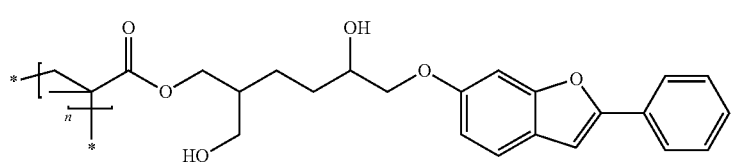
P-80
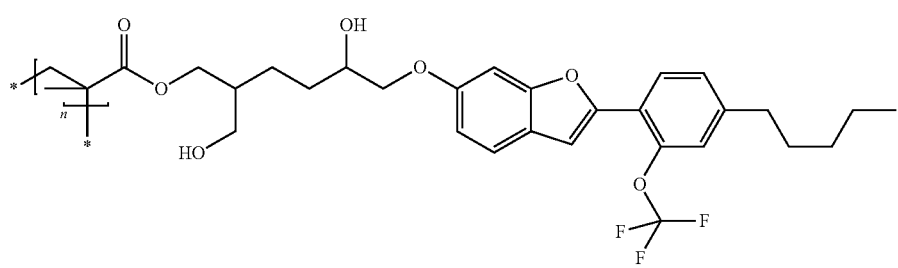
P-81
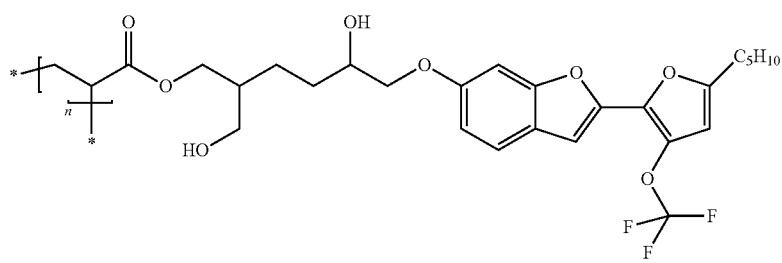
P-82
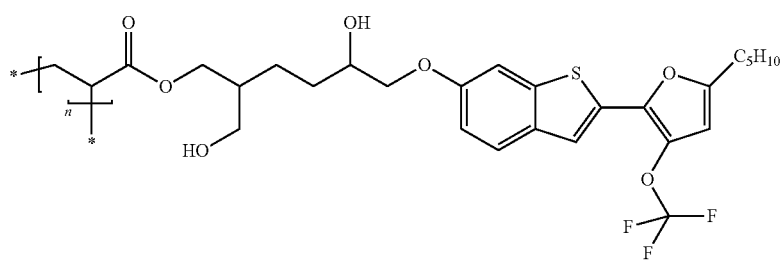

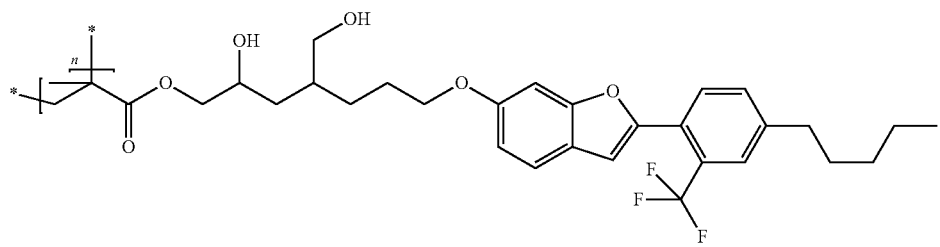
P-83
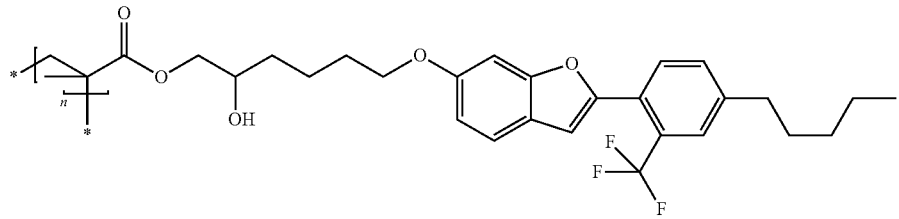
P-84
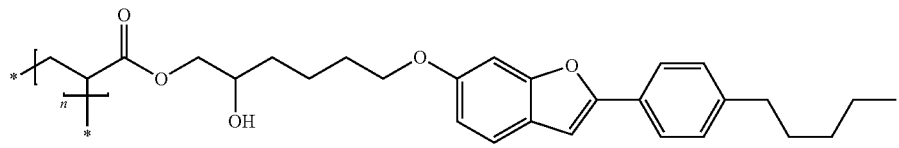
P-85
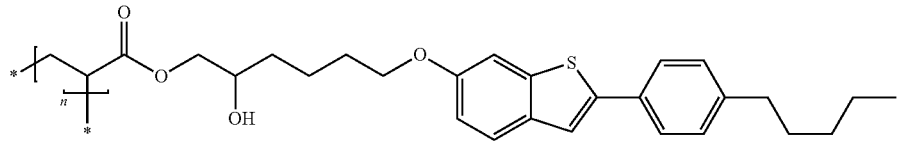
P-86
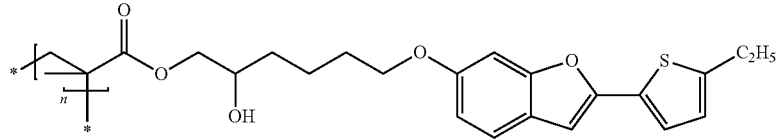
P-87
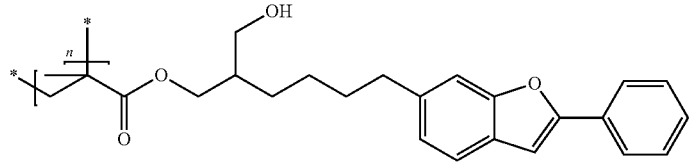
P-88
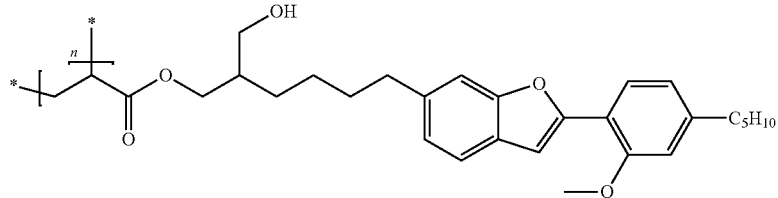
P-89
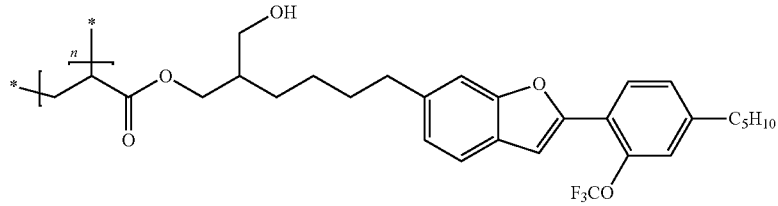
P-90

-continued
P-91
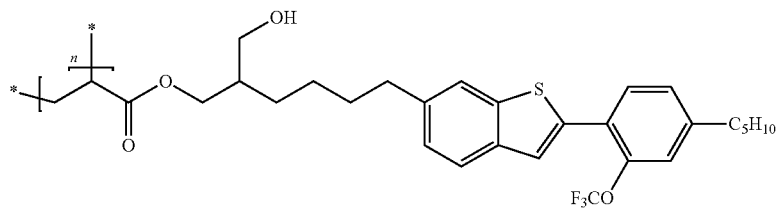
P-92
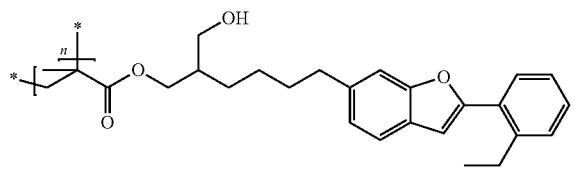
P-93
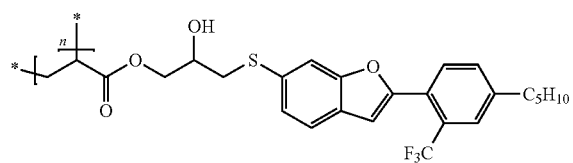
P-94
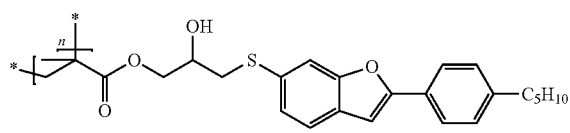
P-95
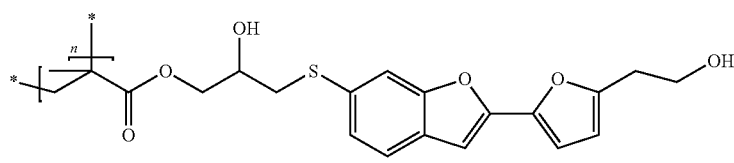
P-96
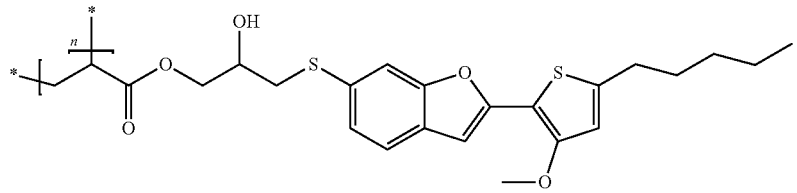
P-97
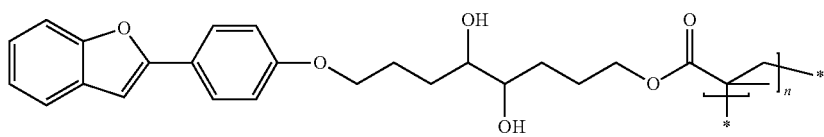
P-98
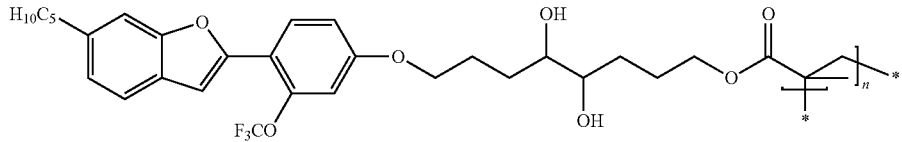
P-99
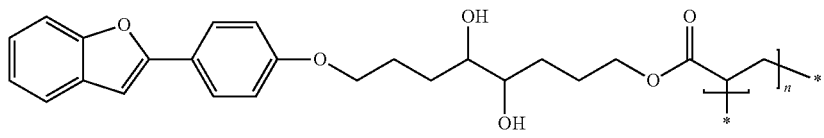
P-100
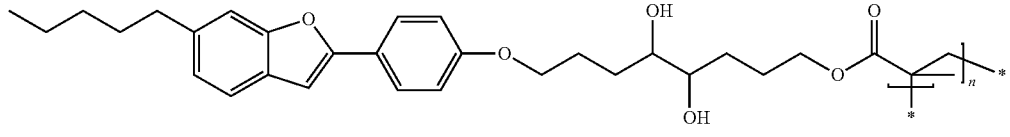
P-101

-continued
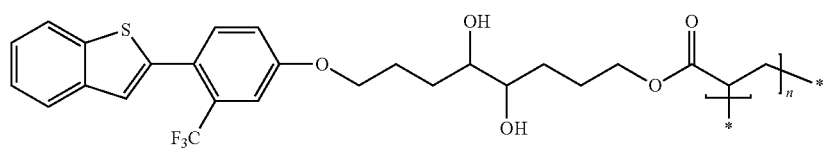 P-102
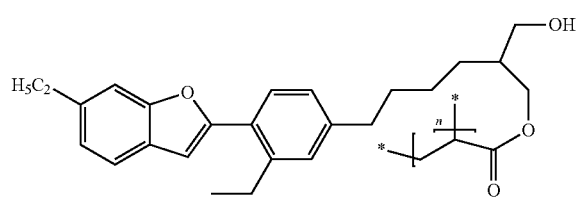 P-103
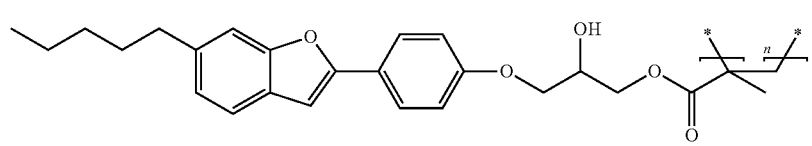 P-104
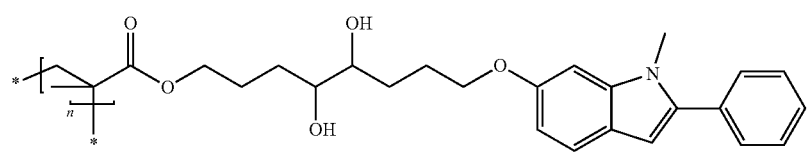 P-105
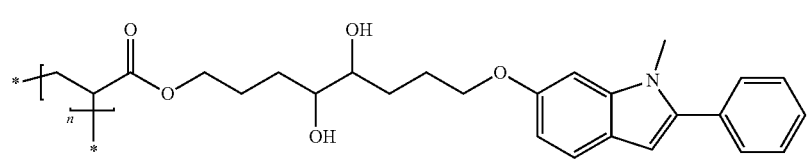 P-106
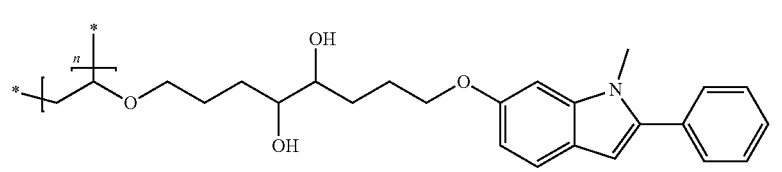 P-107
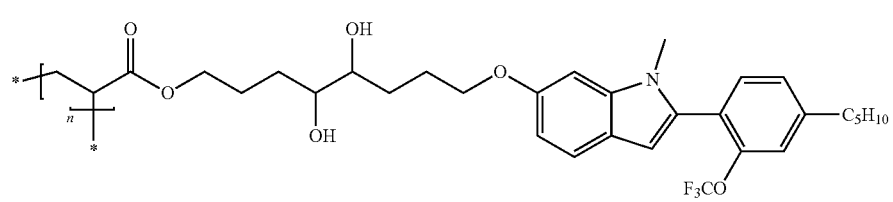 P-108
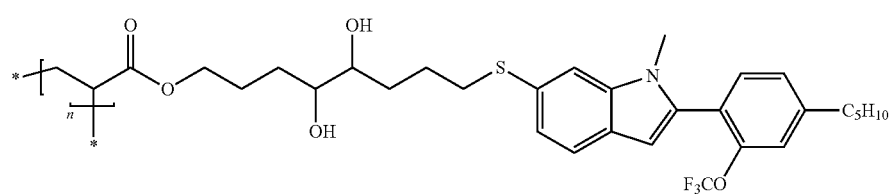 P-109
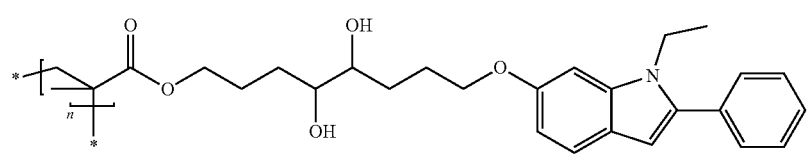 P-110

-continued
P-111
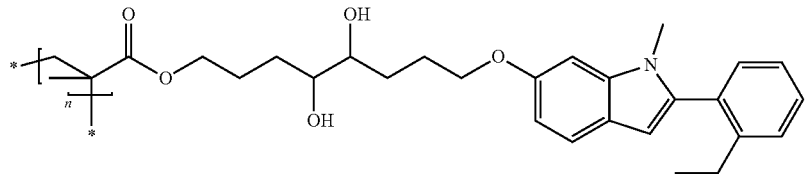
P-112
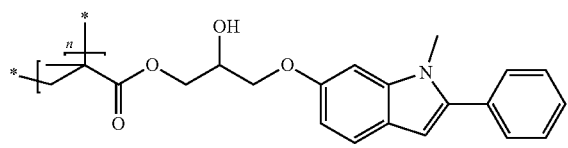
P-113
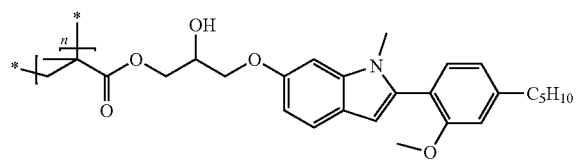
P-114
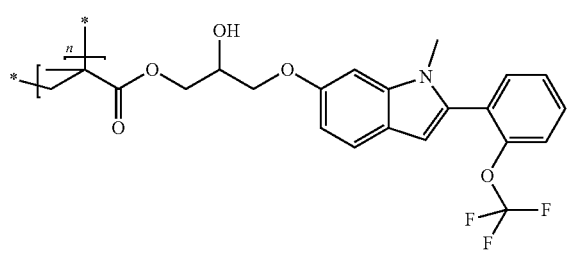
P-115
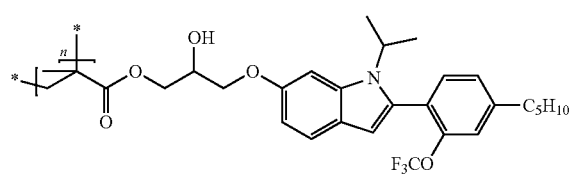
P-116
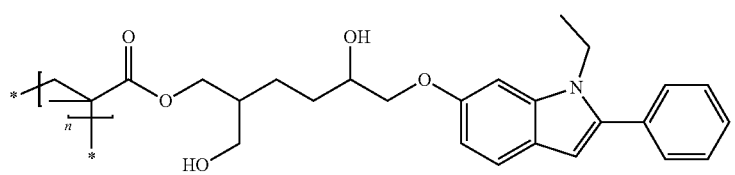
P-117
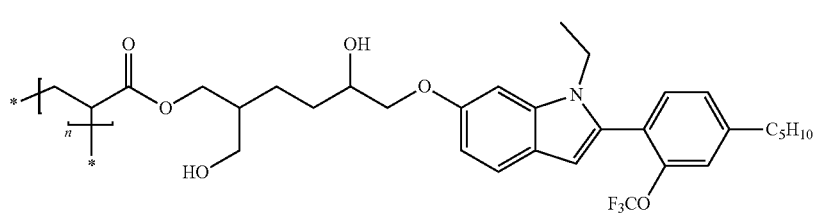
P-118
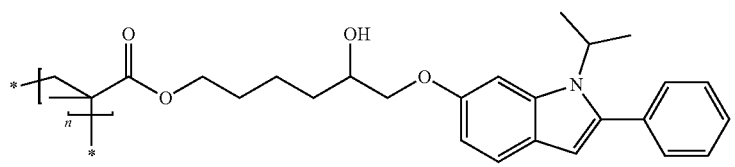
P-119
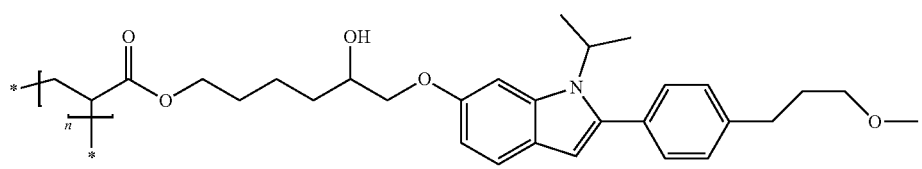
P-120
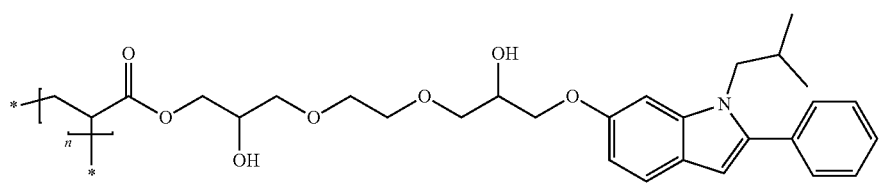

-continued
P-121
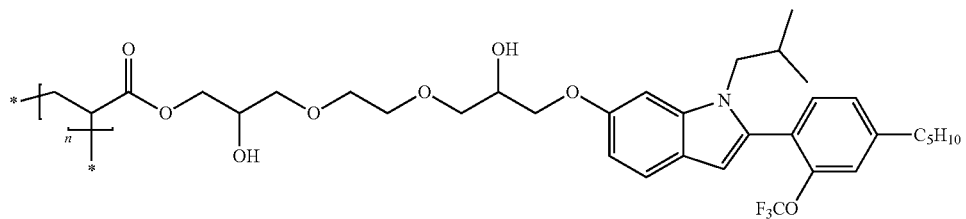
P-122
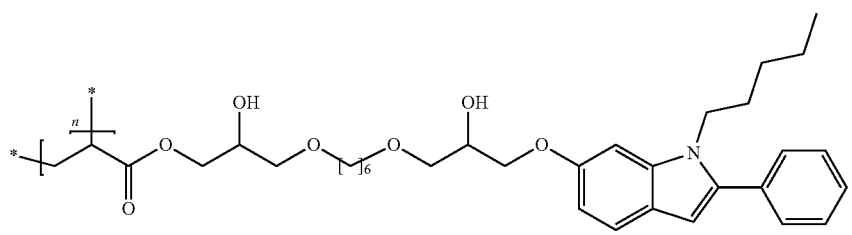
P-123
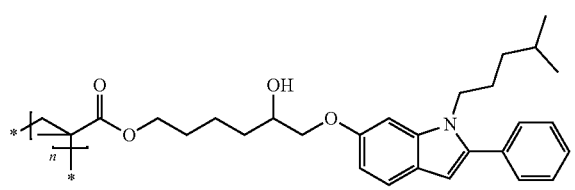
P-124
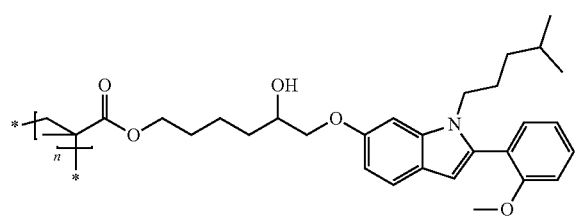
P-125
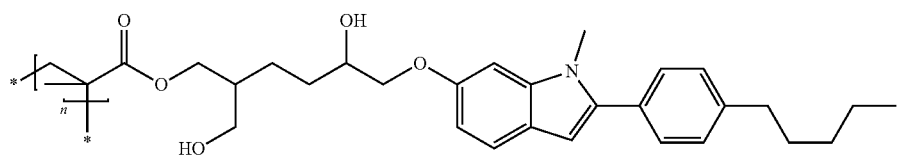
P-126
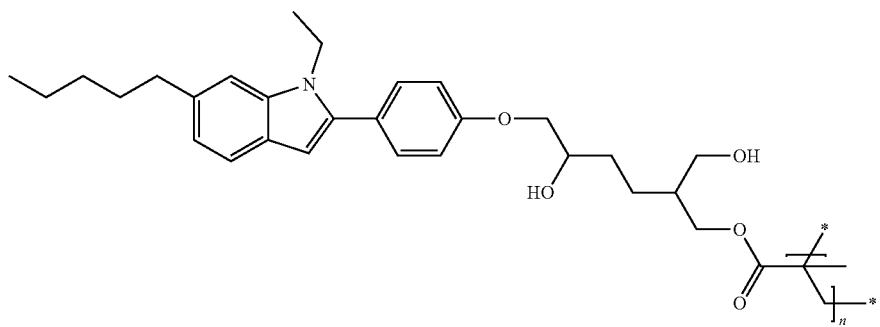
P-127
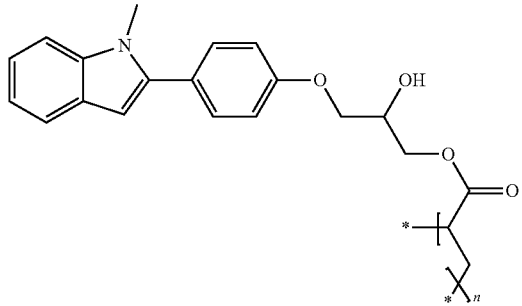
P-128
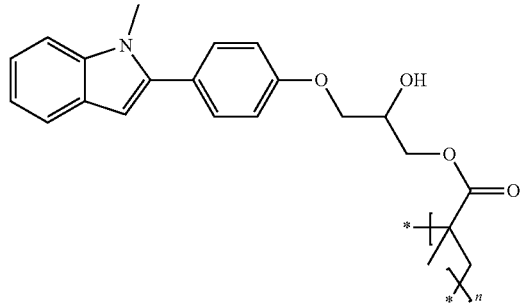

-continued
P-130
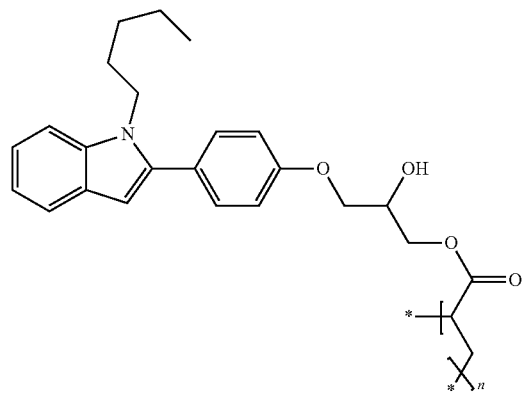
P-131
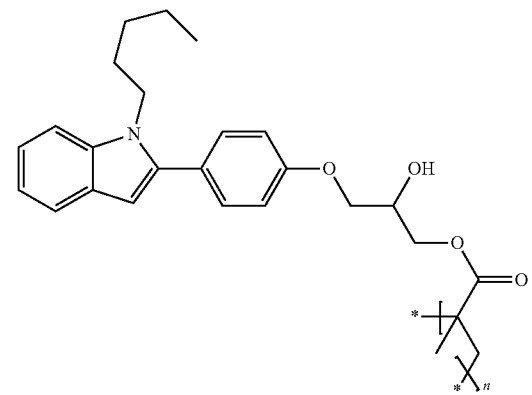
P-132
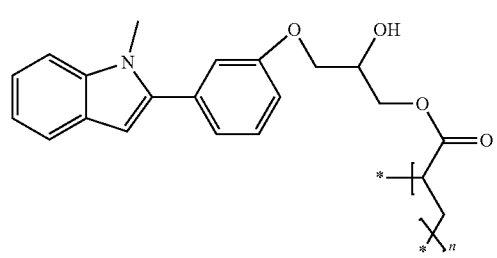
P-133
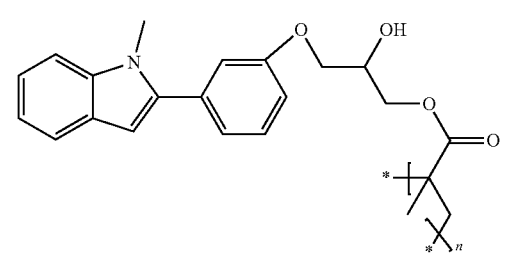
P-134
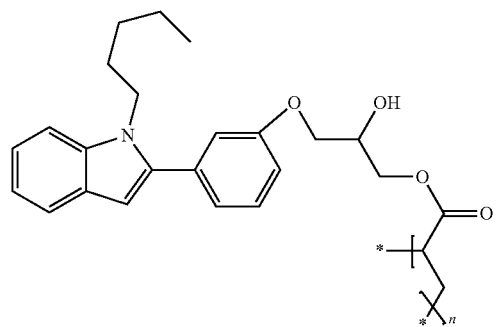
P-135
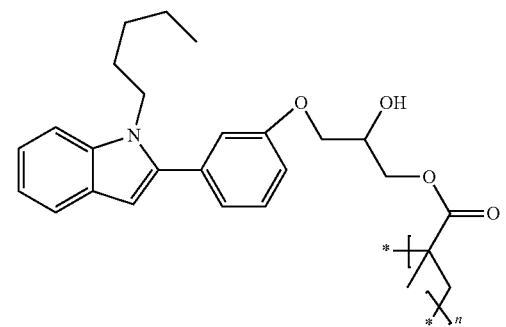
P-136
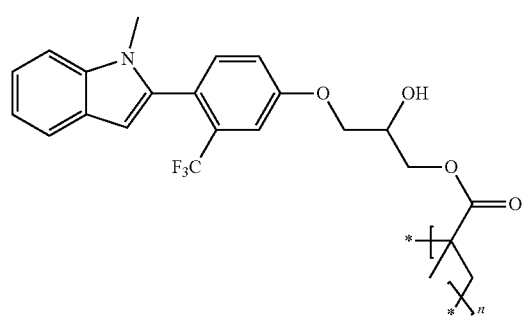
P-137
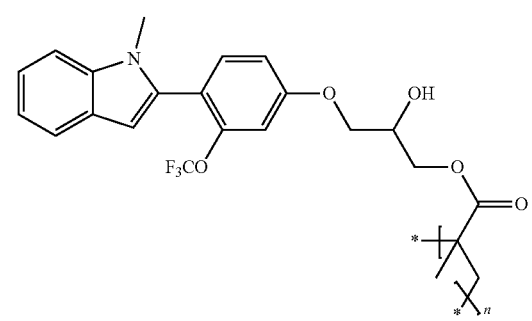
P-138
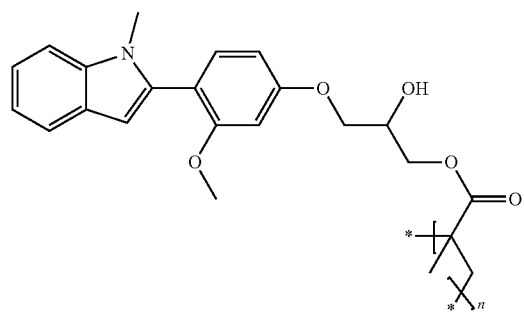
P-139
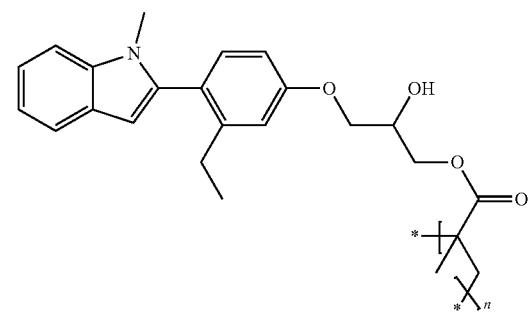

-continued
P-140
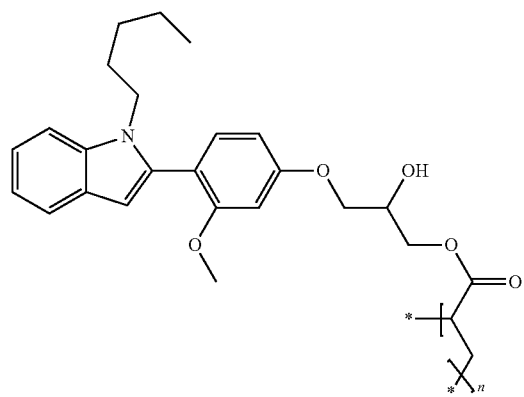
P-141
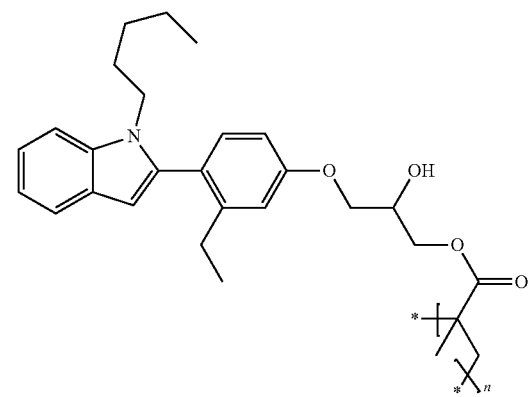
P-142
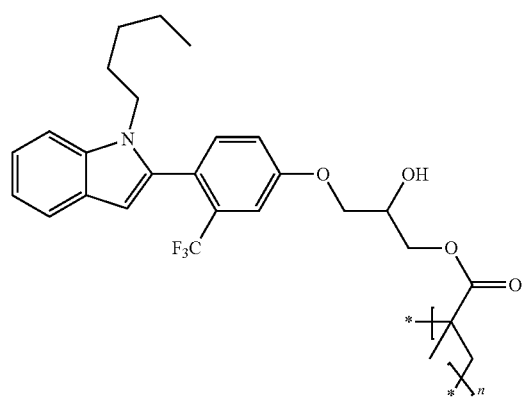
P-143
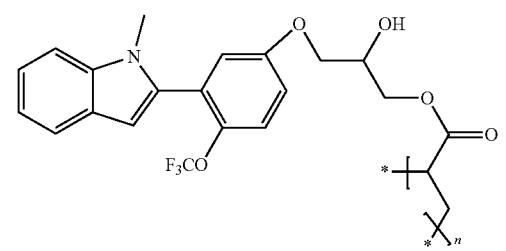
P-144
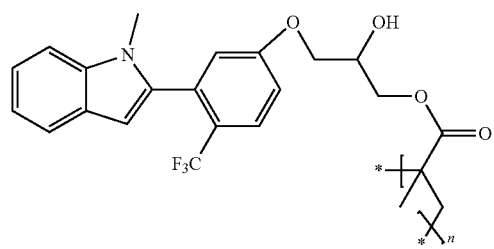
P-145
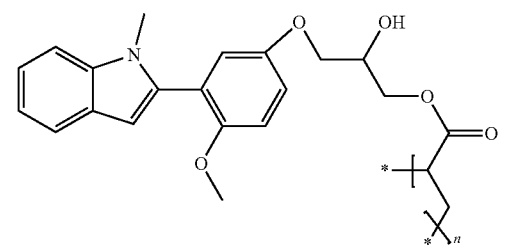
P-146
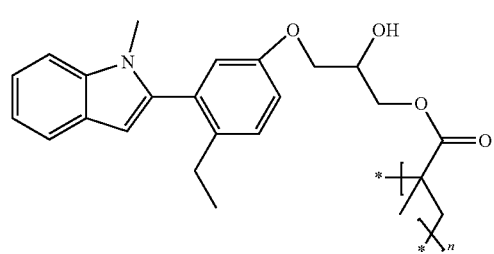
P-147
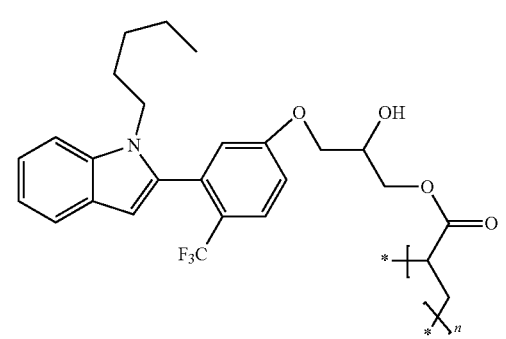

P-148
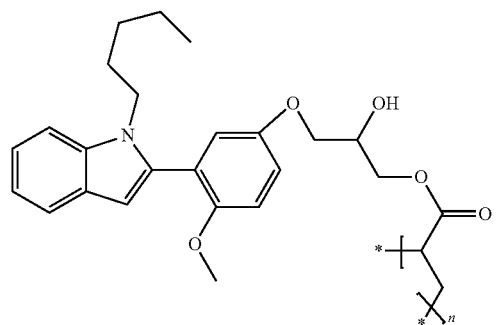
P-149
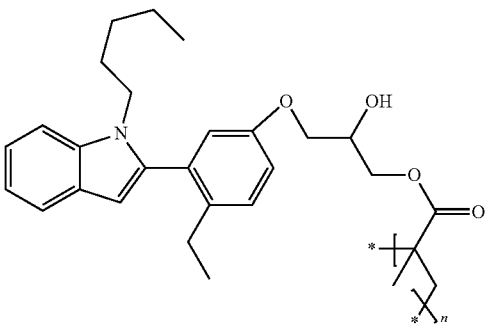
P-150
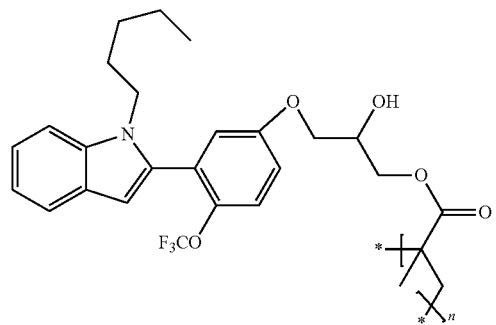
P-151
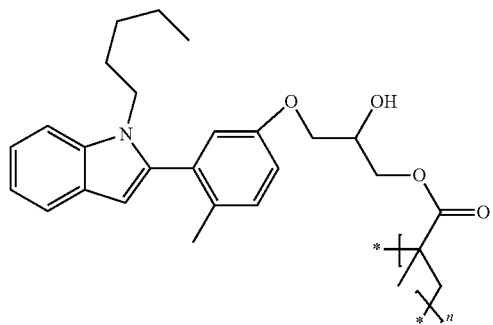
P-152
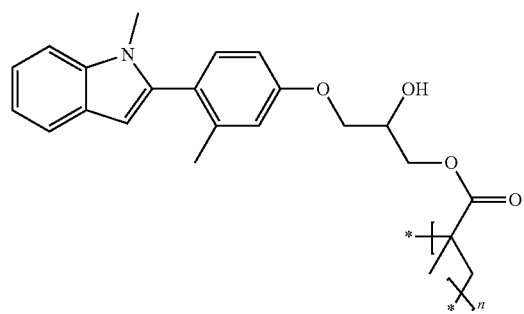
P-153
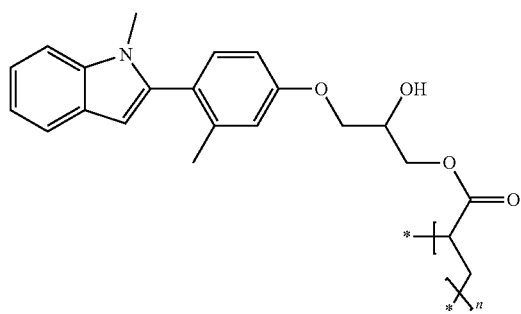
P-154
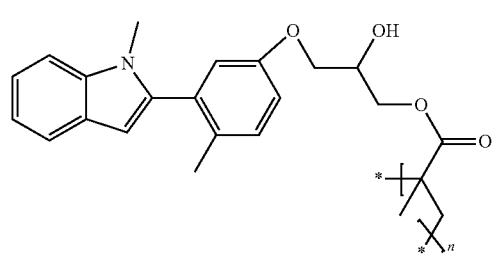
P-155
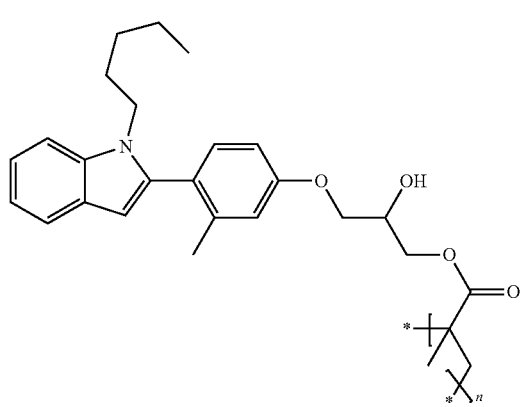

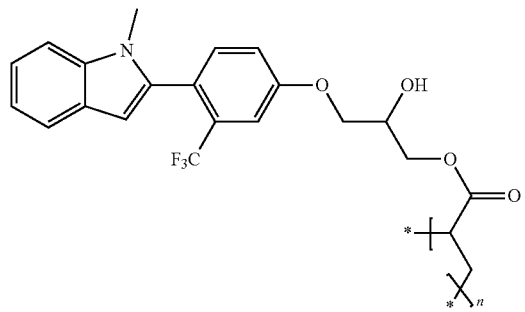

P-156

The letter n gives the degree of polymerization as explained before.

Preferably a co-polymer according to the invention as described before or preferably described before comprises the one or more constitutional units $M^0$ in a molar ratio m1 and the one or more constitutional units $M^2$ in a molar ratio m2, wherein the ratio m1:m2 is at least 0.01 and at most 100.

The oligomers or polymers according to the invention as described before or preferably described may be cross-linked.

The oligomers and polymers of the present invention may be made by any suitable method. It is, however, preferred that the present oligomers and polymers are made by radical polymerization, wherein the polymerization reaction is started by means of a suitable radical polymerization initiator. For the purposes of the present invention the type of radical polymerization initiator is not particularly limited and may be any suitable radical generating compound. Such compounds are well known to the skilled person. Suitable polymerization initiators may be selected from thermal initiators or photoinitiators, i.e. compounds that generate radicals by exposure to heat or irradiation with light of a suitable wavelength. Examples of suitable thermal polymerization initiators may be selected from the groups of compounds comprising one or more peroxide groups, i.e. compounds comprising a group —O—O—, and/or compounds comprising one or more azo groups, i.e. compounds comprising a group —N═N—.

Suitable polymerization initiators comprising one or more peroxide groups may, for example, be selected from the groups consisting of t-butyl(peroxy-2-ethyl-hexanoate), di-(tert-butylcyclohexyl)peroxydicarbonate and benzoylperoxide.

Suitable polymerization initiators comprising one or more azo groups may, for example, be selected from the group consisting of 1,1'-azobis(cyclohexancarbonitrile) and 2,2'azobis(cyclohexanecarbonitrile) (AIBN).

A suitable example of a photoinitiator is dimethylaminobenzoate/camphorquinone.

If a photoinitiator is used as polymerization initiator, it is preferred that the wavelength required to decompose said photoinitiator is different from the wavelength needed to irradiate the compound of the present application so as to change its optical properties.

Preferably, the radical initiators are used in an amount of at least 0.0001 eq and of at most 0.1 eq of the main monomer. Such radical initiators could be thermal initiators, e.g. azobisisobutyronitrile (AIBN) or photochemical initiators like dimethylaminobenzoate/camphorquinone.

The present invention is also directed to a composition comprising at least one compound of formula (I), (I'), (I'') or (I''') as described or preferably described before and/or an oligomer or polymer as described before or preferably described before.

A composition comprising at least one compound of formula (I), (I'), (I'') or (I''') as described or preferably described before and an oligomer or polymer as described before is primarily used for the synthesis of block co-polymers with the condition that the oligomer or polymer has at least one reactive group left which may react with the monomers.

Depending upon the intended use such composition may comprise further different components. Such further components may, for example, be selected from the group consisting of UV absorbers, antioxidants and cross-linkers.

The compositions may include or comprise, essentially consist of or consist of the said requisite or optional constituents. All compounds or components which can be used in the compositions are either known and commercially available or can by synthesized by known processes.

The UV absorber that may be used in the present composition is not particularly limited and can easily be selected from those generally known to the skilled person. Generally suitable UV absorbers are characterized by being unsaturated compounds, preferably compounds comprising one or more selected from group consisting of olefinic groups, aryl groups and heteroaryl groups; these groups may be present in any combination.

Suitable UV-absorbers for use in the present composition may, for example, be selected from those comprising a group selected from benzotriazole, benzophenone and triazine. Suitable UV-absorbers are, for example, disclosed in U.S. Pat. Nos. 5,290,892; 5,331,073 and 5,693,095. Suitable cross-linkers may be used to impart elastomeric properties to the present composition and the articles produced therewith. Typically any suitable di- or tri-functional monomer may be used as crosslinker. Such monomers are generally well known to the skilled person including at least one compound of formula (I''') as described before or preferably described before.

Preferred cross-linker may be selected from the following group of compounds

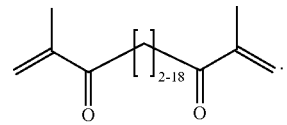

Ethylene glycol dimethacrylate (EGDMA) is particularly preferred.

Suitable antioxidants are phenyl acrylate derivatives bearing a hindered phenol moiety. A preferred antioxidant is

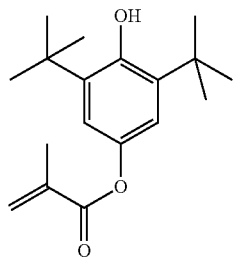 [SMILES: C=C(C)C(=O)Oc1cc(C(C)(C)C)c(O)c(C(C)(C)C)c1]

The compounds of formula (I) according to the invention and their oligomers or polymers as described before or preferably described before are particularly well suited for use in optically active devices.

Hence the present invention is also directed to articles e.g. blanks which may be transformed into optically active devices comprising at least one compound of formula (I) as described before or preferably described before or at least one oligomer or polymer as described before or preferably described before.

Preferred articles are blanks which may be transformed into optically active devices or the optically active devices as such. Preferred optically active devices are ophthalmic devices. Examples of such ophthalmic devices include lenses, keratoprostheses, and cornea inlays or rings. More preferably, said article is a blank which may be transformed into an eye-implant or the eye-implant as such. More preferably, said eye-implant is a lens. Most preferably, such article is a blank which may be transformed into an intraocular lens or the intraocular lens as such, which may, for example, be a posterior chamber intraocular lens or an anterior chamber intraocular lens.

A blank of this invention may be produced as a step in the manufacturing process used to create an intraocular lens. For example, without limitation, a manufacturing process may include the steps of polymer synthesis, polymer sheet casting, blank cutting, optic lathe cutting, optic milling, haptic milling or attachment, polishing, solvent extraction, sterilization and packaging.

The present articles according to the invention as described before or preferably described before may be formed by a process comprising the steps of
  providing a composition comprising at least one compound of formula (I) as defined herein and/or an oligomer or polymer as defined herein; and
  subsequently forming the article of said composition.

Intraocular lenses in accordance with the present invention are believed to show particularly advantageous properties in that they are flexible enough so as to be rolled or folded and consequently requiring a much smaller incision for them to be inserted into the eye. It is believed that this will allow for improved healing of the eye, particularly in respect to the time for the eye to heal.

The type of intraocular lens is not limited in any way. It may, for example, comprise one or more optic and one or more haptic components, wherein the one or more optic components serve as lens and the one or more haptic components are attached to the one or more optic components and hold the one or more optic components in place in the eye. The present intraocular lens may be of a one-piece design or of multi-piece design, depending on whether the one or more optic components and the one or more haptic components are formed from a single piece of material (one-piece design) or are made separately and then combined (multi-piece design). The present intraocular lens is also designed in such a way that it allows to be, for example, rolled up or folded small enough so that it fits through an incision in the eye, said incision being as small as possible, for example, at most 3 mm in length.

Additionally, intraocular lenses in accordance with the present invention allow for the non-invasive adjustment of the optical properties, particularly the refractive power, after implantation of the lens into the eye, thus reducing the need for post-surgery vision aids or reducing or totally avoiding follow-up surgery.

In order to change the optical properties and particularly the refractive power of the intraocular lens it is exposed to irradiation having a wavelength of at least 200 nm and of at most 1500 nm. Hence, the present invention is also directed to a process of changing the optical properties of an article as defined or preferably defined herein, said process comprising the steps of
  providing an article as defined herein; and
  subsequently exposing said article to irradiation having a wavelength of at least 200 nm and at most 1500 nm.

Preferably, said irradiation has a wavelength of at least 250 nm or 300 nm, more preferably of at least 350 nm, even more preferably of at least 400 nm, still even more preferably of at least 450 nm, and most preferably of at least 500 nm. Preferably, said irradiation has a wavelength of at most 1400 nm or 1300 nm or 1200 nm or 1100 nm or 1000 nm, more preferably of at most 950 nm or 900 nm, even more preferably of at most 850 nm, still even more preferably of at most 800 nm and most preferably of at most 750 nm.

EXAMPLES

The following examples are intended to show the advantages of the present compounds in a non-limiting way.

Unless indicated otherwise, all syntheses are carried out under an inert atmosphere using dried (i.e. water-free) solvents. Solvents and reagents are purchased from commercial suppliers.

DCM is used to denote dichloromethane. DMF is used to denote dimethylformamide. EE is used to denote ethyl acetate. THF is used to denote tetrahydrofuran.

Co-polymer-properties can be investigated on blanks, prepared by bulk polymerization of the monomers. Co-monomers, cross-linkers and initiators therefore can be purchased from commercial sources. All chemicals are of highest purity available and can be used as received.

Synthesis of Precursor Materials

Example 1—Bromo-(5-bromo-thiophen-2-yl)-acetic acid methyl ester

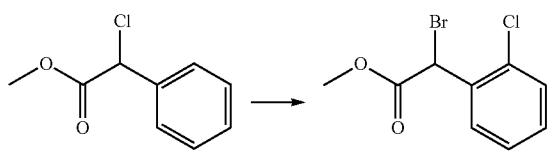

To a stirred solution of the Methyl 2-chlorophenylacetate (0.86 ml; 5.31 mmol) in dichloromethane (10.2 ml; 159 mmol) are added N-bromosuccinimide (1.04 g; 5.84 mmol)

and azobisisobutyronitrile (43.6 mg; 0.27 mmol) at room temperature and the mixture is stirred at 100° C. for 16 h under argon atmosphere. The reaction mixture is cooled down to room temperature. The mixture is diluted with diethyl ether and filtered. The filtrate is evaporated to dryness. The oily residue containing solid succinimid is diluted with heptane and filtered again. The solvent is removed to afford Bromo-(2-chloro-phenyl)-acetic acid methyl ester (1.38 g; 4.56 mmol; 86% of theory).

1H NMR (500 MHz, Chloroform-d) δ 7.69 (dd, J=7.6, 1.8 Hz, 1H), 7.31 (dd, J=7.6, 1.7 Hz, 1H), 7.24 (td, J=7.6, 1.7 Hz, 1H), 7.21 (dd, J=7.5, 1.8 Hz, 1H), 5.84 (s, 1H), 3.74 (s, 3H).

Analogously, other derivatives are prepared in the same manner:

| No. | Reactant 1 | Product | Yield |
|---|---|---|---|
| 1a | CAS: 41841-16-1 | | 75% |
| 1b | CAS: 1805558-53-5 | | 53% |
| 1c | CAS: 95299-14-2 | | 52% |
| 1d | CAS: 1227090-87-0 | | 45% |
| 1e | CAS: 67137-56-8 | | 74% |

Example 2—6-Methoxy-2-phenyl-benzofuran

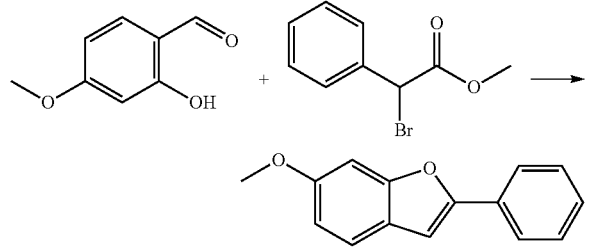

2-Hydroxy-4-methoxybenzaldehyde (1.52 g; 9.99 mmol) and α-bromophenylacetatic acid methyl ester (1.72 ml; 11.0 mmol) are dissolved in dimethylformamide (50.5 ml; 649 mmol). To the solution is added potassium carbonate (6.90 g; 49.9 mmol). The mixture is stirred at 100° C. for 2 h. The mixture is cooled to 25° C. and portioned to ethyl acetate and HCl (1 N, aq.). The organic layer is separated, washed with brine and dried over $MgSO_4$. Evaporation of solvent gave brownish oily residue. The residue is dissolved in ethanol (40.9 ml; 699 mmol). To the solution is added potassium hydroxide (5.04 g; 89.9 mmol). The mixture is refluxed for 2 h. The mixture is cooled to ambient temperature and acidified with HCl (conc.). The precipitating solid is filtered off and recrystallized from toluene to give 6-methoxy-2-phenyl-benzofuran (1.07 g; 4.78 mmol; 48% of theory).

1H NMR (500 MHz, DMSO-d6) δ 7.86 (d, J=8.4 Hz, 2H), 7.53 (d, J=8.5 Hz, 1H), 7.49 (t, J=7.8 Hz, 2H), 7.38 (t, J=7.4 Hz, 1H), 7.26 (d, J=1.9 Hz, 1H), 6.91 (dd, J=8.5, 2.2 Hz, 1H), 3.84 (s, 3H).

Analogously, other derivatives are prepared in the same manner: R1 means reactant 1, R2 means reactant 2, [P] means product

| No. | | | Yield [%] |
|---|---|---|---|
| | [P] | (structure) | 42 |
| 2f | R1 | (structure) | |
| | R2 | (structure) | |
| | [P] | (structure) | 56 |
| 2g | R1 | (structure) | |
| | R2 | (structure) | |
| | [P] | (structure) | 30 |
| 2h | R1 | (structure) | |
| | R2 | (structure) | |
| | [P] | (structure) | 39 |

| No. | | | Yield [%] |
|---|---|---|---|
| 2i | R1 | (structure) | |
| | R2 | (structure) | |
| | [P] | (structure) | 25 |

2-(2-Chloro-phenyl)-6-methoxy-benzofuran

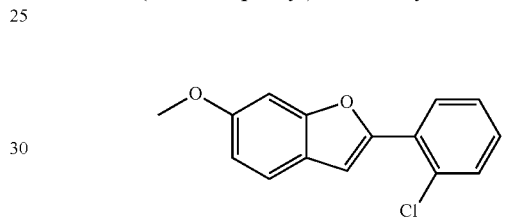

1H NMR (500 MHz, Chloroform-d) δ 8.04 (dd, J=7.9, 1.8 Hz, 1H), 7.54-7.46 (m, 3H), 7.39 (t, J=7.7 Hz, 1H), 7.27 (t, J=7.2 Hz, 1H), 7.10 (d, J=2.4 Hz, 1H), 6.92 (d, J=8.5 Hz, 1H), 3.91 (d, J=1.4 Hz, 3H).

2-(4-Bromo-phenyl)-6-methoxy-benzo[b]thiophene

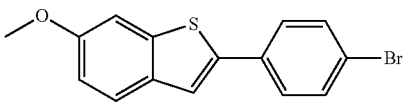 [SMILES: COc1ccc2cc(-c3ccc(Br)cc3)sc2c1]

1H NMR (500 MHz, Chloroform-d) δ 7.67 (d, J=8.8 Hz, 1H), 7.55-7.52 (m, 4H), 7.46-7.43 (m, 1H), 7.32-7.30 (m, 1H), 7.01 (d, J=8.6 Hz, 1H), 3.91 (s, 3H).

Example 3—6-Methoxy-2-(4-pentyl-phenyl)-benzofuran

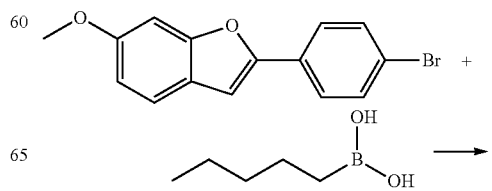

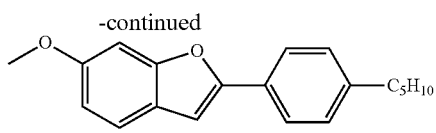

2-(4-Bromo-phenyl)-6-methoxy-benzofuran (550 mg; 1.81 mmol), pentylboronic acid (463 mg; 3.99 mmol) and tripotassium phosphate monohydrate (1.75 g; 7.62 mmol) are dissolved in toluene (19.2 ml; 181 mmol). Then 2-dicyclohexylphosphino-2',6'-dimethoxybiphenyl [SPhos](149 mg; 359 μmol) and palladium(II) acetate (40.7 mg; 180 μmol) are added and the reaction mixture is heated to 120° C. for 1 d. The cooled reaction mixture is diluted with ethyl acetate and HCl solution (2 M). The solution is transferred to a separatory funnel. The organic phase is extracted with HCl solution (2 M) and water and brine. The organic phase is dried over MgSO$_4$, filtered and concentrated under reduced pressure. The residue is purified by silica gel column chromatography (heptane/ethyl acetate, 5/1) to yield 6-Methoxy-2-(4-pentyl-phenyl)-benzofuran (512 mg; 1.7 mmol; 96% of theory).

1H NMR (500 MHz, Chloroform-d) δ 7.65 (d, J=8.2 Hz, 2H), 7.35 (d, J=8.5 Hz, 1H), 7.17 (d, J=8.1 Hz, 2H), 6.99 (d, J=2.1 Hz, 1H), 6.82 (s, 1H), 6.79 (dd, J=8.5, 2.3 Hz, 1H), 3.80 (s, 3H), 2.59-2.54 (m, 2H), 1.58 (p, J=7.5 Hz, 2H), 1.32-1.24 (m, 4H), 0.83 (t, J=6.9 Hz, 3H).

Analogously, other derivatives are prepared in the same manner: R1 means reactant 1, R2 means reactant 2, [P] means product

| No. | | | Yield |
|---|---|---|---|
| 3a | R1 | (6-methoxybenzofuran-2-yl)(2-chlorophenyl) structure | |
| | R2 | ethylboronic acid | |
| | [P] | (6-methoxybenzofuran-2-yl)(2-ethylphenyl) structure | 42% |
| 3b | R1 | (6-mercaptobenzofuran-2-yl)(4-bromophenyl) structure | |
| | R2 | pentylboronic acid | |
| | [P] | (6-mercaptobenzofuran-2-yl)(4-pentylphenyl) structure | 90% |
| 3c | R1 | (6-methoxybenzothiophen-2-yl)(4-bromophenyl) structure | |
| | R2 | ethylboronic acid | |
| | [P] | (6-methoxybenzothiophen-2-yl)(4-ethylphenyl) structure | 76% |

-continued
| No. | | | Yield |
|---|---|---|---|
| 3d | R1 | 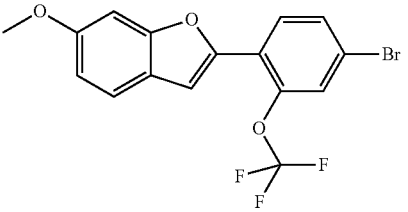 [SMILES: COc1ccc2cc(-c3ccc(Br)cc3OC(F)(F)F)oc2c1] | |
| | R2 | 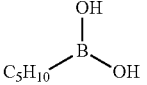 | |
| | [P] | 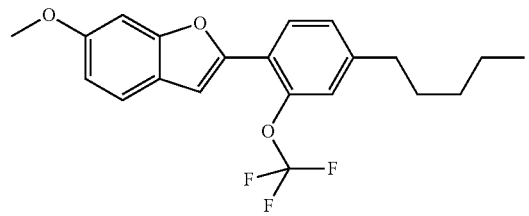 [SMILES: CCCCCc1ccc(-c2cc3ccc(OC)cc3o2)c(OC(F)(F)F)c1] | 95% |
| 3e | R1 | 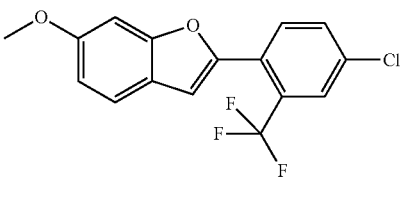 [SMILES: COc1ccc2cc(-c3ccc(Cl)cc3C(F)(F)F)oc2c1] | |
| | R2 | 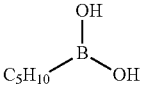 | |
| | [P] | 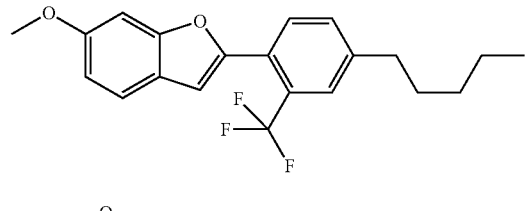 | 75% |
| 3f | R1 | 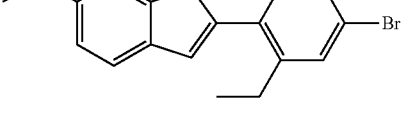 | |
| | R2 | 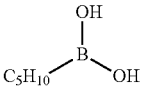 | |
| | [P] | 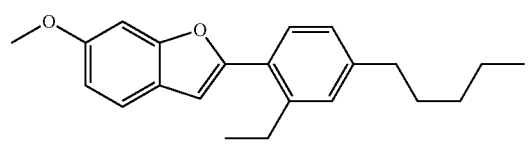 [SMILES: CCCCCc1ccc(-c2cc3ccc(OC)cc3o2)c(CC)c1] | 72% |
| 3g | R1 | 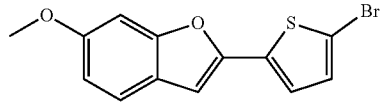 [SMILES: COc1ccc2cc(-c3ccc(Br)s3)oc2c1] | |

| No. | | Yield |
|---|---|---|
| | R2 attached to C5H10-B(OH)2 reagent | |
| [P] | 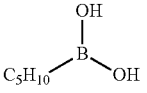 | 86% |

2-(2-Ethyl-phenyl)-6-methoxy-benzofuran

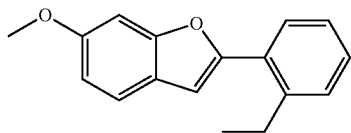 [SMILES: CCc1ccccc1-c1cc2ccc(OC)cc2o1]

1H NMR (500 MHz, Chloroform-d) δ 7.75 (d, J=7.5 Hz, 1H), 7.50 (d, J=8.5 Hz, 1H), 7.36 (d, J=3.8 Hz, 2H), 7.32 (dq, J=8.7, 3.8 Hz, 1H), 7.10 (d, J=1.9 Hz, 1H), 6.92 (dd, J=8.5, 2.2 Hz, 1H), 6.82 (s, 1H), 3.91 (s, 3H), 2.95 (q, J=7.5 Hz, 2H), 1.32 (t, J=7.5 Hz, 3H).

2-(4-Ethyl-phenyl)-6-methoxy-benzo[b]thiophene

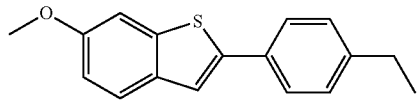

¹H NMR (500 MHz, Chloroform-d) δ 7.66 (d, J=8.7 Hz, 1H), 7.62 (d, J=8.1 Hz, 2H), 7.44 (s, 1H), 7.33 (d, J=2.2 Hz, 1H), 7.27 (d, J=8.0 Hz, 2H), 7.00 (dd, J=8.7, 2.3 Hz, 1H), 3.91 (s, 3H), 2.71 (q, J=7.6 Hz, 2H), 1.30 (t, J=7.6 Hz, 3H).

Example 4—2-Phenyl-benzofuran-6-ol

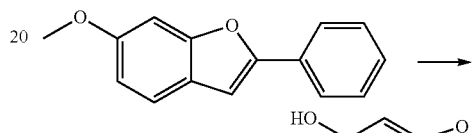

6-Methoxy-2-phenyl-benzofuran (1.07 g; 4.8 mmol) is dissolved in dichloromethane (15 ml) and cooled to 5° C. Boron tribromide (454 μl; 4.8 mmol) is added dropwise to this solution, and stirring is continued overnight. Water is subsequently slowly added to the mixture, and the organic phase is diluted with ethyl acetate, washed three times with water, dried over MgSO₄, evaporated under reduced pressure and filtered through a pad of silica gel with dichloromethane to yield 2-phenyl-benzofuran-6-ol (600 mg; 2.9 mmol; 60% of theory).

1H NMR (500 MHz, DMSO-d6) δ 9.59 (s, 1H), 7.84 (d, J=8.4 Hz, 2H), 7.47 (t, J=7.8 Hz, 2H), 7.43 (d, J=8.4 Hz, 1H), 7.35 (t, J=7.4 Hz, 1H), 7.28 (s, 1H), 6.76 (dd, J=8.4, 2.1 Hz, 1H).

Analogously, other derivatives are prepared in the same manner:

| No. | Reactant 1 | Product | Yield |
|---|---|---|---|
| 4a | 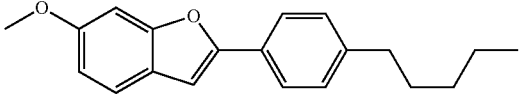 [SMILES: CCCCCc1ccc(-c2cc3ccc(OC)cc3o2)cc1] | 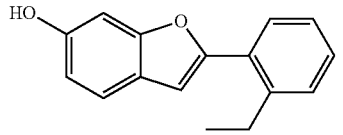 | 86% |
| 4b | 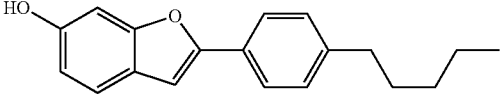 | 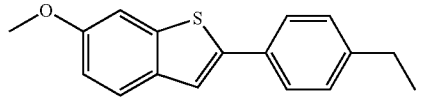 | 99% |
| 4c | 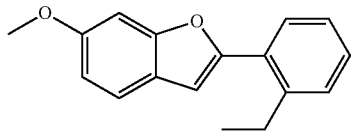 [SMILES: CCc1ccccc1-c1cc2ccc(OC)cc2o1] | 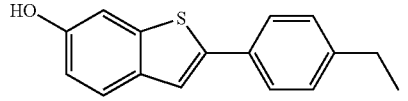 [SMILES: CCc1ccc(-c2cc3ccc(O)cc3s2)cc1] | 88% |

-continued

| No. | Reactant 1 | Product | Yield |
|---|---|---|---|
| 4d | | | 77% |
| 4e | | | 67% |
| 4f | | | 80% |
| 4g | | | 73% |

Example 5—6-[((E)-Octa-4,7-dienyl)oxy]-2-phenyl-benzofuran

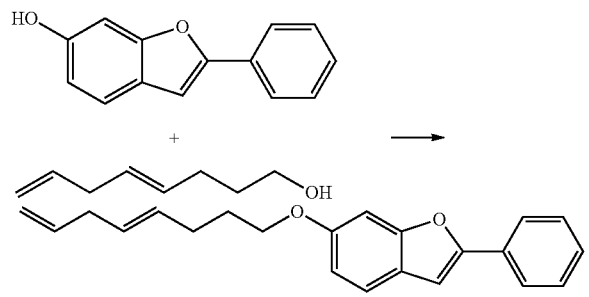

To an ice-cooled solution of 2-phenyl-benzofuran-6-ol (7.70 g; 36.6 mmol), (4E)-octa-4,7-dien-1-ol (4.85 g; 38.5 mmol), triphenylphosphine (12.6 g; 47.6 mmol) in tetrahydrofuran (61.4 ml; 758 mmol), diisopropyl azodicarboxylate (9.57 ml; 47.6 mmol) is added dropwise under argon atmosphere. After stirring at room temperature over night, a further portion of reagents is added. After further 2 h, the reaction mixture is evaporated to put the crude product on silica gel. Column chromatography (ethyl acetate/heptane, 1/5) gave 6-[((E)-octa-4,7-dienyl)oxy]-2-phenyl-benzofuran (8.30 g; 26.1 mmol; 71% of theory). For further purification, the product is recrystallized in ethanol.

Analogously, other derivatives are prepared in the same manner: R1 means reactant 1, R2 means reactant 2 and [P] means product

| No. | | | Yield |
|---|---|---|---|
| 5a | R1 | | |
| | R2 | , CAS: 16652-26-9 | |

| No. | | Yield |
|---|---|---|
| | [P] 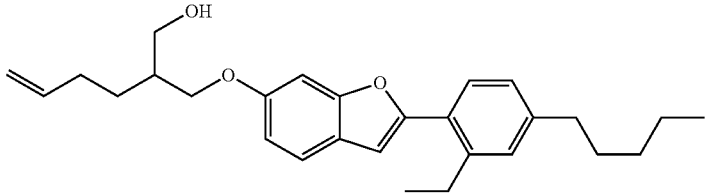 [SMILES: C=CCCC(CO)COc1ccc2cc(-c3ccc(CCCCC)cc3CC)oc2c1] | 35% |
| 5b | R1 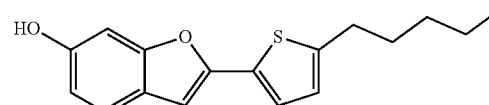 | |
| | R2 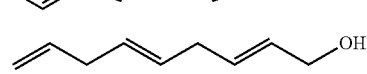<br>CAS: 83413-33-6 | |
| | [P] 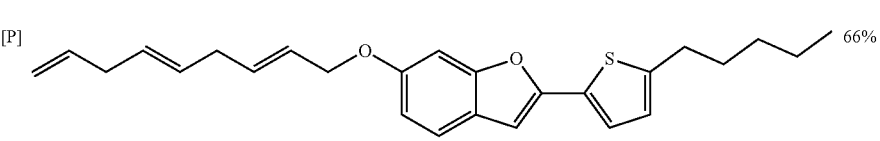 | 66% |
| 5c | R1 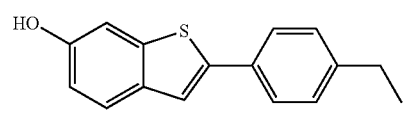 | |
| | R2 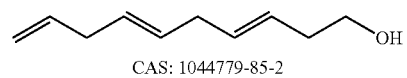<br>CAS: 1044779-85-2 | |
| | [P] 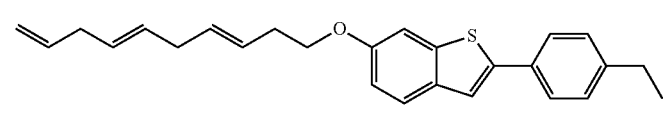 [SMILES: C=CC/C=C/C/C=C/CCOc1ccc2cc(-c3ccc(CC)cc3)sc2c1] | 78% |
| 5d | R1 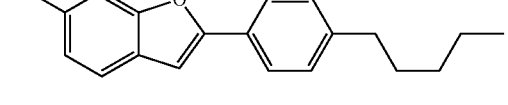 | |
| | R2 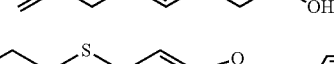 | |
| | [P] 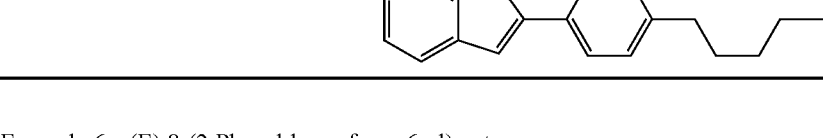 | 73% |

Example 6—(E)-8-(2-Phenyl-benzofuran-6-yl)-oct-4-en-1-ol

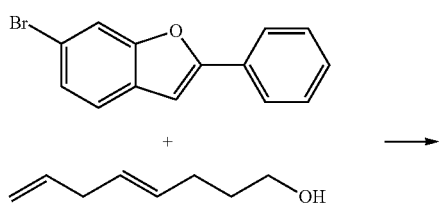

→

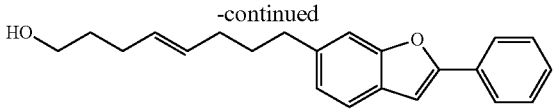

A solution of (E)-octa-4,7-dien-1-ol (2.77 ml; 18.3 mmol) in tetrahydrofuran (34.1 ml; 421 mmol) under argon at room temperature is treated dropwise with 9-borabicyclo[3.3.1]nonane (0.5 M in THF) (43.9 ml; 22.0 mmol). The reaction is then heated 30 min at 90° C. The resulting solution is then transferred into a stirred mixture of 6-bromo-2-phenyl-benzofuran (5.00 g; 18.3 mmol) and tripotassium phosphate monohydrate (4.64 g; 20.1 mmol) in dimethylformamide (34.2 ml; 439 mmol) and water (6.93 ml; 384 mmol) under argon. Tetrakis(triphenylphosphine)palladium(0) (1.06 g;

915 µmol) is added and the reaction mixture is heated to 80° C. for 12 h. The cooled reaction mixture is concentrated in vacuo, diluted with dichloromethane and aqueous ammonia solution. The organic phase is separated, washed with brine, dried over MgSO$_4$ and concentrated in vacuo. Chromatography on silica gel (heptane/ethyl acetate, 5/1) yields (E)-8-(2-phenyl-benzofuran-6-yl)-oct-4-en-1-ol (3.34 g; 10.4 mmol; 57% of theory).

Analogously, other derivatives are prepared in the same manner: R1 means reactant 1, R2 means reactant 2 and [P] means product

| No. | | Yield |
|---|---|---|
| 6a | R 1 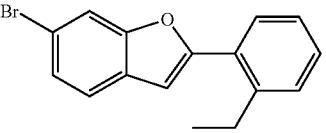 R 2 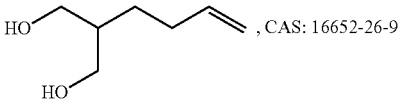, CAS: 16652-26-9 [P] 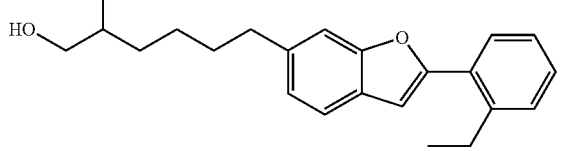 | 47% |

Example 7—(E)-8-(2-Phenyl-benzofuran-6-yloxy)-oct-4-en-1-ol

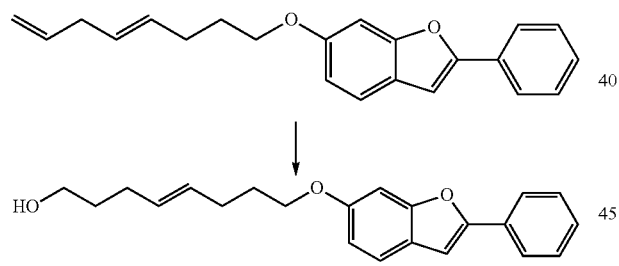

A Schlenk flask is charged with tetrahydrofuran (60.1 ml; 741 mmol) and 6-[((E)-octa-4,7-dienyl)oxy]-2-phenyl-benzofuran (10.0 g; 31.4 mmol) and the solution is cooled to 0° C. After 10 min, 9-borabicyclo[3.3.1]nonane (0.5 M in THF) (62.8 ml; 31.4 mmol) is added dropwise via syringe over 30 min. The reaction is stirred for 1 h at 0° C. and then 1 h at 25° C. Sodium hydroxide solution (2 M) (45.1 ml; 90.1 mmol) is added, the reaction cooled to 0° C. Then hydrogen peroxide (30%) (26.3 ml; 258 mmol) is added dropwise over the course of 10 min. The reaction is then stirred for 30 min, diluted with diethyl ether (10 ml) and filtered through celite. The filtrate is neutralized, extracted with diethyl ether, washed with brine, dried (MgSO$_4$) and concentrated. Column chromatography on silica gel (heptane/EE, gradient) yields (E)-8-(2-phenyl-benzofuran-6-yloxy)-oct-4-en-1-ol (4.12 g; 12.2 mmol; 39% of theory).

Analogously, other derivatives are prepared in the same manner: R1 means reactant 1 and [P] means product

| No. | | Yield |
|---|---|---|
| 7a | R1 — [structure: octadienyl-O-benzofuran-thiophene-pentyl] | |
| | [P] HO—[structure: hydroxyoctadienyl-O-benzofuran-thiophene-pentyl] | 51% |
| 7b | R1 — [structure: octadienyl-O-benzothiophene-ethylphenyl] | |
| | [P] HO—[structure: hydroxyoctadienyl-O-benzothiophene-ethylphenyl] | 62% |
| 7c | R1 — [structure: TBS-protected ether with benzofuran-pentylethylphenyl] | |
| | [P] HO—[structure: TBS-protected alcohol with benzofuran-pentylethylphenyl] | 56% |
| 7d | R1 — [structure: heptenyl-S-benzofuran-pentylphenyl] | |
| | [P] HO—[structure: hydroxyheptenyl-S-benzofuran-pentylphenyl] | 49% |

Example 8—tert-Butyl-dimethyl-[(E)-8-(2-phenyl-benzofuran-6-yloxy)-oct-4-enyloxy]-silane

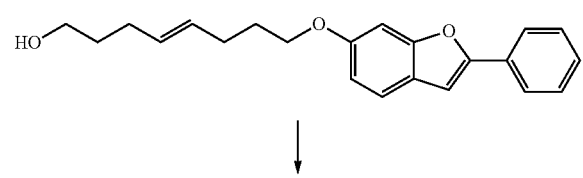

↓

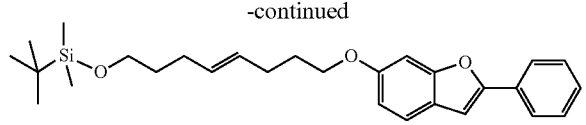

(E)-8-(2-Phenyl-benzofuran-6-yloxy)-oct-4-en-1-ol (3.00 g; 8.9 mmol), imidazole (1.21 g; 17.8 mmol) and dichloromethane (57.0 ml; 892 mmol) are combined under an argon atmosphere. tert-Butyldimethylsilyl chloride (1.48 g; 9.8 mmol) is dissolved in dichloromethane (28.5 ml; 446 mmol) and then added dropwise over 5 min to the reaction mixture, maintaining the temperature below 30° C. The reaction mixture is stirred over night at room temperature. The precipitated solid is filtered off and the filtrate is washed with water and brine. The organic phase is separated and dried with Na$_2$SO$_4$. The solvent is removed under reduced pressure yielding tert-butyl-dimethyl-[(E)-8-(2-phenyl-benzofuran-6-yloxy)-oct-4-enyloxy]-silane (2.97 g; 6.6 mmol; 74% of theory).

Analogously, other derivatives are prepared in the same manner: R means reactant and [P] means product

| No. | | | Yield |
|---|---|---|---|
| 8a | R | | |
| | [P] | | 81% |
| 8b | R | | |
| | [P] | | 95% |
| 8c | R | | |
| | [P] | | 89% |
| 8d | R | | |
| | [P] | | 67% |
| 8e | R | | |

| No. | | Yield |
|---|---|---|
| [P] | | 78% |

Example 9—1-(tert-Butyl-dimethyl-silanyloxy)-8-(2-phenyl-benzofuran-6-yloxy)-octane-4,5-diol

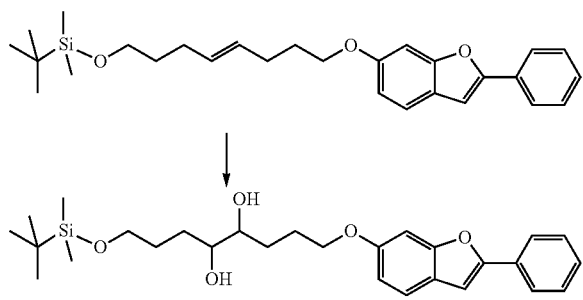

tert-Butyl-dimethyl-[(E)-8-(2-phenyl-benzofuran-6-yloxy)-oct-4-enyloxy]-silane (2.91 g; 6.5 mmol) is dissolved in a mixture of acetone (54.6 ml; 743 mmol) and water (5.82 ml; 323 mmol). The mixture is cooled to 0° C. To the colorless solution is added osmium tetroxide [aq., 4 wt %] (205 µl; 32.3 µmol), followed by N-methylmorpholine N-oxide [aq., 50%] (1.39 ml; 6.8 mmol) at room temperature. The reaction mixture is stirred over night. Then $Na_2SO_3$-solution is added and the mixture is stirred for 10 min to reduce osmium-species. The resulting aqueous solution is extracted with ethyl acetate and n-butanol. The organic phase is separated, dried with $Na_2SO_4$ and concentrated to yield 1-(tert-butyl-dimethyl-silanyloxy)-8-(2-phenyl-benzofuran-6-yloxy)-octane-4,5-diol (3.04 g; 6.3 mmol; 97% of theory).

Analogously, other derivatives are prepared in the same manner: R means reactant and [P] means product

| No. | | | Yield |
|---|---|---|---|
| 9a | R | | |
| | [P] | | 37% |
| 9b | R | | |
| | [P] | | 44% |
| 9c | R | | |

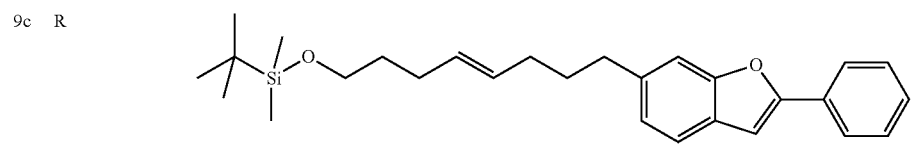

| No. | | Yield |
|---|---|---|
| [P] | (structure: tBuMe2Si-O-CH2CH2CH2-CH(OH)-CH(OH)-CH2CH2-benzofuran-2-phenyl) | 74% |
| 9d R | (structure: tBuMe2Si-O-(CH2)3-CH=CH-(CH2)2-S-benzofuran-2-(4-pentylphenyl)) | |
| [P] | (structure: tBuMe2Si-O-CH2CH2CH2-CH(OH)-CH(OH)-CH2CH2-S-benzofuran-2-(4-pentylphenyl)) | 83% |

Example 10—3-{2,2-Dimethyl-5-[3-(2-phenyl-benzofuran-6-yloxy)-propyl-]1,3]dioxolan-4-yl}-propan-1-ol

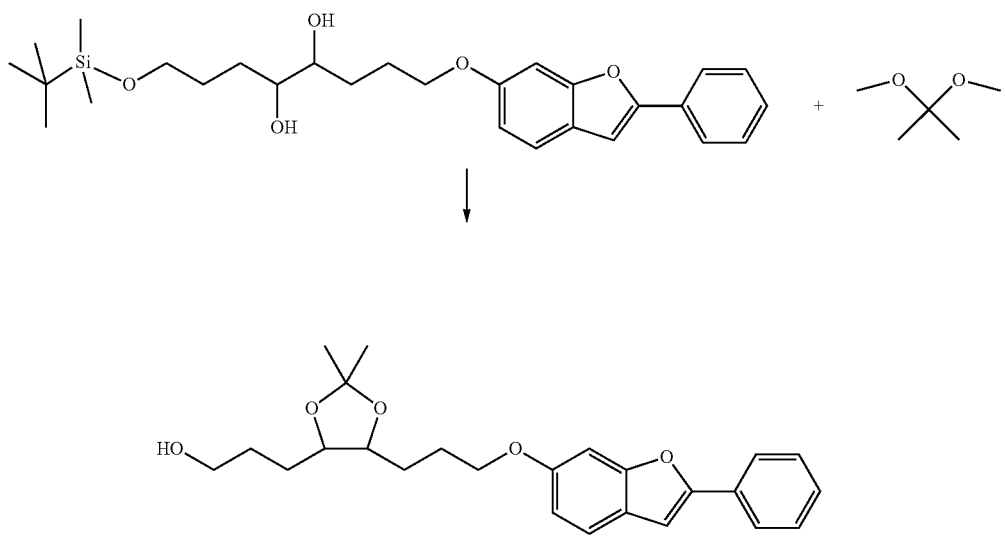

To a solution of 1-(tert-butyl-dimethyl-silanyloxy)-8-(2-phenyl-benzofuran-6-yloxy)-octane-4,5-diol (3.02 g; 6.2 mmol) in acetone (22.9 ml; 312 mmol) at room temperature are added 2,2-dimethoxypropane (850 μl; 6.9 mmol) and p-toluenesulfonic acid monohydrate (4.79 mg; 24.9 μmol) and the resulting mixture is stirred for 3 d. Potassium carbonate (60.3 mg; 436 μmol) is then added and stirring is continued for a further 30 min. The mixture is then concentrated and poured into saturated aqueous NaHCO$_3$ solution, and extracted with diethyl ether. The organic phase is washed with brine, dried with Na$_2$SO$_4$, and concentrated in vacuo. The residue is chromatographed on silica gel (hexane/ethyl acetate, 5/1), to yield 3-{2,2-dimethyl-5-[3-(2-phenyl-benzofuran-6-yloxy)-propyl]-[1,3]dioxolan-4-yl}-propan-1-ol (1.23 g; 3.0 mmol; 48% of theory)

Analogously, other derivatives are prepared in the same manner: R means reactant, [P] means product
| No. | | Yield |
|---|---|---|
| 10a | R 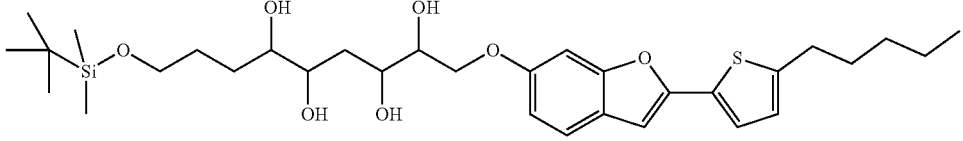 | |
| | [P] 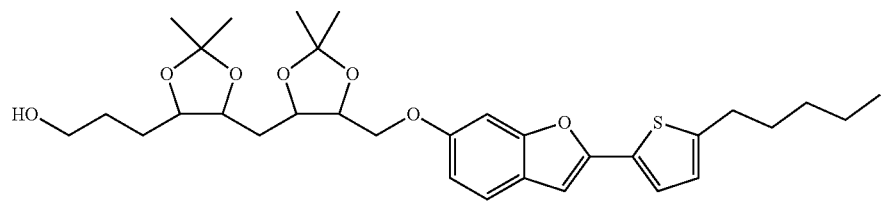 | 39% |
| 10b | R 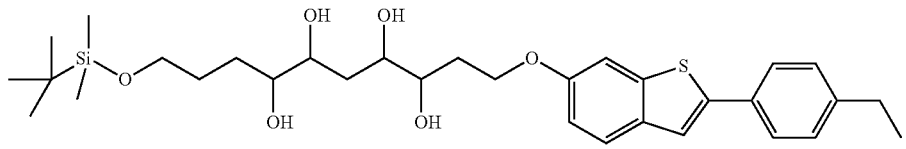 | |
| | [P] 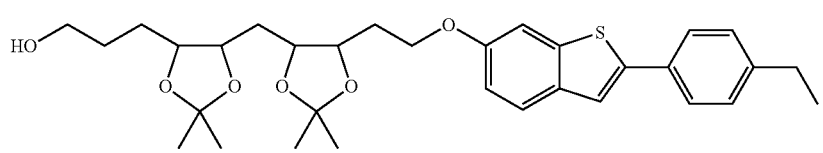 | 48% |
| 10c | R 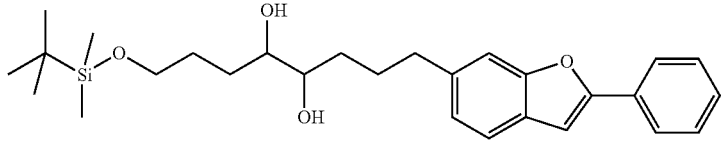 | |
| | [P] 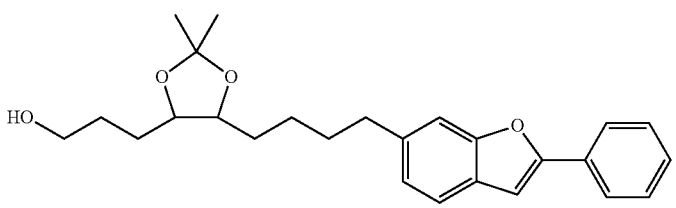 | 59% |
| 10d | R 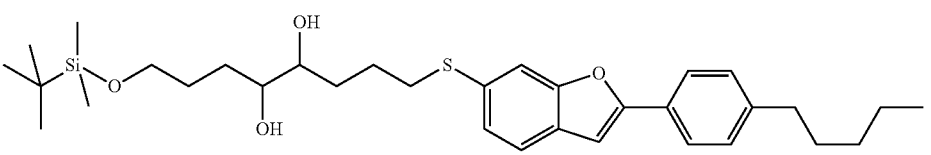 | |
| | [P] 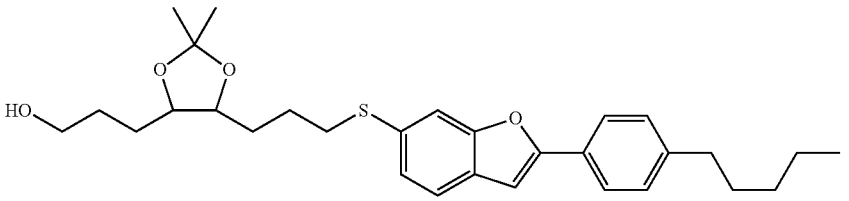 | 60% |

Preparation of compounds according to the invention wherein some hydroxyl groups may still be protected by protecting groups. Once the protecting groups are removed, the below described compounds are compounds according to the invention.

Example 11—2-Methyl-acrylic acid 3-{2,2-dimethyl-5-[3-(2-phenyl-benzofuran-6-yloxy)-propyl]-[1,3]dioxolan-4-yl}-propyl ester

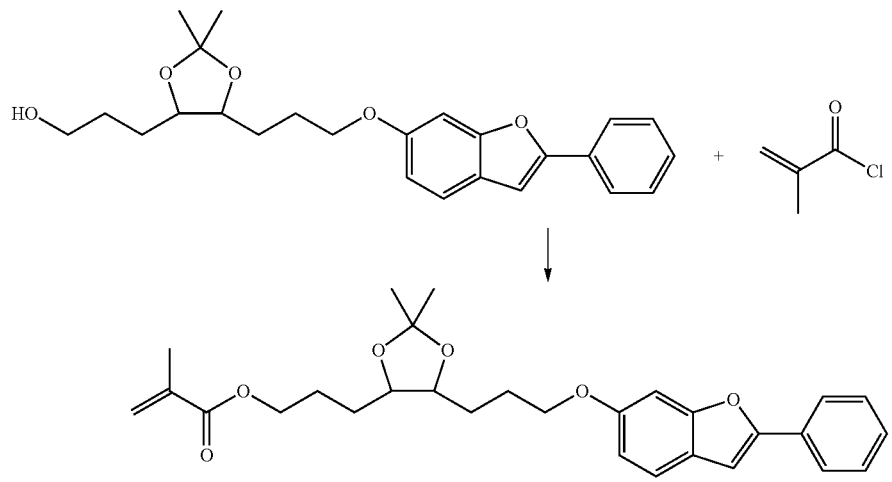

Methacryloyl chloride (486 µl; 4.8 mmol) is slowly added to an ice-cooled solution of 3-{2,2-dimethyl-5-[3-(2-phenyl-benzofuran-6-yloxy)-propyl]-[1,3]dioxolan-4-yl}-propan-1-ol (1.14 g; 2.8 mmol) in tetrahydrofuran (22.4 ml; 277 mmol) and triethylamine (2.32 ml; 16.6 mmol). Then the reaction is left to stir for 1 d at room temperature. The reaction mixture is filtered and evaporated to dryness. The residue is filtered through a short column (SiO$_2$, heptane/ethyl acetate, 2/1). The product fraction is evaporated to dryness yielding acrylic acid 4,5-dihydroxy-8-(2-phenyl-benzofuran-6-yloxy)-octyl ester (1.05 g; 2.2 mmol; 79% of theory).

Analogously, other derivatives are prepared in the same manner: R1 means reactant 1, R2 means reactant 2, [P] means product -continued

| No. | | | Yield |
|---|---|---|---|
| | [P] | (structure: methacrylate ester with hydroxymethyl branch, linked via ether to benzofuran–phenyl with ethyl and pentyl substituents) | 80% |
| 11b | R1 | (structure: HO-propyl-bis(dioxolane)-CH2-O-benzofuran-thiophene-pentyl) | |
| | R2 | methacryloyl chloride | |
| | [P] | (structure: methacrylate ester-propyl-bis(dioxolane)-CH2-O-benzofuran-thiophene-pentyl) | 84% |
| 11c | R1 | (structure: HO-propyl-bis(dioxolane)-CH2CH2-O-benzothiophene-phenyl-ethyl) | |
| | R2 | methacryloyl chloride | |
| | [P] | (structure: methacrylate ester-propyl-bis(dioxolane)-CH2CH2-O-benzothiophene-phenyl-ethyl) | 73% |
| 11d | R1 | 2-(but-3-en-1-yl)propane-1,3-diol (CAS: 16652-26-9) | |
| | R2 | methacryloyl chloride | |

-continued

| No. | | | Yield |
|---|---|---|---|
| | [P] | (structure: methacrylate ester with pendant hydroxymethyl and allyl group) | 28% |
| 11e | R1 | (structure: HO-propyl-dioxolane(dimethyl)-butyl-6-(2-phenylbenzofuran)) | |
| | R2 | methacryloyl chloride | |
| | [P] | (structure: methacrylate ester of R1 alcohol, dioxolane-linked to 2-phenylbenzofuran) | 86% |
| 11f | R1 | (diol: HOCH2-CH(CH2OH)-butyl-6-(2-phenylbenzofuran)) | |
| | R2 | methacryloyl chloride | |
| | [P] | (mono-methacrylate of 11f diol) | 23% |
| 11g | R1 | (diol: HOCH2-CH(CH2OH)-butyl-6-[2-(2-ethylphenyl)benzofuran]) | |
| | R2 | methacryloyl chloride | |

-continued

| No. | | | Yield |
|---|---|---|---|
| | [P] | (structure: methacrylate-CH2-CH(CH2OH)-(CH2)3-benzofuran-phenyl-ethyl) | 37% |
| 11h | R1 | (structure: HO-(CH2)3-dioxolane-(CH2)3-S-benzofuran-2-(4-pentylphenyl)) | |
| | R2 | methacryloyl chloride | |
| | [P] | (structure: methacrylate-(CH2)3-dioxolane-(CH2)3-S-benzofuran-2-(4-pentylphenyl)) | 84% |

Example 12—Acrylic acid 4,5-dihydroxy-8-(2-phenyl-benzofuran-6-yloxy)-octyl ester

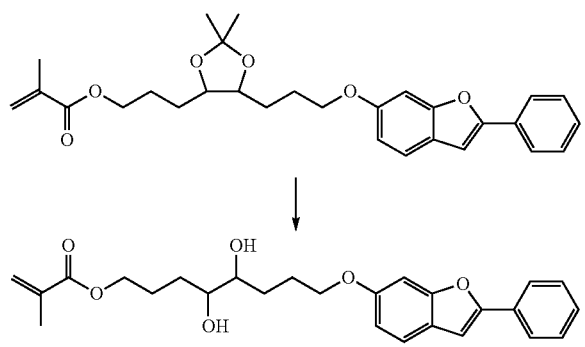

2-Methyl-acrylic acid 3-{2,2-dimethyl-5-[3-(2-phenyl-benzofuran-6-yloxy)-propyl]-[1,3]dioxolan-4-yl}-propyl ester (200 mg; 406 μmol) and p-toluenesulfonic acid monohydrate (54.6 mg; 284 μmol) are dissolved in methanol (5.43 ml; 134 mmol), and the solution is stirred for 18 h at room temperature. After consumption of the substrate, the reaction mixture is diluted with diethyl ether. The organic phase is washed with brine and dried with MgSO$_4$. After filtration, the solvent is removed in vacuo and the residue is purified by column chromatography (silica gel, heptane/ethyl acetate [1/2]) yielding acrylic acid 4,5-dihydroxy-8-(2-phenyl-benzofuran-6-yloxy)-octyl ester (69% of theory).

Analogously, other derivatives are prepared in the same manner: R means reactant [P] means product

| No. | | | Yield |
|---|---|---|---|
| 12a | R | (structure: methacrylate-(CH2)3-bis-dioxolane-CH2-O-benzofuran-2-(5-pentylthiophene)) | |

-continued
| No. | | | Yield |
|---|---|---|---|
| | [P] | 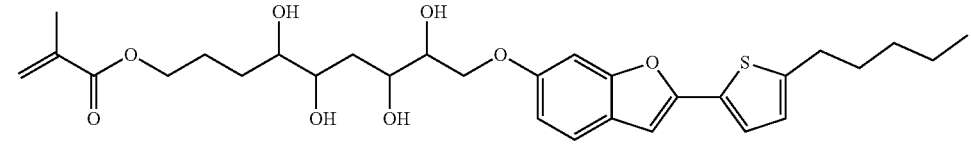 [SMILES: C=C(C)C(=O)OCCCC(O)C(O)CC(O)C(O)COc1ccc2cc(-c3ccc(CCCCC)s3)oc2c1] | 75% |
| 12b | R | 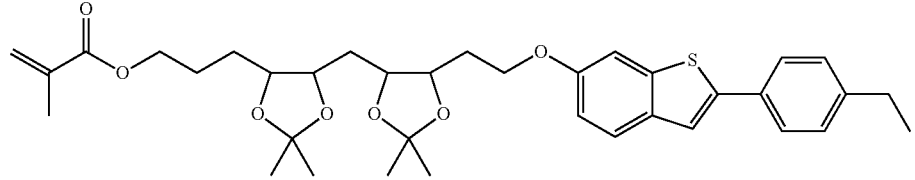 [SMILES: C=C(C)C(=O)OCCCC1OC(C)(C)OC1CC1OC(C)(C)OC1CCOc1ccc2cc(-c3ccc(CC)cc3)sc2c1] | |
| | [P] | 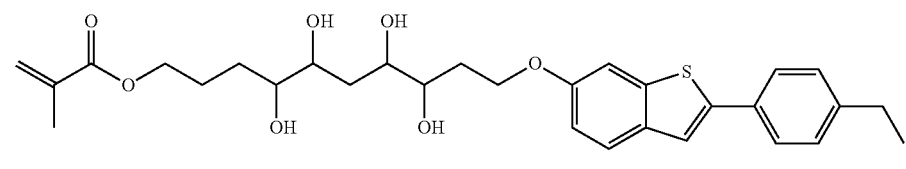 [SMILES: C=C(C)C(=O)OCCCC(O)C(O)CC(O)C(O)CCOc1ccc2cc(-c3ccc(CC)cc3)sc2c1] | 82% |
| 12c | R | 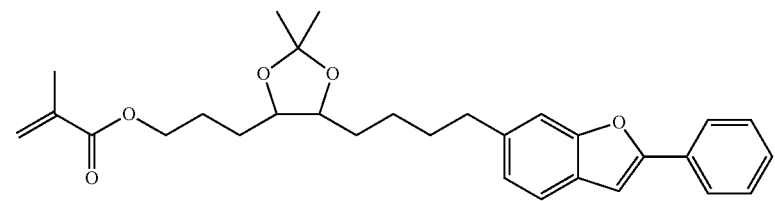 [SMILES: C=C(C)C(=O)OCCCC1OC(C)(C)OC1CCCCc1ccc2cc(-c3ccccc3)oc2c1] | |
| | [P] | 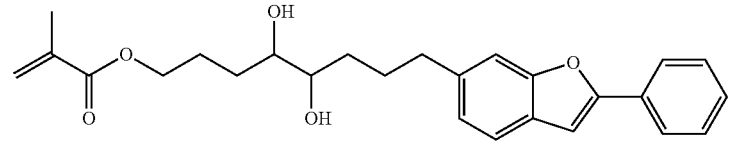 [SMILES: C=C(C)C(=O)OCCCC(O)C(O)CCCc1ccc2cc(-c3ccccc3)oc2c1] | 79% |
| 12d | R | 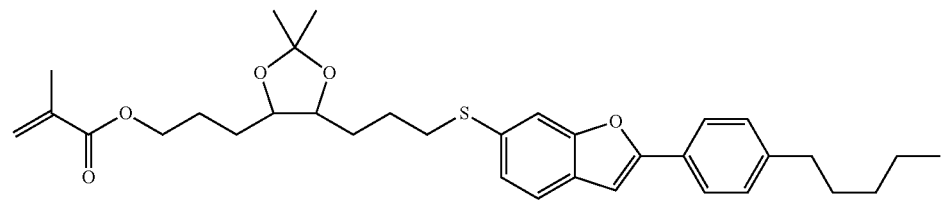 [SMILES: C=C(C)C(=O)OCCCC1OC(C)(C)OC1CCCSc1ccc2cc(-c3ccc(CCCCC)cc3)oc2c1] | |
| | [P] | 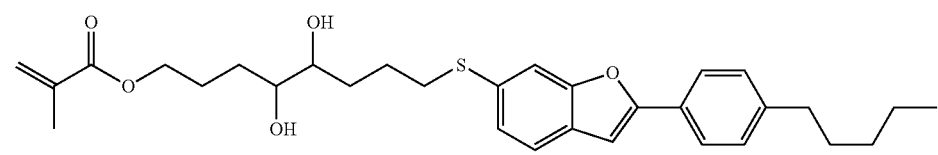 [SMILES: C=C(C)C(=O)OCCCC(O)C(O)CCCSc1ccc2cc(-c3ccc(CCCCC)cc3)oc2c1] | 91% |

Examples for Precursor Materials

Example 13—4-Oxiranyl-2-(2-phenyl-benzofuran-6-yloxymethyl)-butan-1-ol

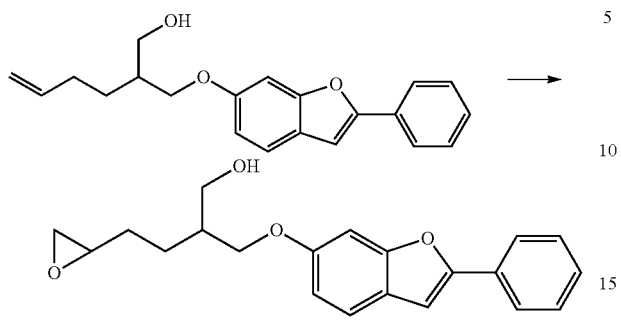

2-(2-Phenyl-benzofuran-6-yloxymethyl)-hex-5-en-1-ol (3.22 g; 10.0 mmol) is added in small portions to a vigorously stirred solution of meta-chloroperoxybenzoic acid (2.47 g; 11.0 mmol) in diethyl ether (15.6 ml; 150 mmol) at 0° C. Stirring is continued for 24 h. The solution is then extracted with sodium hydroxide solution [2 M] and water. The organic phase is dried over MgSO$_4$ and concentrated. The residue is purified by column chromatography on silica gel (heptane/ethyl acetate 5/1) to yield 4-oxiranyl-2-(2-phenyl-benzofuran-6-yloxymethyl)-butan-1-ol (2.37 g; 7.0 mmol; 70% of theory).

Analogously, other derivatives are prepared in the same manner:

| No. | | | Yield |
|---|---|---|---|
| 13a | R | (structure) | |
| | [P] | (structure) | 31% |
| 13b | R | (structure) | |
| | [P] | (structure) | 47% |
| 13c | R | (structure) CAS: 132868-28-1 | |
| | [P] | (structure) | 43% |

Preparation of compounds according to the invention wherein some hydroxyl groups may still be protected by protecting groups. Once the protecting groups are removed, the below described compounds are compounds according to the invention.

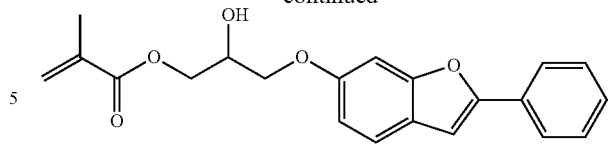

Example 14—2-Methyl-acrylic acid 2-hydroxy-3-(2-phenyl-benzofuran-6-yloxy)-propyl ester

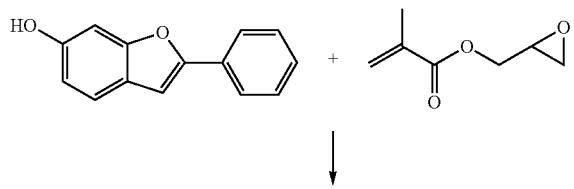

2-Phenyl-benzofuran-6-ol (12.6 g; 60.0 mmol) is dissolved in acetone (300 ml; 4.1 mol). To this solution potassium hydroxide (3.37 g; 60.0 mmol), dissolved in water (15.0 ml; 832 mmol) is added. The reaction mixture is stirred for 1 h at 40° C. Glycidyl methacrylate (9.30 ml; 70.0 mmol) is added dropwise via syringe. The reaction mixture is then heated to reflux for 12 h. The solvent is removed under reduced pressure and the remaining solid is dissolved in ethyl acetate and extracted with water twice. The organic phase is dried with MgSO$_4$, filtered and the concentrated. The residue is purified by column chromatography on silica gel (dichloromethane/methanol; 30/1), yielding 2-methyl-acrylic acid 2-hydroxy-3-(2-phenyl-benzofuran-6-yloxy)-propyl ester (8.88 g; 25.2 mmol; 42% of theory).

Analogously, other derivatives are prepared in the same manner: R1 means reactant 1, R2 means reactant 2, [P] means product

| No. | | | Yield |
|---|---|---|---|
| 14a | R1 | (HO-benzofuran-phenyl structure) | |
| | R2 | (methacrylate epoxide structure) CAS: 62066-42-6 | |
| | [P] | (product structure) | 31% |
| 14b | R1 | (HO-benzofuran-phenyl-pentyl structure) | |
| | R2 | (acrylate diether epoxide structure) CAS: 129904-08-1 | |
| | [P] | (product structure) | 64% |

-continued
| No. | | | Yield |
|---|---|---|---|
| 14c | R1 | 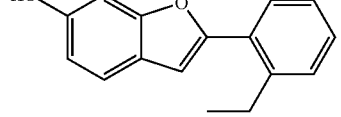 | |
| | R2 | 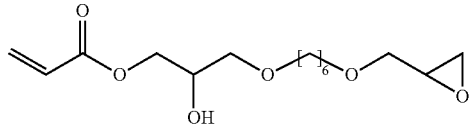 CAS: 166743-84-6 | |
| | [P] | 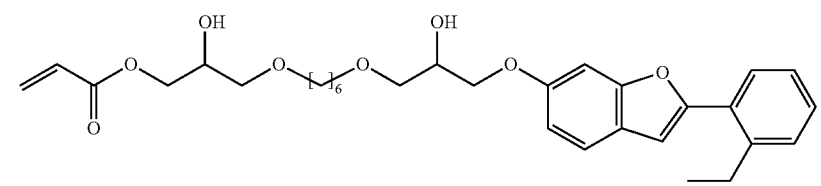 | 73% |
| 14d | R1 | 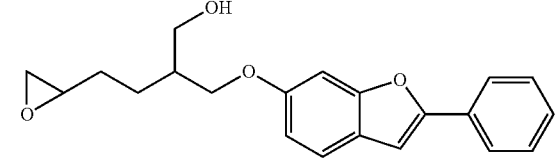 [SMILES: OCC(CCC1CO1)COc1ccc2cc(-c3ccccc3)oc2c1] | |
| | R2 | 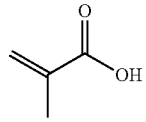 | |
| | [P] | 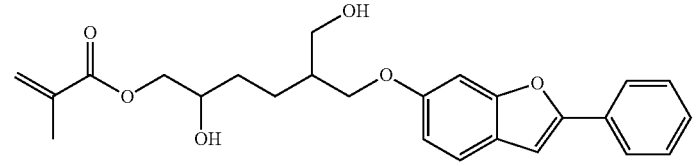 [SMILES: C=C(C)C(=O)OCC(O)CCC(CO)COc1ccc2cc(-c3ccccc3)oc2c1] | 86% |
| 14e | R1 | 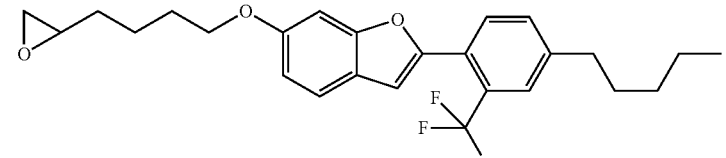 | |
| | R2 | 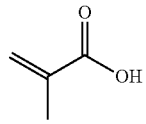 | |
| | [P] | 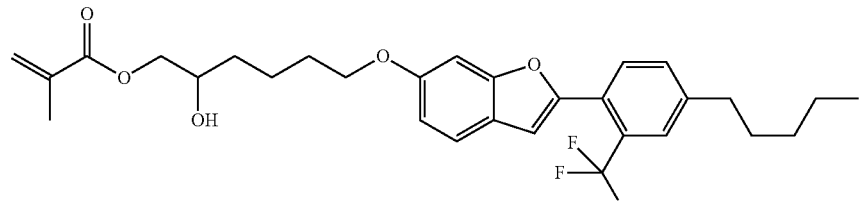 | 68% |

-continued

| No. | | Yield |
|---|---|---|
| 14f | R1: [structure: 6-hydroxybenzofuran-2-yl group attached to phenyl ring bearing pentyl and OCF$_3$ substituents] | |
| | R2: [structure: methacrylate ester of a diol containing an epoxide and hydroxymethyl group] | |
| | [P]: [structure: product of R1 + R2 ring-opened adduct] | 55% |
| 14g | R1: [structure: 6-hydroxybenzofuran-2-yl group attached to phenyl ring bearing pentyl and CF$_3$ substituents] | |
| | R2: [structure: bis-epoxide with central hydroxymethyl] | |
| | [P]: [structure: ring-opened adduct product] | 42% |
| 14h | R1: [structure: epoxide-containing ether-linked benzofuran with pentyl and CF$_3$-substituted phenyl] | |
| | R2: methacrylic acid | |

| No. | | Yield |
|---|---|---|
| [P] | 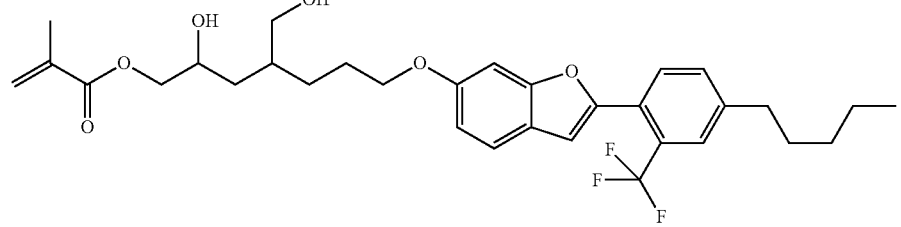 | 50% |
| 14i R1 | 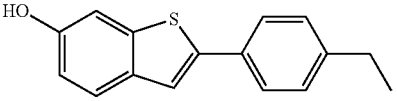 | |
| R2 | 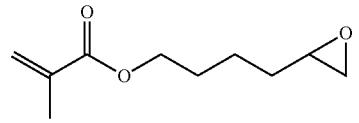\
CAS: 62066-42-6 | |
| [P] | 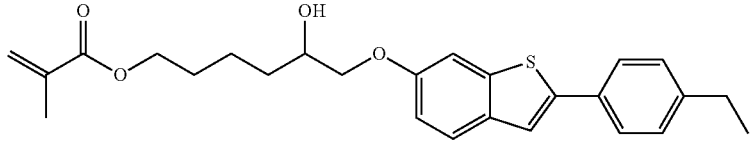 [SMILES: C=C(C)C(=O)OCCCCC(O)COc1ccc2cc(-c3ccc(CC)cc3)sc2c1] | 57% |

Example 15—General Polymerization Procedure

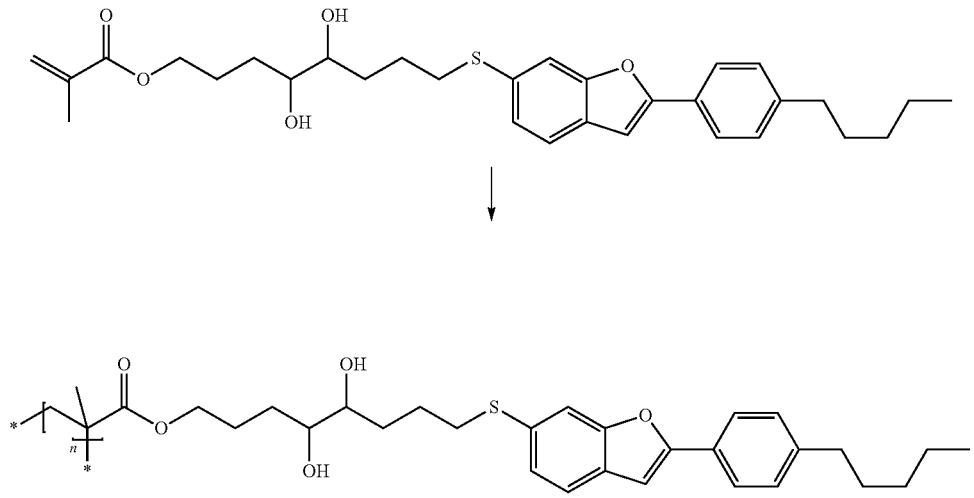

2-Methyl-acrylic acid 4,5-dihydroxy-8-[2-(4-pentyl-phenyl)-benzofuran-6-ylsulfanyl]-octyl ester (1.00 g; 1.9 mmol) is dissolved in dimethylformamide (11.9 ml; 153 mmol). The solution is degassed by three freeze-evacuate-thaw cycles. Azobisisobutyronitrile (12.5 mg; 76.2 µmol) is added to the solution and the reaction vessel is then placed in a 65° C. preheated oil bath for 3 d. At the end of the reaction, the mixture is poured into cold methanol (773 ml; 19.1 mol). The precipitated polymer (740 mg; 1.4 mmol; 74% of theory) is collected by filtration.

Analogously, other polymers are prepared in the same manner: R means reactant, [P] means product
| No. | | | Yield |
|---|---|---|---|
| 15a | R | 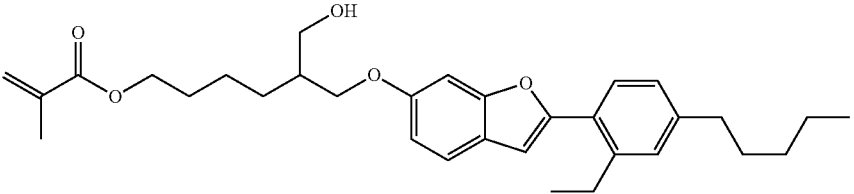 [SMILES: C=C(C)C(=O)OCCCCC(CO)COc1ccc2cc(-c3ccc(CCCCC)cc3CC)oc2c1] | |
| | [P] | 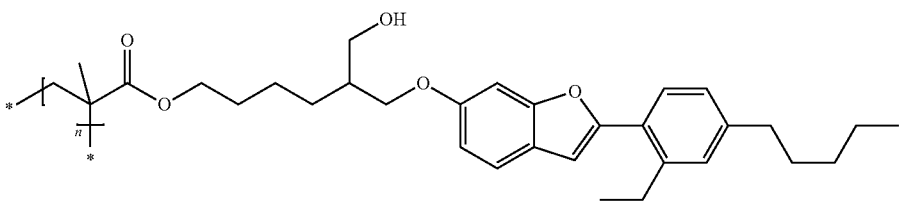 | 71% |
| 15b | R | 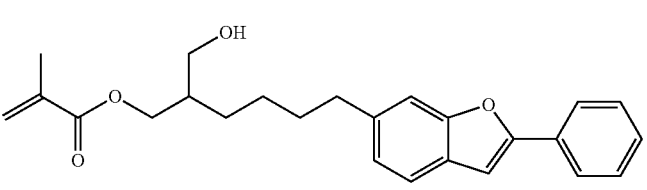 [SMILES: C=C(C)C(=O)OCC(CO)CCCCc1ccc2cc(-c3ccccc3)oc2c1] | |
| | [P] | 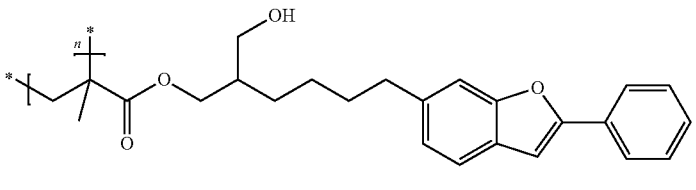 | 62% |
| 15c | R | 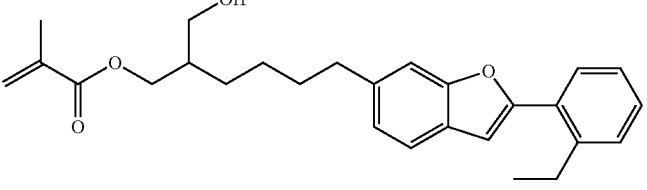 | |
| | [P] | 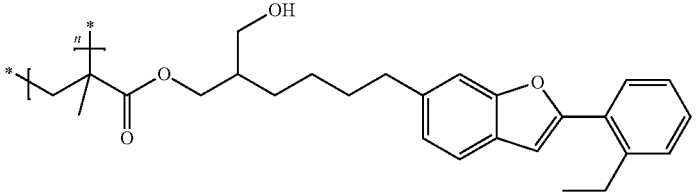 | 56% |
| 15d | R | 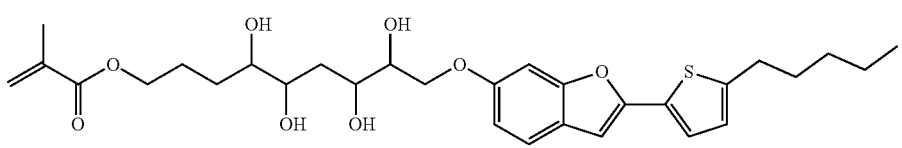 [SMILES: C=C(C)C(=O)OCCCC(O)C(O)CC(O)C(O)COc1ccc2cc(-c3ccc(CCCCC)s3)oc2c1] | |
| | [P] | 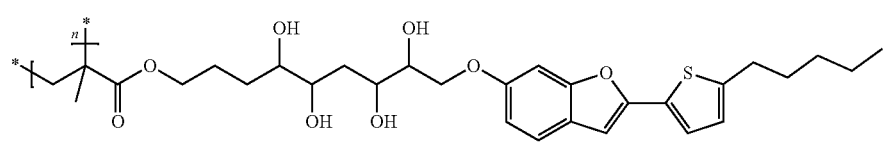 | 72% |

-continued
| No. | | | Yield |
|---|---|---|---|
| 15e | R | 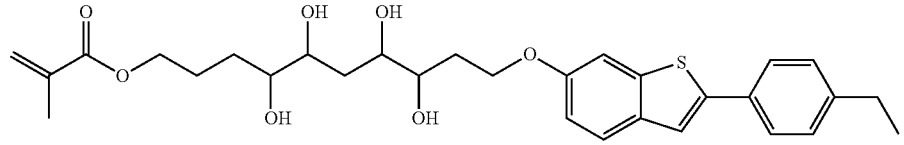 [SMILES: C=C(C)C(=O)OCCCC(O)C(O)CC(O)C(O)CCOc1ccc2cc(-c3ccc(CC)cc3)sc2c1] | |
| | [P] | 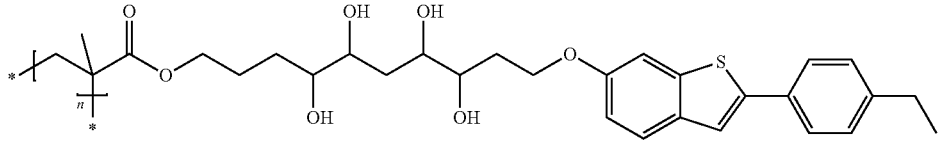 | 69% |
| 15f | R | 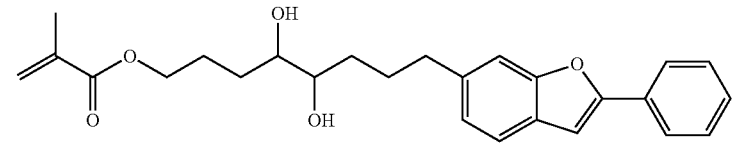 [SMILES: C=C(C)C(=O)OCCCC(O)C(O)CCCc1ccc2cc(-c3ccccc3)oc2c1] | |
| | [P] | 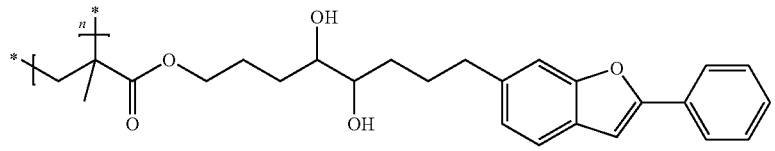 | 66% |
| 15g | R | 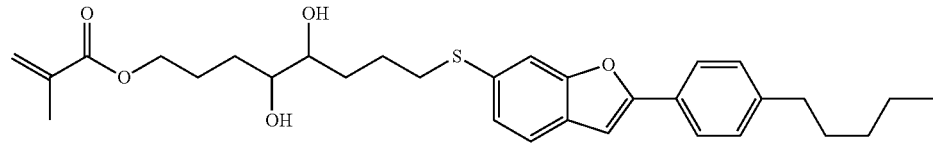 [SMILES: C=C(C)C(=O)OCCCC(O)C(O)CCCSc1ccc2cc(-c3ccc(CCCCC)cc3)oc2c1] | |
| | [P] | 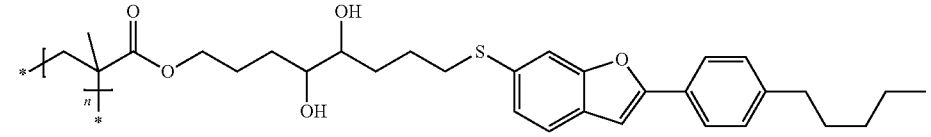 | 73% |
| 15h | R | 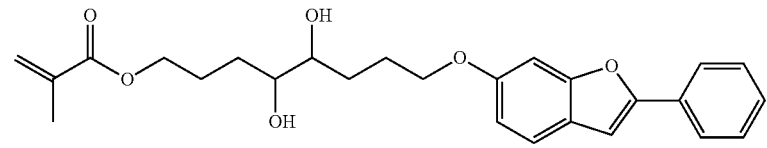 [SMILES: C=C(C)C(=O)OCCCC(O)C(O)CCCOc1ccc2cc(-c3ccccc3)oc2c1] | |
| | [P] | 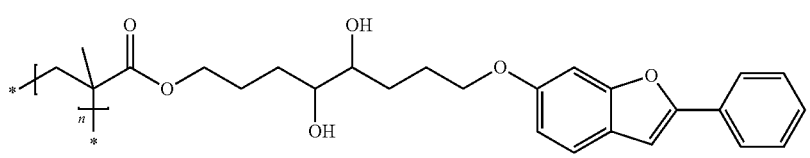 | 59% |
| 15i | R | 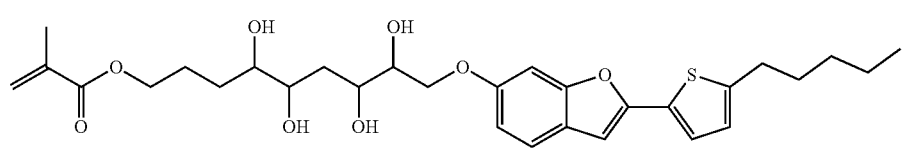 [SMILES: C=C(C)C(=O)OCCCC(O)C(O)CC(O)C(O)COc1ccc2cc(-c3ccc(CCCCC)s3)oc2c1] | |
| | [P] | 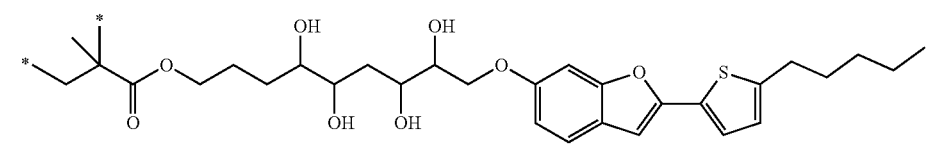 [SMILES: CCCCCc1ccc(-c2cc3ccc(OCC(O)C(O)CC(O)C(O)CCCOC(=O)C(C)(C)CC)cc3o2)s1] | 63% |

-continued
| No. | | | Yield |
|---|---|---|---|
| 15j | R | 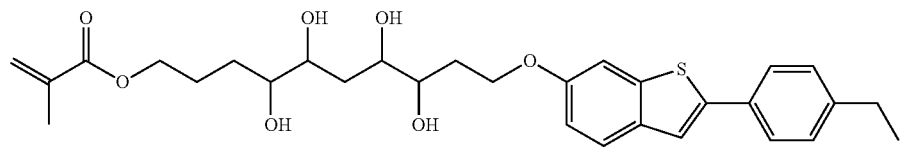 [SMILES: C=C(C)C(=O)OCCCC(O)C(O)CC(O)C(O)CCOc1ccc2cc(-c3ccc(CC)cc3)sc2c1] | |
| | [P] | 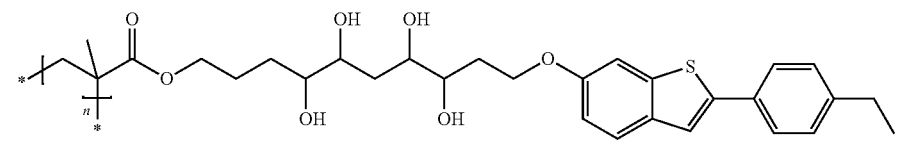 | 73% |
| 15k | R | 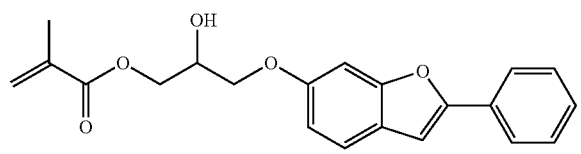 [SMILES: C=C(C)C(=O)OCC(O)COc1ccc2cc(-c3ccccc3)oc2c1] | |
| | [P] | 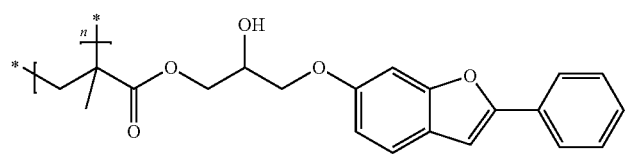 | 57% |
| 15l | R | 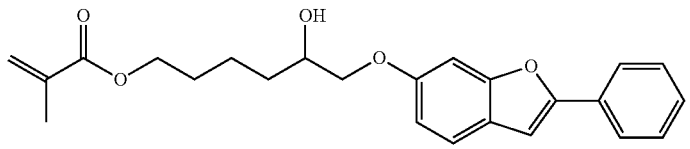 [SMILES: C=C(C)C(=O)OCCCCC(O)COc1ccc2cc(-c3ccccc3)oc2c1] | |
| | [P] | 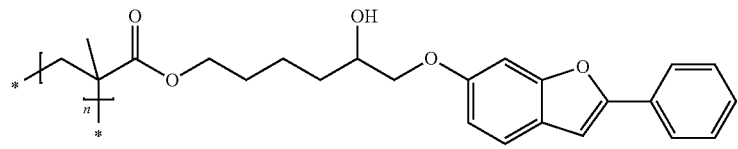 | 69% |
| 15m | R | 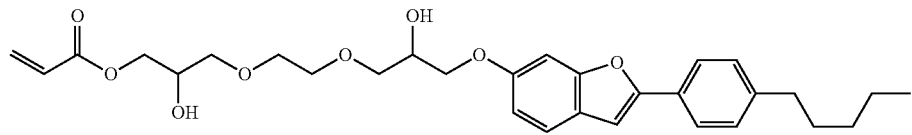 [SMILES: C=CC(=O)OCC(O)COCCOCC(O)COc1ccc2cc(-c3ccc(CCCCC)cc3)oc2c1] | |
| | [P] | 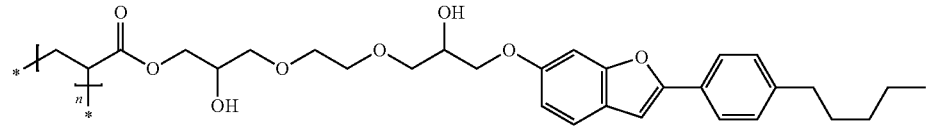 | 67% |
| 15n | R | 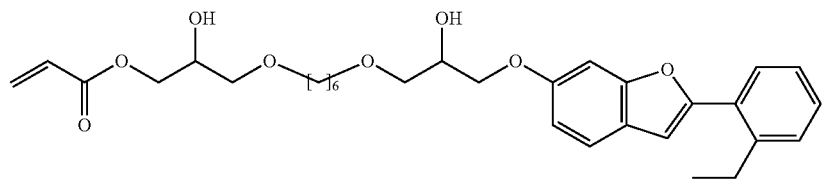 | |

-continued
| No. | | Yield |
|---|---|---|
| | [P] 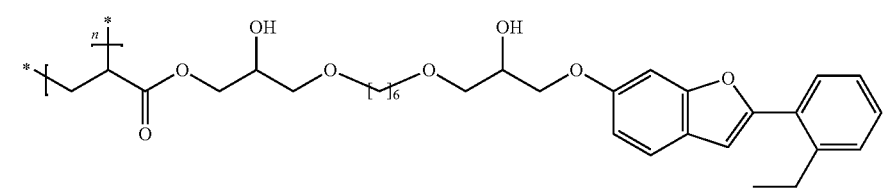 | 71% |
| 15o | R 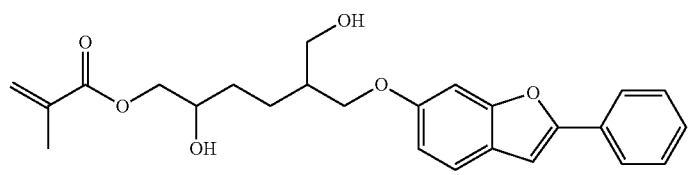 [SMILES: C=C(C)C(=O)OCC(O)CCC(CO)COc1ccc2cc(-c3ccccc3)oc2c1] | |
| | [P] 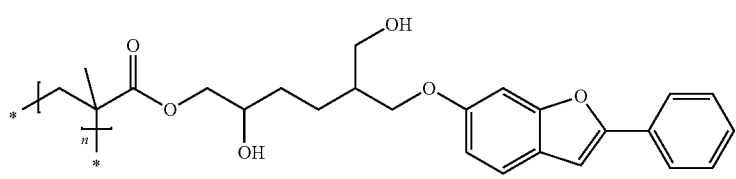 | 55% |
| 15p | R 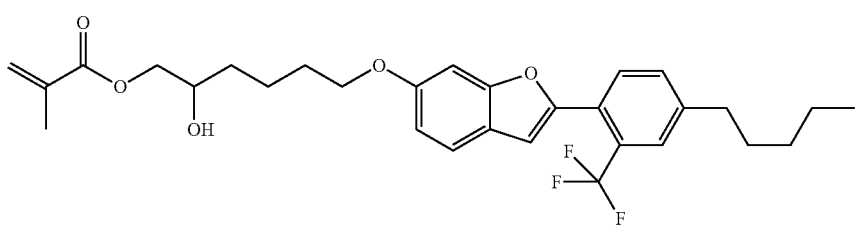 [SMILES: C=C(C)C(=O)OCC(O)CCCCOc1ccc2cc(-c3ccc(CCCCC)cc3C(F)(F)F)oc2c1] | |
| | [P] 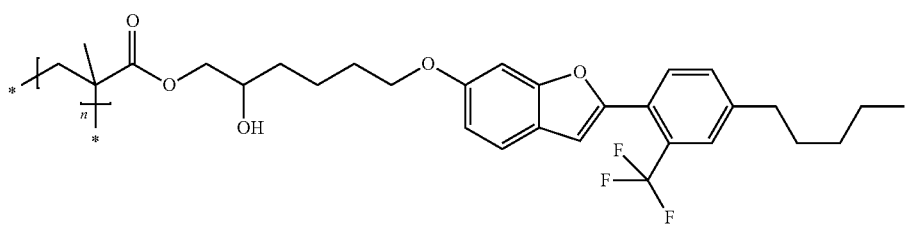 | 66% |
| 15q | R 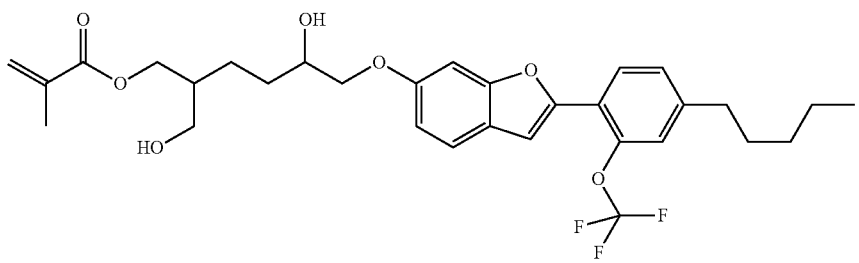 [SMILES: C=C(C)C(=O)OCC(CO)CCC(O)COc1ccc2cc(-c3ccc(CCCCC)cc3OC(F)(F)F)oc2c1] | |
| | [P] 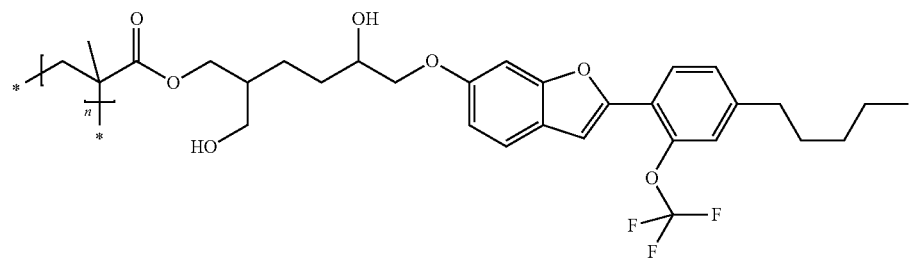 | 67% |

| No. | | Yield |
|---|---|---|
| 15r | R 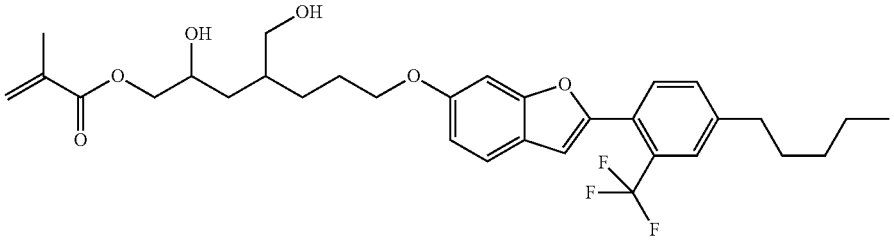 | |
| | [P] 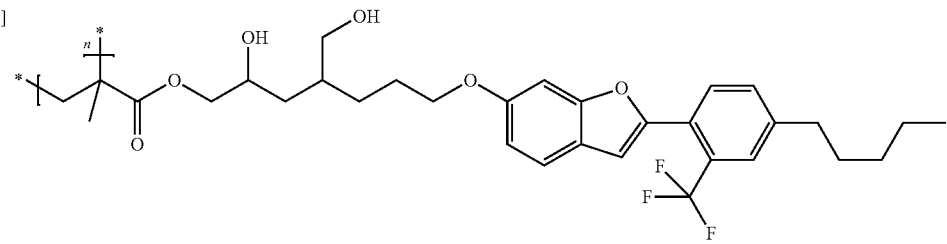 | 71% |

Preparation of Precursor Materials

Example 16—5-Methoxy-2-(phenylethynyl)aniline

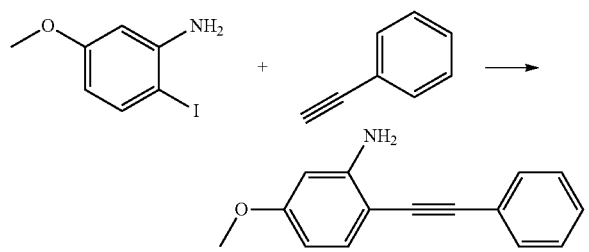

Bis(triphenylphosphine)palladium(II) dichloride (32.1 mg; 45.8 μmol), copper(I) iodide (17.8 mg; 91.5 μmol), 2-Iodo-5-methoxyaniline (1.2 g; 4.6 mmol), phenylacetylene (573 ml; 5.5 mmol), and diethylamine (10 ml) are refluxed for 2 h. The residue is chromatographed on silica gel (heptane/EE, 10/1) to afford 5-methoxy-2-(phenylethynyl)aniline (818 mg; 3.7 mmol; 80% of theory).

1H NMR (500 MHz, Chloroform-d) δ 7.54 (d, J=6.7 Hz, 2H), 7.36 (q, J=8.9, 7.7 Hz, 2H), 7.32 (q, J=8.9, 8.5 Hz, 2H), 6.34 (dd, J=8.5, 2.4 Hz, 1H), 6.30 (d, J=2.3 Hz, 1H), 3.82 (s, 3H).

Analogously, other derivatives are prepared in the same manner:

| No. | Reactant 1 | Reactant 2 | Product | Yield |
|---|---|---|---|---|
| 16a | 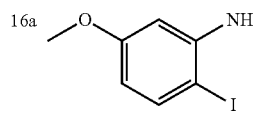 | 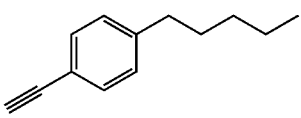 | 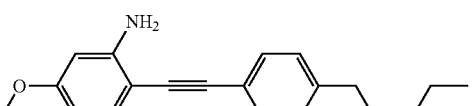 CAS: 79887-10-8 | 76% |
| 16b | 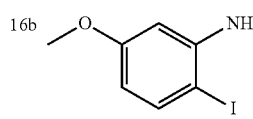 | 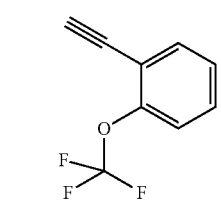 CAS: 886363-40-2 | 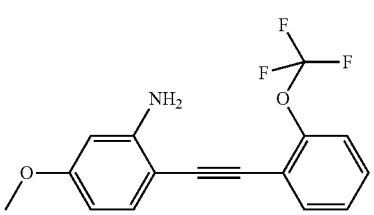 [SMILES: COc1ccc(C#Cc2ccccc2OC(F)(F)F)c(N)c1] | 67% |

Example 17—6-Methoxy-2-phenylindole

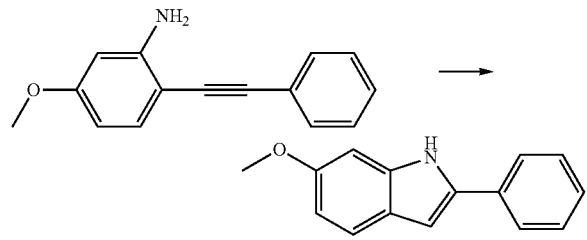

To a refluxing solution of 5-methoxy-2-(phenylethynyl) aniline (826 mg; 3.7 mmol) in toluene (40 ml) is added zinc bromide (420.8 mg; 1.8 mmol) in one portion. After refluxing for 3 d, the reaction mixture is washed with water and extracted with dichloromethane. The combined extracts are dried over MgSO$_4$, filtered, and the solvent is removed under reduced pressure. The solid is passed through a pad of silica gel (heptane/dichloromethane; 5/1) to afford 6-methoxy-2-phenylindole (585 mg; 2.6 mmol; 71% of theory) and is used in the next step without further analyses.

Analogously, other derivatives are prepared in the same manner: R means reactant, [P] means product

| No. | | | Yield |
|---|---|---|---|
| 17a | R | ![structure] | |
| | [P] | ![structure] | 65% |
| 17b | R | ![structure] | |
| | [P] | ![structure] | 49% |

Example 18—6-Methoxy-1-methyl-2-phenylindole

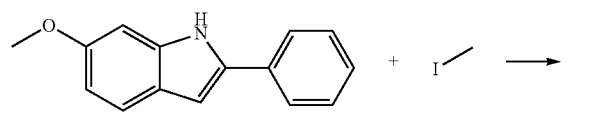

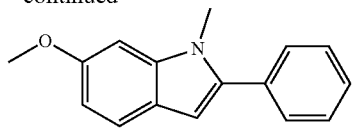

To a solution of 6-Methoxy-2-phenylindole (488 mg; 2.2 mmol) in dimethylformamide (25 ml) is added methyl iodide (304 µl; 4.8 mmol) followed by sodium hydride (182 mg; 4.6 mmol). The mixture is stirred at room temperature for 16 h. Then the mixture is poured onto an ice/NaOH (2M) mixture and the resulting emulsion is extracted with dichloromethane. After drying over MgSO$_4$, the solution is evaporated to dryness. The residue is purified by column chromatography over silica gel eluting with dichloromethane to yield 198 mg (826 µmol; 38% of theory) of 6-methoxy-1-methyl-2-phenyl-1H-indole.

1H NMR (500 MHz, Chloroform-d) δ 7.54 (d, J=8.2 Hz, 1H), 7.52 (d, J=7.0 Hz, 2H), 7.48 (t, J=7.6 Hz, 2H), 7.41 (d, J=7.3 Hz, 1H), 6.86 (s, 1H), 6.85 (dd, J=8.4, 1.4 Hz, 1H), 6.52 (s, 1H), 3.94 (s, 3H), 3.73 (s, 3H).

Analogously, other derivatives are prepared in the same manner: R1 means reactant 1, R2 means reactant 2, [P] means product

| No. | | | Yield |
|---|---|---|---|
| 18a | R1 | ![structure] | |
| | R2 | ![structure] | |
| | [P] | ![structure] | 67% |
| 18b | R1 | ![structure] | |
| | R2 | ![structure] | |
| | [P] | ![structure] | 75% |
| 18c | R1 | ![structure] | |
| | R2 | ![structure] | |

-continued

| No. | | | Yield |
|---|---|---|---|
| 18d | [P] R1 R2 [P] | 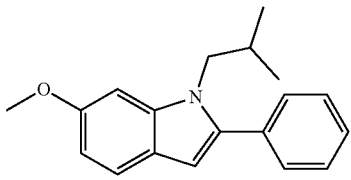 [SMILES: COc1ccc2cc(-c3ccccc3)n(CC(C)C)c2c1] | 74% 85% |
| 18e | R1 R2 [P] | 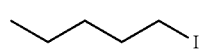 | 83% |
| 18f | R1 R2 [P] | 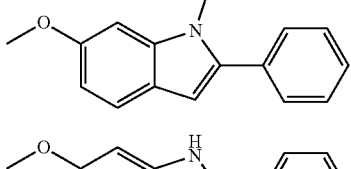 | 42% |

-continued

| No. | | | Yield |
|---|---|---|---|
| 18g | R1 R2 [P] | 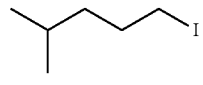 | 45% |

Example 19—6-Hydroxy-1-methyl-2-phenylindole

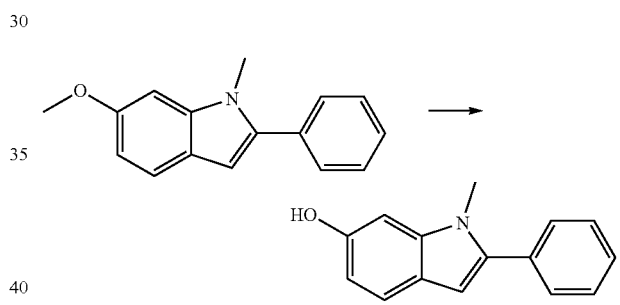

6-Methoxy-1-methyl-2-phenylindole (184 mg; 775 µmol) is dissolved in dichloromethane (10 ml) and cooled to 5° C. Boron tribromide (96.6 µl; 1.0 mmol) is added dropwise to this solution and stirring is continued overnight. Water is slowly added to the mixture, and the organic phase is diluted with ethyl acetate, washed three times with water, dried over $MgSO_4$, evaporated under reduced pressure and filtered through a pad of silica gel with dichloromethane to yield 6-hydroxy-1-Methyl-2-phenylindole (117 mg; 524 µmol; 68% of theory).

1H NMR (500 MHz, Chloroform-d) δ 7.54-7.46 (m, 5H), 7.41 (t, J=6.4 Hz, 1H), 6.84 (d, J=2.2 Hz, 1H), 6.72 (dd, J=8.4, 2.3 Hz, 1H), 6.51 (s, 1H), 4.62 (s, 1H), 3.70 (s, 3H).

Analogously, other derivatives are prepared in the same manner:

| No. | Reactant 1 | Product | Yield |
|---|---|---|---|
| 19a | 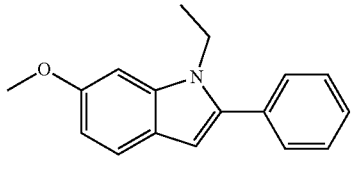 [SMILES: CCn1c(-c2ccccc2)cc2ccc(OC)cc21] | 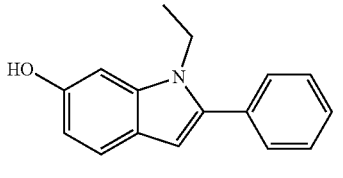 [SMILES: CCn1c(-c2ccccc2)cc2ccc(O)cc21] | 92% |

-continued
| No. | Reactant 1 | Product | Yield |
|---|---|---|---|
| 19b | | | 56% |
| 19c | | | 60% |
| 19d | | | 95% |
| 19e | | | 89% |
| 19f | | | 76% |
| 19g | | | 85% |
Example 20—12-(1-Methyl-2-phenylindol-6-yloxy)-dodecan-1-ol
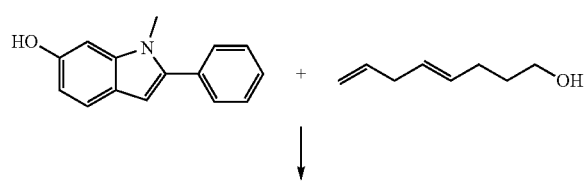
To an ice-cooled solution of 1-methyl-2-phenyl-1H-indol-6-ol (7.70 g; 34.5 mmol), (4E)-octa-4,7-dien-1-ol (4.57 g; 36.2 mmol), triphenylphosphine (11.9 g; 44.8 mmol) in tetrahydrofuran (57.8 ml; 714 mmol), diisopropyl azodicarboxylate (9.01 ml; 44.8 mmol) is added dropwise under argon atmosphere. After stirring at room temperature overnight, the reaction mixture is evaporated to put the crude product on silica gel. Column chromatography (ethyl acetate/heptane, 1/5) gave 1-Methyl-6-[((E)-octa-4,7-dienyl)oxy]-2-phenyl-1H-indole (6.97 g; 21.0 mmol; 61% of theory). Analogously, other derivatives are prepared in the same manner: R1 means reactant 1, R2 means reactant 2, [P] means product

| No. | | Yield |
|---|---|---|
| 20a R1 ![structure] CAS 1013932-64-3 R2 ![structure] [P] ![structure] | | 77% |

Example 21—(E)-8-(1-Methyl-2-phenyl-1H-indol-6-yloxy)-oct-4-en-1-ol

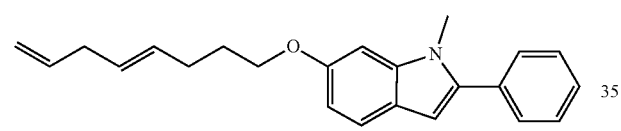

↓

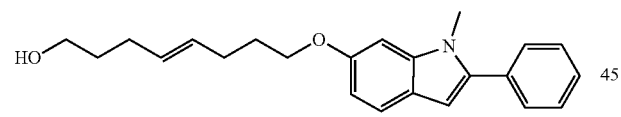

A Schlenk flask is charged with tetrahydrofuran (40.4 ml; 498 mmol) and 1-methyl-6-[((E)-octa-4,7-dienyl)oxy]-2-phenyl-1H-indole (7.00 g; 21.1 mmol) and the solution is cooled to 0° C. After 10 min, 9-borabicyclo[3.3.1]nonane (0.5 M in THF) (42.2 ml; 21.1 mmol) is added dropwise via syringe over 30 min. The reaction is stirred for 1 h at 0° C. and then 1 h at 25° C. Sodium hydroxide solution (2 M) (30.3 ml; 60.6 mmol) is added, the reaction cooled to 0° C. Then hydrogen peroxide (30%) (17.7 ml; 173 mmol) is added dropwise over the course of 10 min. The reaction is then stirred for 30 min, diluted with diethyl ether (10 ml) and filtered through celite. The filtrate is neutralized, extracted with diethyl ether, washed with brine, dried (MgSO$_4$) and concentrated. Column chromatography on silica gel (heptane/EE, gradient) yields (E)-8-(1-Methyl-2-phenyl-1H-indol-6-yloxy)-oct-4-en-1-ol (3.47 g; 9.9 mmol; 47% of theory).

Analogously, other derivatives are prepared in the same manner: R means reactant, [P] means product

| No. | | Yield |
|---|---|---|
| 21a | R 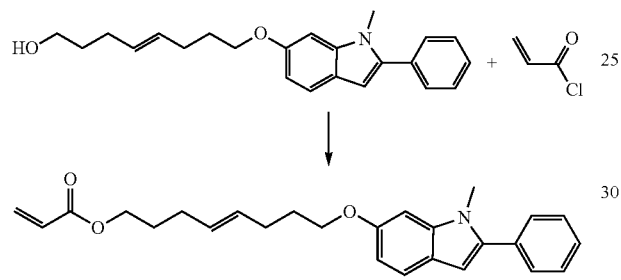 | |
| [P] | | 36% |

Example 22—Acrylic acid (E)-8-(1-methyl-2-phenyl-1H-indol-6-yloxy)-oct-4-enyl ester Acryloyl chloride (858 μl; 10.3 mmol) is slowly added to an ice-cooled solution of (E)-8-(1-Methyl-2-phenyl-1H-indol-6-yloxy)-oct-4-en-1-ol (3.00 g; 8.6 mmol) in tetrahydrofuran (125 ml; 1.54 mol) and triethylamine (4.76 ml; 34.3 mmol). Then the reaction is left to stir for 1 d at room temperature. The reaction mixture is filtered and evaporated to dryness. The residue is filtered through a short column ($SiO_2$, heptane/ethyl acetate, 2/1). The product fraction is evaporated to dryness yielding acrylic acid (E)-8-(1-methyl-2-phenyl-1H-indol-6-yloxy)-oct-4-enyl ester (2.70 g; 6.7 mmol; 78% of theory).

Analogously, other derivatives are prepared in the same manner: R1 means reactant 1, R2 means reactant 2, [P] means product

| No. | | Yield |
|---|---|---|
| 22a | R1 | |
| | R2 | |

| No. | | Yield |
|---|---|---|
| [P] | (structure) | 66% |

Preparation of compounds according to the invention wherein some hydroxyl groups may still be protected by protecting groups. Once the protecting groups are removed, the below described compounds are compounds according to the invention.

Example 23—Acrylic acid 4,5-dihydroxy-8-(1-methyl-2-phenyl-1H-indol-6-yloxy)-octyl ester

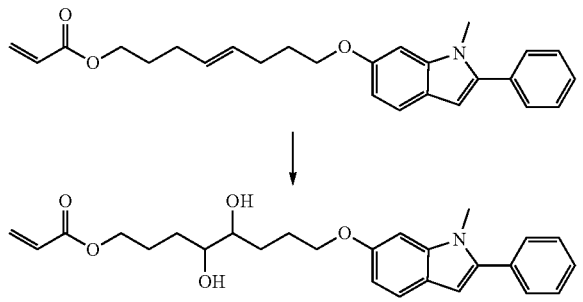

Acrylic acid (E)-8-(1-methyl-2-phenyl-1H-indol-6-yloxy)-oct-4-enyl ester (1.00 g; 2.5 mmol) is dissolved in a mixture of acetone (21.0 ml; 285 mmol) and water (2.23 ml; 124 mmol). The mixture is cooled to 0° C. To the colorless solution is added osmium tetroxide [aq., 4 wt %] (315 µl; 49.6 µmol), followed by N-methylmorpholine N-oxide [aq., 50%] (535 µl; 2.6 mmol) at room temperature. The reaction mixture is stirred over night. Then Na$_2$SO$_3$-solution is added and the mixture is stirred for 10 min to reduce osmium-species. The resulting aqueous solution is extracted with ethyl acetate and n-butanol. The organic phase is separated, dried with Na$_2$SO$_4$ and concentrated to yield Acrylic acid 4,5-dihydroxy-8-(1-methyl-2-phenyl-1H-indol-6-yloxy)-octyl ester (358 mg; 818 µmol; 33% of theory).

Analogously, other derivatives are prepared in the same manner: R means reactant, [P] means product

| No. | | Yield |
|---|---|---|
| 23a R | (structure) | |
| [P] | (structure) | 37% |

Example 24—Methacrylic acid 2-hydroxy-3-(1-methyl-2-phenylindol-6-yloxy)-propyl ester

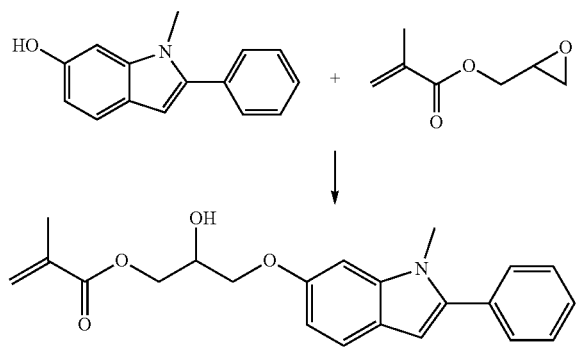

1-Methyl-2-phenyl-1H-indol-6-ol (6.70 g; 30.0 mmol) is dissolved in acetone (154 ml; 2.1 mol). To this solution potassium hydroxide (1.68 g; 30.0 mmol), dissolved in water (7.57 ml; 420 mmol) is added. The reaction mixture is stirred for 1 h at 40° C. Glycidyl methacrylate (4.78 ml; 36.0 mmol) is added dropwise via syringe. The reaction mixture is then heated to reflux for 12 h.

The solvent is removed under reduced pressure and the remaining solid is dissolved in ethyl acetate and extracted with water twice. The organic phase is dried with MgSO$_4$, filtered and the concentrated. The residue is purified by column chromatography on silica gel (dichloromethane/methanol; 30/1), yielding 2-methyl-acrylic acid 2-hydroxy-3-(1-methyl-2-phenyl-1H-indol-6-yloxy)-propyl ester (5.59 g; 15.3 mmol; 51% of theory).

Analogously, other derivatives are prepared in the same manner: R1 means reactant 1, R2 means reactant 2, [P] means product

| No. | | Yield |
|---|---|---|
| 24a | R1 | |
| | R2 | |
| | [P] | 69% |
| 24b | R1 | |
| | R2 CAS: 62066-42-6 | |
| | [P] | 55% |

| No. | | Yield |
|---|---|---|
| 24c | R1 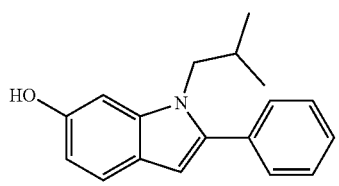 | |
| | R2 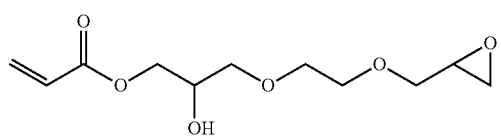<br>CAS: 129904-08-1 | |
| | [P] 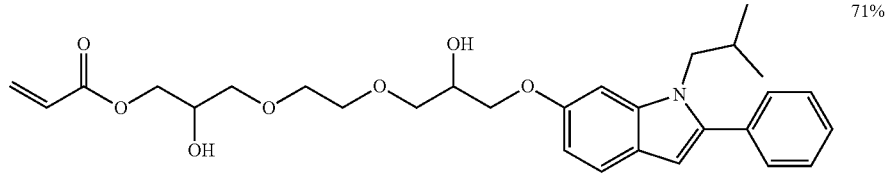 | 71% |
| 24d | R1 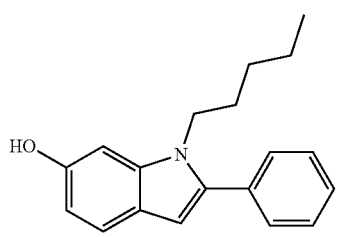 | |
| | R2 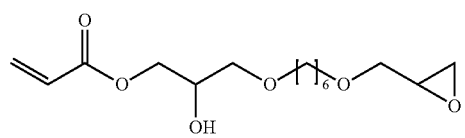<br>CAS: 166743-84-6 | |
| | [P] 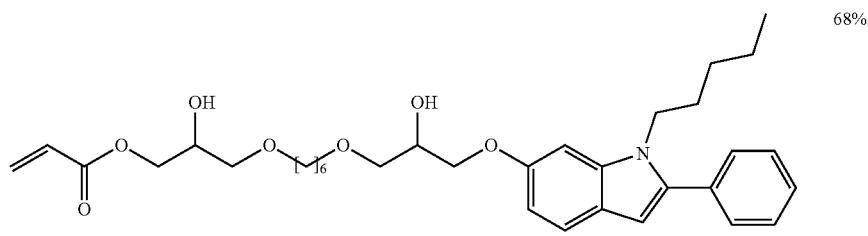 | 68% |
| 24e | R1 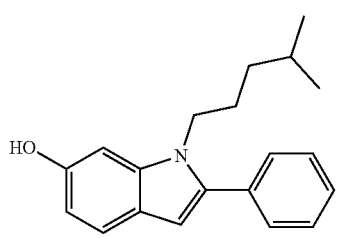 | |

| No. | | Yield |
|---|---|---|
| | R2 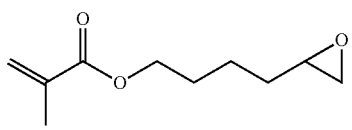  CAS: 62066-42-6 | |
| | [P] 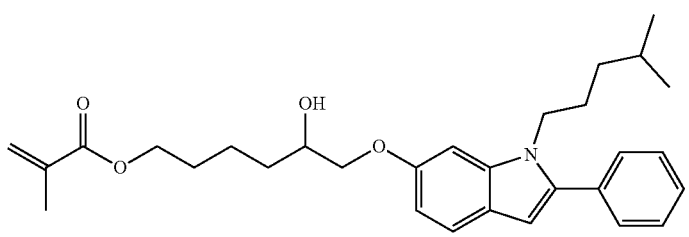 [SMILES: C=C(C)C(=O)OCCCCC(O)COc1ccc2cc(-c3ccccc3)n(CCCC(C)C)c2c1] | 72% |
| 24f | R1 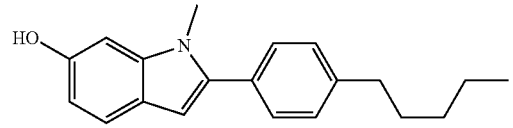 [SMILES: CCCCCc1ccc(-c2cc3ccc(O)cc3n2C)cc1] | |
| | R2 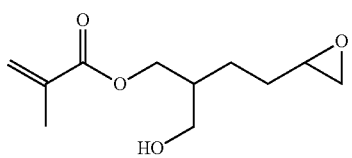 | |
| | [P] 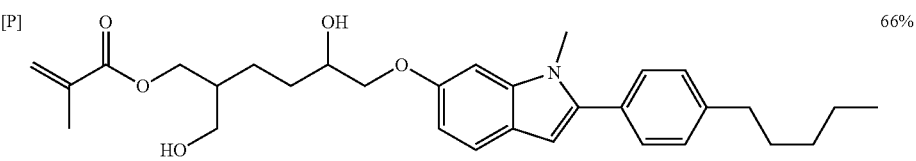 | 66% |
| 24g | R1 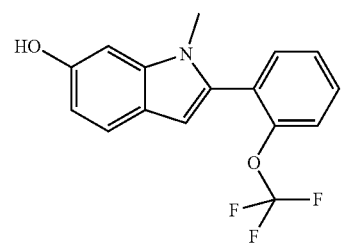 [SMILES: Cn1c(-c2ccccc2OC(F)(F)F)cc2ccc(O)cc21] | |
| | R2 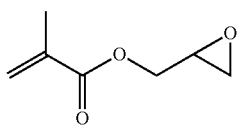 | |
| | [P] 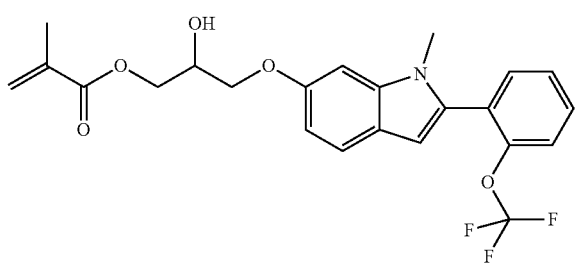 [SMILES: C=C(C)C(=O)OCC(O)COc1ccc2cc(-c3ccccc3OC(F)(F)F)n(C)c2c1] | 70% |

Example 25—General Synthesis of Homopolymers

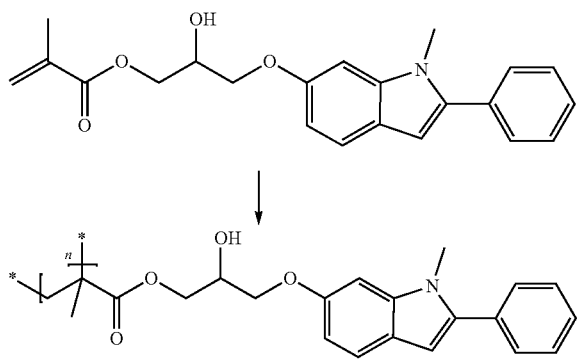

Methacrylic acid 2-hydroxy-3-(1-methyl-2-phenylindol-6-yloxy)-propyl ester (1.00 g; 2.7 mmol) is dissolved in dimethylformamide (17.0 ml; 219 mmol). The solution is degassed by three freeze-evacuate-thaw cycles. Azobisisobutyronitrile (18.0 mg; 110 µmol) is added to the solution and the reaction vessel is then placed in a 65° C. preheated oil bath for 3 d. At the end of the reaction, the mixture is poured into cold methanol (1.11 l; 27.4 mol). The precipitated polymer (680 mg; 1.9 mmol; 68%) is collected by filtration.

Analogously, other polymers are prepared in the same manner: R means reactant, [P] means product

| No. | | Yield |
|---|---|---|
| 25a | R | |
| | [P] | 66% |
| 25b | R | |
| | [P] | 63% |
| 25c | R | |
| | [P] | 78% |

| No. | | Yield |
|---|---|---|
| 25d | R = [methacrylate-O-(CH2)3-CH(OH)-CH2-O-indole(N-iPr)(2-Ph)] | |
| | [P] = poly[methacrylate-O-(CH2)3-CH(OH)-CH2-O-indole(N-iPr)(2-Ph)] | 75% |
| 25e | R = [acrylate-O-CH2-CH(OH)-CH2-O-CH2CH2-O-CH2-CH(OH)-CH2-O-indole(N-iBu)(2-Ph)] | |
| | [P] = polymer form | 71% |
| 25f | R = [acrylate-O-CH2-CH(OH)-CH2-O-(CH2)6-O-CH2-CH(OH)-CH2-O-indole(N-pentyl)(2-Ph)] | |
| | [P] = polymer form | 59% |
| 25g | R = [methacrylate-O-(CH2)3-CH(OH)-CH2-O-indole(N-isohexyl)(2-Ph)] | |

| No. | | Yield |
|---|---|---|
| | [P] (structure: polymer with methacrylate linker, hydroxy, O-linked to 6-position of 1-(4-methylpentyl)-2-phenyl-1H-indole) | |
| 25h | (structure: methacrylate ester with hydroxymethyl branch, hydroxy, O-linked to 6-position of 1-methyl-2-(4-pentylphenyl)-1H-indole) | |
| | [P] (polymer version of 25h) | |
| 25i | (structure: glycidyl methacrylate-type linker with OH, O-linked to 6-position of 1-methyl-2-(2-(trifluoromethoxy)phenyl)-1H-indole) | |
| | [P] (polymer version of 25i) | |

Preparation of Precursor Materials

Example 26

General Experimental Procedure

The following indole compounds are synthesized according to a recently published literature procedure: "Room Temperature and Phosphine Free Palladium Catalyzed Direct C-2 Arylation of Indoles" by Larrosa et al, *J. Am. Chem. Soc.*, 2008, 130 (10), 2926-2927:

1-alkyl-1H-indole derivative, iodo-phenol derivative (2.0 equiv.) and 2-nitrobenzoic acid (1.5 equiv.) are dissolved in dry dimethylformamide (15 volume equivs.). Then palladium(II)-acetate (5 mol-%) and silver(I)oxide (0.75 equiv.) are added and the reaction mixture is stirred at room temperature upon completion checked via TLC. H$_2$O and ethyl acetate are added to the reaction mixture and the phases are separated. The aqueous phase is extracted two times with ethyl acetate. The combined organic phases are dried over magnesium sulfate and are evaporated. The crude residue is purified by column chromatography on silica gel using (heptane/ethyl acetate; 30/1).

The following compounds are prepared using the general procedure: R1 means reactant 1, R2 means reactant 2, [P] means product

| No. | | Yield |
|---|---|---|
| 26a | R1 | (1-methyl-1H-indole structure) |

-continued

| No. | | | Yield |
|---|---|---|---|
| 26b | R1 R2 | (structures: 4-iodophenol; 1-pentyl-indole; 2-(4-hydroxyphenyl)-1-pentyl-indole [P]) | 49% / 33% |
| 26c | R1 R2 | (structures: 3-iodophenol; 1-methyl-indole; 2-(3-hydroxyphenyl)-1-methyl-indole [P]) | 51% |
| 26d | R1 | (structure: 1-pentyl-indole) | |

-continued

| No. | | Yield |
|---|---|---|
| 5 | R2 [P] (structures: 3-iodophenol; 1-pentyl-2-(3-hydroxyphenyl)-indole) | 74% |

4-(1-Methyl-1H-indol-2-yl)-phenol

1H NMR (500 MHz, DMSO-d$_6$) δ 9.71 (s, 1H), 7.53 (d, J=7.8 Hz, 1H), 7.45 (d, J=8.2 Hz, 1H), 7.40 (d, J=8.6 Hz, 2H), 7.18-7.12 (m, 1H), 7.08-7.01 (m, 1H), 6.91 (d, J=8.6 Hz, 2H), 6.44-6.43 (m, 1H), 3.71 (s, 3H).

4-(1-Pentyl-1H-indol-2-yl)-phenol

1H NMR (500 MHz, DMSO-d$_6$) δ 9.70 (s, 1H), 7.52 (d, J=7.7 Hz, 1H), 7.47 (d, J=8.1 Hz, 1H), 7.33 (d, J=8.6 Hz, 2H), 7.16-7.11 (m, 1H), 7.06-7.01 (m, 1H), 6.90 (d, J=8.6 Hz, 2H), 6.39 (s, 1H), 4.20-4.10 (m, 2H), 1.55 (p, J=7.4 Hz, 2H), 1.13 (p, J=7.3, 6.7 Hz, 2H), 1.06 (p, J=13.9, 6.7 Hz, 2H), 0.74 (t, J=7.2 Hz, 3H).

3-(1-Methyl-1H-indol-2-yl)-phenol

1H NMR (500 MHz, DMSO-d$_6$) δ 9.65 (s, 1H), 7.56 (d, J=7.8 Hz, 1H), 7.48 (d, J=8.2 Hz, 1H), 7.31 (t, J=7.9 Hz, 1H), 7.21-7.16 (m, 1H), 7.09-7.05 (m, 1H), 7.00 (d, J=7.7 Hz, 1H), 6.97-6.94 (m, 1H), 6.84 (dd, J=8.1, 1.7 Hz, 1H), 6.52 (s, 1H), 3.74 (s, 3H).

3-(1-Pentyl-1H-indol-2-yl)-phenol

1H NMR (500 MHz, DMSO-d$_6$) δ 9.64 (s, 1H), 7.55 (d, J=7.8 Hz, 1H), 7.50 (d, J=8.2 Hz, 1H), 7.31 (t, J=7.8 Hz, 1H), 7.19-7.14 (m, 1H), 7.05 (t, J=7.1 Hz, 1H), 6.94 (d, J=6.8 Hz, 1H), 6.92-6.90 (m, 1H), 6.84 (dd, J=7.4, 2.4 Hz, 1H), 6.46 (s, 1H), 4.25-4.15 (m, 2H), 1.57 (p, J=7.4 Hz, 2H), 1.17-1.10 (m, 2H), 1.10-1.02 (m, 2H), 0.74 (t, J=7.2 Hz, 3H).

Preparation of Compounds According to the Invention

Example 27

The 3-substituted or 4-substituted-(1-alkyl-1H-indol-2-yl)-phenol derivative is dissolved in acetone (10 volume equivs.) and the solution is cooled with an ice-bath. Then 2-methyl-acrylic acid oxiranylmethyl ester or oxiran-2-yl methyl acrylate (5.0 equivs.) and potassium carbonate (1.1 equiv.) are added. The solution is stirred for approximately 10 minutes at low temperature and then heated to 55° C. for id. The reaction was monitored via TLC and, if necessary, further acrylate or methacrylate is added until completion of the reaction. Water is added to the reaction mixture, and the aqueous phase is diluted with saturated sodium chloride solution. The mixture is extracted two times with tert-butyl methyl ether, the combined organic phases are dried over magnesium sulfate and evaporated. The crude residue is purified by column chromatography on silica gel using (heptane/ethyl acetate; 20/1).

The following compounds are prepared using the general procedure: R1 means reactant 1, R2 means reactant 2, [P] means product

| No. | | Yield |
|---|---|---|
| 27a | R1 | |
| | R2 | |
| | [P] | 45% |
| 27b | R1 | |
| | R2 | |
| | [P] | 41% |
| 27c | R1 | |
| | R2 | |
| | [P] | 39% |
| 27d | R1 | |
| | R2 | |
| | [P] | 32% |
| 27e | R1 | |
| | R2 | |
| | [P] | 37% |

| No. | | | Yield |
|---|---|---|---|
| 27f | R1 | 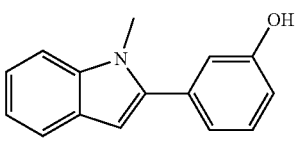 [SMILES: Cn1c(-c2cccc(O)c2)cc2ccccc21] | |
| | R2 | 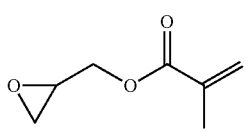 | |
| | [P] | 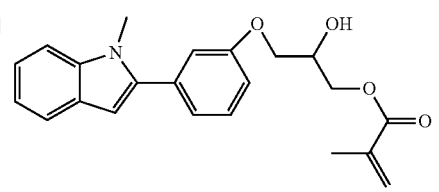 | 33% |
| 27e | R1 | 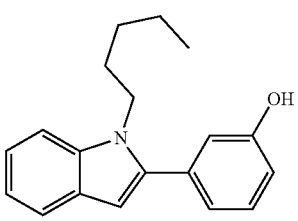 [SMILES: CCCCCn1c(-c2cccc(O)c2)cc2ccccc21] | |
| | R2 | 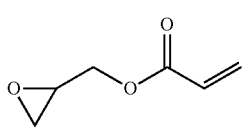 | |
| | [P] | 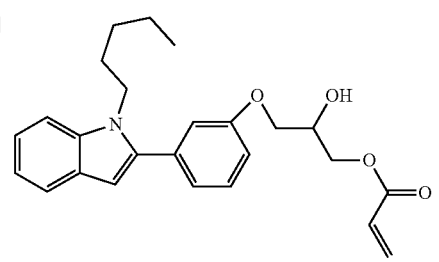 | 15% |
| 27f | R1 | 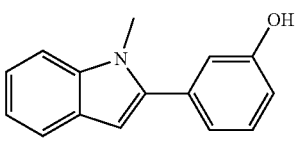 [SMILES: Cn1c(-c2cccc(O)c2)cc2ccccc21] | |
| | R2 | 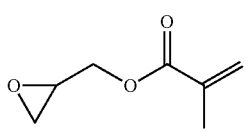 | |

| No. | | Yield |
|---|---|---|
| | [P] 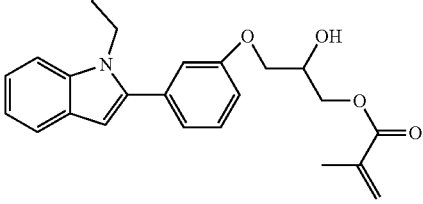 | 34% |

2-hydroxy-3-(4-(1-methyl-1H-indol-2-yl)phenoxy) propyl methacrylate

1H NMR (500 MHz, DMSO-d$_6$) δ 7.55 (d, J=7.8 Hz, 1H), 7.52 (d, J=8.7 Hz, 2H), 7.47 (d, J=8.1 Hz, 1H), 7.19-7.15 (m, 1H), 7.10 (d, J=8.7 Hz, 2H), 7.08-7.03 (m, 1H), 6.49 (s, 1H), 6.10 (s, 1H), 5.75-5.66 (m, 1H), 5.44 (d, J=5.2 Hz, 1H), 4.27-4.17 (m, 2H), 4.16-4.03 (m, 3H), 3.73 (s, 3H), 1.91 (s, 3H).

m.p.: 103-106° C.

m.p. (DSC): 102° C.

2-Hydroxy-3-(3-(1-methyl-1H-indol-2-yl)phenoxy) propyl methacrylate

1H NMR (500 MHz, DMSO-d$_6$) δ 7.57 (d, J=7.8 Hz, 1H), 7.50 (d, J=8.2 Hz, 1H), 7.44 (t, J=7.9 Hz, 1H), 7.22-7.15 (m, 2H), 7.15-7.13 (m, 1H), 7.10-7.06 (m, 1H), 7.04 (dd, J=8.0, 2.2 Hz, 1H), 6.59 (s, 1H), 6.09 (s, 1H), 5.71-5.67 (m, 1H), 5.42 (d, J=5.1 Hz, 1H), 4.26-4.16 (m, 2H), 4.15-4.04 (m, 3H), 3.76 (s, 3H), 1.89 (s, 3H).

2-hydroxy-3-(3-(1-pentyl-1H-indol-2-yl)phenoxy) propyl methacrylate

1H NMR (500 MHz, DMSO-d$_6$) δ 7.56 (d, J=7.8 Hz, 1H), 7.52 (d, J=8.2 Hz, 1H), 7.43 (t, J=7.9 Hz, 1H), 7.20-7.15 (m, 1H), 7.12 (d, J=7.7 Hz, 1H), 7.09-7.02 (m, 3H), 6.53 (s, 1H), 6.08 (s, 1H), 5.69-5.66 (m, 1H), 5.42 (d, J=4.8 Hz, 1H), 4.25-4.03 (m, 7H), 1.88 (s, 3H), 1.56 (p, J=7.4 Hz, 2H), 1.15-1.08 (m, 2H), 1.08-1.01 (m, 2H), 0.72 (t, J=7.2 Hz, 3H).

2-hydroxy-3-(4-(1-pentyl-1H-indol-2-yl)phenoxy) propyl methacrylate

1H NMR (500 MHz, DMSO-d$_6$) δ 7.54 (d, J=7.8 Hz, 1H), 7.49 (d, J=8.2 Hz, 1H), 7.46 (d, J=8.7 Hz, 2H), 7.18-7.13 (m, 1H), 7.10 (d, J=8.7 Hz, 2H), 7.07-7.02 (m, 1H), 6.44 (s, 1H), 6.10 (s, 1H), 5.74-5.68 (m, 1H), 5.43 (d, J=5.0 Hz, 1H), 4.28-4.09 (m, 7H), 1.91 (s, 3H), 1.55 (p, J=7.5 Hz, 2H), 1.12 (p, J=7.2, 6.7 Hz, 2H), 1.05 (p, J=7.3 Hz, 2H), 0.73 (t, J=7.2 Hz, 3H).

m.p. (DSC): 90.5

Example 28—General Synthesis of Homopolymers According to Example 25
Analogously are Prepared: R Means Reactant, [P] Means Product
| No. | | Yield |
|---|---|---|
| 28a | R 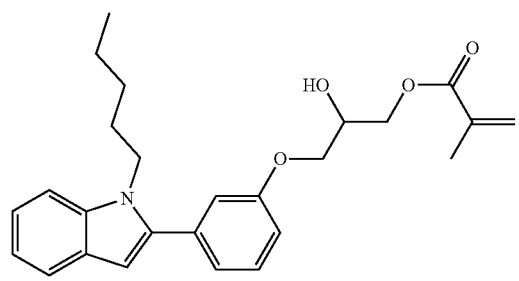 | |
| | [P] 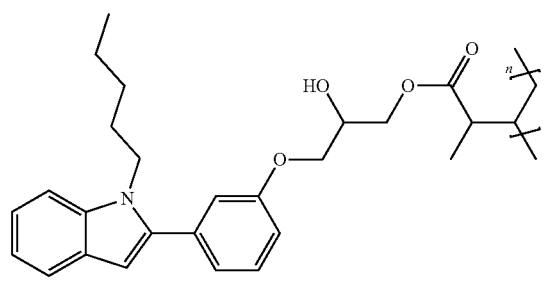 | 61% |
| 28b | R 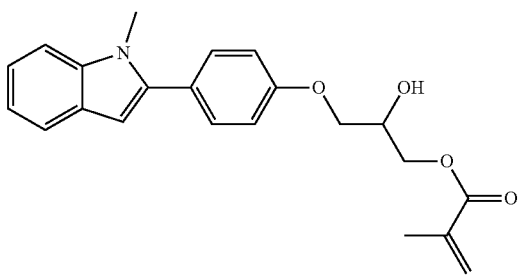 | |
| | [P] 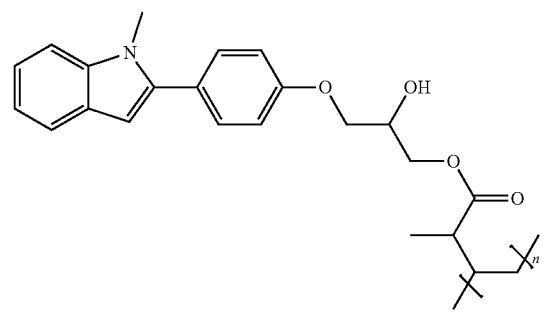 | 19% |

| No. | | Yield |
|---|---|---|
| 28c | R 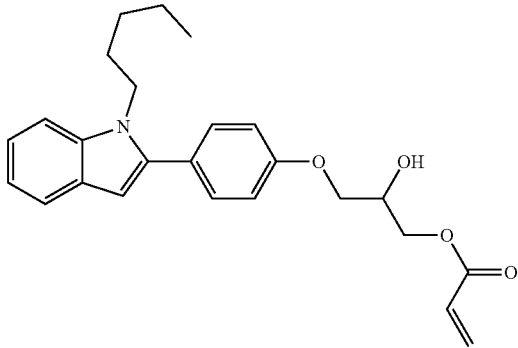 | |
| [P] | 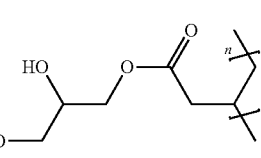 | 24% |

Examples of Application

Example 29: General Bulk Polymerization Procedure to Produce Blank

A composition of acrylic acid 4,5-dihydroxy-8-(2-phenyl-benzofuran-6-yloxy)-octyl ester as described in example 12, initiator azobisisobutyronitrile (0.04 eq) and crosslinker ethylene glycol dimethacrylate (0.1-0.4 eq) in different ratios is degassed by three freeze-pump-thaw cycles.

Two glass plates are coated with a polyethylene sheet and a 0.5 mm thick cell is created between the polyethylene sheets using a silicone rubber gasket. The coated faces of the glass sheets are clipped together using spring clips with a syringe needle being placed between the gasket and the polyethylene sheets. The cavity is then filled with the above formulation through the needle using a gastight syringe. Once the cavity is filled the syringe needle is removed, a final clip is used to seal the mould and the assembly is placed in an oven at 60° C. for 24 hours before the oven is ramped to a temperature of 90° C. for a period of 3 hours. The moulds are allowed to cool to room temperature before the film is removed from the mould.

Examples Directed to the Properties of the Compounds

Example 30—Photoinduced Refractive Index Change and Glass Transition Temperature The phase transition temperatures are determined with a TA Instruments Q2000 differential scanning calorimeter during heating in the second heating run with 20 K/min from −100° C. to 200° C. in a hermetic aluminum pans.

Irradiations of the blanks are performed with a Coherent Avia 355-7000 UV-Laser.

Common photoactive polymers that undergo refractive index change upon irradiation with UV-light exhibit glass transition temperatures as low as 34° C.

Polymer films for refractive index measurements are prepared by spin coating or drop casting from 1-8 wt % solutions of the polymers in chloroform onto silicon wafers or quartz plates. For production of bulk polymer blanks, the monomers are melted under vacuum. Appropriate amounts of a radical initiator and cross-linker are mixed in and quickly filled into a heated polymerization chamber. Cross-linked polymer plates are obtained.

Refractive index change is induced by irradiation at 340-365 nm. The refractive indices (n) of the polymer films and blanks at 590 nm are measured on Schmidt+Haensch AR12 before and after irradiation. The following table shows the refractive indices before and after irradiation as well as the change in refractive index (max. Δn).

| Polymer No | $T_g$ [° C.] | $M_n$ | $M_w$ | D | n | Δn |
|---|---|---|---|---|---|---|
| P-02 | 33.8 | — | — | — | 1.572 | 0.033 |
| P-106 | −10.4 | — | — | — | 1.596 | 0.020 |
| P-128 | 66.3 | 9.422 g/mol | 40.869 g/mol | 4.34 | 1.602 | 0.003 |
| P-135 | 53.4 | 11.783 g/mol | 4.4434.390 g/mol | 376 | 1.610 | 0.003 |

The invention claimed is:

1. A compound of formula (I)

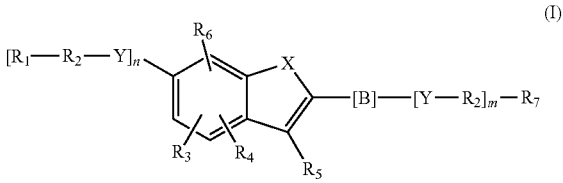

wherein
X is O, S or NR$_0$,
Y is independently of each other O, S or a bond,
n is 0 or 1,
m is 0 or 1,
n+m is 1 or 2,
—[B]— is selected from formula (1) to formula (4),

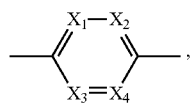 (1)

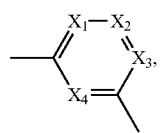 (2)

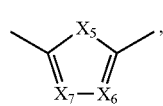 (3)

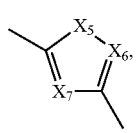 (4)

$X_1$, $X_2$, $X_3$, $X_4$ are each independently of each other CR' or N,
$X_5$ is each independently O, S, C=O or NR$_0$,
$X_6$, $X_7$ are each independently CR' or N,
R is at each occurrence independently selected from the group consisting of H, OH or a linear or branched hydroxyalkyl group having 1 to 4 C atoms,
R' is at each occurrence independently selected from the group consisting of H, F, a linear or branched, non-halogenated, partially or completely halogenated alkyl group having 1 to 20 C atoms, a linear or branched hydroxyalkyl group having 1 to 20 C atoms, a non-halogenated, partially or completely halogenated cycloalkyl group having 3 to 6 C atoms, a linear or branched, non-halogenated, partially or completely halogenated alkoxy group having 1 to 20 C atoms, or a linear or branched, non-halogenated, partially or completely halogenated thioalkyl group having 1 to 20 C atoms,
R$_0$ is at each occurrence independently selected from the group consisting of a linear or branched alkyl group having 1 to 10 C atoms, or a cycloalkyl group having 3 to 6 C atoms,
R$_1$ is a polymerizable group selected from an alkenyl group of formula (5),

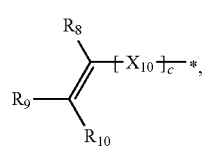 (5)

wherein
$X_{10}$ is O, S, C(=O), or C(=O)O,
$R_8$, $R_9$, $R_{10}$ are at each occurrence independently of each other H, F, a linear or branched, non-fluorinated, partially or completely fluorinated alkyl having 1 to 20 C atoms, or aryl with 6 to 14 C atoms,
c is 0 or 1;
trialkoxysilyl groups or dialkoxyalkylsilyl groups where the alkyl and/or alkoxy groups are each independently linear or branched having 1 to 6 C atoms; and
silyl groups of formula (6), (7) or (8),

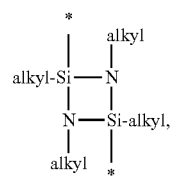 (6)

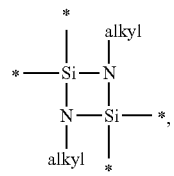 (7)

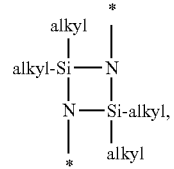 (8)

where alkyl means at each occurrence independently of each other a linear or branched alkyl group having 1 to 6 C atoms and the asterisk "*" denotes at each occurrence independently of each other a linkage to the linker [—R$_2$—Y]$_n$ and/or [Y—R$_2$—]$_m$,
—R$_2$— is —(C(R)$_2$)$_o$— or —(C(R)$_2$)$_p$—X$_8$—(C(R)$_2$)$_q$—(X$_9$)$_s$—(C(R)$_2$)$_r$—, wherein at least one R is OH or a linear or branched hydroxyalkyl group having 1 to 4 C atoms,
o is selected from 1 to 20,
$X_8$, $X_9$ are at each occurrence independently O, S or NR$_0$,
s is 0 or 1,
p, q are at each occurrence independently selected from 1 to 10,
r is at each occurrence independently selected from 0 to 10, wherein the overall number of atoms for —(C(R)$_2$)$_p$—X$_8$—(C(R)$_2$)$_q$—(X$_9$)$_s$—(C(R)$_2$)$_r$—is up to 20 atoms,
$R_3$, $R_4$, $R_5$, $R_6$ are at each occurrence independently R',
$R_7$ is R' in case m is 0, and
$R_7$ is $R_1$ in case m is 1.

2. The compound according to claim 1, wherein —[B]— corresponds to formula (1) or formula (2).

3. The compound according to claim 1, wherein $X_1$, $X_3$ and $X_4$ in formulae (1) or (2) are CR'.

4. The compound according to claim 1, wherein $X_2$ is CR'.

5. The compound according to claim 1, wherein at least one R' within $X_1$, $X_2$, $X_3$, $X_4$, $X_6$ or $X_7$ in formulae (1) to (4) is not H.

6. The compound according to claim 1, wherein n is 1 and m is 0, said compounds being of formula (I')

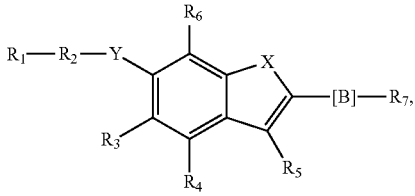

wherein $R_1$, —$R_2$—, Y, $R_3$, $R_4$, $R_5$, $R_6$, X, —[B]— and $R_7$ have a meaning as indicated in claim 1.

7. The compound according to claim 1, wherein n is 0 and m is 1, said compounds being of formula (I'')

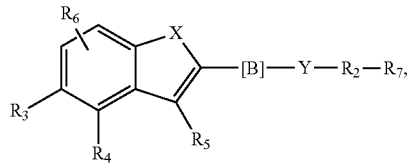

wherein $R_1$, —$R_2$—, Y, $R_3$, $R_4$, $R_5$, $R_6$, X, —[B]— and $R_7$ have a meaning as indicated for the compound of formula (I).

8. The compound according to claim 1, wherein n is 1 and m is 1, said compounds being of formula (I''')

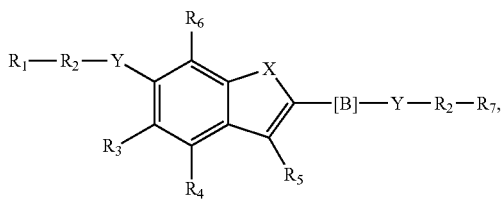

wherein $R_1$, —$R_2$—, Y, $R_3$, $R_4$, $R_5$, $R_6$, X, —[B]— and $R_7$ have a meaning as indicated for the compound of formula (I).

9. The compound according to claim 1, wherein —$R_2$— is at each occurrence independently —$(C(R)_2)_o$—, wherein at least one R is OH or a linear or branched hydroxyalkyl group having 1 to 4 C atoms.

10. The compound according to claim 1, wherein $R_1$ is at each occurrence independently an acryl or methacryl radical.

11. An oligomer or polymer comprising a polymerized compound of formula (I) according to claim 1.

12. A composition comprising at least one compound of formula (I) according to claim 1.

13. An article comprising at least one oligomer or polymer according to claim 11.

14. The article according to claim 13, wherein said article is a blank which may be transformed into an eye implant or an eye implant.

15. A process of forming an article of claim 13, said process comprising:

providing a composition comprising at least one polymerized compound of formula (I), and
subsequently forming the article from said composition.

16. A process of changing the optical properties of an article according to claim 13, said process comprising:
providing an article according to claim 13, and
subsequently exposing said article to irradiation having a wavelength of at least 200 nm and at most 1500 nm.

17. A composition comprising an oligomer or polymer according to claim 11.

18. The article according to claim 13, wherein said article is an intraocular lens.

19. The article according to claim 13, wherein said article is an ophthalmic device.

20. The article according to claim 19, wherein said ophthalmic device is a lens, a keratoprosthesis, a cornea inlay, or a cornea ring.

21. A process of forming an article, said process comprising:
introducing a compound according to claim 1 into a mold and polymerizing said compound to form a blank,
transforming the blank into the article, wherein said article is an ophthalmic device.

22. A process of forming an article, said process comprising:
polymerizing a compound according to claim 1 to form an oligomer or polymer composition,
introducing the oligomer or polymer composition into a mold to form a blank,
shaping the blank by cutting, optic lathe cutting, optic milling, and/or haptic milling to form the article.

23. A copolymer comprising a polymerized compound of formula (I) according to claim 1 wherein the polymerizable group $R_1$ forms part of a co-polymer backbone.

24. The copolymer according to claim 23, wherein said copolymer comprises one or more constitutional units $M^0$ of formulae (5-p-1), (5-p-2), or (5-p-3):

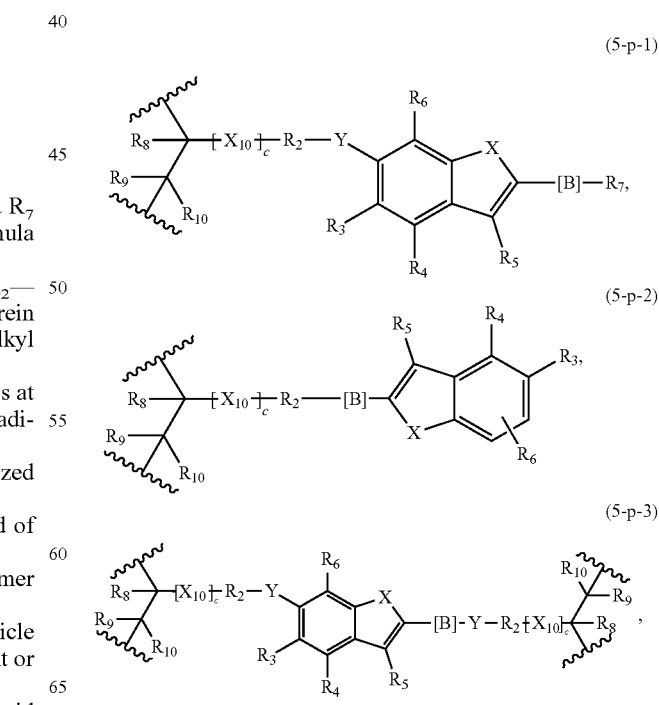

wherein —$R_2$—, Y, $R_3$, $R_4$, $R_5$, $R_6$, X, —[B]—, $R_7$, $X_{10}$, $R_8$, $R_9$, $R_{10}$ and c meanings as defined in claim 1.

25. The copolymer according to claim 24, wherein said copolymer further comprises one or more constitutional units $M^2$ which are chemically different from the units $M^0$.

26. The copolymer according to claim 25, wherein said one or more constitutional units $M^2$ which are derived by polymerization of one or more monomers selected from
styrene, ethoxyethyl methacrylate, methyl methacrylate, n-alkyl methacrylates wherein the n-alkyl groups contain 2-20 C-atoms, n-alkyl methacrylates wherein the n-alkyl groups contain 2-20 C-atoms, ethoxyethoxy ethylacrylate, 2-hydroxyethyl methacrylate, tetrahydrofuryl methacrylate, glycidylmethacrylate, 16-hydroxyhexadecyl acrylate, 16-hydroxyhexadecyl methacrylate, 18-hydroxyoctadecyl acrylate, 18-hydroxyoctadecyl methacrylate, 2-phenoxyethyl acrylate, bisphenol A diacrylate-1 EO/Phenol, 2-[3'-2'H-benzotriazol-2'-yl)-4'-hydroxyphenyl] ethyl methacrylate, trialkoxyalkenylsilane, dialkoxyalkylalkenylsilane, and
silanes of formula (9) and (10),

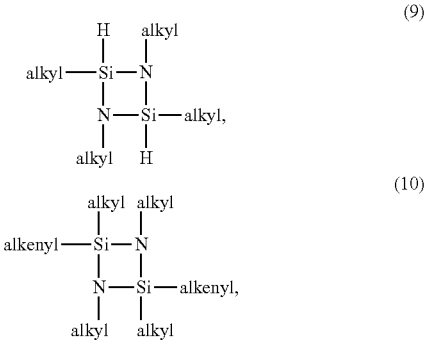

where the alkyl and/or alkoxy groups are at each occurrence independently of each other linear or branched having 1 to 6 C atoms and the alkenyl group is at each occurrence independently linear having 2 to 4 C atoms.

27. An article comprising at least one copolymer according to claim 24.

28. An article comprising at least one copolymer according to claim 25.

29. An article comprising at least one copolymer according to claim 26.

30. The article according to claim 27, wherein said copolymer is cross-linked.

31. The article according to claim 28, wherein said copolymer is cross-linked.

32. The article according to claim 29, wherein said copolymer is cross-linked.

33. The copolymer according to claim 25, wherein said copolymer comprises the one or more constitutional units $M^0$ in a molar ratio m1 and the one or more constitutional units $M^2$ in a molar ratio m2, wherein the ratio m1:m2 is at least 0.01 and at most 100.

34. An article comprising at least one copolymer according to claim 33.

35. An article according to claim 19, wherein the ophthalmic device comprises one or more optic components and one or more haptic components, wherein the one or more optic components serve as a lens and the one or more haptic components are attached to the one or more optic components and hold the one or more optic components in place in the eye.

36. An article according to claim 18, wherein the article has a one-piece design.

37. An article according to claim 18, wherein the article has a multi-piece design.

38. An article produced by the process according to claim 16.

\* \* \* \* \*